United States Patent
Butora et al.

(10) Patent No.: US 7,598,243 B2
(45) Date of Patent: Oct. 6, 2009

(54) HETEROCYCLIC CYCLOPENTYL TETRAHYDROISOQUINOLINE AND TETRAHYDROPYRIDOPYRIDINE MODULATORS OF CHEMOKINE RECEPTOR ACTIVITY

(75) Inventors: Gabor Butora, Martinsville, NJ (US); Stephen D. Goble, Edsion, NJ (US); Alexander Pasternak, Princeton, NJ (US); Lihu Yang, Edison, NJ (US); Changyou Zhou, Plainsboro, NJ (US); Christopher R. Moyes, Hertford (GB)

(73) Assignee: Merck & Co., Inc., Rahway, NJ (US)

( * ) Notice: Subject to any disclaimer, the term of this patent is extended or adjusted under 35 U.S.C. 154(b) by 951 days.

(21) Appl. No.: 10/260,008

(22) Filed: Oct. 15, 2004

(65) Prior Publication Data

US 2008/0081803 A1    Apr. 3, 2008

Related U.S. Application Data

(63) Continuation-in-part of application No. PCT/US2004/011463, filed on Apr. 14, 2004.
(60) Provisional application No. 60/463,673, filed on Apr. 17, 2003.

(51) Int. Cl.
*A61K 31/5377* (2006.01)
*C07D 413/08* (2006.01)
*C07D 413/14* (2006.01)
(52) U.S. Cl. .................. 514/234.5; 544/127
(58) Field of Classification Search .......... 544/127; 514/234.5
See application file for complete search history.

(56) References Cited

FOREIGN PATENT DOCUMENTS

| WO | WO 02/13824 A1 | 2/2002 |
|---|---|---|
| WO | WO 03/093231 A2 | 11/2003 |
| WO | WO 2004/094371 | 11/2004 |
| WO | WO 2004/110376 A2 * | 12/2004 |

* cited by examiner

*Primary Examiner*—Rebecca L Anderson
(74) *Attorney, Agent, or Firm*—Mark R. Daniel; James L. McGinnis

(57) ABSTRACT

The present invention is directed to compounds of the formula I:

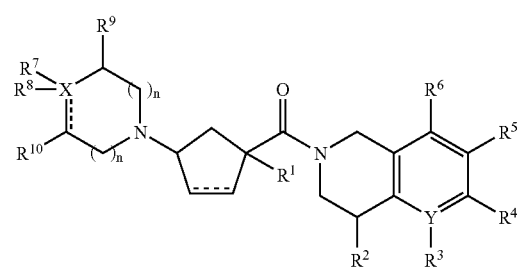

Wherein $R_1$, $R_2$, $R_3$, $R_4$, $R_5$, $R_6$, $R_7$, $R_8$, $R_9$, X, n and the broken lines are as defined herein which are useful as modulators of chemokine receptor activity. In particular, these compounds are useful as modulators of the chemokine receptor CCR-2.

11 Claims, No Drawings

HETEROCYCLIC CYCLOPENTYL TETRAHYDROISOQUINOLINE AND TETRAHYDROPYRIDOPYRIDINE MODULATORS OF CHEMOKINE RECEPTOR ACTIVITY

RELATED APPLICATION DATA

This is a filing under 35 U.S.C. § 111(a) and is a continuation-in-part of PCT/US2004/011463, filed Apr. 14, 2004, which claims priority from U.S. Ser. No. 60/463,673, filed Apr. 17, 2003.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165-183 (1991) and Murphy, *Rev. Immun.*, 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661-666 (1996)).

The chemokines are secreted by a wide variety of cell types and bind to specific G-protein coupled receptors (GPCRs) (reviewed in Horuk, *Trends Pharm. Sci.*, 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123-22128 (1995); Beote, et al, *Cell*, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908-928 (1997)); CCR-4 (or "CKR-4" or "CC-CKR-4") [MIP-1α, RANTES, MCP-1] (Rollins, et al., *Blood*, 90, 908-928 (1997)); CCR-5 (or "CKR-5" or "CC-CKR-5") [MIP-1α, RANTES, MIP-1β] (Sanson, et al., *Biochemistry*, 35, 3362-3367 (1996)); and the Duffy blood-group antigen [RANTES, MCP-1] (Chaudhun, et al., *J. Biol. Chem.*, 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.*, 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601-608 (1998); Kurihara et al. *J. Exp. Med.*, 186, 1757-1762 (1997); Boring et al. *J. Clin. Invest.*, 100, 2552-2561 (1997); Kuziel et al. *Proc. Natl. Acad. Sci.*, 94, 12053-12058 (1997)). Furthermore, these animals show reduced monocyte infiltration into granulomatous lesions induced by the injection of schistosomal or mycobacterial antigens (Boring et al. *J. Clin. Invest.*, 100, 2552-2561 (1997); Warmington et al. *Am J. Path.*, 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1−/− or CCR24−/− mice backcrossed to APO-E −/−, LDL-R −/− or Apo B transgenic mice maintained on high fat diets (Boring et al. *Nature*, 394, 894-897 (1998); Gosling et al. *J. Clin. Invest.*, 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

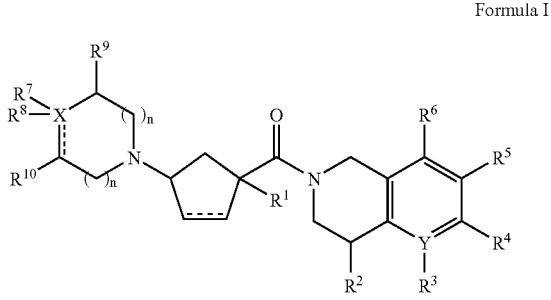

Formula I

X is selected from:
  C, N, O, S and $SO_2$;
Y is selected from N or C.
$R^1$ is selected from:
  hydrogen, —$C_{1-6}$alkyl, —$C_{0-6}$alkyl-O—$C_{1-6}$alkyl, —$C_{0-6}$alkyl-S—$C_{1-6}$alkyl,
  —($C_{0-6}$alkyl)-($C_{3-7}$cycloalkyl)-($C_{0-6}$alkyl), hydroxy, heterocycle,
  —CN, —$NR^{12}R^{12}$, —$NR^{12}COR^{13}$, —$NR^{12}SO_2R^{14}$, —$COR^{11}$, —$CONR^{12}R^{12}$, and phenyl,
  where $R^{11}$ is independently selected from: hydroxy, hydrogen,
    $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-16}$ alkyl, and trifluoromethyl, and
  where $R^{12}$ is selected from: hydrogen, $C_{1-6}$ alkyl, benzyl, phenyl,
    $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, and
  where $R^{13}$ is selected from: hydrogen, $C_{1-6}$ alkyl, —O—$C_{1-6}$alkyl, benzyl, phenyl, $C_{3-6}$ cycloalkyl
    where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, and
  where $R^{14}$ is selected from: hydroxy, $C_{1-6}$ alkyl, —O—$C_{1-6}$alkyl, benzyl, phenyl, $C_{3-6}$ cycloalkyl
    where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, and
  where the alkyl and the cycloalkyl are unsubstituted or substituted with 1-7 substituents where the substituents are independently selected from:
    (a) halo,
    (b) hydroxy,
    (c) —O—$C_{1-3}$alkyl,
    (d) trifluoromethyl,
    (f) $C_{1-3}$alkyl,
    (g) —O—$C_{1-3}$alkyl,
    (h) —$COR^{11}$,
    (i) —$SO_2R^{14}$,
    (j) —$NHCOCH_3$,
    (k) —$NHSO_2CH_3$,
    (l) -heterocycle,
    (m) =O,
    (n) —CN,
  and where the phenyl and heterocycle are unsubstituted or substituted with 1-3 substituents where the substituents are independently selected from: halo, hydroxy, $C_{1-3}$alkyl, $C_{1-3}$alkoxy and trifluoromethyl;
$R^2$ is selected from:
  (a) hydrogen,
  (b) hydroxy,
  (c) halo,
  (d) $C_{1-3}$alkyl, where the alkyl is unsubstituted or substituted with 1-6 substituents independently selected from: fluoro, and hydroxy,
  (e) —$NR^{12}R^{12}$,
  (f) —$COR^{11}$,
  (g) —$CONR^{12}R^{12}$,
  (h) —$NR^{12}COR^{13}$,
  (i) —$OCONR^{12}R^{12}$,
  (j) —$NR^{12}CONR^{12}R^{12}$,
  (k) -heterocycle,
  (l) —CN,
  (m) —$NR^{12}$—$SO_2$—$NR^{12}R^{12}$,
  (n) —$NR^{12}$—$SO_2$—$R^{14}$,
  (o) —$SO_2$—$NR^{12}R^{12}$, and
  (p) =O, where $R^2$ is connected to the ring via a double bond;
$R^3$ is oxygen or is absent when Y is N;
$R^3$ is selected from the following list when Y is C:
  (a) hydrogen,
  (b) hydroxy,
  (c) halo,
  (d) $C_{1-3}$alkyl, where the alkyl is unsubstituted or substituted with 1-6 substituents independently selected from: fluoro, hydroxy, and —$COR^{11}$,
  (e) —$NR^{12}R^{12}$,
  (f) —$COR^{11}$,
  (g) —$CONR^{12}R^{12}$,
  (h) —$NR^{12}COR^{13}$,
  (i) —$OCONR^{12}R^{12}$,
  (j) —$NR^{12}CONR^{12}R^{12}$,
  (k) -heterocycle, (l) —CN,
(m) —NR$^{12}$—SO$_2$—NR$^{12}$R$^{12}$,
(n) —NR$^{12}$—SO$_2$—R$^{14}$,
(o) —SO$_2$—NR$^{12}$R$^{12}$ and
(p) nitro;

R$^4$ is selected from:
  (a) hydrogen,
  (b) C$_{1-6}$alkyl,
  (c) trifluoromethyl,
  (d) trifluoromethoxy,
  (e) chloro,
  (f) fluoro,
  (g) bromo, and
  (h) phenyl;

R$^5$ is selected from:
  (a) C$_{1-6}$alkyl, where alkyl may be unsubstituted or substituted with 1-6 fluoro and optionally substituted with hydroxyl,
  (b) —O—C$_{1-6}$alkyl, where alkyl may be unsubstituted or substituted with 1-6 fluoro,
  (c) —CO—C$_{1-6}$alkyl, where alkyl may be unsubstituted or substituted with 1-6 fluoro,
  (d) —S—C$_{1-6}$alkyl, where alkyl may be unsubstituted or substituted with 1-6 fluoro,
  (e) -pyridyl, which may be unsubstituted or substituted with one or more substituents selected from the group consisting of: halo, trifluoromethyl, C$_{1-4}$alkyl, and COR$^{11}$,
  (f) fluoro,
  (g) chloro,
  (h) bromo,
  (i) —C$_{4-6}$cycloalkyl,
  (j) —O—C$_{4-6}$cycloalkyl,
  (k) phenyl, which may be unsubstituted or substituted with one or more substituents selected from the group consisting of: halo, trifluoromethyl, C$_{1-4}$alkyl, and COR$^{11}$,
  (l) —O-phenyl, which may be unsubstituted or substituted with one or more substituents selected from the group consisting of: halo, trifluoromethyl, C$_{1-4}$alkyl, and COR$^{11}$,
  (m) —C$_{3-6}$cycloalkyl, where alkyl may be unsubstituted or substituted with 1-6 fluoro,
  (n) —O—C$_{3-6}$cycloalkyl, where alkyl may be unsubstituted or substituted with 1-6 fluoro,
  (o) -heterocycle,
  (p) —CN, and
  (q) —COR$^{11}$;

R$^6$ is selected from:
  (a) hydrogen,
  (b) C$_{1-6}$alkyl, and
  (c) trifluoromethyl
  (d) fluoro
  (e) chloro, and
  (f) bromo;

R$^7$ is selected from:
  nothing (when X=O), hydrogen, (C$_{0-6}$alkyl)-phenyl, (C$_{0-6}$alkyl)-heterocycle, (C$_{0-6}$alkyl)-C$_{3-7}$cycloalkyl, (C$_{0-6}$alkyl)-COR$^{11}$, (C$_{0-6}$alkyl)-(alkene)-COR$^{11}$, (C$_{0-6}$alkyl)-SO$_3$H, (C$_{0-6}$alkyl)-W—C$_{0-4}$alkyl, (C$_{0-6}$alkyl)-CONR$^{12}$-phenyl, (C$_{0-6}$alkyl)-CONR$^{15}$—V—COR$^{11}$, and nothing (when X is O, S, or SO$_2$), where V is selected from C$_{1-6}$alkyl or phenyl, and where W is selected from: a single bond, —O—, —S—, —SO—, —SO$_2$—, —CO—, —CO$_2$—, —CONR$^{12}$— and —NR$^{12}$—, and where the R$^{15}$ can be hydrogen, C$_{1-4}$alkyl, or where R$^{15}$ is joined via a 1-5 carbon tether to one of the carbons of V to form a ring, and where the C$_{0-6}$alkyl is unsubstituted or substituted with 1-5 substituents, where the substituents are independently selected from:
  (a) halo,
  (b) hydroxy,
  (c) —C$_{0-6}$alkyl
  (d) —O—C$_{1-3}$alkyl,
  (e) trifluoromethyl, and
  (f) —C$_{0-2}$alkyl-phenyl, and where the phenyl, heterocycle, cycloalkyl, and C$_{0-4}$alkyl is unsubstituted or substituted with 1-5 substituents where the substituents are independently selected from:
  (a) halo,
  (b) trifluoromethyl,
  (c) hydroxy,
  (d) C$_{1-3}$alkyl,
  (e) —O—C$_{1-13}$alkyl,
  (f) —C$_{0-3}$—COR$^{11}$,
  (g) —CN,
  (h) —NR$^{12}$R$^{12}$,
  (i) —CONR$^{12}$R$^{12}$, and
  (j) —C$_{0-3}$-heterocycle,
  or where the phenyl and heterocycle may be fused to another heterocycle, which itself may be unsubstituted or substituted with 1-2 substituents independently selected from hydroxy, halo, —COR$^{11}$, and —C$_{1-3}$alkyl, and where alkene is unsubstituted or substituted with 1-3 substituents which are independently selected from:
  (a) halo,
  (b) trifluoromethyl,
  (c) C$_{1-3}$alkyl,
  (d) phenyl, and
  (e) heterocycle;

R$^8$ is selected from:
  (a) hydrogen,
  (b) nothing when X is either O, S, SO$_2$ or N or when a double bond joins the carbons to which R$^7$ and R$^{10}$ are attached,
  (c) hydroxy,
  (d) C$_{1-6}$alkyl,
  (e) C$_{1-6}$alkyl-hydroxy,
  (f) —O—C$_{1-3}$alkyl,
  (g) —COR$^{11}$,
  (h) —CONR$^{12}$R$^{12}$, and
  (i) —CN;

or where R$^7$ and R$^8$ may be joined together to form a ring which is selected from:
  (a) 1H-indene,
  (b) 2,3-dihydro-1H-indene,
  (c) 2,3-dihydro-benzofuran,
  (d) 1,3-dihydro-isobenzofuran,
  (e) 2,3-dihydro-benzothiofuran,
  (f) 1,3-dihydro-isobenzothiofuran,
  (g) 6H-cyclopenta[d]isoxazol-3-ol
  (h) cyclopentane, and
  (i) cyclohexane, where the ring formed may be unsubstituted or substituted with 1-5 substituents independently selected from:
  (a) halo,
  (b) trifluoromethyl,
  (c) hydroxy,
  (d) C$_{1-3}$alkyl, (e) —O—$C_{1-3}$alkyl,
(f) —$C_{0-3}$—$COR^{11}$,
(g) —CN,
(h) —$NR^{12}R^{12}$,
(i) —$CONR^{12}R^{12}$, and
(j) —$C_{0-3}$-heterocycle, or where $R^7$ and $R^9$ or $R^8$ and $R^{10}$ may be joined together to form a ring which is phenyl or heterocycle,
wherein the ring is unsubstituted or substituted with 1-7 substituents where the substituents are independently selected from:
(a) halo,
(b) trifluoromethyl,
(c) hydroxy,
(d) $C_{1-3}$alkyl,
(e) —O—$C_{1-13}$alkyl,
(f) —$COR^{11}$,
(g) —CN,
(h) —$NR^{12}R^{12}$, and
(i) —$CONR^{12}R^{12}$;

$R^9$ and $R^{10}$ are independently selected from:
(a) hydrogen,
(b) hydroxy,
(c) $C_{1-6}$alkyl,
(d) $C_{1-6}$alkyl-$COR^{11}$,
(e) $C_{1-6}$alkyl-hydroxy,
(f) —O—$C_{1-13}$alkyl,
(g) =O, when $R^9$ or $R^{10}$ is connected to the ring via a double bond
(h) halo;

n is selected from 0, 1 and 2;
the dashed line represents a single or a double bond;
and pharmaceutically acceptable salts thereof and individual diastereomers thereof.

Another embodiment of the present invention includes compounds of formula Ia:

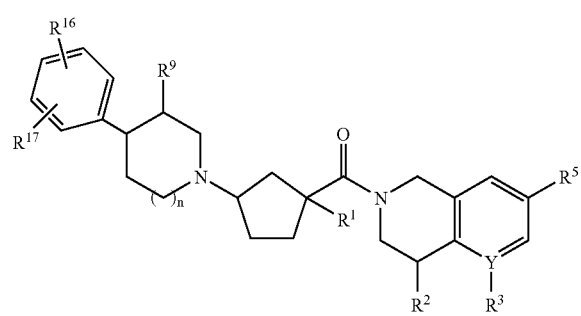

Ia wherein $R^1$, $R^2$, $R^3$, $R^5$, $R^9$, Y, and n are defined herein,
and wherein $R^{16}$ and $R^{17}$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$C_{0-3}$—$CO_2H$,
(h) —$C_{0-3}$—$CO_2C_{1-3}$alkyl,
(i) —CN, and
(j) —$C_{0-3}$-heterocycle, or where the $R^{16}$ and $R^{17}$ are joined together to form a heterocycle which is fused to the phenyl ring, and which itself may be unsubstituted or substituted with 1-2 substituents independently selected from hydroxy, halo, —$COR^{11}$, and —$C_{1-3}$alkyl;
and pharmaceutically acceptable salts and individual diastereomers thereof.

Another embodiment of the present invention also includes compounds of formula Ib:

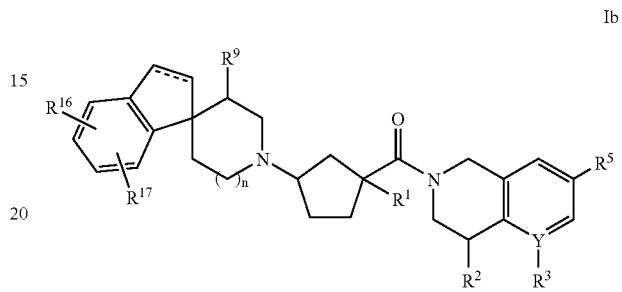

Ib wherein the dashed line represents a single or a double bond and $R^1$, $R^2$, $R^3$, $R^5$, $R^9$, $R^{16}$, $R^{17}$, Y, and n are defined herein;
and pharmaceutically acceptable salts and individual diastereomers thereof.

A still further embodiment of the present invention includes compounds of formula Ic:

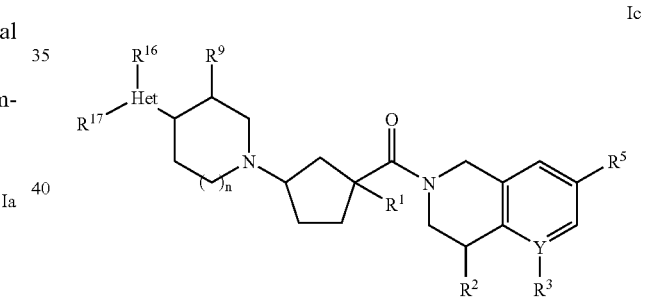

Ic wherein $R^1$, $R^2$, $R^3$, $R^5$, $R^9$, $R^{16}$, $R^{17}$, Y, and n are defined herein,
and where Het is a heterocycle
and pharmaceutically acceptable salts and individual diastereomers thereof.

Another embodiment of the present invention include compounds of formula Id:

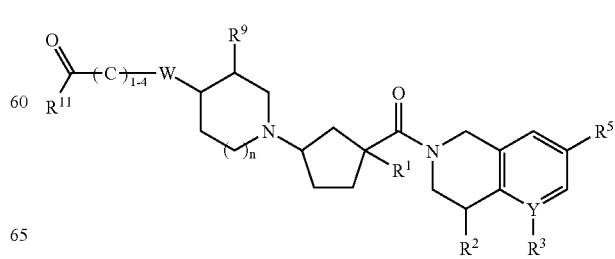

Id wherein $R^1$, $R^2$, $R^3$, $R^5$, $R^9$, $R^{11}$, Y, W, and n are defined herein
and where the $C_{1-4}$ carbon chain may be unsubstituted, or substituted with 1-4 substituents which are independently selected from:
(a) halo,
(b) hydroxy,
(c) —$C_{0-6}$alkyl
(d) —O—$C_{1-13}$alkyl,
(e) trifluoromethyl, and
(f) —$C_{0-2}$alkyl-phenyl,
or where the $C_{1-4}$ carbon chain may be included within a $C_{3-7}$cycloalkyl ring,
and pharmaceutically acceptable salts and individual diastereomers thereof.

A further embodiment of the present invention includes compounds of formula Ie:

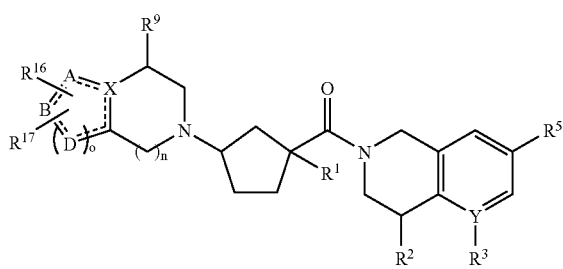

Ie wherein $R^1$, $R^2$, $R^3$, $R^5$, $R^9$, $R^{16}$, $R^{17}$, X, Y, and n are defined herein, and
where the dotted lines can represent either a single or double bond, and
where o can be 1 or 2, and
where A, B, and D, can independently be selected from C, N, O, or S, to make a phenyl ring (when X, A, B, D, are all C, and o=2) or to make a heterocycle when at least one of X, A, B, D are N, O, or S and not C,
and pharmaceutically acceptable salts and individual diastereomers thereof.

A still further embodiment of the present invention includes compounds of formula If:

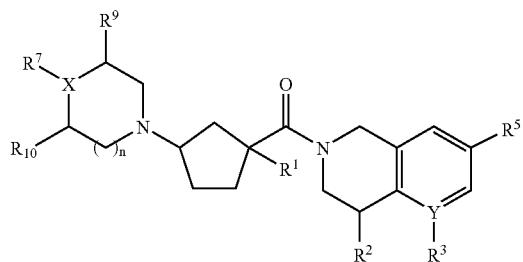

If wherein $R^1$, $R^2$, $R^3$, $R^5$, $R^7$, $R^9$, $R^{10}$, Y, and n are defined herein, and X is either N, or O (in which case $R^7$ is nothing) and pharmaceutically acceptable salts and individual diastereomers thereof.

Another embodiment of the present invention includes compounds of formula Ig:

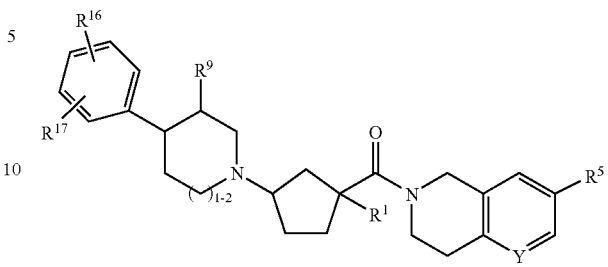

Ig wherein $R^1$, $R^5$, $R^9$, $R^{16}$, $R^{17}$, and Y are defined herein,
or where the $R^{16}$ and $R^{17}$ are joined together to form a heterocycle which is fused to the phenyl ring, and which itself may be unsubstituted or substituted with 1-2 substituents independently selected from hydroxy, halo, —$COR^{11}$, and —$C_{1-3}$alkyl;

and pharmaceutically acceptable salts and individual diastereomers thereof.

A further embodiment of the present invention includes compounds of formula Ih:

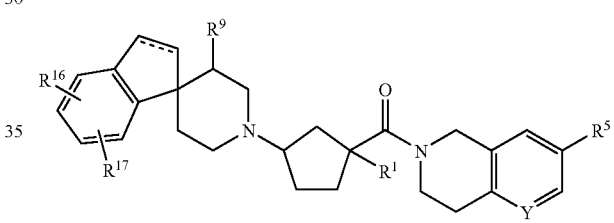

Ih wherein the dashed line represents a single or a double bond and $R^1$, $R^5$, $R^9$, $R^{16}$, $R^{17}$, and Y are defined herein;

and pharmaceutically acceptable salts and individual diastereomers thereof.

An additional embodiment of the present invention includes compounds of formula Ii:

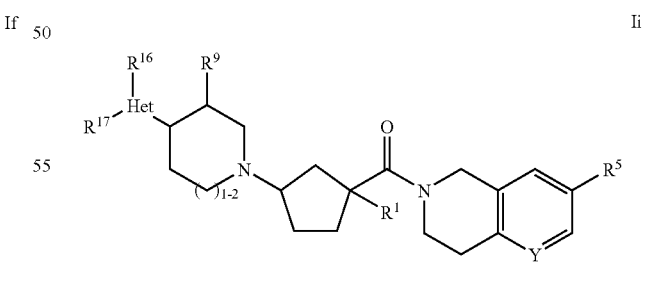

Ii wherein $R^1$, $R^5$, $R^9$, $R^{16}$, $R^{17}$, and Y are defined herein,
and where Het is a heterocycle;
and pharmaceutically acceptable salts and individual diastereomers thereof.

A still further embodiment of the present invention includes compounds of formula Ij:

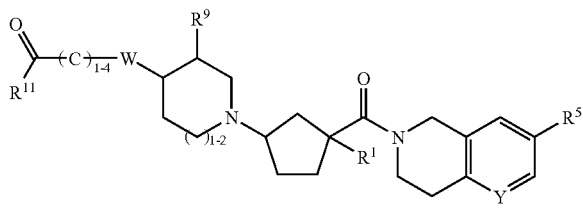

wherein $R^1$, $R^5$, $R^9$, $R^{11}$, Y, and W are defined herein and where the $C_{1-4}$ carbon chain may be unsubstituted, or substituted with 1-4 substituents which are independently selected from:
(a) halo,
(b) hydroxy,
(c) —$C_{0-6}$alkyl
(d) —O—$C_{1-3}$alkyl,
(e) trifluoromethyl, and
(f) —$C_{0-2}$alkyl-phenyl,
and pharmaceutically acceptable salts and individual stereoisomers thereof.

Another embodiment of the present invention includes compounds of formula Ik:

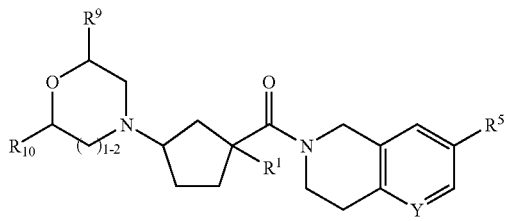

Formula Ik wherein $R^1$, $R^5$, $R^9$, $R^{10}$, and Y are defined herein, and pharmaceutically acceptable salts and individual diastereomers thereof.

In a still further embodiment of the present invention X is C, O or N.

In another embodiment of the present invention X is C or O.

In another embodiment of the present invention $R^1$ is selected from:
—$C_{1-6}$alkyl, —$C_{0-6}$alkyl-O—$C_{1-6}$alkyl, and
—($C_{0-6}$alkyl)-($C_{3-7}$cycloalkyl)-($C_{0-6}$alkyl),
where the alkyl and the cycloalkyl are unsubstituted or substituted with 1-7 substituents where the substituents are independently selected from:
(a) halo,
(b) hydroxy,
(c) —O—$C_{1-13}$alkyl,
(d) trifluoromethyl,
(f) $C_{1-3}$alkyl,
(g) —O—$C_{1-13}$alkyl,
(h) —$COR^{11}$,
(i) —CN,
(j) —$NR^{12}R^{12}$, and
(k) —$CONR^{12}R^{12}$.

In another aspect of the present invention $R^1$ is selected from:

(1) —$C_{1-6}$alkyl, which is unsubstituted or substituted with 1-6 substituents where the substituents are independently selected from:
(a) halo,
(b) hydroxy,
(c) —O—$C_{1-13}$alkyl,
(d) trifluoromethyl, and
(e) —$COR^{11}$,
(2) —$C_{0-6}$alkyl-O—$C_{1-6}$alkyl-, which is unsubstituted or substituted with 1-6 substituents where the substituents are independently selected from:
(a) halo,
(b) trifluoromethyl, and
(c) —$COR^{11}$,
(3) —($C_{3-5}$cycloalkyl)-($C_{0-6}$alkyl), which is unsubstituted or substituted with 1-7 substituents where the substituents are independently selected from:
(a) halo,
(b) hydroxy,
(c) —O—$C_{1-3}$alkyl,
(d) trifluoromethyl, and
(e) —$COR^{11}$.

In still another aspect of the present invention $R^1$ is selected from:
(a) $C_{1-6}$alkyl,
(b) $C_{1-6}$alkyl substituted with hydroxy
(c) $C_{1-6}$alkyl substituted with 1-6 fluoro.

In a still further aspect of the present invention $R^1$ is selected from:
(a) —$CH(CH_3)_2$,
(b) —$CH(OH)CH_3$, and
(c) —$CH_2CF_3$.

In another aspect of the present invention $R^2$ is selected from:
(a) hydroxy
(b) hydrogen
(c) =O, where $R^2$ is connected to the ring via a double bond.

In another aspect of the present invention $R^2$ is hydrogen.

In a still further aspect of the present invention when Y is N, $R^3$ is nothing or O (to give a N-oxide)

In a further aspect of the present invention when Y is N, $R^3$ is nothing.

In a still further aspect of the present invention when Y is C, $R^3$ is selected from:
(a) hydrogen
(b) halo
(c) hydroxy
(d) $C_{1-3}$alkyl, where the alkyl is unsubstituted or substituted with 1-6 substituents independently selected from: fluoro, and hydroxy,
(e) —$COR^{11}$,
(f) —$CONR^{12}R^{12}$,
(g) -heterocycle,
(h) —$NR^{12}$—$SO_2$—$NR^{12}R^{12}$,
(i) —$NR^{12}$—$SO_2$—$R^{14}$,
(j) —$SO_2$—$NR^{12}R^{12}$,
(k) -nitro, and
(l) —$NR^{12}R^{12}$;

In another aspect of the present invention when Y is C, $R^3$ is hydrogen.

In another aspect of the present invention $R^4$ is hydrogen.

In another aspect of the present invention $R^5$ is selected from:
(a) $C_{1-6}$alkyl substituted with 1-6 fluoro,
(b) —O—$C_{1-6}$alkyl substituted with 1-6 fluoro, (c) chloro,
(d) bromo, and
(e) phenyl.

In another aspect of the present invention $R^5$ is selected from:
(a) trifluoromethyl,
(b) trifluoromethoxy,
(c) chloro,
(d) bromo, and
(e) phenyl.

In another aspect of the present invention $R^5$ is trifluoromethyl.

In another aspect of the present invention $R^6$ is hydrogen

In another aspect of the present invention $R^7$ is phenyl, heterocycle, $C_{3-7}$cycloalkyl, $C_{1-6}$alkyl, —$COR^{11}$, and —CONH—V—$COR^{11}$,
where V is selected from $C_{1-6}$alkyl or phenyl, and
where the phenyl, heterocycle, $C_{3-7}$cycloalkyl, and $C_{1-6}$alkyl is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$COR^{11}$,
(g) —CN,
(h)-heterocycle, and
(i) —$CONR^{12}R^{12}$.

In still another aspect of the present invention (when X is not O) that $R^7$ is phenyl, heterocycle, $C_{1-4}$alkyl, —$COR^{11}$, and —CONH—V—$COR^{11}$,
where V is selected from $C_{1-6}$alkyl or phenyl, and
where the phenyl, heterocycle, and $C_{1-4}$alkyl is unsubstituted or substituted with 1-3 substituents where the substituents are independently selected from:
(a) halo,
(b) hydroxy,
(c) $C_{1-3}$alkyl,
(d) —O—$C_{1-13}$alkyl,
(e) —$COR^{11}$, and
(f)-heterocycle In still another aspect of the present invention (when X is C), $R^7$ is selected from:

(a) 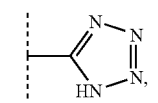
(b) para-fluorophenyl,
(c) 3-carboxyphenyl,
(d) 3-carboxy-4-fluorophenyl,
(e) phenyl,
(f) —$CO_2CH_2CH_3$,
(g) —$CO_2H$,
(h) —$CONHCH_3$,
(i) -hydroxy

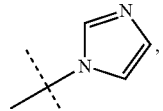 (j)

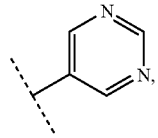 (k)

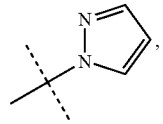 (l)

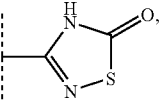 (m)

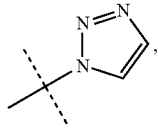 (n)

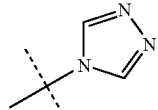 (o)

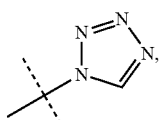 (p)

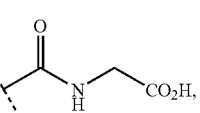 (q)

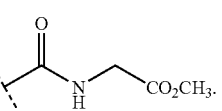 (r)

In another aspect of the present invention when X is C, $R^8$ is selected from:
(a) hydrogen,
(b) hydroxy,
(c) —CN, and
(d) —F In another aspect of the present invention $R^7$ and $R^8$ may be joined together to form a ring which is selected from:
(a) 1H-indene,
(b) 2,3-dihydro-1H-indene,
where the ring formed may be unsubstituted or substituted with 1-3 substituents independently selected from:
(a) halo,
(b) hydroxy, (c) $C_{1-3}$alkyl,
(d) —O—$C_{1-13}$alkyl,
(e) —$COR^{11}$, and
(f) -heterocycle.

In another aspect of the present invention $R^9$ and $R^{10}$ are independently selected from:
(a) hydrogen,
(b) hydroxy,
(c) —$CH_3$,
(d) —O—$CH_3$, and
(e) =O (where $R^9$ and/or $R^{10}$ are joined to the ring via a double bond).

In yet another aspect of the present invention n=1 or 2.

Representative compounds of the present invention include those presented in the Examples and pharmaceutically acceptable salts and individual diastereomers thereof.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of one aspect of the compounds of this invention, where the substituents on the cyclopentyl ring (amide and amine units) are cis, as depicted:

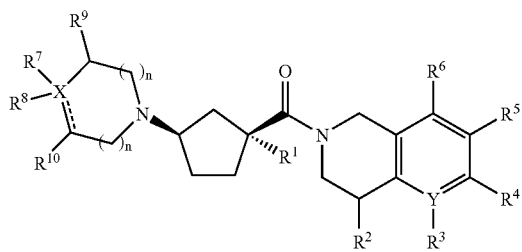

The absolute configurations of a still further aspect of the compounds of this invention are those of the orientation as depicted:

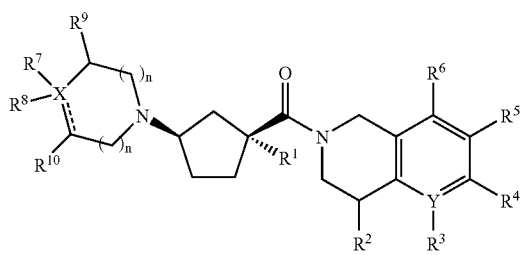

wherein the carbon bearing the amine substituent is designated as being of the (R) absolute configuration and the carbon bearing the amide subunit can be designated as being of either the (S) or (R) absolute configuration depending on the priority for $R^1$. For example if R is isopropyl then the absolute stereochemistry at the carbon bearing the amide subunit would be (S) since the amide and amine units are preferred to have the cis arrangement on the cyclopentyl ring.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are used. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 µM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 3 µM, preferably less than about 11M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In one embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, COPD, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, stroke, Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis, Hookworm, Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In an aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

The term "substituted" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups.

It is understood that the definition of a substituent at a particular location in a molecule is independent of its definition at other locations in the molecule. Thus, for example, when R3=alkyl substituted with 1-5 of R12 (defined elsewhere), each R12 is independently selected from the possible values thereof; i.e., each R12 can be the same as or different from any other R12.

The term "optionally substituted" is intended to include both substituted and unsubstituted. Thus, for example, optionally substituted aryl could represent a pentafluorophenyl or a phenyl ring.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is typically employed. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. The dosage level will be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, 2.0 to 500, 3.0 to 200, or 1, 5, 10, 15, 20, 25, 30, 50, 75, 100, 125, 150, 175, 200, 250, 300, 400, 500, 600, 750, 800, 900 and/or 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are commercially available, made by known procedures, or prepared as illustrated herein.

One of the principal routes used for preparation of compounds within the scope of the instant invention which bear a 1,1,3-trisubstituted cyclopentane framework 1-5 is depicted in Scheme 1. According to this route, keto acids 1-1 (preparation described in Schemes 2A, 2B, 2C, and 2D) is coupled to amines 1-2 (preparation described in Schemes 3A-G). This can be accomplished in various ways, including by first converting the acid to its acid chloride with a reagent such as oxalyl chloride, and then combining with amine 1-2 in the presence of a base such as triethylamine. Reductive amination of 1-3 with an amine 1-4 using, for example, NaB(OAc)$_3$H or NaBH$_3$CN as the reducing agent gives chemokine receptor modulators 1-5. The compounds 1-9, which can be synthesized according to the chemistry described in Scheme 1 represent stereoisomeric mixtures (Eliel, E. E., Wilen, S. H., *Stereochemistry of Organic Compounds*, John Wiley & Sons, Inc., New York). In particular, compounds 1-5 are often obtained as a mixture of cis and trans isomers. When 1-1 is a single stereoisomer (1-1a) only 2 possible isomers of 1-5 can result (cis and trans); these can be separated by a variety of methods, including by preparative TLC, flash chromatography, MPLC, or by HPLC using a column with a chiral stationary phase. When 1-1 is racemic, a total of 4 possible isomers of 1-5 can be obtained. Again, these may be separated by HPLC using a column with a chiral stationary phase, or by a combination of the methods above. The synthesis of racemic 1-1 is detailed in Scheme 2A, while syntheses of the chiral 1-1a are described in Schemes 2B and 2C.

Furthermore, compounds 1-5 can themselves be modified to give new chemokine receptor modulators 1-5.1. For example, an ester functional group within a compound 1-5 can be hydrolyzed to the corresponding carboxylic acid, which also can be a chemokine receptor modulator.

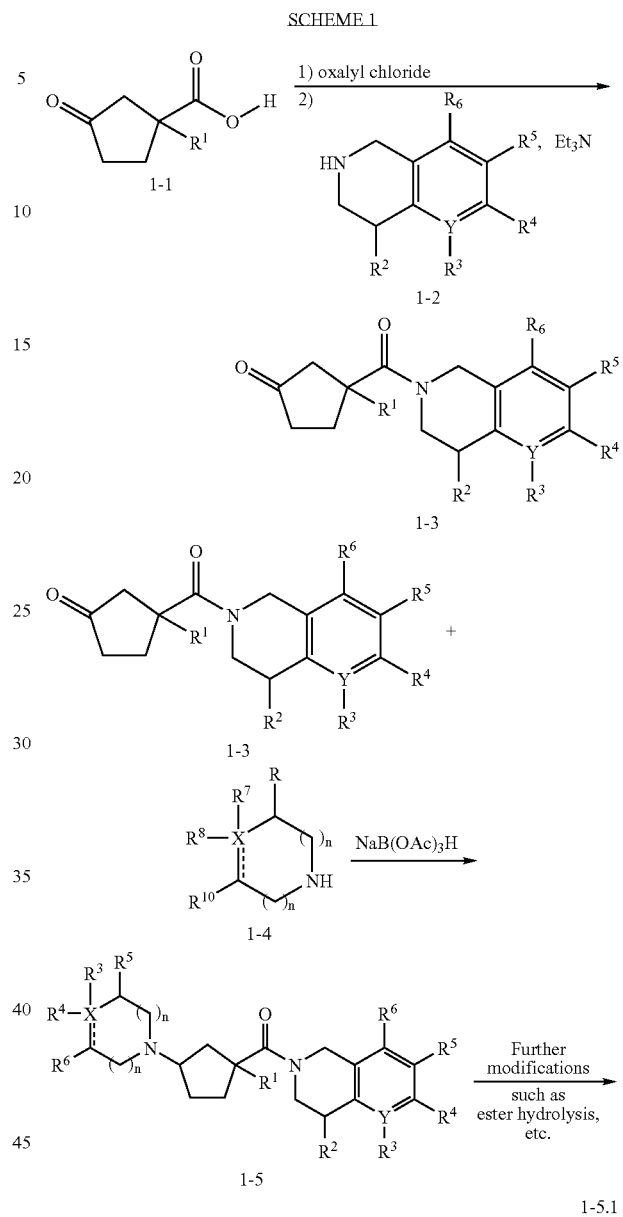

As depicted in Scheme 1A, the keto-ester 1-6 could be reductively aminated with amine 1-4 to form the amino ester 1-7 under a variety of conditions, including sodium triacetoxyborohydride or sodium cyanoborohydride. Alkylation of the ester 1-7 with an alkylating agent such as an alkyl chloride, bromide or iodide in the presence of an appropriate base such as lithium bis(trimethylsilyl)amide, affords the intermediate esters 1-8. These esters formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 1-8 were hydrolytically cleaved to yield the respective acids 1-9. This hydrolysis was readily accomplished under usual conditions, including lithium, sodium or potassium hydroxide, at ambient to elevated temperatures, depending on the nature of the ester group and substituent R¹. These diastereoisomers could be separated by crystallization from a variety of solvents, taking advantage of the finding, that the cis-diastereoisomeric acids are less soluble, when compared to their trans-epimers.

The compounds of formula 1-5 are then formed from the acids 1-9 and tetrahydroisoquinoline derivatives 1-2 under standard amide-bond forming reaction conditions, including carbodimide reagents, such as DCC, EDC and catalysts such as DMAP, HOAT or HOBT.

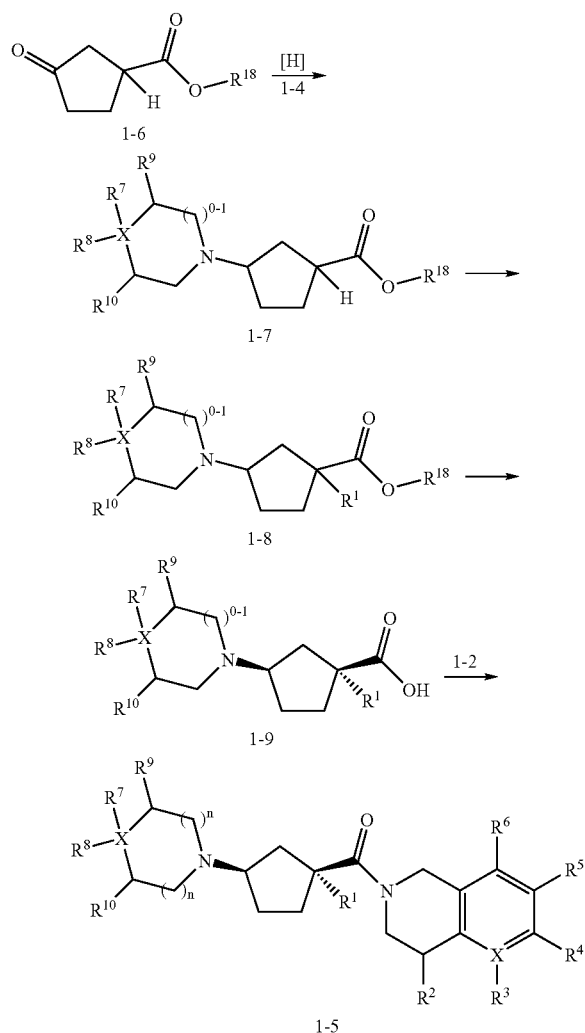

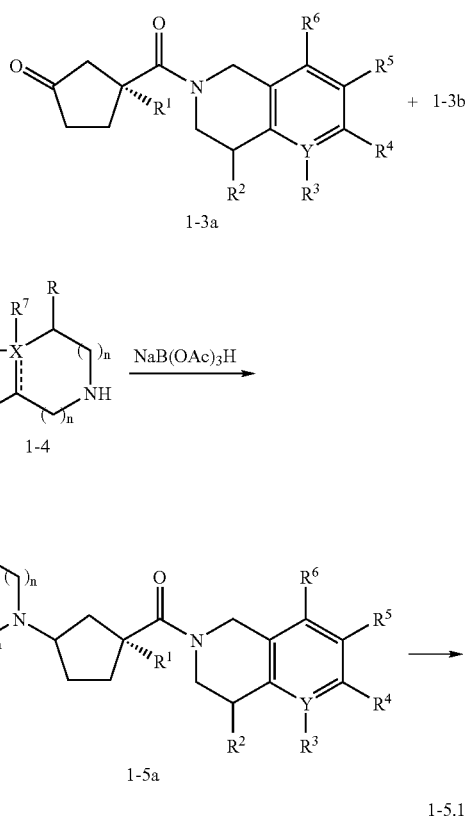

Intermediate 1-3 can also be resolved by Chiral HPLC to give 1-3a and 1-3b (Scheme 1B). This then would give cis/trans isomers 1-5a and 1-5b.

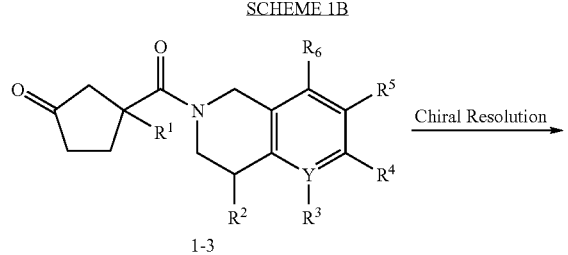

One of the principal routes used for preparation of Intermediate 1-1 and Intermediate 1-6 is outlined in Scheme 2A. According to this route, 3-oxocyclopentanecarboxylic acid (2-1), which can be synthesized following a known procedure (Stetter, H., Kuhlman, H., *Liebigs Ann. Chim.*, 1979, 944) is esterified under standard conditions. When $R^{18}$ represents a tert-Butyl group, the respective ester 1-6 can be prepared by reacting the appropriate alcohol, in this case tert-butanol, with acid 2-1 in the presence of sulfuric acid. Protection of the oxo-group in 2-1 can be achieved by a number of ways (Greene, T., Wuts, P. G. M., *Protective Groups in Organic Chemistry*, John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{18}$ being a methyl group, the acid 2-1 can be converted to 2-3 directly by using trimethyl orthoformate and an acidic catalyst, such as para-toluenesulfonic acid. An alkylation of esters 2-3 with an alkylating agent such as an alkyl chloride, bromide or iodide in the presence of an appropriate base such as lithium diisopropylamide, produces compounds 2-4. The ester protecting group present in 2-4 can be removed in a number of ways, depending on the nature of the ester. Methyl esters ($R^{18}$=methyl) can be hydrolyzed in the presence of an acid or base at ambient or elevated temperatures, whereas tert-butyl esters ($R^{18}$=tert-butyl) can be easily cleaved under acidic conditions. Under these conditions, the dimethyl acetal is simultaneously deprotected to give 1-1.

SCHEME 2A

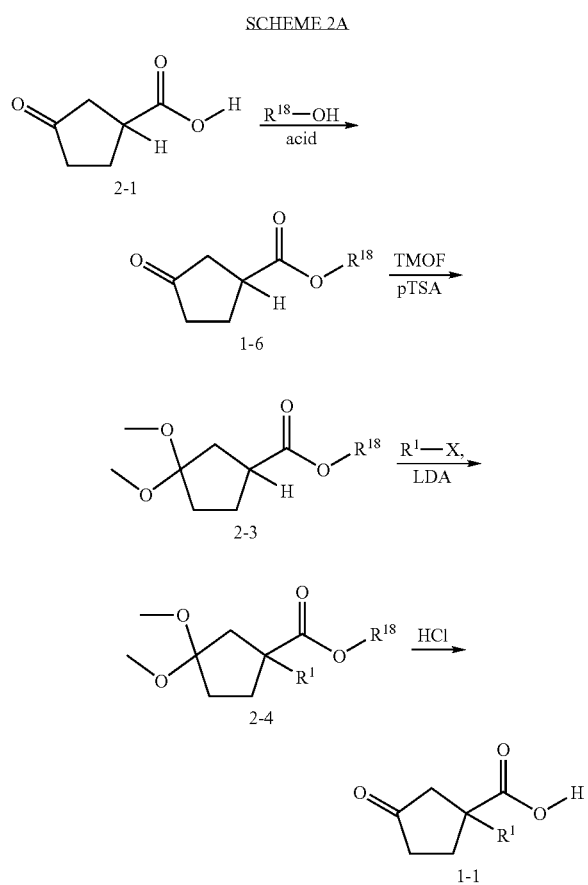

Intermediate 1-1 can be prepared as a single stereoisomer (1-1a) in various ways including those depicted in Schemes 2B and 2C. According to Scheme 2B, racemic 1-1 can be converted to its benzyl ester. There are many ways to effect this esterification, one of which being by a sequence involving conversion to the corresponding acid chloride with, for example oxalyl chloride, followed by treatment with benzyl alcohol in the presence of a base such as triethylamine. Then the racemic benzyl ester 2-5 can be separated by chiral preparative HPLC to give 2-5a as a single stereoisomer. Removal of the benzyl group to give the chiral ketoacid 1-1a can be accomplished in several ways. One convenient way is by hydrogenolysis in the presence of a catalyst such as Pd/C.

SCHEME 2B

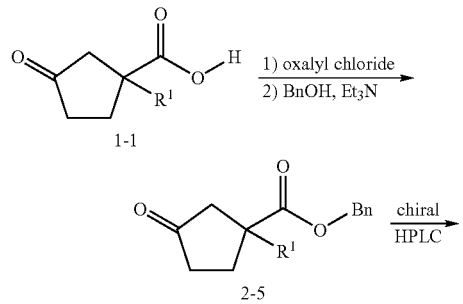

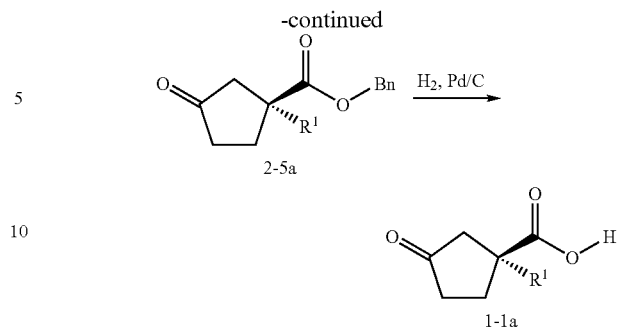

According to Scheme 2C, chiral ketoacid compound 1-1a can be prepared starting from commercially available optically pure amino acid 2-6. Protection of the carboxylic acid group can be achieved in a variety of ways. When $R^{18}$ is methyl, esterification can be accomplished by treatment with methanol in the presence of an acid catalyst such as HCl. Treatment with Boc$_2$O results in protection of the amine group of 2-7. Stereoselective alkylation of ester 2-8 with an alkylating agent such as an alkyl chloride, bromide or iodide in the presence of an appropriate base such as lithium bis(trimethylsilyl)amide, produces compounds 2-9. Hydrogenation in the presence of a catalyst such as Pd/C affords 2-10. Hydrolysis of the ester to give 2-11 can be achieved under standard conditions depending on the $R^{18}$ group. For example, when $R^{18}$ is methyl (methyl ester), hydrolysis can be accomplished by treatment with a base such as sodium hydroxide, lithium hydroxide, or potassium hydroxide, with or without heating. The Boc protecting group can be removed under standard acidic conditions, such as with HCl in a solvent such as dioxane, or with TFA. Oxidation of 2-12 to give 1-1a (as a single stereoisomer if constituent $R^1$ is achiral, or as a mixture of stereoisomers if constituent $R^1$ has a chiral center) can be achieved in several ways, including by treatment with NBS, followed by treatment with sodium methoxide.

SCHEME 2C

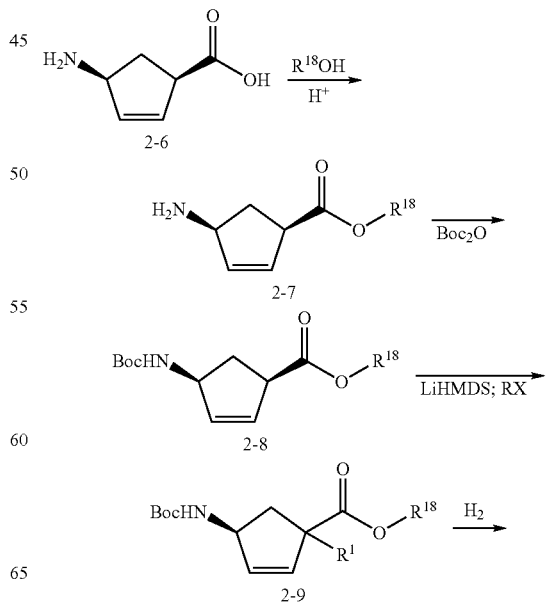

-continued

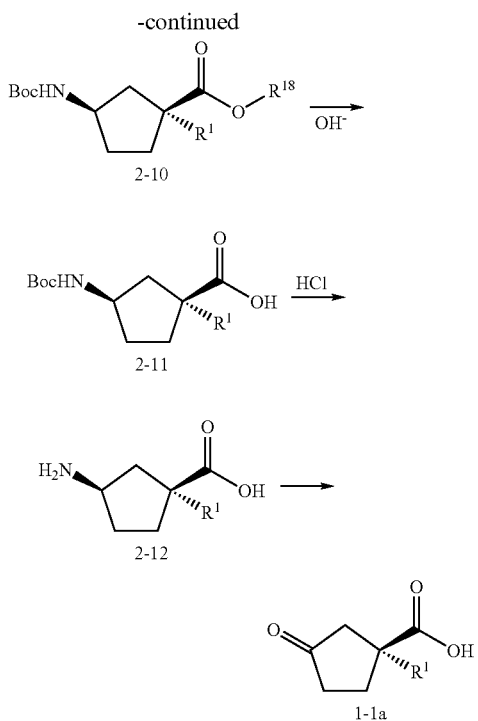

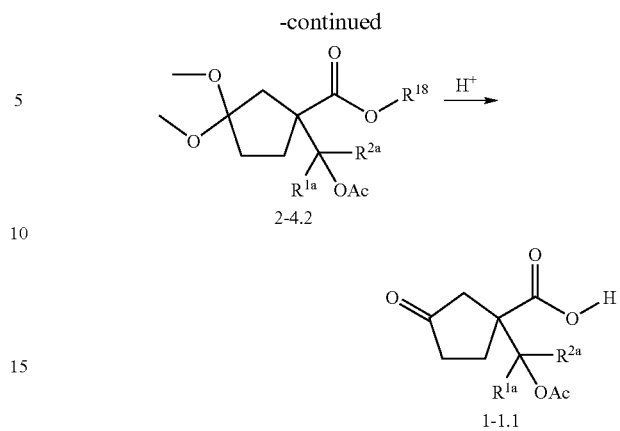

Amines 1-2 can be prepared in several ways as shown in schemes 3A-3G. The 5-aza-tetrahydroisoquinoline fragment can be prepared in accordance to the literature methods of MarCoux, J-F. et al. (*J. Chem. Lett.*, 2000, 2 (15), 2339-2341). Alternatively, it can be prepared as outlined in Scheme 3A. Compound 3-1, normally obtained from commercial sources, is brominated ($Br_2$, AcOH) to give 3-2. Metal halogen exchange (NaH, t-butyl lithium) followed by treatment with DMF provides aldehyde 3-3. Conversion of the aldehyde group to a nitrile can be achieved with sodium formate, hydroxylamine hydrochloride and formic acid. The resulting nitrile 3-4 can be treated with phosphorous oxychloride to give 2-chloropyridine 3-5. Displacement of the chloro group can be achieved with the sodium salt of a dialkylmalonate. Reduction of the nitrile group of 3-6 with hydrogen and Raney Ni catalyst is accompanied by cyclization to afford compound 3-7. Decarboxylation can be achieved in a variety of ways depending on the ester. In the case represented in Scheme 3A, the t-butyl ester was decarboxylated with TFA to give 3-8. Reduction ($BH_3$), followed by protection of the resulting amine using $Boc_2O$, gives 3-9, which can be conveniently purified. Removal of the Boc protecting group to give 1-2a can be achieved in various ways, including by treatment with anhydrous HCl in dioxane or some other solvent.

The enolate generated from ester 2-3 ($R^{18}$ being a benzyl or tert-Butyl group) in the presence of a strong base such as lithium diisopropylamide can be reacted with aldehydes ($R^{1a}CHO$) or ketones ($R^{1a}R^{2a}CO$) to produce the appropriate hydroxyalkyl substituted compounds 2-4.1 as indicated in Scheme 2D. The resulting hydroxy group can be protected in various ways, including by treatment with acetic anhydride in the presence of a base such as triethylamine to give compounds 2-4.2. Once again the ester protecting group is removed under conditions suitable for the particular protecting group. In the case of the tert-butyl esters ($R^{18}$ is t-butyl), deprotection is achieved under acidic conditions. The latter usually induces cleavage of the acetal protecting group as well, and the keto acids 1-1.1 can be prepared this way in an one-pot procedure. Their conversion to the final modulators of chemokine activity 1-9 can be achieved as described previously, with minor modifications to accommodate the protected hydroxy in 1-1.1.

SCHEME 2D

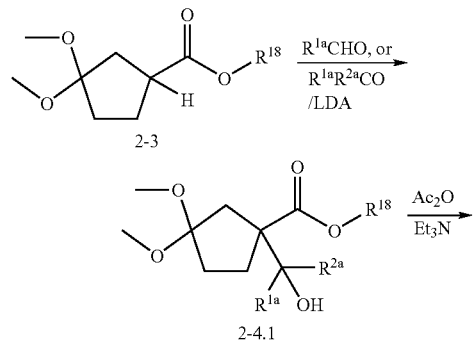

SCHEME 3A

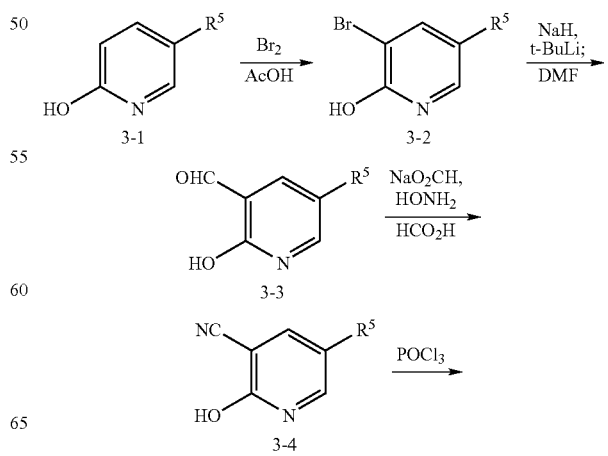

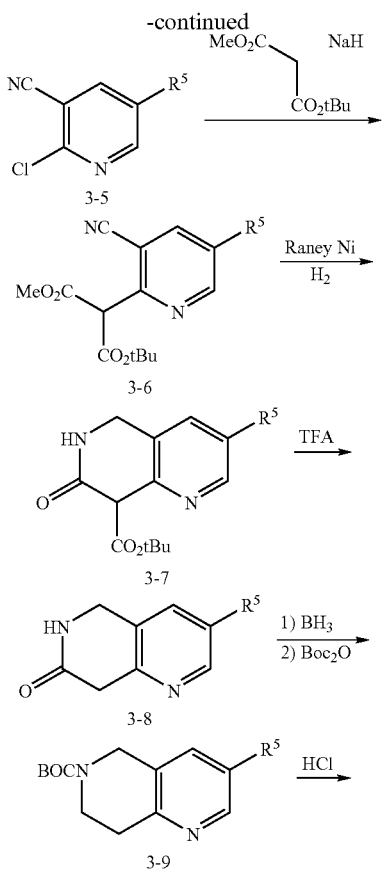

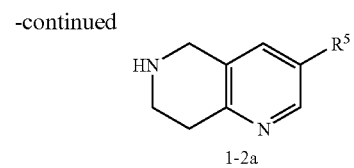

Compounds of the type 1-2a could also be prepared according to Scheme 3B. Commercially available 3-10 can be methylated with methyl iodide in the presence of a base such as $K_2CO_3$ to give 3-11. Cycloaddition with a protected piperidinone in the presence of $NH_3$ in methanol furnishes 5-aza-tetrahydroiso-quinoline 3-12 ($R^{10c}$ can be various protecting groups such as benzyl or benzoyl). Hydrogenation of the nitro group of compound 3-12 with hydrogen and a catalyst such as Pd/C gives 3-13. Diazonium salt formation followed by warming with sulfuric acid provides 5-aza-7-hydroxytetrahydroisoquinoline 3-14. Removal of the protecting group $R^{10c}$ is achieved in different ways depending upon the nature of $R^{10c}$. If $R^{10c}$ is benzyl, hydrogenation in the presence of HCl and a catalyst such as Pd/C can be applied. If $R^{10c}$ is benzoyl, hydrolysis can be achieved by heating in concentrated HCl solution. Installation of a Boc protecting group on to 3-15 can be easily achieved with $Boc_2O$ to give 3-16. Various $R^{10d}$ can then be incorporated generating ethers (see Scheme 3C). The Boc protecting group on the resulting compounds 3-17 can finally be removed with HCl or TFA to give 1-2b. Alternatively, Compound 3-14 itself can be converted to ethers (according to Scheme 3C). The resulting ether 3-18 can be converted to compound 3-19 by removal of $R^{10c}$ as described above.

SCHEME 3B

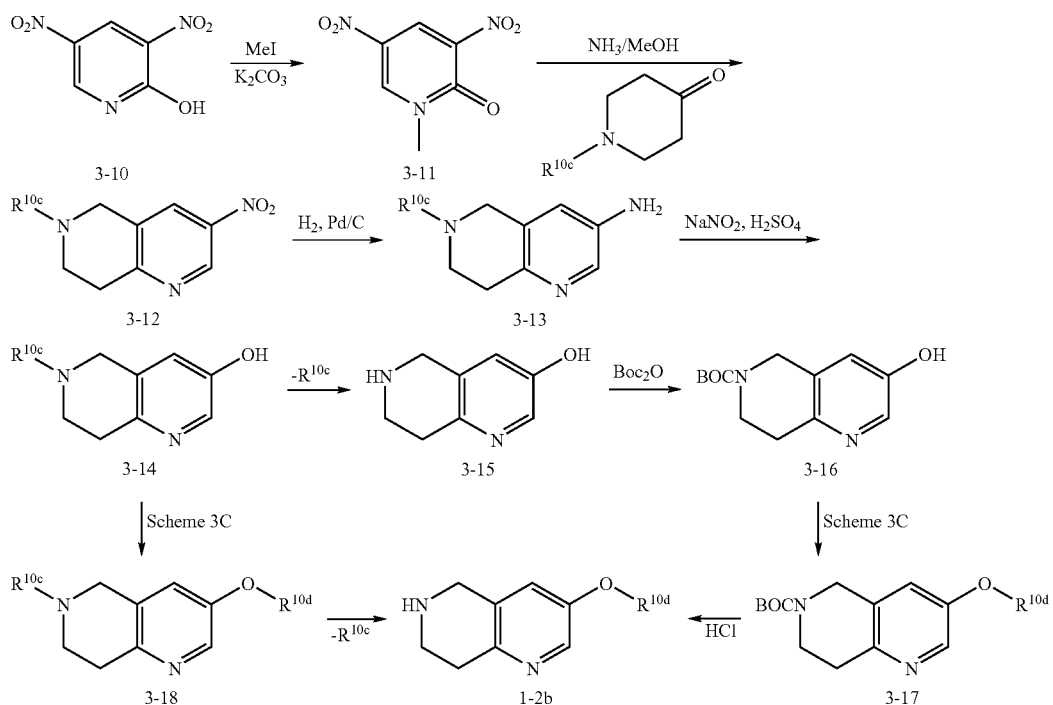

The 5-aza-7-hydroxytetrahydroisoquinolines 3-14 and 3-16 in Scheme 3B can be converted to various ethers (see Scheme 3C). Alkyl ethers can be generated from an alkyl halide and a base (such as $K_2CO_3$, NaOH, or NaH) giving compounds 3-19 and 3-22. A trifluoromethyl ether can be prepared by initial methyl xanthate formation (NaH, $CS_2$; MeI), followed by sequential treatment with 1,3-dibromo-5,5-dimethylhydantoin (or NBS) and HF/pyridine solution giving 3-20. Aryl ethers can be prepared by a number of methods, including reaction of arylboronic acids in the presence of copper (II) acetate and triethylamine, to give compounds 3-21.

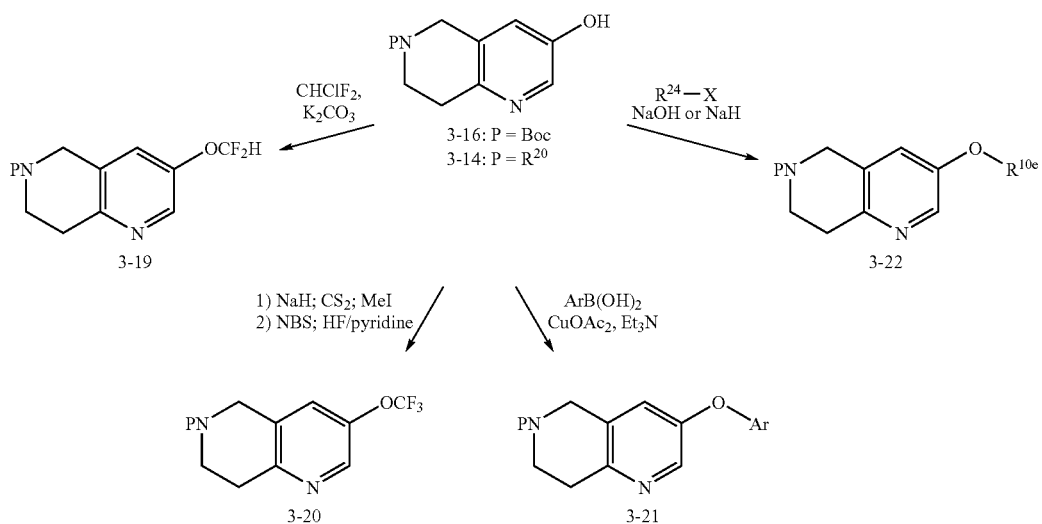

Compounds 1-2c where $R^5$ is a halide (IVc) can be prepared according to Scheme 3D. Compound 3-13 can be converted to the halide 3-22 according to classical procedures via the diazonium salt. Alternatively the known cycloaddition reaction to a suitably protected piperidinone can be applied. Removal of the protecting group $R^{10c}$ can be achieved as described previously.

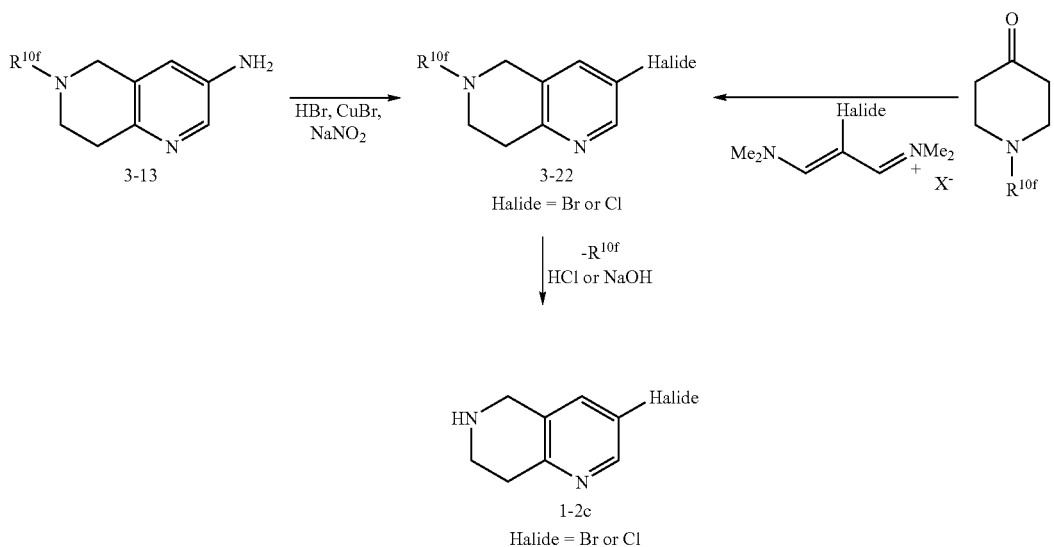

Furthermore, after incorporation into advanced intermediates, fragments 1-2c can be further modified so as to prepared 7-aryl-5-azotetrahydroisoquinoline containing analogs. This can be accomplished by coupling of the 5-aza-7-halotetrahydroisoquinoline intermediates to aryl boronic acids (or aryl stannanes), mediated by transition metal catalysts such as Pd(OAc)$_2$.

The preparation of tetrahydroisoquinoline amine components is outlined in Schemes 3E-3G. The tetrahydroisoquinolines incorporated into the amide portion of 1-5 often contain one or two substituted groups on various positions. Most of these are not available commercially, however, can be obtained through synthesis, representative examples of which are shown in Schemes 3F and 3G.

An example of a synthesis of the simple tetrahydroisoquinoline (1-2d) is depicted in Scheme 3E. According to this, the commercially available 4-trifluoromethyl phenylacetonitrile (3-23) is converted to the corresponding amine (3-24) using hydrogenation in the presence of Ra—Ni, and trifluoroacetic anhydride is then used to cap the amine. The resultant amide (3-25) is treated with formaldehyde in the presence of sulfuric acid to give the cyclic compound (3-26) which is further converted into tetrahydroisoquinoline (1-2d).

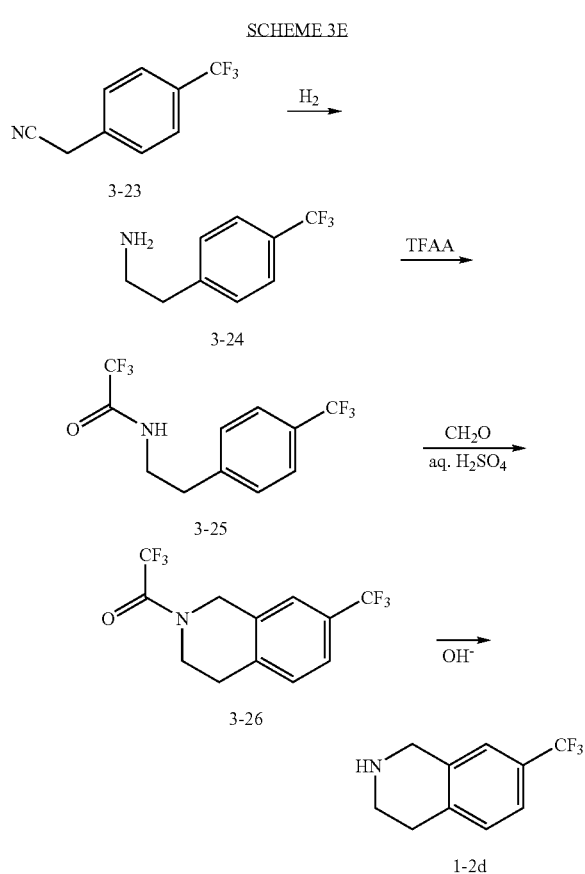

Many 5-substituted atetrahydroisoquinolines can also be prepared based on 3-26 (Scheme 3F). Iodonization on the 5-position yields compound 3-28. After conversion to the cyano compound (3-29) under palladium (0) catalyzed conditions, the amide is cleaved to the amine 3-30 which can be converted into amino ester 1-2ein high yield by a two step sequence. The iodo compound 3-28 can also be converted to other compounds as shown in the experimental section.

Modification of these substituents can also be made after the assembly of the final framework (1-5) to make new chemokine modulators of the form 1-5.1 (see Scheme 1). An example of this would be the hydrolysis of a methyl ester (from 1-2e) to make the corresponding carboxylic acid (see examples).

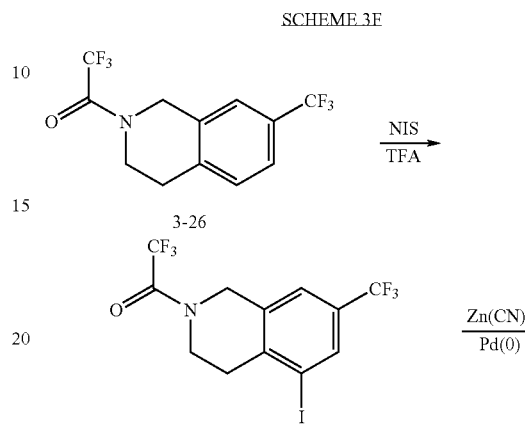

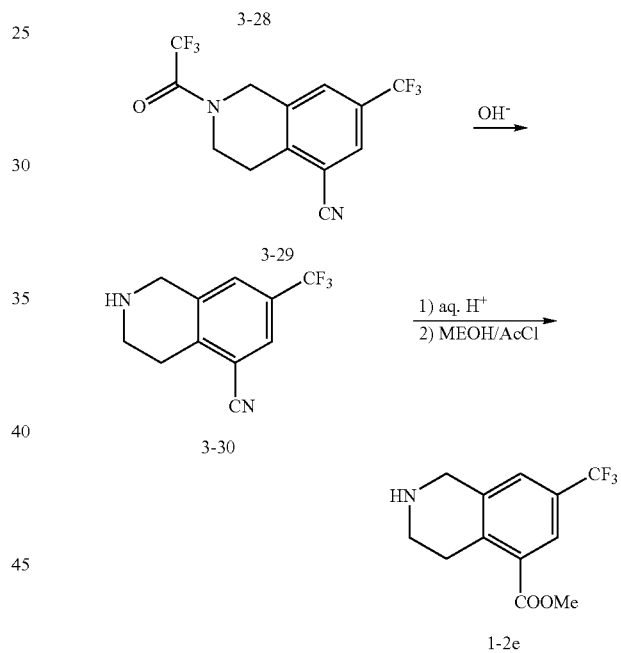

Heterocyclic 7-substituted tetrahydroisoquinolines could be obtained by utilizing commercially available tetrahydroisoquinoline. As described is Scheme 3G, tetrahydroisoquinoline (3-32) is nitrated by treatment with potassium nitrate in the presences of concentrated sulfuric acid. The 7-nitro-tetrahydroisoquinoline 3-33 is treated with trifluoroacetic anhydride to protect the amine and the resulting amide then hydrogenated with 10% palladium on carbon under hydrogen at 50 psi pressure to afford the aniline derivative 3-34. Base hydrolysis yields a 7-amino substituted tetrahydroisoquinoline (3-35) which could be used in the synthesis of further CCR2 antagonist or other tetrahydroisoquinoline derivatives. Protection of 3-35 with benzylchloroformate in the presence of an organic base such as triethylamine or diisopropylethyl amine affords the carbamate 3-37. This intermediate could be utilized to make the tetrazole and substituted tetrazoles such as 1-2 g. Intermediate 3-37 is treated with trifluoroacetic anhydride to form the trifluoroacetyl protected amide which then is converted to the trifluoromethyl substituted tetrazole by sequential reactions with triphenylphosphine heated to reflux for 15 hours followed by sodium azide in DMF at room temperature. Hydrogenation with 10% palladium on carbon under hydrogen atmosphere affords the heterocyclic substituted tetrahydroisoquinoline 1-2 g.

Alternatively 3-34 can be directly derivatized as shown to the triazole 3-36 with N,N-dimethylforamide azine in the presences of a catalytic amount of an acid such as toluene sulfonic acid heated to reflux for 24 to 48 hours. Basic hydrolysis of this intermediate gives amine component 1-2f.

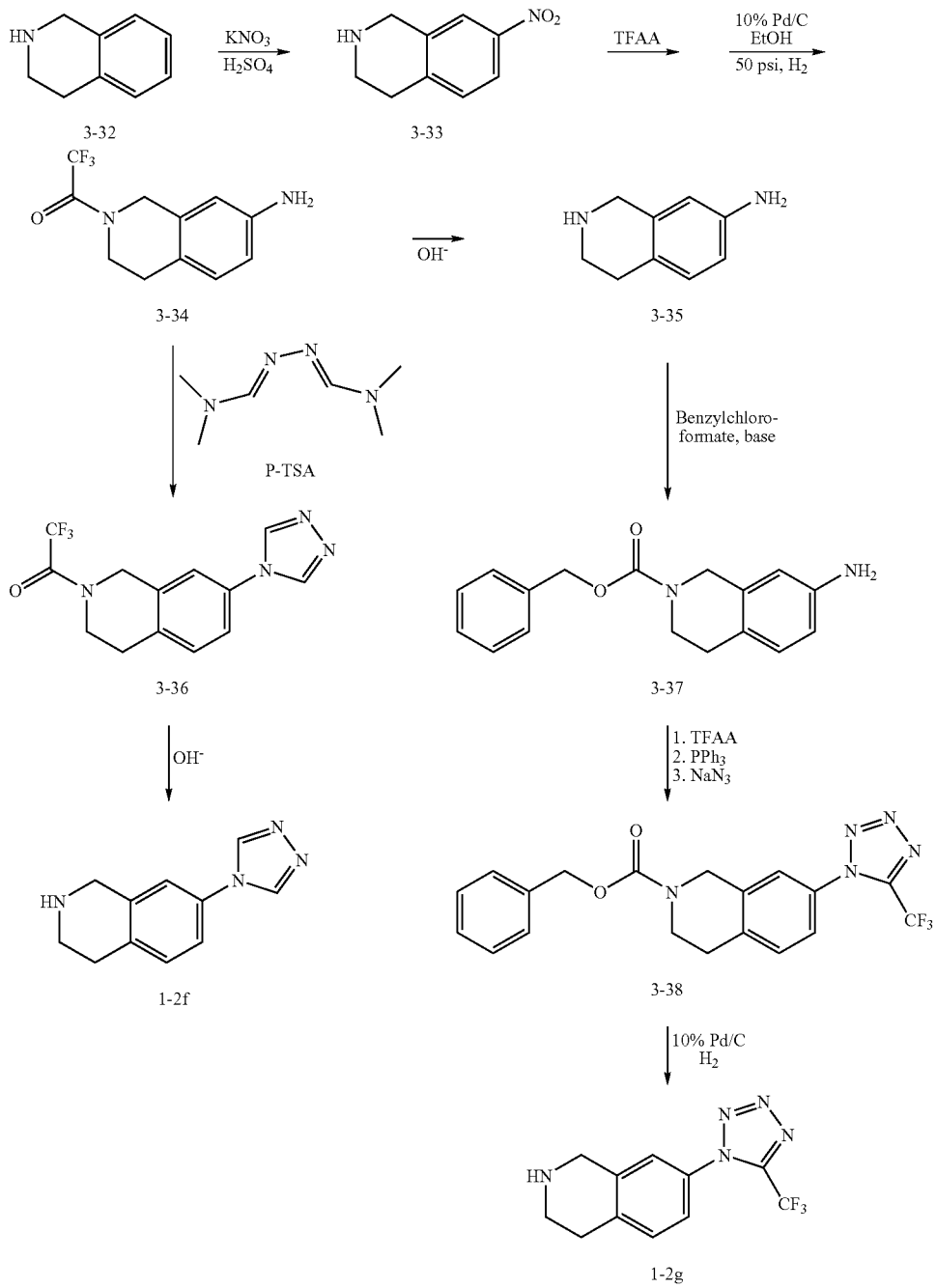

Additional examples of tetrhydroisoquinolines incorporated into the amide portion of compounds within the scope of the instant invention, as well as their syntheses are further described in the Experimental section.

Amines 1-4 were obtained from various sources. Most were commercially available, some were known from the literature and could be prepared according to published procedures, and some were prepared as described herein. Since their structures and the methods for their preparation are diverse, only two schemes will be outlined in this section; individual syntheses of amines 1-4 can be found in the Experimental Section. Scheme 4A shows one method for the synthesis of 4-aryl substituted piperidines. Enol triflate 4-1 (prepared according to Wustrow, D. J., Wise, L. D., *Synthesis*, (1991), 993-995.) could be coupled to boronic acids 4-2 as described by Wustrow and Wise. Hydrogenation of the olefin in 4-3 could be achieved using hydrogen in the presence of a catalyst such as Pd(OH)$_2$/C. Removal of the Boc protecting group could be achieved using standard acidic conditions, such as HCl in dioxane or TFA/DCM to afford piperidine 1-4.1.

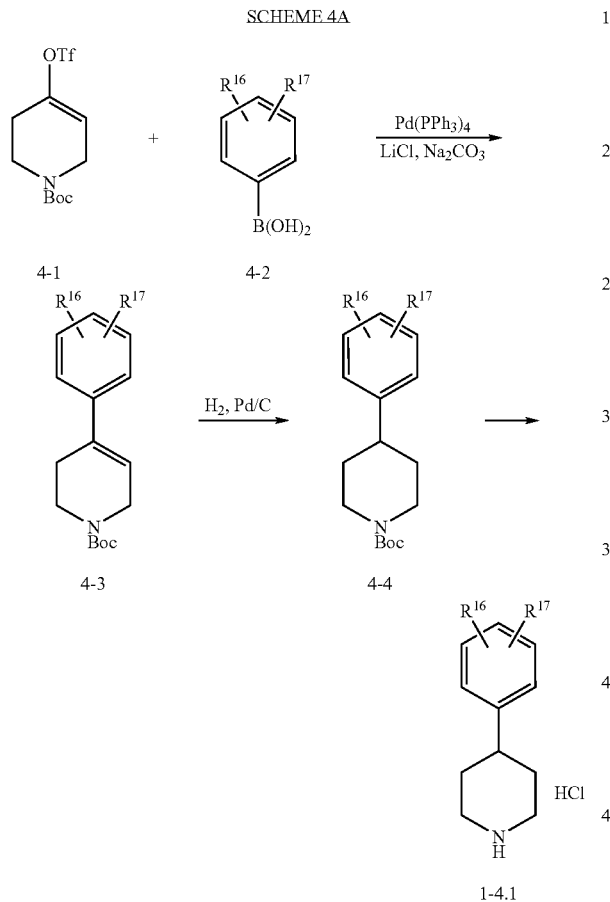

Another example of the synthesis of amine 1-4 is shown in Scheme 4B. Commercially available alcohol (4-5) is first sulfonylated with methanesulfonyl chloride to give compound 4-6 which can be directly substituted with tetrazole to give heteroaryl piperidine 4-7. Removal of the Boc protecting group under the standard conditions gives the amine hydrochloride 4-8.

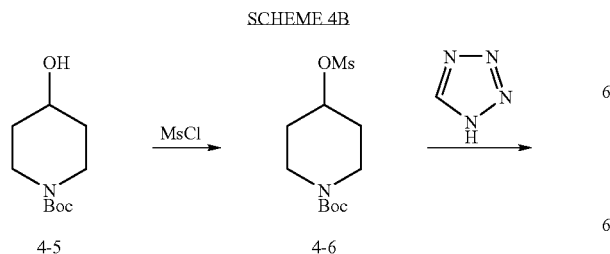

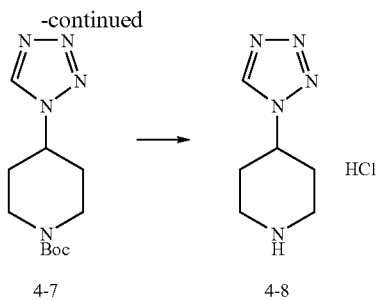

Another principal route for the synthesis of chemokine receptor modulators is depicted in Scheme 5. According to this route, compound 2-11 (described in Scheme 2C) is condensed with amine 1-2 (described in Scheme 1) using a peptide coupling reagent such as EDC to give 5-1. The Boc protecting group is removed under standard conditions such as with HCl in a solvent such as dioxane followed by treatment of the resulting amine 5-2 with a dialdehyde 5-3 in the presence of a reducing agent such as sodium triacetoxyborohydride leads to a double reductive alkylation sequence with concomitant cyclization to give 1-5.2. In accord with Scheme 1, further modifications, such as hydrolysis of an ester group present within 1-5.2 can be effected to give new chemokine receptor modulators 1-5.3.

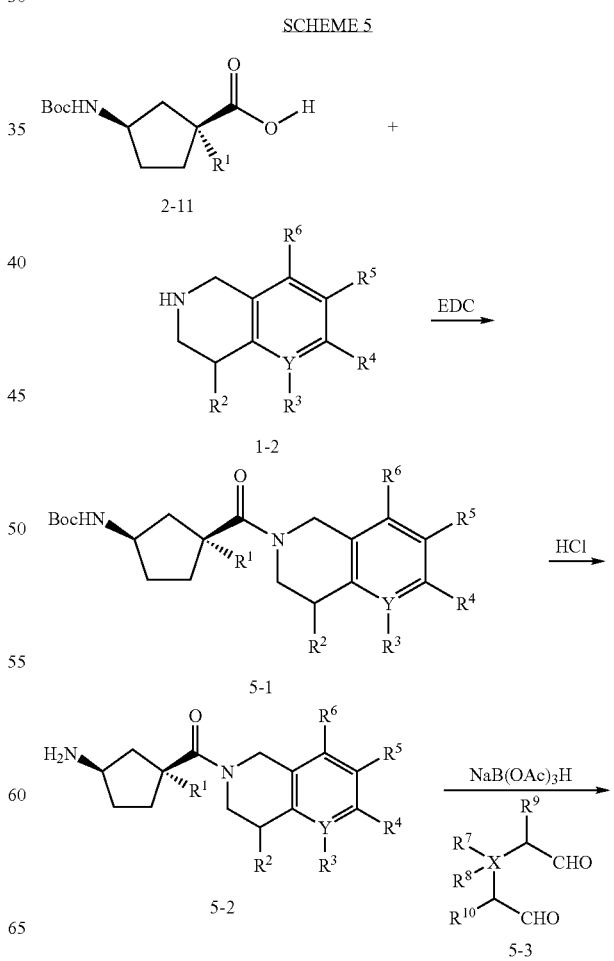

-continued

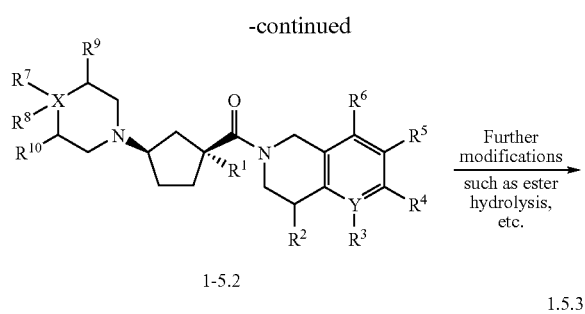

1-5.2

One way of preparing dialdehydes 5-3 is outlined in Scheme 6. According to this route, a cycloalkene 6-1 is oxidatively cleaved with, for example, ozone followed by dimethylsulfide, to give the dialdehyde. Alternatively, in place of the dialdehydes 5-3 the intermediate ozonides 6-2 can themselves be used directly in the double reductive amination reaction leading to 1-5.2.

SCHEME 6

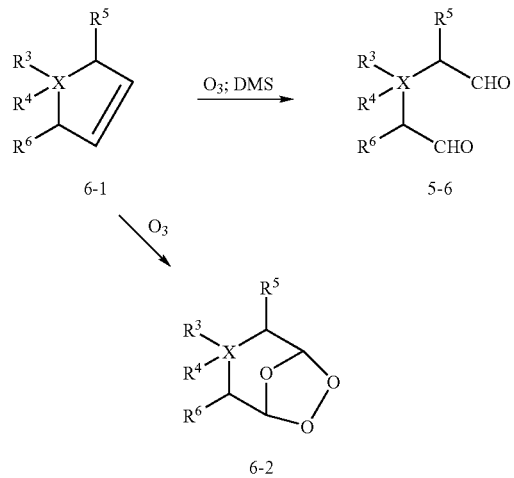

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

INTERMEDIATE 1

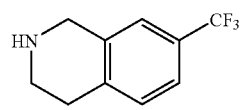

Step A:

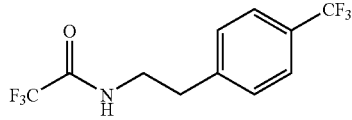

A solution of 4-trifluoromethylphenylacetonitrile (10 g, 49 mmol) in a mixture of ethanol (100 mL) and ammonium hydroxide (20 mL of a 29.3% aqueous solution) was hydrogenated over Raney nickel (1 g) for 16 h. The catalyst was removed by filtration through celite and the filtrate evaporated to dryness. The neat residue was added in a dropwise manner to trifluoroacetic anhydride (25 mL, 180 mmol) cooled at 0° C. and the resulting mixture stirred at 0° C. for 30 minutes. The reaction mixture was poured onto ice (250 mL) and the resulting mixture stirred for 30 minutes after which the precipitate was removed by filtration and air dried to give the product as a white solid (13.4 g, 90%).

Step B:

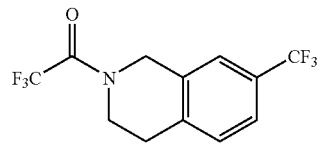

To a mixture of the product from step A (13.4 g, 44.0 mmol) and paraformaldehyde (2 g, 50 mmol) was added in one portion a mixture of concentrated sulfuric acid (90 mL) and glacial acetic acid (60 mL) and the resulting mixture stirred at room temperature for 16 hours. The reaction mixture was poured onto a mixture of ice and water (1 L) and extracted with ethyl acetate (3×150 mL); the combined ethyl acetate layers were washed with water (3×500 mL), saturated NaHCO$_3$ (200 mL), and sat NaCl (100 mL), dried over MgSO$_4$, filtered and evaporated in vacuo. The residue was purified by column chromatography on silica elution with 10% Et$_2$O in hexanes to give the product (8.29 g, 60%).

Step C:

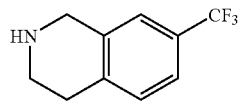

To a solution of the trifluoroacetamide formed in Step B (8.29 g, 26.0 mmol) in ethanol (200 mL) was added a solution of potassium carbonate (20 g, 150 mmol) in water (50 mL), and the resulting mixture stirred at reflux for 1 hour. The ethanol was removed by rotary evaporation and water (150 mL) was added to the residue. Extracted with CH$_2$Cl$_2$ (3×100 mL), the combined CH$_2$Cl$_2$ layers were washed with sat NaCl (100 mL), dried over Na$_2$SO$_4$, filtered and evaporated in vacuo to give the product (5.2 g, 91%); $^1$H NMR 500 MHz (CDCl$_3$) δ=1.81 (1H, br s), 2.84 (2H, d, J=6.0 Hz), 3.15 (2H, t, J=6.0 Hz), 4.05 (2H, s), 7.19 (1H, d, J=8.0 Hz), 7.27 (1H, s), 7.37 (1H, d, J=8.0 Hz).

INTERMEDIATE 2

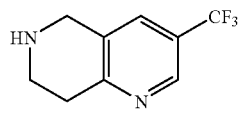

Step A:

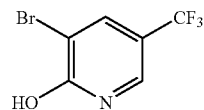

To a solution of 5-trifluoromethyl-2-pyridinol (51.0 g, 307 mmol) and sodium acetate (26.2 g, 319 mmol) in glacial acetic acid (200 mL) was added bromine (16.7 mL, 325 mmol) and the resulting mixture was heated at 80° C. for 2.5 hours. The reaction was allow to cool to room temperature and then was evaporated under reduced pressure. The residue was neutralized with saturated NaHCO$_3$ solution and extracted with ethyl acetate (3×200 mL). The organic layers were combined, dried over MgSO$_4$, filtered, and evaporated in vacuo to yield 74.45 g (98.7%) of the crude product. $^1$H NMR (400 MHz, CDCl$_3$) δ 8.04 (d, J=2.6 Hz, 1H), 7.89 (m, 1H).

Step B:

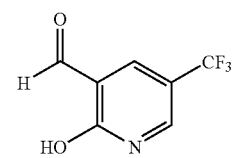

Under nitrogen, the substituted pyridine, described in Step A (48.8 g, 202 mmol) was added by small portions to a suspension of NaH (8.9 g, 220 mmol) in anhydrous THF (500 mL). After complete addition of the intermediate, the reaction mixture was cooled to −78° C. and treated with tert-butyllithium (260 mL, 444 mmol) added dropwise via syringe. After stirring for 5 minutes, DMF (50 mL, 707 mmol) was added slowly to maintain the temperature below −50° C. The resulting mixture was then stirred for 10 hours allowing to warm to room temperature. The mixture was quenched with 2N HCl and then diluted with ethyl acetate (1000 mL). The organic layer was separated, washed with brine, dried over MgSO$_4$, and evaporated in vacuo. The desired product was precipitated out of ethyl acetate and hexane and filtered to yield a light brown solid (28.55 g, 73.8%). $^1$H NMR (500 MHz, CD$_3$OD) δ 10.13 (s, 1H), 8.21 (s, 2H).

Step C:

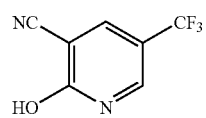

A mixture of the compound from Step B (18 g, 95 mmol), sodium formate (7.1 g, 105 mmol), hydroxylamine hydrochloride (7.3 g, 110 mmol), and formic acid (150 mL) was stirred at room temperature for 2 hours and then refluxed overnight. The reaction mixture was cooled and let stand at room temperature for 7 days. The reaction was poured into water and extracted with ethyl acetate (3×). Combined organic layers were washed with water (2×), saturated NaHCO$_3$ and brine, dried over Na$_2$SO$_4$, filtered, and concentrated in vacuo to yield the desired product as a brown powder (17.84 g, 89.8%). $^1$H NMR (400 MHz, CD$_3$OD) δ 8.37 (d, J=2.7 Hz, 1H), 8.19 (q, J=0.7 Hz, 0.3??/Hz, 1H).

Step D:

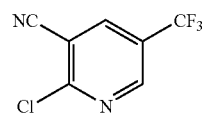

To a mixture of phosphorous oxychloride (13.4 mL, 144 mmol) and quinoline (8.7 mL, 73.4 mmol) was added the product from Step C (24.6 g, 131 mmol) and the resulting mixture was refluxed for 3 hours. The reaction was cooled to 100° C. before water (70 mL) was slowly added. The mixture was further cooled to room temperature and neutralized carefully with saturated NaHCO$_3$ solution. The aqueous layer was extracted with ethyl acetate (3×) and the organic layers were combined, dried over MgSO$_4$, filtered, and evaporated in vacuo. The crude product was purified by flash chromatography to afford (23.5 g, 87.0%) of the desired compound. $^1$H NMR (500 MHz, CDCl$_3$) δ 8.88 (d, J=2.0 Hz, 1H), 8.26 (d, J=2.5 Hz, 1H).

Step E:

To a suspension of NaH (7.8 g, 200 mmol) in THF (100 mL) under nitrogen was added dropwise a solution of tert-butyl methyl malonate (20 mL, 120 mmol) in anhydrous THF (100 mL) via syringe. The reaction mixture was stirred for 0.5 h before a solution of the compound prepared in Step D (20.1 g, 97.6 mmol) in THF (200 mL) was added slowly via syringe. The reaction was stirred at room temperature overnight, then quenched with a saturated solution of NH$_4$Cl. The organic layer was separated and the aqueous layer extracted with ethyl acetate (3×). The combined organic layers were washed with water (3×), dried over Na$_2$SO$_4$, filtered, and evaporated in vacuo. Flash chromatography afforded 31.76 g (94.6%) of the pure desired product. $^1$H NMR (500 MHz, CDCl3) δ 9.03 (d, J=1.5 Hz, 1H), 8.25 (d, J=2.0 Hz, 1H), 5.25 (s, 1H), 3.86 (s, 3H), 1.52 (s, 9H).

Step F:

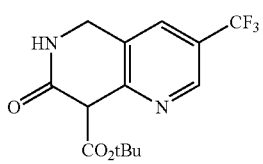

A suspension of Raney Ni (1 g) and the product from Step E (18.2 g, 52.9 mmol) in ethanol (130 mL) was placed on a Parr Apparatus and hydrogenated at 40 psi overnight. The suspension was filtered through celite and the filtrate evaporated in vacuo to afford 16.35 g (97.8%) of crude product. $^1$H NMR (500 MHz, CDCl$_3$) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G:

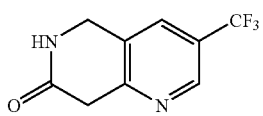

To the mixture of the product from Step F (16 g, 51 mmol) in DCM (60 mL) was added TFA (30 mL) and the resulting mixture stirred at room temperature for 0.5 h. The solution was evaporated under reduced pressure and the residue was dissolved in DCM. The mixture was neutralized by slow addition of a solution of saturated sodium bicarbonate and the organic layer removed. The aqueous was extracted with DCM (4×) and then all organic layers were combined, dried over Na$_2$SO$_4$, filtered, and evaporated in vacuo to afford 10.42 g (95.2%) of the desired product. $^1$H NMR (400 MHz, CDCl$_3$) δ 8.81 (s, 1H), 7.78 (s, 1H), 7.30 (s, 1H), 4.63 (s, 2H), 3.90 (s, 2H).

Step H:

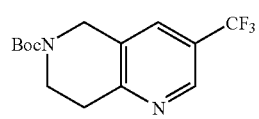

To a solution of the product from Step G (18.0 g, 83.3 mmol) in THF (50 mL) was added 1.0 M Borane in THF (417 mL, 420 mmol) and the resulting solution stirred at room temperature overnight. The solution was evaporated under reduced pressure and then the residue was treated with 1% HCl/MeOH solution in which the resulting mixture was heated at 50° C. overnight to breakdown the borane complex. Treatment with acidic methanol was repeated twice to insure that the borane complex was eliminated. The crude product from this reaction was then immediately used for the next reaction. A solution of crude product described immediately above (83.3 mmol, assuming 100% conversion) and DIEA (43 mL, 250 mmol) in DCM was treated with di-tert-butyl dicarbonate (36.4 g, 167 mmol) and the resulting mixture stirred at room temperature overnight. The solution was washed with saturated sodium bicarbonate solution, water, and brine. The aqueous layers were combined and back-washed with DCM (2×). The combined organic layers were then dried over Na$_2$SO$_4$, filtered, and evaporated to dryness. The crude product was purified by flash chromatography and MPLC to afford (11.89 g, 47.2% for last two steps) as a yellow solid. $^1$H NMR (500 MHz, CDCl$_3$) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H).

Step I:

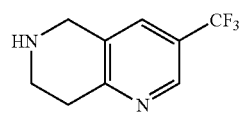

The product described in Step H (11.89 g) was treated with a solution of 4 M HCl in dioxane. The solution was stirred at room temperature for 2 hours and then evaporated in vacuo to afford Intermediate 2 (10.85 g, 99%) as a yellow powder. LC-MS for C$_9$H$_{10}$F$_3$N$_2$[M$^+$H$^+$] calculated 202.07, found 203.0.

INTERMEDIATE 3

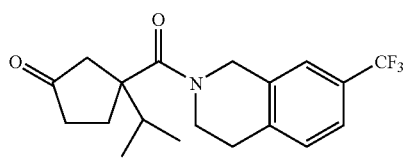

Step A:

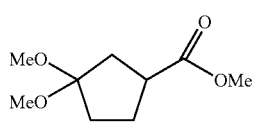

A solution of methyl-3-oxocyclopentane-carboxylate (20 g, 160 mmol) and trimethyl orthoformate (85 mL, 780 mmol) in methanol was treated with a catalytic amount of p-toluene-sulfonic acid (3.00 g, 15.6 mmol) and the resulting solution was stirred for 4 h at room temperature. The solvent was evaporated under reduced pressure and the residue was then dissolved in ether (600 mL). The solution was washed with saturated sodium bicarbonate (2×200 mL), water (150 mL), brine (200 mL), dried over anhydrous sodium sulfate, filtered, and the solvent evaporated as before. Purification by flash column chromatography (eluant: 25% ether/pentane) afforded 21.52 g (73%) of the desired product as a clear oil. ¹H NMR (500 MHz, CDCl₃) δ 3.68 (s, 3H), 3.21 (d, J=9.9 Hz, 6H), 2.89 (p, J=8.5 Hz, 1H), 2.14-2.05 (m, 2H), 2.02-1.80 (m, 4H).

Step B:

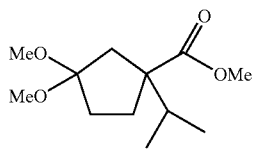

A flame dried 500 mL round bottom flask was charged with 150 mL of dry THF, and then, set under nitrogen and cooled to −78° C. using an acetone/dry ice bath. Diisopropylamine (19.2 mL, 137 mmol) was added to the cooled solvent via syringe followed by the slow addition of 2.5M n-butyllithium in hexane (55 mL, 140 mmol). After 5 minutes stirring, the methyl ketal described in Step A, Intermediate 3 (21.52 g, 114.4 mmol) in 50 mL of THF was added dropwise via syringe and the resulting mixture stirred at −78° C. for 2 hours. 2-Iodopropane (34.3 mL, 343 mmol) was then added dropwise via syringe and the resulting mixture was stirred overnight allowing to warm slowly to room temperature. The reaction was quenched with a solution of 10% citric acid and the organics separated. The aqueous layer was extracted with ether (3×150 mL) and all the organics combined, dried over anhydrous sodium sulfate, filtered, and evaporated under reduced pressure. The crude product was purified by flash column using an eluant of 20% ether/pentane to afford 16.74 g (64%) of the desired product. ¹H NMR (400 MHz, CDCl₃) δ 3.69 (s, 3H), 3.18 (d, J=20.5 Hz, 6H), 2.57 (d, J=13.9 Hz, 1H), 2.29-2.20 (m, 1H), 1.90 (p, J=6.8 Hz, 1H), 1.88-1.80 (m, 2H), 1.69-1.61 (m, 2H), 0.89 (dd, J=11.9 Hz, 6.8 Hz, 6H).

Step C:

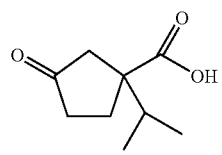

A solution of the ester (described in Step B, Intermediate 3, 16.7 g, 72.7 mmol) in ethanol (30 mL) was treated with 5 M NaOH (55 mL) and the resulting mixture heated to reflux for three days. The mixture was then cooled to room temperature and acidified with concentrated hydrochloric acid. The organic solvent was evaporated under reduced pressure and the aqueous layer was then extracted with DCM (5×100 mL). The organic extracts were combined, dried over anhydrous magnesium sulfate, filtered, and evaporated in vacuo to yield the crude 3-oxocyclopentane carboxylic acid (11.07 g, 90%) as a yellow oil. ¹H NMR (500 MHz, CDCl₃) δ 2.70 (d, J=18.1 Hz, 1H), 2.44-2.39 (m, 1H), 2.30-2.15 (m, 2H), 2.14 (dd, J=18.1, 1.0 Hz, 1H), 2.06 (p, J=6.9 Hz, 1H), 1.98 (m, 1H), 0.98 (dd, J=11.4, 6.9 Hz, 6H).

Step D:

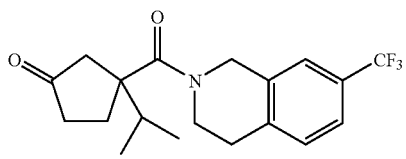

Procedure A:

To a solution of acid (described in Step C, Intermediate 3, 2.00 g, 11.8 mmol) in DCM (50 mL) was added oxalyl chloride (1.54 mL, 17.6 mmol) followed by 2 drops of DMF. The solution was stirred at room temperature for 80 minutes and then evaporated under reduced pressure. The residue was dissolved in DCM (2 mL) and added via syringe to a prepared solution of Intermediate 1 (2.36 g, 11.8 mmol) and triethylamine (2.13 mL, 15.3 mmol) in DCM (40 mL). The resulting mixture was stirred at room temperature for 18 hours and then quenched with water (25 mL). The organics were separated, washed with 1 N HCl, saturated sodium bicarbonate, and brine, dried over anhydrous magnesium sulfate, filtered, and evaporated. The crude product was purified by MPLC using an eluant of 60% ethyl acetate/hexane to afford Intermediate 3 (3.18 g, 77%). ¹H NMR (500 MHz, CDCl₃) δ 7.46 (d, J=7.3 Hz, 1H), 7.39 (s, 1H), 7.29 (d, J=7.7 Hz, 1H), 4.81 (m, 2H), 3.93 (m, 1H), 3.82 (m, 1H), 2.94 (m, 3H), 2.54 (m, 1H), 2.43 (d, J=8.5 Hz, 1H), 2.32 (m, 2H), 2.26 (p, J=6.6 Hz, 1H), 2.16 (m, 1H), 0.93 (dd, J=19.7 Hz, 6.8 Hz, 6H). LC-MS for $C_{19}H_{23}F_3NO_2$ calculated 353.16, found [M⁺H⁺] 354.25.

Procedure B:

A mixture of the acid prepared in Step C, Intermediate 3 (1.0 g, 5.9 mmol), Intermediate 1 (1.18 g, 5.88 mmol), DMAP (71 mg, 0.59 mmol), and N,N-diisopropyl ethylamine (1.02 mL, 5.88 mmol) in dichloromethane (20 mL) was treated with 1-[3-(dimethylamino)propyl]-3-ethylcarbodiimide hydrochloride (EDC, 2.25 g, 11.7 mmol) and stirred at room temperature overnight. The reaction mixture was diluted with dichloromethane (30 mL), washed with water (2×20 mL), brine (1×30 mL), dried over anhydrous sodium sulfate and the solvent was evaporated. The pure compound was obtained by MPLC purification (eluant 60% ethyl acetate/hexane), 1.08 g (52%). LC-MS for $C_{19}H_{23}F_3NO_2$ calculated 353.16, found [M+H⁺] 354.25.

INTERMEDIATE 4

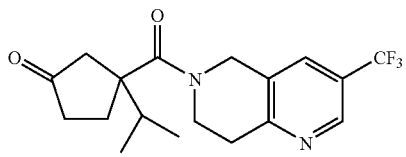

To a solution of acid (described in Step C, Intermediate 3, 540 mg, 3.20 mmol) in DCM (50 mL) was added oxalyl chloride (0.834 mL, 9.60 mmol) followed by 2 drops of DMF. The solution was stirred at room temperature for 80 minutes and then evaporated under reduced pressure. The residue was dissolved in DCM (2 mL) and added via syringe to a prepared solution of Intermediate 2 (880 mg, 3.20 mmol) and triethylamine (0.820 mL, 6.50 mmol) in DCM (20 mL). The resulting mixture was stirred at room temperature for 18 hours and then quenched with water (25 mL). The organics were separated, washed with saturated sodium bicarbonate and brine, dried over anhydrous sodium sulfate, filtered, and evaporated. The crude product was purified by MPLC using a step-wise gradient eluant of 0-70% ethyl acetate/hexane to afford Intermediate 2 (720 mg, 64%). ESI-MS calculated for C18H21F3N2O2: 354.16; found 355 (M+H)

INTERMEDIATE 5

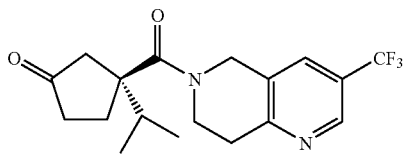

Resolution of Intermediate 4 to its individual enantiomers was accomplished by chiral separation using HPLC equipped with a Preparative ChiralPak AD column. The separation was completed by injecting 100 mg/run and using an eluant of 25% isopropanol and 75% heptane with a flow rate of 9 mL/min.

INTERMEDIATE 6

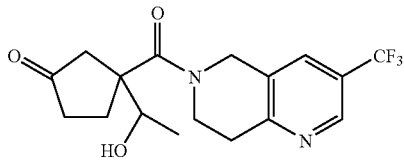

Step A:

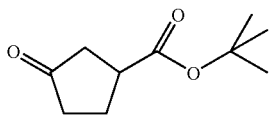

Procedure A:

A solution of 3-oxo-cyclopentane carboxylic acid (Stetter, H., Kuhlmann, H. Liebigs Ann. Chem., 1979, 7, 944-9) (5.72 g, 44.6 mmol) in dichloromethane (30 mL) was treated with N,N'-diisopropyl-O-tert-butyl-iso-urea (21.2 mL, 89.3 mmol) and the reaction mixture was stirred at ambient temperature overnight. The precipitated N,N'-diisopropyl urea was filtered off, the filtrate concentrated in vacuo and the residue was purified by distillation (bp: 125-129° C. @ 18 mmHg) to yield 4.74 g (58%) of the pure product. $^1$H NMR (500 MHz, CDCl$_3$): δ 3.02 (p, J=7.8 Hz, 1H), 2.05-2.50 (m, 6H), 1.45 (s, 9H). $^{13}$C NMR (125 MHz, CDCl$_3$): δ 217.00, 173.47, 80.99, 41.88, 41.14, 27.94, 26.57.

Procedure B:

A 2 L round RBF was charged with anhydrous magnesium sulfate (113 g, 940 mmol) and dichloromethane (940 mL) was added. While stirring, the suspension was treated with concentrated sulfuric acid (12.5 mL, 235 mmol) followed in 15 minutes by 3-oxo-cyclopentane carboxylic acid (30.1 g, 235 mmol). After stirring for 15 minutes, tert-butanol (87 g, 1.2 mol) was added. The reaction vessel was closed with a stopper to aid retention of isobutylene, and stirred at ambient temperature for 72 hours. The solid was filtered off through a plug of celite, volume of the filtrate was reduced to approximately 500 mL, and washed with saturated solution of sodium bicarbonate (2×150 mL). The organic phase was dried with anhydrous magnesium sulfate, filtered, and the solvent was removed by distillation at reduced pressure (180 mmHg). The crude product was purified by distillation to yield 39.12 g (90%) of pure product.

Step B:

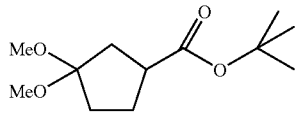

A solution of tert-Butyl 3-oxocyclopentane carboxylate (11.54 g, 62.64 mmol) in dichloromethane (200 mL) was treated with trimethyl orthoformate (41.4 mL, 251 mmol) in the presence of p-toluenesulfonic acid (400 mg) and stirred at room temperature for 48 hours. The dark reaction mixture was poured onto saturated solution of sodium bicarbonate, and the crude product was extracted with dichloromethane. The combined organic extracts were dried with anhydrous magnesium sulfate, the solvent was removed in vacuo, and the crude product was purified by distillation (bp.: 104° C. @ 4 mmHg) to yield 12.32 g (85%) of the desired product. $^1$H NMR (500 MHz, CDCl$_3$): δ 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): δ 174.9, 111.2, 80.3, 67.8, 49.2, 42.5, 37.4, 33.8, 28.3, 22.0.

Step C:

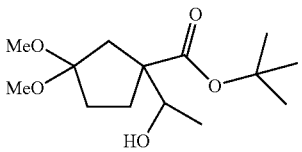

A flame dried 500 mL round bottom flask was charged with 100 mL of dry THF, and then, set under nitrogen and cooled to −78° C. using an acetone/dry ice bath. Diisopropylamine (7.9 mL, 56 mmol) was added to the cooled solvent via syringe followed by the slow addition of 2.5 M n-butyllithium in hexane (22.6 mL, 56.45 mmol). After 5 minutes stirring, the acetal (described in Step B, Intermediate 6, 10.0 g, 43.4 mmol) in 50 mL of THF was added dropwise via syringe and the resulting mixture stirred at −78° C. for 2 hours. Acetaldehyde (7.3 mL, 130 mmol) was then added dropwise via syringe and the resulting mixture was stirred for 2 h at −78° C. The reaction was quenched by pouring the mixture into a solution of 10% citric acid (300 mL) and then extracting with dichloromethane (2×150 mL). The organics were combined, dried over anhydrous magnesium sulfate, filtered, and evaporated under reduced pressure. During the reaction or work-up some of the acetal was hydrolyzed to the ketone, therefore, the crude mixture was taken onto the next step without purification.

Step D:

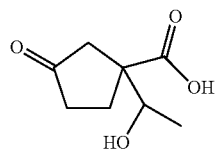

The crude intermediate (described in Step C, Intermediate 6, 56.45 mmol assumed 100% conversion for Step C) was treated with a solution of 10% trifluoroacetic acid in dichloromethane and the resulting mixture stirred overnight at room temperature. The reaction was concentrated in vacuo, then diluted with water, and extracted with dichloromethane. The organics were combined, dried over anhydrous magnesium sulfate, filtered, and evaporated under reduced pressure to afforded 8.04 g (83%) of the crude product that was used without further purification.

Step E:

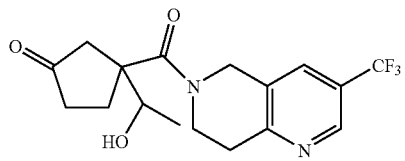

A mixture of the acid (described in Step D, Intermediate 6, 300 mg, 1.74 mmol), Intermediate 2 (486, 1.74 mmol), HOAt (237 mg, 1.74 mmol), and N,N-diisopropyl ethylamine (0.606 mL, 3.48 mmol) in dichloromethane (15 mL) was treated with 1-[3-(dimethylamino)propyl]-3-ethylcarbodiimide hydrochloride (EDC, 667 mg, 3.48 mmol) and stirred at room temperature for five days. The reaction mixture was diluted with dichloromethane (30 mL), washed with water (20 mL), brine (20 mL), dried over anhydrous sodium sulfate, filtered, and the solvent was evaporated in vacuo. The product, Intermediate 6, was obtained by preparative plate purification (eluant 100% ethyl acetate), 260 mg (42%).

INTERMEDIATE 7

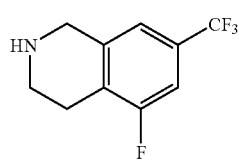

Step A

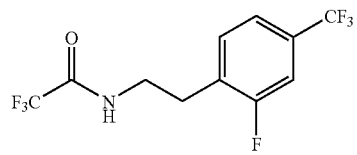

A solution of 2-fluoro-4-trifluoromethylphenylacetonitrile (10 g, 49 mmol) in a mixture of ethanol (100 mL) and ammonium hydroxide (20 mL of a 29.3% aqueous solution) was hydrogenated over Raney nickel (1 g) for 16 h. The catalyst was removed by filtration through celite and the filtrate evaporated to dryness. The neat residue was added in a dropwise manner to trifluoroacetic anhydride (25 mL, 180 mmol) cooled at 0° C. and the resulting mixture was stirred at 0° C. for 30 minutes. The reaction mixture was poured onto ice (250 g) and the resulting mixture was stirred for 30 minutes after which time the precipitate was removed by filtration and air dried to give the product as a white solid (13.4 g, 90%); $^1$H NMR 500 MHz (CDCl$_3$) δ=3.02 (2H, t, J=7.0 Hz), 3.66 (2H, q, J=6.6 Hz), 6.44 (1H, br s), 7.34 (2H, m), 7.41 (1H, d, J=7.8 Hz).

Step B

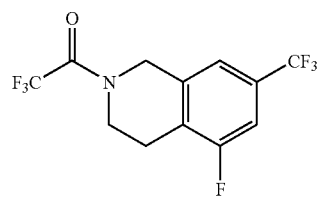

To a mixture of the product from Step A (13 g, 44 mmol) and paraformaldehyde (2.0 g, 48 mmol) was added in one portion a mixture of concentrated sulfuric acid (90 mL) and glacial acetic acid (60 mL) and the resulting mixture was stirred at room temperature for 16 h. The reaction mixture was poured onto a mixture of ice and water (1 L) and extracted with ethyl acetate (3×150 mL); the combined ethyl acetate layers were washed with water (3×500 mL), saturated NaHCO$_3$ (200 mL), and saturated NaCl (100 mL), dried over MgSO$_4$, filtered and evaporated in vacuo. The residue was purified by column chromatography on silica elution with 10% Et$_2$O in hexanes to give the product (8.29 g, 60%); $^1$H NMR 500 MHz (CDCl$_3$) δ=3.01 (2H, m), 3.91 and 3.97 (2H, t, J=6.2 Hz), 4.83 and 4.88 (2H, s), 7.21-7.28 (3H, m).

Step C

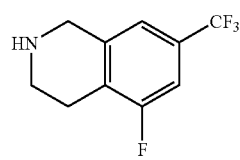

To a solution of the trifluoroacetamide formed in Step B (8.3 g, 26 mmol) in ethanol (200 mL) was added a solution of potassium carbonate (20 g, 150 mmol) in water (50 mL), and the resulting mixture was stirred at reflux for 1 h. The ethanol was removed under reduced pressure and water (150 mL) was added to the residue and extracted with $CH_2Cl_2$ (3×100 mL). The combined $CH_2Cl_2$ layers were washed with saturated NaCl (100 mL), dried over $Na_2SO_4$, filtered and evaporated in vacuo to give the product (5.2 g, 91%); $^1$H NMR 500 MHz ($CDCl_3$) δ=1.74 (1H, br s), 2.78 (2H, d, J=6.0 Hz), 3.17 (2H, t, J=6.0 Hz), 4.05 (2H, s), 7.04-7.14 (3H, m).

INTERMEDIATE 8

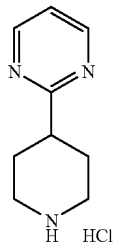

Step A

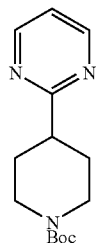

A 3-neck round bottomed flask equipped with an addition funnel and condenser and containing zinc dust (2.45 g, 37.4 mmol) was flame dried. After cooling, and purging the system with nitrogen gas, 6 mL of THF was added, followed by 1,2-dibromoethane (0.298 mL, 3.46 mmol). The mixture was warmed to a vigorous reflux using a heat gun and stirred at reflux for ~30 seconds (gas evolution was observed), then cooled to room temperature. The warming and cooling was repeated two more times. Then chlorotrimethylsilane (0.402 mL, 3.17 mmol) was added and the mixture was stirred at room temperature for 20 minutes. N-t-butoxycarbonyl-4-iodo-piperidine (known: Billotte, S. *Synlett* (1998), 379, 8.97 g, 28.8 mmol) in 15 mL of THF was added over a period of about 1 minutes. The reaction mixture was stirred at 50° C. for 1.5 h, then was cooled to room temperature. Meanwhile, a mixture of tri-2-furylphosphine (267 mg, 1.15 mmol) and Tris(dibenzylideneacetone)-dipalladium(0) chloroform adduct (298 mg, 0.288 mmol) was dissolved in 6 mL of THF under a nitrogen atmosphere, stirred for 15 minutes at room temperature, and added to the organozinc solution. Then a solution of 2-bromopyrimidine (5.50 g, 34.6 mmol) in a mixture of 58 mL of THF and 20 mL of N,N-dimethylacetamide was added. The reaction mixture was warmed to 80° C. and stirred for 3.5 h, then was cooled to room temperature and stirred for 36 h. The reaction mixture was filtered through celite and the filter cake was washed with ethyl acetate. The filtrate was diluted further with ethyl acetate, and washed with saturated $NaHCO_3$ solution. The aqueous layer was back extracted with ethyl acetate, the organic layers were combined and washed twice with water and once with brine. The organic phase was dried over anhydrous $MgSO_4$, filtered, and concentrated. Purification by flash chromatography (silica, stepwise gradient: 25% ethyl acetate/hexane, 40% ethyl acetate/hexane, 60% ethyl acetate/hexane, 80% ethyl acetate/hexane, 100% ethyl acetate) to afford 4.92 g of pure 4-(2-pyrimidyl)-piperidine product (65%). $^1$H NMR (500 MHz, $CDCl_3$): δ 8.70 (d, J=5.0 Hz, 2H), 7.16 (app t, J=4.5 Hz, 1H), 4.24 (br s, 2H), 3.05 (m, 1H), 2.89 (br m, 2H), 2.01 (br d, J=13 Hz, 2H), 1.84 (dq, J=4.5, 12.5 Hz, 2H), 1.49 (s, 9H).

Step B

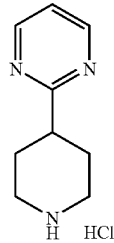

The N-t-butoxycarbonylpiperidine prepared in Step A (4.64 g, 17.6 mmol) was dissolved in 4 N HCl in dioxane (50 mL) and stirred at room temperature for 2.25 h. The reaction mixture was concentrated to afford 4.16 g of piperidine hydrochloride (100%) which required no further purification. $^1$H NMR (500 MHz, $CD_3OD$): δ 8.95 (d, J=5.5 Hz, 2H), 7.60 (t, J=5.0 Hz, 1H), 3.53 (dt, J=13, 3.5 Hz, 2H), 3.35 (tt, J=4.0, 11.0 Hz, 1H), 3.20 (br t, J=13.8 Hz, 2H), 2.30 (br d, J=14.0 Hz, 2H), 2.11-2.20 (m, 2H); ESI-MS calc. for C9H13N3: 163; Found: 164 (M+H).

INTERMEDIATE 9

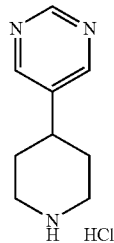

This intermediate was prepared using the procedure described for Intermediate 8 except that 4-bromo pyrimidine was used in place of 2-bromo pyrimidine. LC-MS for $C_9H_{13}N_3$ calculated 163.28, found $[M+H]^+$ 164.

INTERMEDIATE 10

4-(1H-1,2,4-triazol-1-yl)piperidine hydrochloride

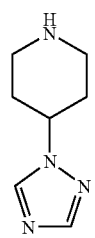

Step A tert-butyl 4-hydroxypiperidine-1-carboxylate

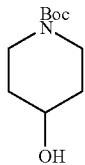

To a stirred solution of 4-hydroxypiperidine (60.8 g) in dichloromethane (500 mL) was added a solution of di-ter-butyl dicarbonate (19 g, 0.55 mol) in dichloromethane (500 mL) very slowly. After the addition, which took 1 h, the resulted mixture was stirred at ambient temperature for 5 h. The mixture was then washed with saturated $NaHCO_3$, 3 N HCl, brine, dried and evaporated to give tert-butyl 4-hydroxypiperidine-1-carboxylate as a thick oil (90 g).

Step B: tert-butyl 4-[(methylsulfonyl)oxy]piperidine-1-carboxylate

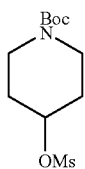

To a stirred solution of tert-butyl 4-hydroxypiperidine-1-carboxylate (21.1 g, 100 mmol) and triethyl amine (22 mL) in dichloromethane (250 mL) at 0° C. was slowly added methanesulfonyl chloride (9.0 mL, 1.1 equiv.). The resulting mixture was stirred for an additional 1 h and during this time white solid was formed. The mixture was then washed with 3 N HCl, dried over $Na_2SO_4$ and evaporated to give: tert-butyl 4-[(methylsulfonyl)oxy]piperidine-1-carboxylate as a white solid (29.2 g). $^1$H NMR (400 MHz, $CDCl_3$): δ 4.92-4.87 (m, 1H), 3.75-3.69 (m, 2H), 3.34-3.28 (m, 2H), 3.05 (s, 3H), 2.01-1.94 (m, 2H), 1.87-1.78 (m, 2H).

Step C: 4-(1H-1,2,4-triazol-1-yl)piperidine hydrochloride

To a stirred solution of: tert-butyl 4-[(methylsulfonyl)oxy] piperidine-1-carboxylate (5.9 g, 21 mmol) and 1,2,4-triazole (1.8 g, 25 mmol equiv.) in DMF at ambient temperature was added sodium hydride (60% in mineral oil, 1.0 g, 25 mmol). The mixture was stirred at 60° C. for 5 days, and the TLC showed no starting mesylate left. The mixture was poured into ice water and extracted with ethyl acetate (3×). The organic layer was dried, evaporated and purified by silica flash column eluting with 0-10% methanol in ethyl acetate to give tert-butyl 4-(1H-1,2,4-triazol-1-yl)piperidine-1-carboxylate as a white solid. The solid was then treated with hydrogen chloride in dioxane (4 N, 10 mL) for 2 h. The mixture was then evaporated to remove most of the dioxane to give a white solid, which was washed with ethyl acetate to give the desired 4-(1H-1,2,4-triazol-1-yl)piperidine hydrochloride salt (5.55 g). $^1$H NMR (300 MHz, $CD_3OD$): δ 10.00 (s, 1H), 8.97 (s, 1H), 5.10-5.00 (m, 1H), 3.63-3.58 (br. d, 2H), 3.33-3.26 (br. d, 2H), 2.50-2.30 (m, 4H).

The following compounds 10-16 were prepared in a similar fashion to Intermediate 10 using: tert-butyl 4-[(methylsulfonyl)oxy]piperidine-1-carboxylate and the appropriate heterocycles.

INTERMEDIATE 11

4-(1H-pyrazol-1-yl)piperidine hydrochloride

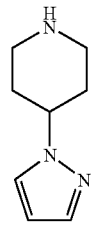

Prepared using pyrazole according to the procedure for Intermediate 10.

INTERMEDIATE 12

4-(1H-imidazol-1-yl)piperidine hydrochloride

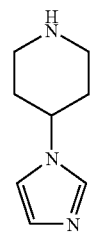

Prepared from imidazole according to the procedure for Intermediate 10: $^1$H NMR (400 MHz, $CD_3OD$): δ 9.18 (s, 1H), 7.86 (s, 1H), 7.65 (s, 1H), 4.9-4.8 (hidden under $CD_3OD$ peak, 1H), 3.61-3.61 (br. d., 2H), 3.33-3.26 (m, 2H), 2.49-2.45 (br. d, 2H), 2.39-2.28 (m, 2H).

INTERMEDIATE 13

4-(1H-1,2,3-triazol-1-yl)piperidine hydrochloride

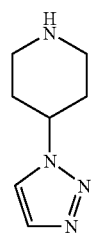

Prepared from 1,2,3-triazole according to the procedure for Intermediate 10.

4-(1H-1,2,3-triazol-1-yl)piperidine hydrochloride: $^1$H NMR (400 MHz, $CD_3OD$): δ 8.77 (s, 1H), 8.54 (s, 1H), 5.26-5.19 (m, 1H), 3.65-3.59 (m, 2H), 3.37-3.29 (m, 2H), 2.60-2.54 (m, 2H), 2.50-2.39 (m, 2H).

INTERMEDIATE 14

4-(2H-1,2,3-triazol-2-yl)piperidine hydrochloride

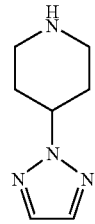

Prepared from 1,2,3-triazole according to the procedure for Intermediate 10.

4-(2H-1,2,3-triazol-2-yl)piperidine hydrochloride: $^1$H NMR (400 MHz, CD$_3$OD): δ 7.72 (s, 2H), 4.94-4.87 (m, 1H), 3.54-3.48 (m, 2H), 3.28-3.22 (m, 2H), 2.46-2.32 (m, 4H).

INTERMEDIATE 15

4-(1H-tetraazol-1-yl)piperidine hydrochloride

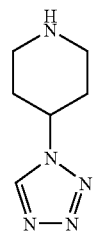

Prepared from tetrazole according to the procedure for Intermediate 10.

4-(1H-tetraazol-1-yl)piperidine hydrochloride: $^1$H NMR (400 MHz, CD$_3$OD): δ 8.77 (s, 1H), 5.30-5.23 (m, 1H), 3.58-3.53 (m, 2H), 3.35-3.29 (m, 2H), 2.58-2.2.52 (m, 2H), 2.48-2.38 (m, 2H).

INTERMEDIATE 16

4-(2H-tetraazol-2-yl)piperidine hydrochloride

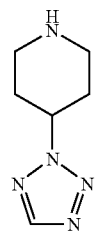

Prepared from tetrazole according to the procedure for Intermediate 10.

4-(2H-tetraazol-2-yl)piperidine hydrochloride: $^1$H NMR (400 MHz, CD$_3$OD): δ 9.32 (s, 1H), 5.08-5.00 (m, 1H), 3.61-3.57 (m, 2H), 3.33-3.28 (m, 2H), 2.52-2.47 (m, 2H), 2.42-2.32 (m, 2H).

INTERMEDIATE 17

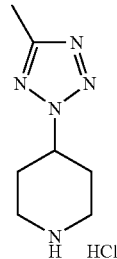

Prepared from 5-methyltetrazole according to the procedure for Intermediate 10.

$^1$H NMR (400 MHz, CD$_3$OD): δ 5.08-5.00 (m, 1H), 3.61-3.57 (m, 2H), 3.33-3.28 (m, 2H), 2.52-2.47 (m, 2H), 2.42-2.32 (m, 2H), 1.68 (s, 3H).

INTERMEDIATE 18

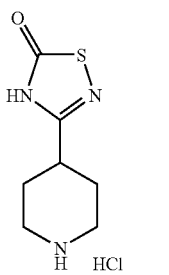

Step A

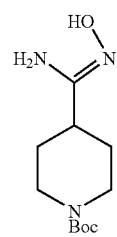

Hydroxylamine hydrochloride (8.26 g, 119 mmol) and triethylamine (16.6 mL, 119 mmol) were combined in 50 mL of DMSO. The suspension was filtered to remove triethylamine hydrochloride and the filter cake was washed with THF. The filtrate was partially concentrated to remove the THF. Then commercially available 1-tert-butoxycarbonyl-4-cyanopiperidine (5.0 g, 24 mmol) was added to the DMSO solution and the resulting reaction mixture was stirred at 75° C. for 3 h, and then at room temperature overnight. The reaction mixture was diluted with ethyl acetate and washed with water. The aqueous layer was back-extracted with more ethyl acetate and the combined organic layers were washed four times with water and once with brine. The organic layer was dried over anhydrous MgSO₄, filtered, and concentrated to give 3.51 g of product.

Step B

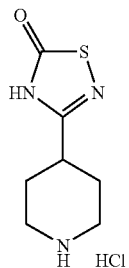

A solution of the compound from Step A (1.02 g, 4.19 mmol) in 20 mL THF was treated with thiocarbonyldiimidazole (897 mg, 5.03 mmol), whereupon gas evolution and an exotherm were noted. The reaction mixture was stirred at room temperature for 1 h, then was transferred to a suspension of silica gel #60 (20 g) in 180 mL of 5:1 CHCl₃/methanol. The reaction mixture was stirred at room temperature for 5 days, then filtered and concentrated. Purification by MPLC (silica, 50% ethyl acetate/hexane) afforded 143 mg of thiodiazolone.

Boc intermediate ¹H NMR (500 MHz, CD₃OD): δ 4.16 (m, 2H), 2.86 (t, J=11.5 Hz, 2H), 2.77 (tt, J=4.0, 11.0 Hz, 1H), 1.98 (dd, J=2.0, 13.0 Hz, 2H), 1.73 (dq, J=4.5, 12.0 Hz, 2H), 1.47 (s, 9H). The Boc intermediate (139 mg, 0.487 mmol) was dissolved in 4 N HCl in dioxane (5 mL) and stirred at room temperature for 1.5 h. The reaction mixture was concentrated to give 94.3 mg of piperidine hydrochloride product.

INTERMEDIATE 19

4-(1H-pyrazol-3-yl)piperidine

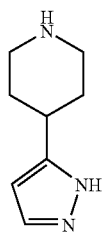

Step A: 4-(1H-pyrazol-3-yl)pyridine

To a mixture of 4-acetylpyridine (75 mL, 0.68 mol) and ethyl formate (109 mL) in anhydrous benzene (1 L) was added sodium methoxide (73 g) and the resulting mixture was refluxed for 18 h. The mixture was cooled and benzene decanted from a sticky solid, which had formed during the reaction. The crude product was dissolved in water (700 mL) and hydrazine dihydrochloride was added and the resulting mixture was stirred at room temperature for 2 h. The mixture was redissolved by addition of 5 N NaOH. Precipitate formed which was removed by filtration and dried to give 4-(1H-pyrazol-3-yl)pyridine (35 g).

Step B: 1-benzyl-4-(1H-pyrazol-3-yl)-1,2,3,6-tetrahydropyridine

To a hot (80° C.) solution of 4-(1H-pyrazol-3-yl)pyridine (9.6 g) in 2-propanol (60 mL) was added benzyl bromide (20 mL, 2.5 equiv.) and the resulting mixture was heated at reflux for 10 minutes. After cooling in an ice bath, the precipitate was filtered and washed with more 2-propanol and air dried. The solid was suspended in ethanol at 0° C. and sodium borohydride (13 g) was added in several portions over 30 minutes, and the mixture was stirred for an additional 30 minutes. The reaction was quenched by the careful addition of water, the ethanol was removed by evaporation, and the residue was partitioned between dichloromethane and water. The organic layer was dried over MgSO₄, filtrated and evaporated to give 1-benzyl-4-(1H-pyrazol-3-yl)-1,2,3,6-tetrahydropyridine (16 g)

Step C: 4-(1H-pyrazol-3-yl)piperidine

A solution of 1-benzyl-4-(1H-pyrazol-3-yl)-1,2,3,6-tetrahydropyridine (16 g) was hydrogenated over palladium on carbon (10%, 1 g) at 40 psi overnight. The catalyst was removed by filtration through celite and the filtrate was evaporated. NMR shows the product is 1-benzyl-4-(1H-pyrazol-3-yl)-piperidine (16 g).

To a solution of 1-benzyl-4-(1H-pyrazol-3-yl)-piperidine (16 g) and formic acid (30 mL) in ethanol (400 mL) was added palladium on carbon (10%, 2 g) and the resulting mixture was stirred at room temperature overnight. The catalyst was removed by filtration and the filtrate evaporated. The product was purified by adding di-tert-butyl dicarbonate (2 equiv.) and triethyl amine (1.5 equiv.) in dichloromethane to give a Boc protected intermediate. Evaporated and purification by column chromatography on silica eluting with 20-40% ethyl acetate in hexane give pure tert-butyl 4-(1H-pyrazol-3-yl)piperidine-1-carboxylate. The Boc intermediate was then treated with methanolic HCl to give 4-(1H-pyrazol-3-yl)piperidine hydrochloride salt (3.5 g). Loss of material was due to the formation of the di-Boc product, which was not collected.
¹H NMR (400 MHz, CDCl₃): δ 8.00 (s, 2H), 3.48 (br. d, J=13 Hz, 2H), 3.28-3.20 (m, 1H), 3.13 (br. t, J=13 Hz, 2H), 2.23 (br. d, J=14 Hz, 2H), 1.97-1.85 (m, 2H).

INTERMEDIATE 20

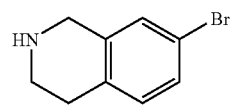

Step A:

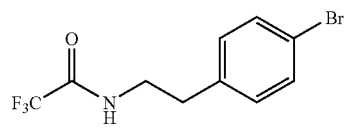

To a mixture of 4-bromophenethylamine hydrobromide (25 g, 89 mmol) and pyridine (36 mL, 445 mmol) in CH₂Cl₂ (100 mL) cooled at 0° C. was added dropwise trifluoroacetic anhydride (18.8 mL, 133 mmol). After complete addition the mixture was stirred at room temperature for 48 hours then poured onto ice (500 g). The mixture was extracted with CH$_2$Cl$_2$ (4×100 mL), the combined CH$_2$Cl$_2$ layers were washed with 1N HCl (4×100 mL), sat NaCl (100 mL), dried over MgSO$_4$, filtered and evaporated in vacuo to give the product (26.13 g, 100%); $^1$H NMR 500 MHz (CDCl$_3$) δ=2.86 (2H, t, J=7.1 Hz), 3.59 (2H, q, J=6.6 Hz), 6.57 (1H, br s), 7.09 (2H, d, J=8.5 Hz), 7.43 (2H, d, J=8.5 Hz).

Step B:

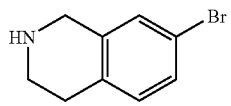

To a mixture of the product from Step A (26 g, 88 mmol) and paraformaldehyde (5.6 g, 130 mmol), was added in one portion a mixture of concentrated sulfuric acid (130 mL) and glacial acetic acid (195 mL), and the resulting mixture stirred at room temperature for 17 hours. The reaction mixture was poured onto ice/water (1.5 L) and extracted with ethyl acetate (3×300 mL), the combined ethyl acetate layers were washed with water (2×600 mL), sat NaHCO$_3$ (300 mL), and saturated NaCl (150 mL), dried over MgSO$_4$, filtered and evaporated in vacuo. The residue was dissolved in ethanol (450 mL), and a solution of potassium carbonate (60 g, 434 mmol) in water (150 ml) was added. The mixture was heated to reflux for 1 hour then cooled and evaporated in vacuo. Water (500 mL) was added to the residue and extracted with CH$_2$Cl$_2$ (3×300 mL); the combined CH$_2$Cl$_2$ layers were washed with water (500 mL), sat NaCl (150 mL), dried over Na$_2$SO$_4$, filtered and concentrated in vacuo. The residue was purified by column chromatography on silica elution with 5% CH$_3$OH in CH$_2$Cl$_2$ containing 0.5% NH$_4$OH to give the product (10 g, 54%); $^1$H NMR 500 MHz (CDCl$_3$) δ=1.77 (1H, br s), 2.77 (2H, d, J=6.0 Hz), 3.11 (2H, t, J=6.0 Hz), 3.97 (2H, s), 6.95 (1H, d, J=8.0 Hz), 7.15 (1H, s) 7.23 (1H, dd, J=1.2 and 8.2 Hz).

INTERMEDIATE 21

Cis racemate

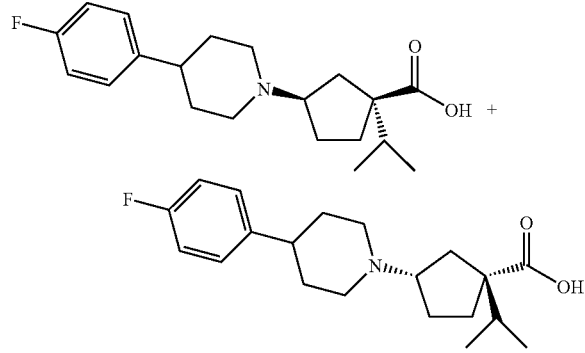

Step A

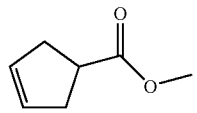

To a solution of 3-cyclopentene-1-carboxylic acid (Org. Synth. 75, p195-200, 1998) (31.5 g, 281 mmol) in anhydrous N,N-dimethylformamide (300 mL), under an atmosphere of nitrogen, was added potassium carbonate (97 g, 710 mmol), and iodomethane (35 mL, 560 mmol). The resulting mixture was stirred at room temperature for 16 h, then poured into water (1 L), and extracted with diethyl ether (3×400 mL). The combined diethyl ether layers were washed with water (3×500 mL), saturated NaCl (200 mL), dried over MgSO$_4$, filtered and concentrated in vacuo, to give 34 g (96%).

$^1$H NMR (CDCl$_3$, 500 MHz): δ 5.64 (s, 2H), 3.68 (s, 3H), 3.11 (quintet, J=8.5 Hz, 1H), 2.63 (d, J=8.3 Hz, 4H).

Step B

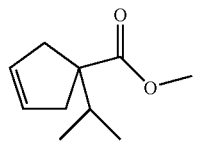

To a cooled (−78° C.) solution of diisopropylamine (34.4 mL, 250 mmol) in anhydrous tetrahydrofuran (250 mL) under an atmosphere of nitrogen was added slowly n-butyllithium (100 mL of a 2.5M solution in hexanes, 250 mmol), and the resulting mixture was stirred at −78° C. for 10 minutes. To this mixture was added methyl-3-cyclopentenecarboxylate (25.8 g, 200 mmol), after stirring for a further 15 minutes 2-iodopropane (41 mL, 410 mmol) was added, and the mixture stirred at −78° C. for 30 minutes then allowed to rise to +4° C. and was left standing at this temperature for 72 h. The reaction mixture was poured in 5% citric acid (700 mL) and extracted with diethyl ether (3×300 mL). The combined diethyl ether layers were washed with water (2×500 mL), saturated NaCl (1×100 mL), dried over MgSO$_4$, filtered and concentrated in vacuo. The residue was purified by vacuum distillation 50° C. @ 5 mmHg to provide 28.9 g (86%) of product.

$^1$H NMR (CDCl$_3$, 500 MHz): δ 5.54 (s, 2H), 3.67 (s, 3H), 2.85 (d, J=15.1 Hz, 2H), 2.30 (dd, J=14.9 Hz, 2H), 2.07 (t, J=6.6 Hz, 1H), 0.82 (d, J=6.6 Hz, 6H).

Step C

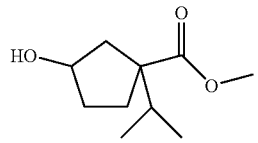

To a cooled (0° C.) solution of borane-methyl sulfide (20 mL, 200 mmol) in anhydrous tetrahydrofuran (100 mL), under an atmosphere of nitrogen, was added, using a double ended needle, a solution of the cyclopentene ester prepared in Step B (28.9 g, 172 mmol). After complete addition the reaction mixture was stirred at room temperature for 20 h. The mixture was cooled in an ice bath and sodium hydroxide (60 mL of a 3 N solution, 181 mmol) was added dropwise, followed by 30% hydrogen peroxide (65 mL) and the resulting mixture was stirred at 40° C. for 1 h. The mixture was poured into water (600 mL) and extracted with diethyl ether (3×200 mL), the combined diethyl ether layers were washed with water (3×500 mL), saturated NaCl (100 mL), dried over MgSO$_4$, filtered and concentrated in vacuo. The residue was purified by column chromatography on silica elution with 20% EtOAc/hexanes to give 18.5 g (58%) of product.

Step D

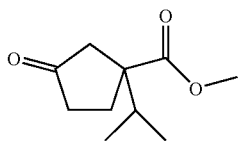

To a (−78° C.) solution of oxalyl chloride (55 mL, 110 mmol) in anhydrous dichloromethane (300 mL) under an atmosphere of nitrogen was added in a dropwise manner dimethyl sulfoxide (15.5 mL, 219 mmol), and the resulting mixture stirred at −78° C. for 10 minutes. To this mixture was added, using a double ended needle, a solution of the product from Step C (18.5 g, 100 mmol) in anhydrous dichloromethane (100 mL). The reaction mixture was stirred at −78° C. for a further 15 minutes, then triethylamine (69 mL, 500 mmol) was added and the resulting mixture was allowed to rise to room temperature over 2 h. The reaction mixture was washed with water (500 mL), saturated NaCl (150 mL), dried over MgSO$_4$, filtered and concentrated in vacuo, to give 18 g of product which was used in the next step without further purification.

Step E

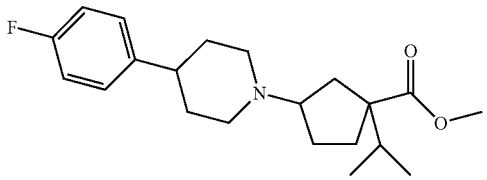

To a solution of the cyclopentanone prepared in Step D (18 g, 98 mmol) in anhydrous 1,2-dichloroethane (500 mL), under an atmosphere of nitrogen, was added 4-(4-fluorophenyl)piperidine hydrochloride (25 g, 120 mmol), diisopropylethylamine (20.4 mL, 116 mmol), sodium triacetoxyborohydride (112 g, 531 mmol), and 4 Å molecular sieves (powder 10 g). The mixture was stirred at room temperature for 48 h, and then diluted with dichloromethane (500 mL), and filtered through celite. The filtrate was washed with saturated NaHCO$_3$ solution (500 mL), water (500 mL), saturated NaCl (200 mL), dried over Na$_2$SO$_4$, filtered and concentrated in vacuo to give 28 g (82%) of product. This material was used in the next step without further purification.

Step F 1-isopropyl-3-(4-(4-fluorophenyl)piperidin-1-yl)cyclopentanecarboxylic acid

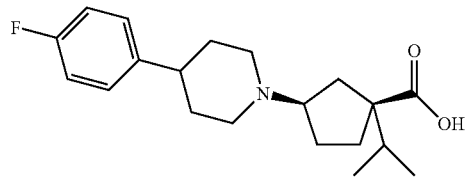

To a solution of the cyclopentane methyl ester prepared in Step E (28 g, 81 mmol) in ethanol (500 mL), was added a solution of potassium hydroxide (30 g, 540 mmol) in water (100 mL), and the resulting mixture was heated at reflux for 18 h. The cooled mixture was concentrated in vacuo to remove the ethanol, and water (200 mL) was added to the residue. The mixture was extracted with diethyl ether (3×200 m/L), and the aqueous layer was neutralized by the addition of concentrated hydrochloric acid. The mixture was extracted with a mixture of 9/1 chloroform/2-propanol (3×150 mL), and the combined organic extracts were dried over Na$_2$SO$_4$, filtered and concentrated in vacuo. To the residue was added acetone (70 mL) and the mixture was heated to reflux briefly and then was left standing at +5° C. for 16 h. The acetone was decanted way from the white solid, and the remaining solid was dried to give 11.5 g (43%) of product which was a 10:1 mixture of cis and trans isomers.

ESI-MS calc. for C20H28FNO2: 333; Found: 334 (M+H).

INTERMEDIATE 22

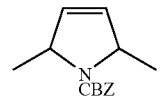

2,5-Dimethyl-3-pyrroline (3.128 g, 32.19 mmol) was dissolved in triethylamine (8.97 mL, 64.4 mmol) and cooled to 0° C. Carbobenzyloxychloride (10.11 mL, 70.83 mmol) in a minimal amount of dichloromethane was added dropwise. The reaction mixture was slowly warmed to room temperature and stirred for 48 h. The reaction was quenched with saturated sodium bicarbonate solution (150 mL), and the organic layer was then washed with saturated sodium bicarbonate solution (2×100 mL) and brine (1×100 mL), dried over MgSO$_4$, filtered, and concentrated. Intermediate 1 (3.844 g) was obtained in a 52% yield through purification by silica gel flash column chromatography using a gradient solvent system of 5% EtOAc in hexanes to 10% EtOAc in hexanes. ESI-MS calculated for C$_{14}$H$_{17}$NO$_2$: 31.29, found 232 (M+H).

INTERMEDIATE 23

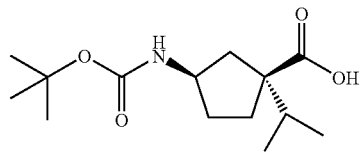

Procedure A:

Step A

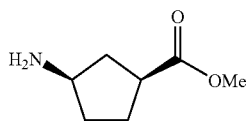

A mixture of (1S)-(+)-2-azabicyclo[2.2.1]hept-5-en-3-one (10.3 g, 94.4 mmol) in ethyl acetate (200 mL) and 10% Pd/C (0.5 g), was hydrogenated at room temperature. After 24 h the reaction mixture was filtered and evaporated leaving behind 10.4 g (100%) of the product that was taken in 250 mL methanol and HCl (12 M, 6 mL). The resultant mixture was stirred at room temperature, until the reaction was complete (72 h). Evaporation of methanol followed by drying under high vacuum, yielded title compound as an off white solid (16.0 g, 96%). $^1$H NMR (500 MHz, D$_2$O): δ 3.70 (s, 3H), 3.01 (m, 1H), 2.38 (m, 1H), 2.16-1.73 (m, 6H).

Step B

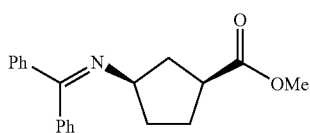

To a suspension of the intermediate from Step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. 1H NMR (500 MHz, CDCl3): δ 7.5-7.18 (m, 10H), 3.75 (m, 1H), 3.7 (s, 3H), 2.78 (m, 1H), 2.26-1.71 (m, 6H).

Step C

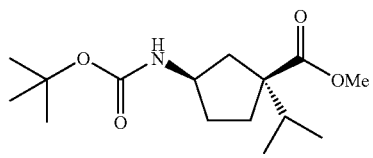

To a solution of lithium diisopropylamide (prepared from diisopropylamine (7.7 g, 76 mmol) and n-butyllithium (30.4 mL, 2.5 M in hexanes, 76 mmol) in tetrahydrofuran (120 mL) at −78° C. was added the ester from Step B (18.0 g, 58.6 mmol). The resultant burgundy colored solution was stirred for 20 min after which it was quenched with 2-iodopropane (14.9 g, 88.0 mmol). The reaction mixture was gradually warmed over 3 h to 0° C. and this temperature was maintained for an additional 3 h. Reaction was quenched with water and extracted with ethyl acetate. The organic layer was washed with water, brine, dried (anhydrous magnesium sulfate) and concentrated to yield an oil. To the solution of the crude Schiff base (20.0 g) in tetrahydrofuran (100 mL) was added HCl (5.0 mL, 12 M). The resulting reaction mixture was allowed to stir at room temperature for 3 h. After the removal of all volatiles, the hydrochloride salt was taken up into dichloromethane (250 mL), saturated solution of sodium bicarbonate (250 mL) and di-tert-butyl dicarbonate (26.0 g, 1.4 Eq.) were added. The resultant mixture was vigorously stirred overnight at room temperature. The organic layer was separated and washed with water, brine, dried (anhydrous magnesium sulfate) and concentrated to yield an oil. Purification by flash column chromatography (eluent: hexanes/ethyl acetate 19:1) gave the desired product (4.91 g, 30%). 1H NMR (500 MHz, CDCl3): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D

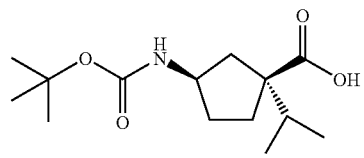

To a solution of the ester from Step C (4.91 g, 17.2 mmol) in methanol (100 mL) was added a solution of LiOH (3.6 g, 85 mmol) in water (20 mL) and tetrahydrofuran (10 mL). The resultant mixture was heated at 80° C. until the reaction was complete (18 h). The methanol was removed in vacuo and the crude product was taken up with water/ethyl acetate (200 mL, 1:4) and cooled to 0° C. The acidity of the mixture was adjusted to pH 6. The ethyl acetate layer was separated, washed with water, brine, dried (anhydrous magnesium sulfate) and concentrated to yield an oil. Purification by flash column chromatography (eluent: hexanes/ethyl acetate 1:1+ 2% AcOH) gave Intermediate 11 (3.9 g, 84%). 1H NMR (500 MHz, CDCl3): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Procedure B:

Step A:

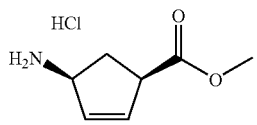

Commercially available (1R,4S)-4-amnocyclopent-2-ene-1-carboxylic acid was converted to its methyl ester hydrochloride salt via classical procedures.

Step B:

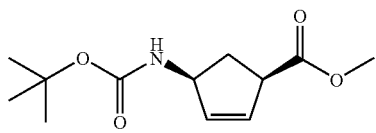

To a suspension of amine from Step A (6.31 g, 35.5 mmol) in acetone (40 mL) and water (20 mL) was added solid NaHCO$_3$ (6.6 g, 78 mmol) in portions. After 5 min, a solution of di-tert-butyl dicarbonate (8.5 g, 39 mmol) in acetone (60 mL) was added and the reaction mixture was stirred at room temperature. After 3 h, acetone was removed in vacuo and the residue was partitioned between ether (500 mL) and saturated aqueous NaHCO$_3$ solution (120 mL). The ether layer was further washed with aqueous NaHCO$_3$ solution (1×100 mL), brine (1×10 mL), dried over anhydrous Na$_2$SO$_4$, concentrated and purified by flash chromatography (15% ethyl acetate/hexanes) to afford the product (7.25 g, 85%).

Step C:

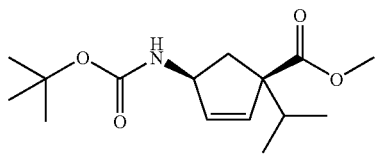

To a solution of lithium bis(trimethylsilyl)amide (10.4 g, 62.1 mmol) in tetrahydrofuran (100 mL) was added a solution of the intermediate from Step B (6.71 g, 27.8 mmol) in tetrahydrofuran (10 mL) over 10 min at −78° C. The resulting solution was stirred at −78° C. for 30 min before isopropyl iodide (3.3 mL, 33 mmol) was added in one portion. The reaction was allowed to warm up to −25° C. and this temperature was maintained overnight. The reaction was then quenched with an aqueous saturated NH$_4$Cl solution (250 mL). The organic layer was separated and the aqueous layer was further extracted with diethyl ether (3×100 mL). The combined organic layers were then washed with brine (1×100 mL), dried over anhydrous Na$_2$SO$_4$, filtered, concentrated and purified by flash chromatography (5-10% ethyl acetate/hexanes) to give the product (5.66 g, 72%) as a clear oil (cis/trans=4.3/1). $^1$H NMR (500 MHz, CDCl$_3$) cis-isomer: δ 5.79 (s, 2H), 4.75 (m, 1H), 3.72 (s, 3H), 2.28-2.20 (m, 2H), 2.0 (dd, J=15, 4 Hz, 1H), 1.45 (s, 9H), 0.85 (d, J=6.6 Hz, 3H), 0.81 (d, J=7 Hz, 3H).

Step D:

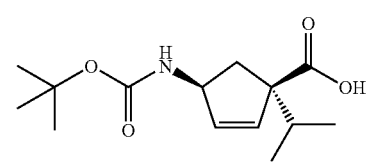

To a solution of the product from Step C (1.6 g, 5.7 mmol) in tetrahydrofuran (50 mL), methanol (50 mL) and water (10 mL) was added LiOH monohydrate (400 mg) and the reaction was heated to reflux overnight until the TLC indicated that the reaction was complete. The organic solvents were removed in vacuo and the aqueous layer was washed with ether (1×) and then acidified slowly with concentrated HCl until the pH reached 4. The resulting suspension was extracted with CH$_2$Cl$_2$ (3×). The combined organic layers were dried over anhydrous MgSO$_4$, filtered and concentrated to give the product as a mixture of two cis/trans isomers (1.5 g) as a foaming yellow solid. This solid was dissolved in ethyl acetate (2 mL) with heating and diluted with hexanes (50 mL) to give a clear solution. This solution was allowed to cool to room temperate slowly over 1 h and then maintained at −25° C. in a freezer overnight. The trans-isomer was crystallized out along with some of the desired cis-isomer (500 mg total). The mother solution was collected and concentrated to give the title compound (1 g, 66%, cis-isomer only). $^1$H NMR (500 MHz, CDCl$_3$) cis-isomer: δ 5.80 (m, 2H), 4.80 (m, 1H), 2.40-2.20 (m, 2H), 2.15-2.0 (m, 1H), 1.5 (m, 9H), 1.0-0.8 (m, 3H).

Step E:

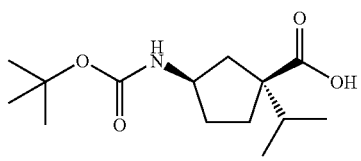

To a solution of the product from Step D (1 g) in ethanol (30 mL) was added 10% Pd/C (100 mg) and the resulting mixture was agitated on a Parr apparatus at 50lb pressure of H2 overnight. The mixture was filtered through celite and concentrated in vacuo to afford the title compound (1 g, 99%). 1H NMR (500 MHz, CDCl3): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

INTERMEDIATE 24

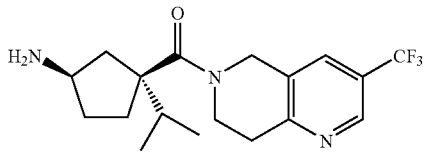

Step A

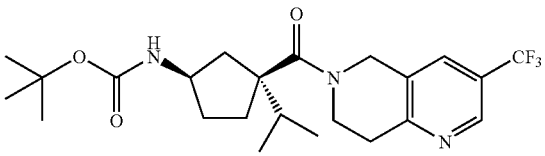

Intermediate 2 (4.6 g, 16 mmol) and Intermediate 23 (4.0 g, 14 mmol) were first dried by azeotropic distillation with toluene (3×50 mL) and placed under high vacuum for 30 min.

Under nitrogen, 4-dimethylaminopyridine (1.08 g, 8.60 mmol), anhydrous dichloromethane (40 mL), and diisopropylethylamine (7.0 mL, 40 mmol) were added sequentially. After the intermediates were in solution, bromo-tris-pyrrolidino-phosphonium hexafluorophosphate (6.80 g, 14.3 mmol) was added, immediately followed by additional diisopropylethylamine (7.0 mL, 40 mmol). The reaction mixture was stirred at room temperature overnight and then quenched with saturated NaHCO$_3$. The aqueous layer was back washed with dichloromethane (3×50 mL) and the organic layers were combined, dried over Na$_2$SO$_4$, filtered, and evaporated in vacuo. The crude product was purified by flash chromatography (stepwise gradient 0-60%, ethyl acetate/hexanes) to afford the product (4.80 g, 74%) as a yellow foam. $^1$H NMR (500 MHz, CDCL$_3$) δ 8.72 (s, 1H), 7.70 (s, 1H), 4.88 (br d, J=17.0 Hz, 1H), 4.78 (d, J=17.6 Hz, 1H), 4.04-3.84 (m, 2H), 3.52 (br s, 1H), 3.12 (br t, J=5.6 Hz, 1H), 2.32-2.06 (m, 3H), 1.98-1.70 (m, 4H), 1.64-1.54 (m, 1H), 1.44 (s, 9H), 0.92-0.82 (m, 6H). LC-MS for C$_{23}$H$_{32}$F$_3$N$_3$O$_3$ calculated 455.24, found [M+H]$^+$ 456.2.

Step B

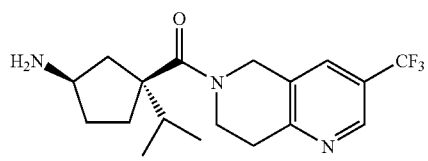

The product from Step A (1.2 g, 2.6 mmol) was dissolved in 4 M HCl in dioxane (50 mL) and the resulting solution was stirred at room temperature for 1 h. The reaction mixture was evaporated under vacuum to afford the product (904 mg, 97%) as a white powder. LC-MS calculated for C$_{18}$H$_{24}$F$_3$N$_3$O is 355.20, found [M+H]$^+$ 356.2.

INTERMEDIATE 25

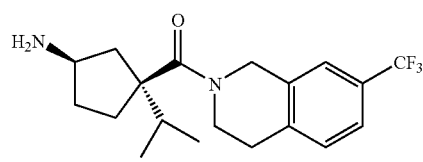

Step A

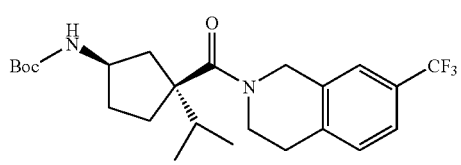

To a flask was added Intermediate 23 (1.1 g, 4.0 mmol), Intermediate 1 (0.944 g, 4.00 mmol), bromo-tris-pyrrolidino-phosphonium hexafluorophosphate (1.85 g, 4.00 mmol), DMAP (0.29 g, 2.4 mmol), DIEA (2.77 mL, 16 mmol) and DCM (20 mL). The resulting mixture was stirred for 36 h under nitrogen. The entire mixture was applied onto a silica gel column and eluted with 20% EtOAc/Hexane. The desired Boc-amide was obtained as a gummy solid (1.5 g, 82%). ESI-MS calc. for C24H33F3N2O3: 454; Found: 455 (M+H).

Step B

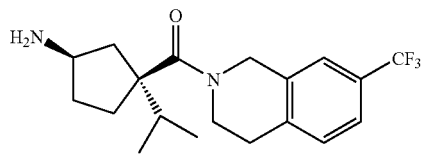

The Boc amino amide from Step A was treated with 10 mL of 4 N HCl/Dioxane for 1 h. the reaction mixture was evaporated and the product was dried under vacuum. Intermediate 25 was obtained as a yellow solid (1.2 g). ESI-MS calc. for C19H25F3N2O: 354; Found: 355 (M+H).

INTERMEDIATE 26

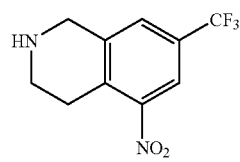

Step A

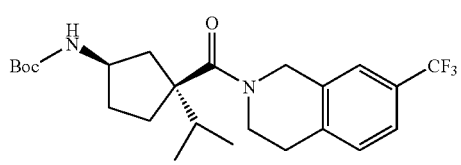

To a flask containing Intermediate 1 (10 g, 50 mmol) was added 30 mL of 70% nitric acid. The mixture was cooled at 0° C., 30 mL of concentrated sulfuric acid was added over 30 min. The resulting solution was stirred at RT overnight, poured into an ice-water mixture, adjusted to pH>10 with solid LiOH—H$_2$O at 0° C. Under vigorous stirring, a solution of di-tert-butyl carbonate (21.8 g, 100 mmol) in 500 mL of DCM was added. The mixture was stirred for 30 min, the organic layer was separated, the aqueous layer was extracted with DCM (2×200 mL). The combined extracts were washed with water (500 mL), dried over Na$_2$SO$_4$, and evaporated. The crude product was purified by flash chromatography (silica gel, 20% EtOAc/Hexane) to afford the title compound as a white solid (17.0 g, 98%). $^1$H NMR (400 MHz, CDCl$_3$) δ 8.05

(s, 1H), 7.62 (s, 1H), 4.72 (s, 2H), 3.67 (t, J=6.0 Hz, 2H), 3.13 (t, J=6.0 Hz, 2H), 1.49 (s, 9H).

Step B

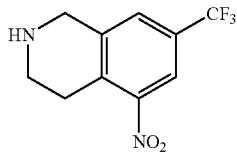

The above intermediate from Step A (17.0 g) was dissolved in 100 mL of 4 M HCl/dioxane, stirred for one hour, evaporated and dried under vacuum. Intermediate 26 was obtained as white solid. $^1$H NMR (400 MHz, CD$_3$OD) δ 8.75 (s, 1H), 8.00 (s, 1H), 2.58 (s, 2H), 3.57 (t, J=6.0 Hz, 2H), 3.42 (t, J=6.0 Hz, 2H).

INTERMEDIATE 27

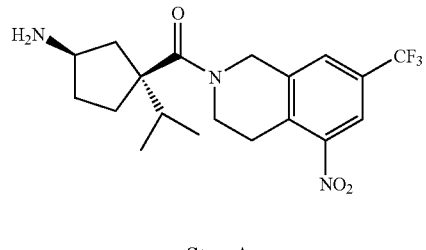

Step A

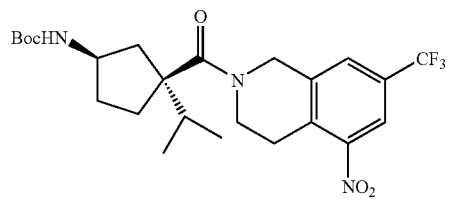

To a flask was added Intermediate 27 (1.10 g, 4.00 mmol), Intermediate 23 (1.15 g, 4.00 mmol), bromo-tris-pyrrolidino-phosphonium hexafluorophosphate (1.85 g, 4.00 mmol), DMAP (0.29 g, 2.4 mmol), DIEA (2.7 mL, 16 mmol) and DCM (20 mL). The resulting mixture was stirred for 36 h under nitrogen. The entire mixture was applied onto a silica gel column and eluted with 20% EtOAc/Hexane to yield the title compound as a gummy solid (1.5 g, 75%). ESI-MS calc. for C24H32F3N3O5: 499; Found: 500 (M+H).

Step B

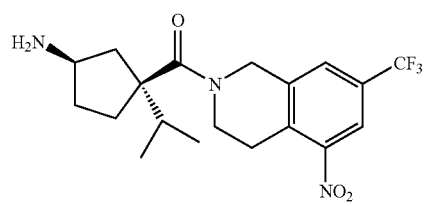

The coupling product from the previous step (1.5 g) was treated with 10 mL of 4N HCl/Dioxane for 1 h, evaporated and dried under high vacuum to yield the title compound as a yellow solid (1.2 g). 1H NMR (400 MHz, CD3OD) δ 8.20 (s, 1H), 7.95 (wide, 1H), 4.98 (s, 2H), 4.00 (dd, 2H), 3.90 (t, 2H), 3.68 (m, 1H), 3.45 (m, 3H), 3.20 (s, 2H), 2.15-2.50 (m, 3H), 1.80-2.10 (m, 2H), 1.80 (m, 2H), 0.90 (m, 6H). ESI-MS calc. for C19H24F3N3O3: 399; Found: 400 (M+H).

INTERMEDIATE 28

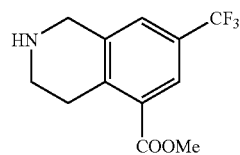

Step A

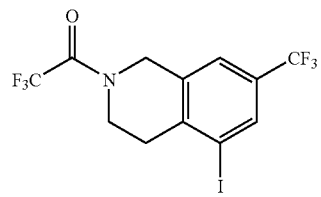

To a stirring mixture of N-trifluoroacetyl-7-trifluoromethyl-1,2,3,4-tetrahydroisoquinoline, from Intermediate 1, Step B (6.0 g, 20 mmol), NIS (6.9 g, 30 mmol) and TFA (15 mL) was added dropwise concentrated sulfuric acid (1.5 mL). A large amount of solid was formed. The mixture was stirred overnight at RT, poured into an ice-water mixture, extracted with ethyl acetate (3×). The combined organic phases were washed with water and brine, dried over Na$_2$SO$_4$, evaporated. The residue was purified on silica gel (eluted with 10% EtOAc/Hexane). The combined fractions were washed with sat. NaHSO$_3$, dried over Na$_2$SO$_4$, evaporated and dried under vacuum to afford the title compound as a white solid (5.0 g). 1H NMR (400 MHz, CDCl3) δ 8.02 (d, J=2.5 Hz, 1H), 7.42 (d, j=3.0 Hz, 1H), 4.85, 4.79 (ss, 2H), 3.95, 3.90 (tt, J=1.5, 1.5 Hz, 2H), 2.97 (m, 2H). ESI-MS calc. For C12H8F6INO: 423; Found: 424 (M+H).

Step B

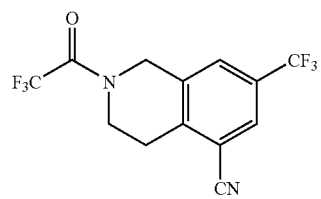

A mixture of the iodo compound (Step A, 4.2 g, 10 mmol), zinc cyanide (2.3 g, 20 mmol) and tetrakis-triphenyl phosphene palladium (0) complex (0.4 g) in 50 mL of DMF was purged with nitrogen several times, then heated at 85° C. overnight under nitrogen. LC-MS showed a complete conversion. The insoluble material was removed by filtration. The filtrate was diluted with water and extracted with ethyl acetate (3×). The ethyl acetate layers were combined, filtered through celite, then washed with water, dried over $Na_2SO_4$, and evaporated. The residue was purified on silica gel (eluted with 10% EtOAc/Hex) to yield the title compound as a white solid (2.5 g). 1H NMR (400 MHz, CDCl3) δ 7.85 (d, J=2.1 Hz, 1H), 7.65 (d, J=2.6 Hz, 1H), 4.91, 4.86 (ss, 2H), 4.00 (m, 2H), 3.25 (m, 2H). ESI-MS calc. For C13H8F6N2O: 323; Found: 323 (M+H).

Step C

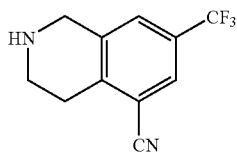

A mixture of the amide Intermediate from Step B (500 mg, 1.55 mmol), potassium carbonate (1.5 g), ethanol (20 mL) and water (0.5 mL) was heated at 80° C. until TLC showed complete cleavage. The solvent was evaporated, diluted with water, extracted with DCM (3×), dried over $Na_2SO_4$, evaporated, and dried under vacuum. The title product was obtained as a white solid (0.41 g). ESI-MS calc. For C11H9F3N2: 226; Found: 227 (M+H).

Step D

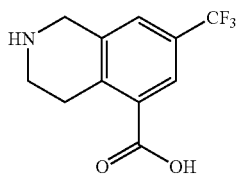

The above cyano intermediate from Step C (1.9 g, 8.5 mmol) was refluxed with 50 mL of concentrated aq. HCl for 48 h. LC-MS showed a complete hydrolysis. The mixture was cooled to RT and the resultant precipitate was collected by filtration and washing with concentrated aq. HCl. The desired product as its HCl salt (1.75 g, 73%) was obtained after drying under high vacuum. $^1$H NMR (CD$_3$OD, 400 MHz): δ 8.20 (s, 1H), 7.80 (s, 1H), 4.51 (s, 2H), 3.55 (m, 4H). LC-MS for C11H10F3NO2 calculated 245, found [M+H]$^+$ 246.

Step E

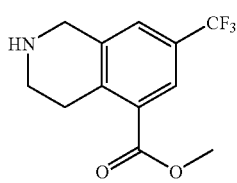

To a suspension of the above amino acid HCl salt from Step D (1.75 g, 6.25 mmol) in 50 mL of methanol was added slowly a neat solution of acetyl chloride (5 mL). The resultant mixture was refluxed until LC-MS showed a complete esterification (~3 h), then the solvent was evaporated and dried under high vacuum to yield the title compound as a white solid (1.85 g, 100%). $^1$H NMR (CD$_3$OD, 400 MHz): 8.19 (s, 1H), 7.82 (s, 1H), 4.50 (s, 2H), 3.94 (s, 3H), 3.53 (s, 4H). LC-MS for C12H12F3NO2 calculated 259, found [M+H]$^+$ 260.

INTERMEDIATE 29

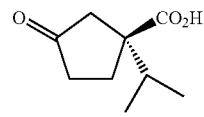

Procedure A:

Step A:

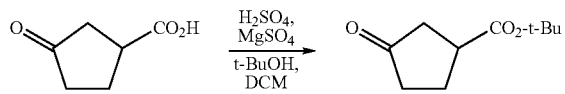

$H_2SO_4$ (conc., 15.3 g, 8.30 mL, 156 mmol) was added dropwise to a vigorously stirred suspension of $MgSO_4$ (75 g, 620 mmol) in DCM (650 mL). The mixture was stirred for 0.5 h, then known cyclopentanone-3-carboxylate (20.0 g, 156 mmol) was added, followed by t-butanol (58 g, 780 mmol). The reaction vessel was tightly sealed and the mixture was stirred overnight at room temperature. The next morning another 30 mL of t-butanol was added. Again the reaction vessel was tightly sealed, and the reaction mixture was stirred over the weekend. The reaction mixture was then filtered through celite. The filtrate was washed with 2 N NaOH. The aqueous layer was back-washed with DCM. The organic layers were combined, washed with water, then brine, dried over anhydrous $MgSO_4$, filtered, and concentrated to afford 19.9 g (69%) of tert-butyl 3-oxocyclopentanecarboxylate. The reaction progress was monitored by TLC using 50% ethyl acetate/hexane and staining with anisaldehyde stain (SM and product stain purple).

$^1$H NMR (500 MHz, CDCl$_3$): 3.02 (p, J=7.8 Hz, 1H), 2.05-2.50 (m, 6H), 1.45 (s, 9H). $^{13}$C NMR (125 MHz, CDCl$_3$): 217.00, 173.47, 80.99, 41.88, 41.14, 27.94, 26.57.

Step B:

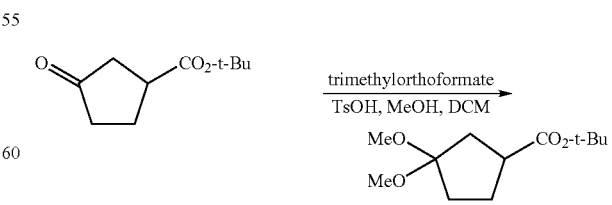

To a solution of tert-butyl 3-oxocyclopentanecarboxylate (19.8 g, 107 mmol) in 1:1 DCM/methanol (150 mL) was added trimethylorthoformate (46.8 mL, 428 mmol), followed by TsOH.H$_2$O (~0.5 g). The reaction mixture was stirred at room temperature for 2 h. Then more TsOH.H$_2$O (~0.25 g) was added and the reaction mixture was stirred overnight. The reaction mixture was concentrated at room temperature and the resulting residue was dissolved in ether and washed with saturated NaHCO$_3$ solution, then with brine. The ethereal layer was dried over anhydrous MgSO$_4$, filtered, and concentrated. Purification by flash chromatography (silica, 15% ethyl acetate/hexane) gave 22.2 g (90%) of tert-butyl 3,3-dimethoxycyclopentanecarboxylate.

$^1$H NMR (500 MHz, CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C:

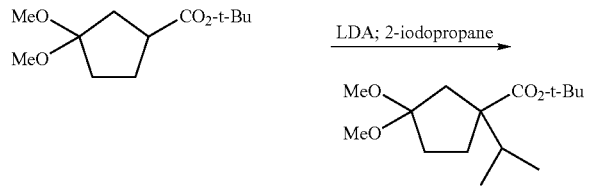

To a cooled (−78° C.) solution of LDA (1.5 M in cyclohexane, 41 mL, 61 mmol) in THF (150 mL) was added dropwise over 10 min tert-butyl 3,3-dimethoxycyclopentanecarboxylate (9.37 g, 40.7 mmol) in 25 mL of THF. The resulting mixture was stirred at −78° C. for 30 min, then was treated dropwise with 2-iodopropane (16.3 mL, 163 mmol). After stirring for an additional 10 min, the reaction mixture was permitted to warm to room temperature. After stirring overnight, the reaction mixture was diluted with ether and washed with brine. The ethereal layer was dried over anhydrous MgSO$_4$, filtered, and concentrated. After storing the crude product under vacuum overnight, it was purified by MPLC (silica, 20% ethyl acetate/hexane) to give 8.32 g of tert-butyl 1-isopropyl-3,3-dimethoxycyclopentanecarboxylate (75%).

$^1$H NMR (500 MHz, CDCl$_3$) δ 3.21 (s, 3H), 3.18 (s, 3H), 2.56 (app d, J=14 Hz, 1H), 2.26 (m, 1H), 1.78-1.89 (m, 3

Step D:

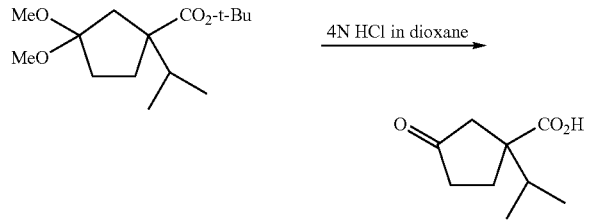

tert-Butyl 1-isopropyl-3,3-dimethoxycyclopentanecarboxylate (8.32 g, 30.5 mmol) was dissolved in 4 N anhydrous HCl in dioxane (50 mL) and water (10 mL) was added. The reaction mixture was stirred at room temperature overnight, then was concentrated. The residue was dissolved in DCM, dried over anhydrous MgSO$_4$, filtered, and concentrated to give 5.44 g of 1-isopropyl-3-oxocyclopentanecarboxylic acid (used without purification).

$^1$H NMR (500 MHz, CDCl$_3$) δ 2.70 (d, J=18.1 Hz, 1H), 2.44-2.39 (m, 1H), 2.30-2.15 (m, 2H), 2.14 (dd, J=18.1, 1.0 Hz, 1H), 2.06 (p, J=6.9 Hz, 1H), 1.98 (m, 1H), 0.98 (dd, J=11.4, 6.9 Hz, 6H).

Step E:

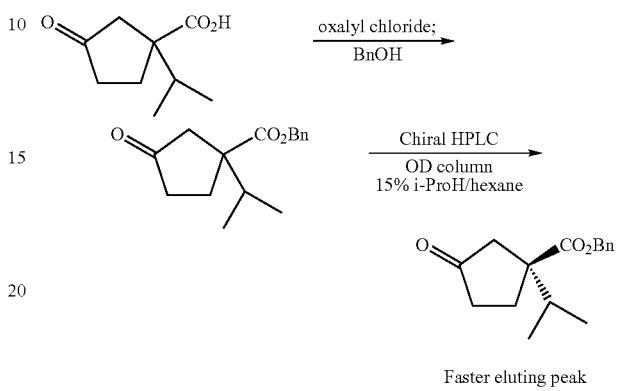

Faster eluting peak

A cooled (0° C.) solution of 1-isopropyl-3-oxocyclopentanecarboxylic acid (5.44 g, 32.0 mmol) in DCM (75 mL) was treated with oxalyl chloride (8.36 mL, 95.9 mmol), followed by 3 drops of DMF. The reaction mixture was permitted to warm to room temperature and stir for 1.75 h. The reaction mixture was then concentrated and stored under vacuum for 30 min. The resulting acid chloride was dissolved in DCM (75 mL), cooled to 0° C., and treated with benzyl alcohol (8.28 mL, 80.0 mmol), followed by triethyl amine (8.92 mL, 64.0 mmol, dropwise). Then approximately 100 mg of DMAP was added and the reaction mixture was warmed to room temperature and stirred for 2 h. The reaction mixture was diluted with DCM and washed with 1 N HCl solution, saturated NaHCO$_3$ solution, and brine. The organic layer was dried over anhydrous MgSO$_4$, filtered, and concentrated. Purification by MPLC (silica, 50% ethyl acetate/hexane) gave 6.11 g (73%) of benzyl 1-isopropyl-3-oxocyclopentanecarboxylate.

$^1$HNMR (CDCl$_3$, 500 MHz): δ 7.36 (m, 5H), 5.17 (d, J=2.5 Hz, 2H), 2.85 (d, J=18.5 Hz, 1H), 2.48 (m, 1H), 2.29 (dd, J=10.0, 3.0 Hz, 1H), 1.98-2.23 (m, 3H), 1.93 (m, 1H), 0.95 (m, 6H). Resolution of the racemic product was accomplished by chiral HPLC using a chiralcel OD column, and eluting with 15% 2-propanol/hexane (100 mg/injection; was accomplished using a programmed Gilson HPLC system). 2.11 g Of the desired faster eluting isomer, benzyl (1S)-1-isopropyl-3-oxocyclopentanecarboxylate, were obtained.

Step F:

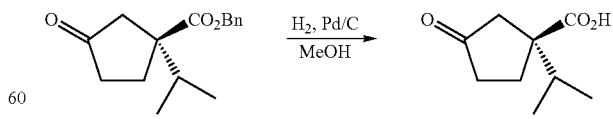

Benzyl (1S)-1-isopropyl-3-oxocyclopentanecarboxylate (1.27 g, 4.88 mmol) was combined with Pd/C (10% Degussa, 500 mg) in 20 mL of methanol and stirred under a hydrogen atmosphere (balloon) for 2 h. The reaction had only proceeded part way (~30% conversion) so the reaction mixture was filtered, another portion of Pd/C (500 mg) was added, and the mixture was stirred under a hydrogen atmosphere for 5 h. Since the reaction had now gone to completion, the reaction mixture was filtered through celite and concentrated to afford 704 mg of (1S)-1-isopropyl-3-oxocyclopentanecarboxylic acid that did not require further purification. Note that the large quantities of catalyst were used because the ester obtained after chiral separation must have been poisoned by an impurity. This was unique to this particular sample. Normally much smaller quantities of catalyst are used. $^1$H NMR was identical to that of the racemic acid above (Step D).

Procedure B:

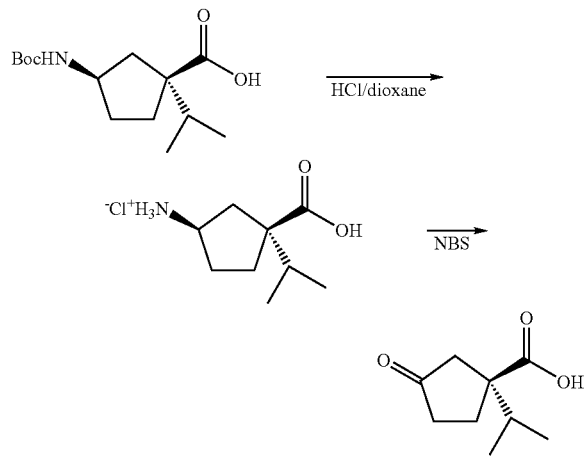

To a solution of (1S,3R)-3-[(tert-butoxycarbonyl)amino]-1-isopropylcyclopentanecarboxylic acid (7.46 g, 27.5 mmol) in dioxane (10 mL) was added 4 N HCl in dioxane (30 mL). The reaction mixture was stirred at room temperature for 2 hours, then concentrated in vacuo to give the corresponding aminoacid salt as a white solid. This solid was then dissolved in $CH_2Cl_2$ (100 mL) and solid $NaHCO_3$ (7.0 g, 82.5 mmol) was added. After cooled to 0° C., a solution of NBS (20.0 g, 110 mmol) in $CH_2Cl_2$ (200 mL) was slowly added to the reaction over 4 hours. After the addition, the reaction was concentrated to dryness in vacuo and then dissolved in ethanol (100 mL). To this ethanol solution was added NaOMe (4.45 g, 82.5 mmol) and the reaction was heated to reflux. After 1 hour at reflux, the reaction was cooled to 0° C. and 2N aqueous $H_2SO_4$ (50 mL) was added. The mixture was stirred at room temperature for 1 hour before concentrating in vacuo to about 60 mL in volume. The remaining mixture was partitioned between water (150 mL) and ethyl acetate (100 mL). The aqueous layer was further extracted with ethyl acetate twice. The organic layers were combined and dried over anhydrous MgSO4, concentrated and purified by flash chromatography (silca, ethyl acetate/hexanes) to give (1S)-1-isopropyl-3-oxocyclopentanecarboxylic acid (3.00 g, 64%).

INTERMEDIATE 30

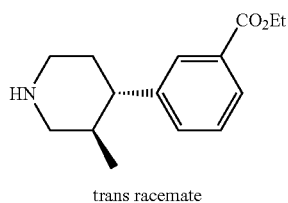

trans racemate

Procedure A

Step A:

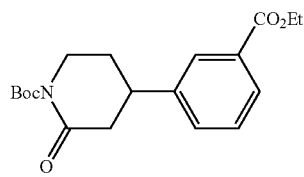

To a stirred solution of tert-butyl 4-[3-(ethoxycarbonyl)phenyl]piperidine-1-carboxylate (48 g, 220 mmol) in chloroform (900 mL) was added ruthenium (IV) oxide hydrate (6.0 g, 45 mmol) followed by a solution of sodium periodate (150 g, 700 mmol) in water (900 mL). The resulting heterogenous reaction mixture was stirred at room temperature for 11 days before being filtered through a short column of celite. The organic layer was removed and the aqueous layer was extracted twice with DCM. The combined organic layers were washed with a 10% solution of sodium thiosulfate in water twice, and once with brine. This solution was dried over $MgSO_4$, filtered, and concentrated under reduced pressure. The product was purified by flash chromatography (silica gel, 20% EA/hexanes) to give 22.5 g (64.8 mmol) of tert-butyl 4-[3-(ethoxycarbonyl)phenyl]-2-oxopiperidine-1-carboxylate (29%).

ESI-MS calculated for C19H25NO5: 347.17; found 370.1 (M+Na).

Step B:

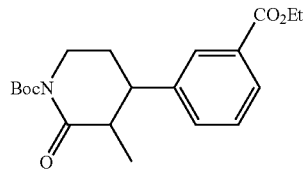

Potassium bis(trimethylsilyl)amide (14 g, 71 mmol) was mixed with 300 mL of THF in a 1000 mL flame-dried round bottomed flask and the resulting mixture was cooled to −78° C. tert-butyl 4-[3-(ethoxycarbonyl)phenyl]-2-oxopiperidine-1-carboxylate (22.5 g, 64.8 mmol) dissolved in 150 mL of THF was added slowly to the mixture, via an addition funnel, and the resulting reaction mixture was stirred at −78° C. for 30 min. Methyl iodide (12.1 mL, 195 mmol) was then added dropwise and the reaction mixture was allowed to stir at −78° C. for 4 h before being allowed to warm to room temperature overnight. The reaction was quenched with saturated ammonium chloride and extracted 3 times with ether. The combined ethereal layers were washed with brine and dried over $MgSO_4$, filtered, and concentrated under reduced pressure. The product was purified by flash chromatography (10-20% EA/hexanes) to give 6.1 g of the trans racemate of tert-butyl 4-[3-(ethoxycarbonyl)phenyl]-3-methyl-2-oxopiperidine-1-carboxylate (26%).

ESI-MS calculated for C20H27NO5: 361.19; found 384.25 (M+Na).

Step C:

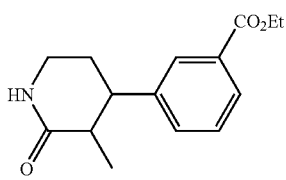

The product from Step B (6.1 g, 17 mmol) was dissolved in 4.0 M HCl in dioxane and stirred at room temperature for 2 h before being concentrated under reduced pressure to give the desired product as an orange solid which was sued directly in the next step without further purification.

ESI-MS calculated for C15H19NO3: 261.14; found 262.1 (M+H).

Step D:

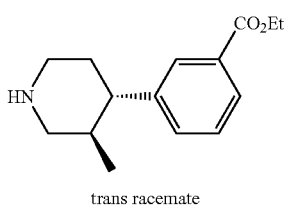

trans racemate

The product from the previous step (entire amount ~17 mmol) was dissolved in THF (100 mL) and treated dropwise with 2.0 M borane-methyl sulfide solution in THF (31 mL, 62 mmol). The resulting solution was stirred at room temperature for 4 h before being stored at 4° C. for 72 h. The solvent was removed under reduced pressure and the resulting residue was dissolved in 0.5 M HCl (aqueous ~38%) in ethanol. This solution was heated to 50° C. and stirred for 4 h. The solvent was removed and the procedure was repeated again to ensure the break up of the borane complex. The solvent was removed and the product was purified by MPLC (0-15% (10% NH4OH/MeOH)/DCM) to give the desired product which was 80% pure. This crude material was dissolved in DCM (100 mL) and treated with di-tert-butyl dicarbonate (2.95 g, 13.5 mmol), diisopropylethylamine (2.30 mL, 13.5 mmol) and DMAP (10 mg). The resulting reaction mixture was stirred overnight at room temperature before being diluted with DCM and washed with 1 N aqueous, aqueous saturated sodium bicarbonate, and brine. The organic layer was dried over MgSO4, filtered and concentrated under reduced pressure. The intermediate was purified by MPLC (0-40% EA/hexanes). The resulting colorless oil was dissolved in 4.0 M HCl in dioxane and the resulting reaction mixture was stirred at room temperature for 1.5 h. The reaction mixture was concentrated to dryness to give 2.13 g (7.52 mmol) of the desired HCl salt. ESI-MS calculated for C15H21NO2: 247.16; found 248.15 (M+H)

Procedure B

Step A:

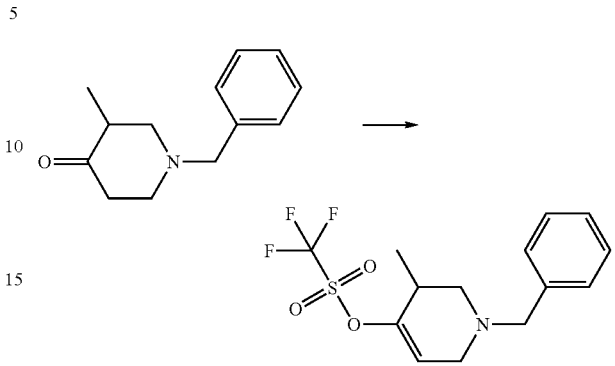

A solution of 1-benzyl-3-methylpiperidin-4-one (48 g, 0.24 mol) in THF (200 mL) was added dropwise to a cooled (−78° C.) solution of sodium bis(trimethylsilyl)amide (2M in THF, 141 mL, 0.28 mol) in THF (100 mL). The resulting dark orange mixture was stirred at −78° C. for 2 hr after which a solution of N-phenyl-bis(trifluoromethanesulfonimide) (100 g, 0.28 mol) in THF (300 mL) was added dropwise. The mixture was allowed to warm to r.t. and stirred for 3 hr. Most of the THF was removed in vacuo. The residue was partitioned between Ether and aqueous 1M NaOH. The organic layer was then washed repeatedly with aqueous 1M NaOH, dried over sodium sulfate, and evaporated to dryness. The dark orange residue was then dissolved in CH2Cl2 and filtered through a silica gel plug eluting with CH2Cl2. The desired 1-benzyl-3-methyl-1,2,3,6-tetrahydropyridin-4-yl trifluoromethanesulfonate (79 g) was obtained as a yellow oil.

Step B:

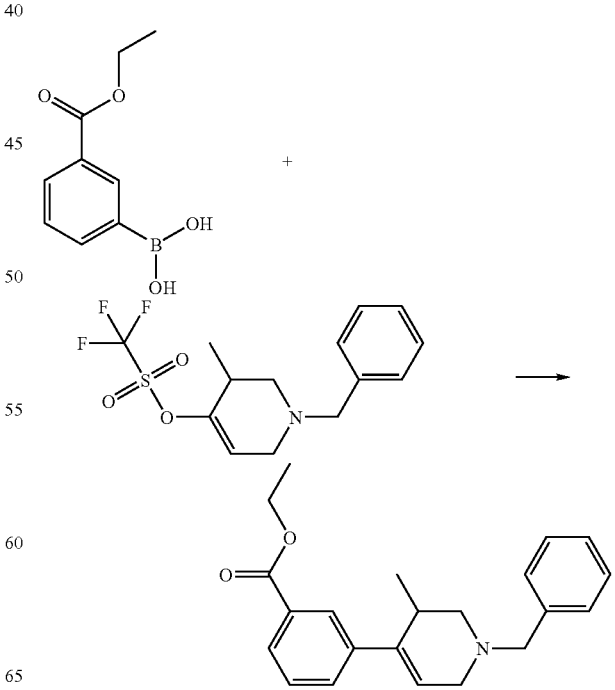

A mixture of 1-benzyl-3-methyl-1,2,3,6-tetrahydropyridin-4-yl trifluoromethanesulfonate (3 g, 9.0 mmol), [3-(ethoxycarbonyl)phenyl]boronic acid (2.26 g, 11.6 mmol), PdCl$_2$(PPh$_3$)$_2$ (315 mg, 0.44 mmol), and potassium carbonate (2.5 g, 18.0 mmol) in Toluene:EtOH (10:1, 50 mL) were heated to 100° C. for 18 hr. The cooled reaction mixture was partitioned between EtOAC and H$_2$O and the aqueous layer was extrated with EtOAc (4×). The organics were combined, dried over sodium sulfate, filtered and evaporated to dryness. The residue was purified by column chromatography on silica gel eluting with a gradient of hexane:EtOAc to yield ethyl 3-(1-benzyl-3-methyl-1,2,3,6-tetrahydropyridin-4-yl)benzoate as a clear oil.

Step C:

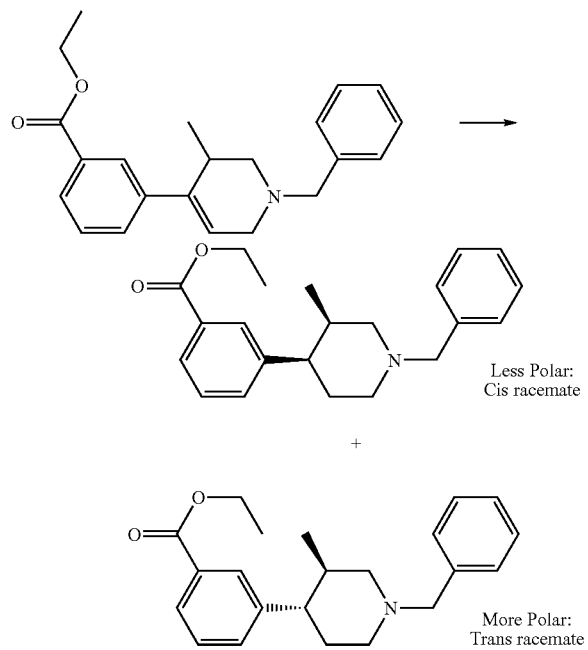

Less Polar: Cis racemate

+

More Polar: Trans racemate

Ethyl 3-(1-benzyl-3-methyl-1,2,3,6-tetrahydropyridin-4-yl)benzoate (32.5 g, 98 mmol) was dissolved in EtOAc (400 mL) and was hydrogenated for 18 hr with a hydrogen balloon in the presence of a catalytic amount (1.1 g) of platinum oxide. Platinum oxide was filtered through a celite plug and the filtrate was evaporated to dryness. The resulting yellow oil was purified by column chromatography on silica gel eluting with a gradient of hexane:EtOAc.

Less polar compound: ethyl 3-[(3R,4R)-1-benzyl-3-methylpiperidin-4-yl]benzoate as a mixture of two diastereomers More polar compound: desired ethyl 3-[(3R,4S)-1-benzyl-3-methylpiperidin-4-yl]benzoate) as a mixture of two diastereomers (9 g, 24%).

Step D:

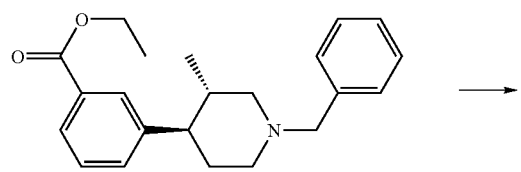

-continued

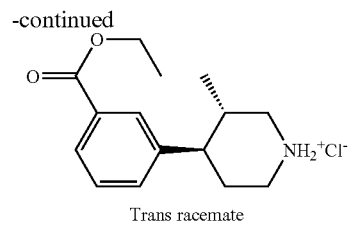

Trans racemate

Ethyl 3-[(3S,4R)-1-benzyl-3-methylpiperidin-4-yl]benzoate (9 g, 26.7 mmol) was dissolved in EtOH: 1M HCl (1:1, 160 mL) and was hydrogenated at 50 psi in the presence of a catalytic amount of palladium on carbon (1 g) for 36 hr. Palladium was filtered through a celite plug and the filtrate was evaporated to dryness to give 7.2 g of ethyl 3-[(3S,4R)-3-methylpiperidin-4-yl]benzoate as an HCl salt.

INTERMEDIATE 31

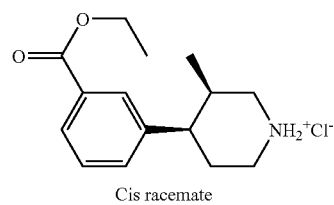

Cis racemate

Ethyl 3-[(3R,4R)-3-methylpiperidin-4-yl]benzoate was synthesized as described for INTERMEDIATE 30 (procedure B, step D) using ethyl 3-[(3R,4R)-1-benzyl-3-methylpiperidin-4-yl]benzoate as starting material.

INTERMEDIATE 32

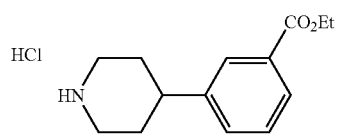

Step A:

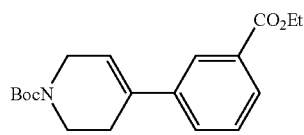

To a mixture of tert-butyl 4-{[(trifluoromethyl)sulfonyl]oxy}-3,6-dihydropyridine-1(2H)-carboxylate (prepared according to Wustrow, D. J., Wise, L. D., *Synthesis*, (1991), 993-995.; 10.5 g, 31.6 mmol), 3-(ethoxycarbonyl)phenylboronic acid (8.59 g, 44.3 mmol), lithium chloride (3.98 g, 94.8 mmol), and 2 M Na$_2$CO$_3$ solution (44 mL) in DME (107 mL) was added Pd(PPh$_3$)$_4$ (1.82 g, 1.58 mmol), and the resulting mixture was stirred at reflux under a nitrogen atmosphere for 3.5 h. The reaction mixture was cooled to rt, stirred overnight, then partially concentrated to remove most of the DME. To the remaining aqueous mixture was added DCM, 2M $Na_2CO_3$ solution, and ~10mL of 28% $NH_4OH$ solution. The layers were separated and the organic layer was washed with brine, dried over anhydrous $MgSO_4$, filtered, and concentrated. Purification by flash chromatography (silica, 10% ethyl acetate/hexanes eluent) afforded tert-butyl 4-[3-(ethoxycarbonyl)phenyl]-3,6-dihydropyridine-1(2H)-carboxylate. $^1$HNMR ($CDCl_3$, 500 MHz): δ 8.07 (s, 1H), 7.95 (d, J=7.5 Hz, 1H), 7.58 (d, J=8.0 Hz, 1H), 7.43 (t, J=8.0 Hz, 1H), 6.13 (br s, 1H), 4.41 (q, J=7.0 Hz, 2H), 4.12 (br s, 2H), 3.68 (t, J=5.5 Hz, 2H), 2.58 (br s, 2H), 1.52 (s, 9H), 1.43 (t, J=7.0 Hz, 3H).

Step B:

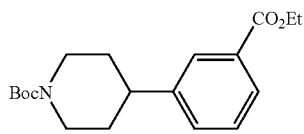

A mixture of tert-butyl 4-[3-(ethoxycarbonyl)phenyl]-3,6-dihydropyridine-1(2H)-carboxylate (6.48 g, 19.6 mmol) and $Pd(OH)_2/C$ (20% Pd, 1 g) in 50 mL of methanol was stirred under a hydrogen atmosphere (balloon) for 18 h. The reaction mixture was then filtered through a celite plug, and the filtrate was concentrated to give tert-butyl 4-[3-(ethoxycarbonyl)phenyl]piperidine-1-carboxylate which did not require further purification. $^1$HNMR ($CDCl_3$, 500 MHz): δ 7.91 (m, 2H), 7.40 (m, 2H), 4.40 (q, J=7.0 Hz, 2H), 4.28 (br s, 2H), 2.83 (m, 2H), 2.73 (tt, J=12.5, 4.0 Hz, 1H), 1.85 (br d, J=13.0 Hz), 1.67 (dq, J=4.0, 12.5 Hz, 2H), 1.51 (s, 9H), 1.42 (t, J=7.0 Hz).

Step C:

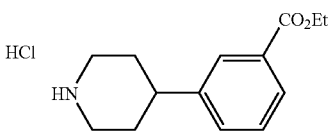

tert-Butyl 4-[3-(ethoxycarbonyl)phenyl]piperidine-1-carboxylate (3.24 g, 9.72 mmol) was dissolved in anhydrous 4N HCl in dioxane (ca. 30 mL) and stirred at rt for 1.5 h. The reaction mixture was concentrated to give ethyl 3-piperidin-4-ylbenzoate hydrochloride as a pale yellow solid that required no further purification.

ESI-MS calc. for C14H19NO2: 233; Found: 234 (M+H).

INTERMEDIATE 33

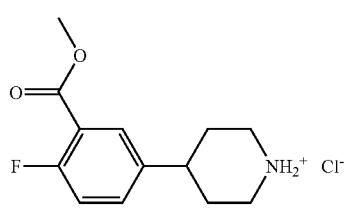

Step A:

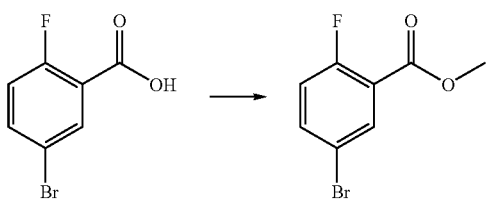

A mixture of 5-bromo-2-fluorobenzoic acid (25 g, 0.11 mol), methyl iodide (8.5 mL, 0.14 mol), and potassium carbonate (31 g, 0.23 mol) in DMF (200 mL) was heated to 50° C. for 18 hr. The cooled reaction mixture was diluted with EtOAc (200 mL) and the organic phase was washed with a saturated aqueous NaCl solution (4×). The organic phase was then dried over sodium sulfate and evaporated to dryness to give 24 g of methyl 5-bromo-2-fluorobenzoate as a yellow oil.

Step B:

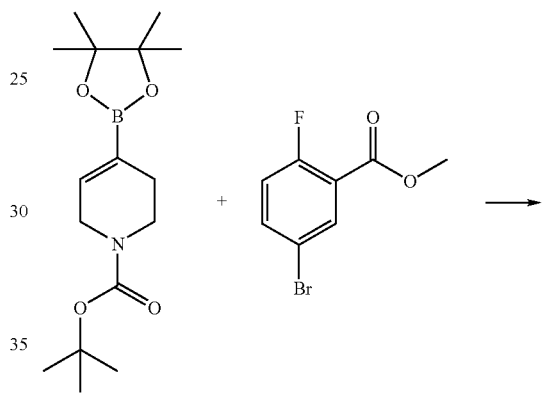

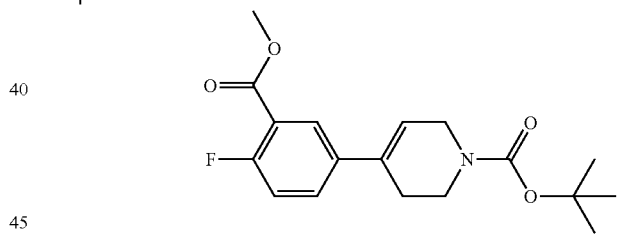

tert-Butyl 4-[4-fluoro-3-(methoxycarbonyl)phenyl]-3,6-dihydropyridine-1(2H)-carboxylate was synthesized as described for INTERMEDIATE 32 using tert-butyl 4-(4,4,5,5-tetramethyl-1,3,2-dioxaborolan-2-yl)-3,6-dihydropyridine-1(2H)-carboxylate (prepared according to Eastwood, P. R. Tetrahedron Lett., 41, 19, 2000, 3705-3708) and methyl 5-bromo-2-fluorobenzoate as starting material and $PdCl_2dppf.CH_2Cl_2$ as a catalyst.

Step C:

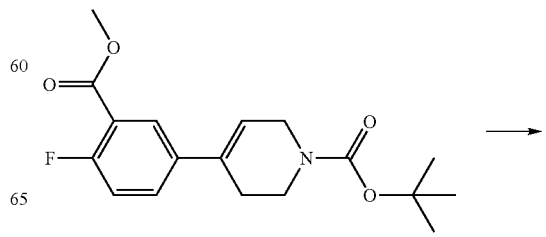

-continued

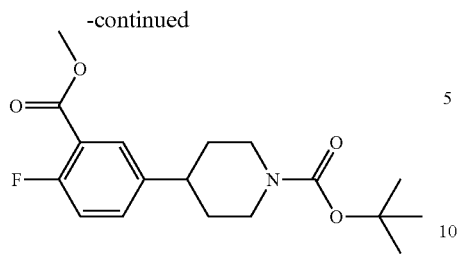

tert-Butyl 4-[4-fluoro-3-(methoxycarbonyl)phenyl]piperidine-1-carboxylate was synthesized as described for INTERMEDIATE 30 (procedure B, step C) using tert-butyl 4-[4-fluoro-3-(methoxycarbonyl)phenyl]-3,6-dihydropyridine-1(2H)-carboxylate as starting material.

Step D:

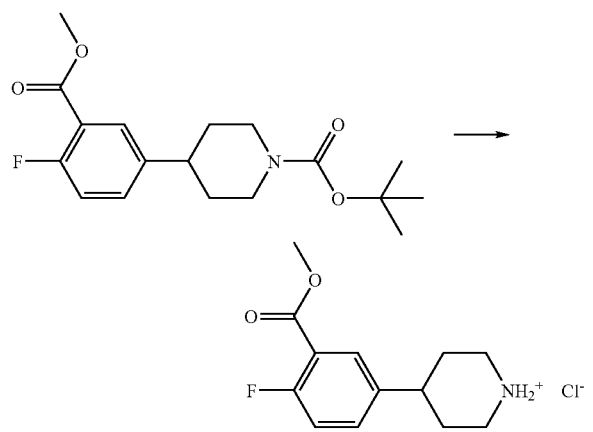

tert-Butyl 4-[4-fluoro-3-(methoxycarbonyl)phenyl]piperidine-1-carboxylate (471 mg, 1.40 mmol) was dissolved in anhydrous 4N HCl in dioxane (5mL) and stirred at r.t. for 40 min. The white solid was filtered and washed with $Et_2O$ to afford methyl 2-fluoro-5-piperidin-4-ylbenzoate.

INTERMEDIATE 34

Methyl 3-fluoro-5-piperidin-4-ylbenzoate.HCl was synthesized as described for INTERMEDIATE 33 using 3-bromo-5-fluorobenzoic acid as starting material.

INTERMEDIATE 35

Methyl 2-methyl-3-piperidin-4-ylbenzoate.HCl was synthesized as described for INTERMEDIATE 33 using 3-bromo-2-methylbenzoic acid as starting material.

INTERMEDIATE 36

Methyl 2-methoxy-5-piperidin-4-ylbenzoate.HCl was synthesized as described for INTERMEDIATE 33 using 3-bromo-6-methoxybenzoic acid as starting material.

INTERMEDIATE 37

Methyl 4-fluoro-3-piperidin-4-ylbenzoate.HCl was synthesized as described for INTERMEDIATE 33 using 3-bromo-4-fluorobenzoic acid as starting material.

INTERMEDIATE 38

Methyl (3-piperidin-4-ylphenyl)acetate HCl was synthesized as described for INTERMEDIATE 33 using (3-bromophenyl)acetic acid as starting material.

INTERMEDIATE 39

A mixture of methyl 5-bromo-2-fluorobenzoate (6.5 g, 27.9 mmol), 4,4,4',4',5,5,5',5'-octamethyl-2,2'-bi-1,3,2-dioxaborolane (8.5 g, 33.5 mmol), $PdCl_2dppf\cdot CH_2Cl_2$ (1.1 g, 1.4 mmol), dppf (0.77 g, 1.4 mol), and KOAc (5.4 g, 55.8 mmol) in DMF (100 mL) was heated to 90° C. for 18 hr. The cooled reaction mixture was diluted with EtOAc (200 mL) and the organic phase was washed with a saturated aqueous NaCl solution (4×). The organic phase was then dried over sodium sulfate and evaporated to dryness. The dark residue was dissolved in CH₂Cl₂, filtered through a silica gel plug, and washed with CH₂Cl₂ (500 mL). The filtrate was evaporated to dryness and the residue was purified by column chromatography on silica gel eluting with a gradient of EtOAc and hexane to afford methyl 2-fluoro-5-(4,4,5,5-tetramethyl-1,3,2-dioxaborolan-2-yl)benzoate (5 g) as a green solid.

INTERMEDIATE 40

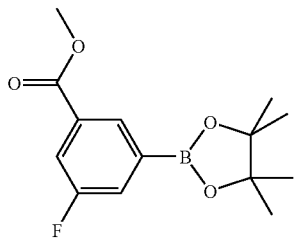

Methyl 3-fluoro-5-(4,4,5,5-tetramethyl-1,3,2-dioxaborolan-2-yl)benzoate was synthesized as described for INTERMEDIATE 39 using 3-bromo-5-fluorobenzoic acid as starting material.

INTERMEDIATE 41

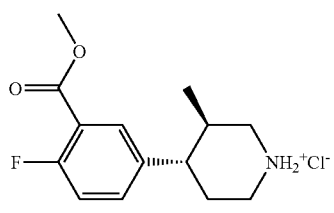

Trans racemate

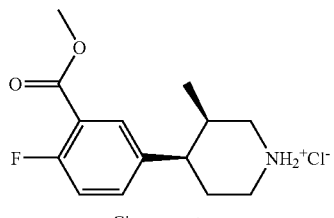

Cis racemate

The HCl salt of methyl 2-fluoro-5-[(3R,4S)-3-methylpiperidin-4-yl]benzoate was synthesized as described for INTERMEDIATE 30 (procedure B) using methyl 2-fluoro-5-(4,4,5,5-tetramethyl-1,3,2-dioxaborolan-2-yl)benzoate as starting material.

INTERMEDIATE 42

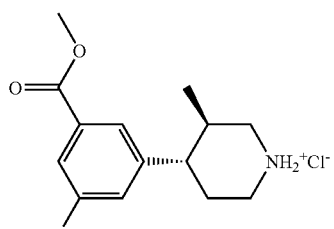

Trans racemate

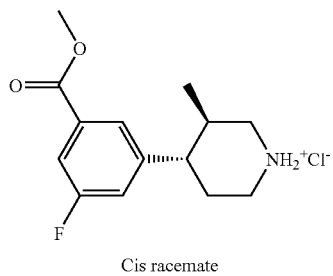

Cis racemate

The HCl salt of methyl 3-fluoro-5-[(3R,4S)-3-methylpiperidin-4-yl]benzoate was synthesized as described for INTERMEDIATE 30 (procedure B) using methyl 3-fluoro-5-(4,4,5,5-tetramethyl-1,3,2-dioxaborolan-2-yl)benzoate as starting material.

INTERMEDIATE 43

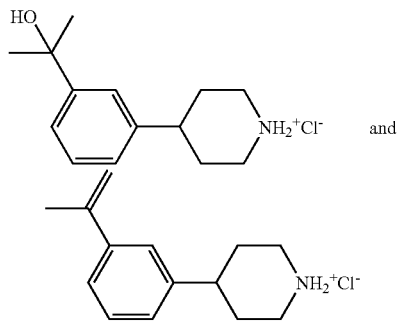

Step A:

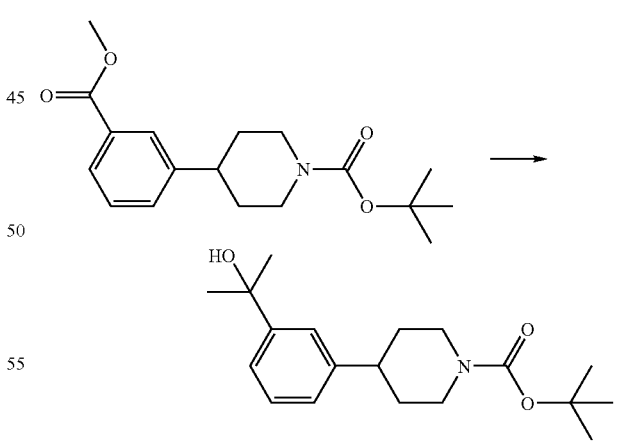

Methyl magnesium bromide (1.4M in toluene/THF, 8 mL, 11 mmol) was added to tert-butyl 4-[3-(methoxycarbonyl)phenyl]piperidine-1-carboxylate (710 mg, 2.22 mmol) in THF (8 mL). The resulting mixture was stirred at r.t. for 18 hr. The reaction mixture was quenched with H₂O and the aqueous was extracted with EtOAc (3×). The organics were combined, dried over sodium sulfate, filtered, and evaporated to dryness to yield tert-butyl 4-[3-(1-hydroxy-1-methylethyl) phenyl]piperidine-1-carboxylate as a clear oil.

Step B:

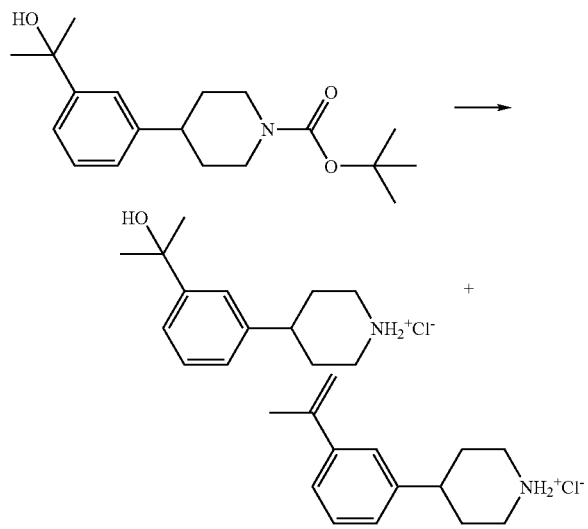

2-(3-Piperidin-4-ylphenyl)propan-2-ol.HCl and 4-(3-isopropenylphenyl)piperidine.HCl were obtained as a mixture following the procedure for INTERMEDIATE 35 (step D).

INTERMEDIATE 44

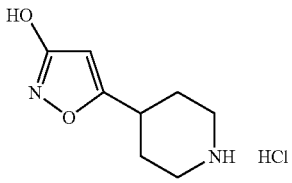

Step A:

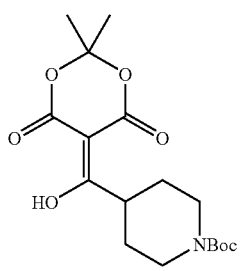

A cooled (0° C.) solution of Boc-isonipecotic acid (5.97 g, 26.0 mmol) and Meldrum's acid (3.75 g, 26.0 mmol) in DMF (54 mL) was treated dropwise with diethyl cyanophosphonate (4.34 mL, 28.6 mmol) and triethylamine (11.2 mL, 80.7 mmol). After stirring at 0° C. for an additional 30 min the reaction mixture was permitted to warm to rt and stir over 3 days. The reaction mixture was concentrated under reduced pressure and ether and 1N HCl solution were added. The aqueous layer was extracted again with ether and the ethereal layers were combined and washed with 1N HCl solution, twice with water, and lastly with brine. He ethereal layer was then dried over anhydrous MgSO$_4$, filtered, and concentrated to give tert-butyl 4-[(2,2-dimethyl-4,6-dioxo-1,3-dioxan-5-ylidene)(hydroxy)methyl]piperidine-1-carboxylate which contained approximately 10% of Boc-isonipecotic acid.

$^1$H NMR (500 MHz, CDCl$_3$) δ 4.24 (br m, 2H), 3.97 (tt, J=12, 3.5 Hz, 1H), 2.84 (br m, 2H), 1.83 (m, 2H), 1.76 (s, 6H), 1.69-1.75 (m, 2H), 1.48 (s, 9H).

Step B:

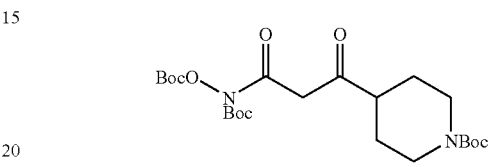

A solution of tert-butyl 4-[(2,2-dimethyl-4,6-dioxo-1,3-dioxan-5-ylidene)(hydroxy)methyl]piperidine-1-carboxylate (8.99 g, 25.3 mmol) and t-butyl N-(t-butoxycarbonyloxy) carbamate (5.90 g, 25.3 mmol) in toluene (200 mL) was stirred at 65° C. for 14 h, then at rt for 36 h. The reaction mixture was concentrated and the residue was purified by flash chromatography (silica, 25% ethyl acetate/hexanes) to afford tert-butyl 4-(3-{(tert-butoxycarbonyl)[(tert-butoxycarbonyl)oxy]amino}-3-oxopropanoyl)piperidine-1-carboxylate. H NMR analysis was consistent with product but complex due to carbamate rotamers.

Step C:

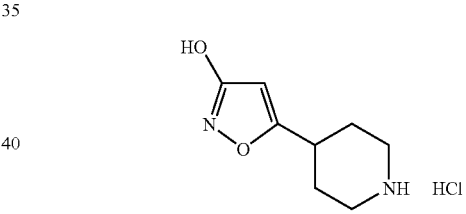

A solution of tert-butyl 4-(3-{(tert-butoxycarbonyl)[(tert-butoxycarbonyl)oxy]amino}-3-oxopropanoyl)piperidine-1-carboxylate (6.2 g, 12.7 mmol) in 100 mL of methanol was treated with 4N HCl solution (150 mL) and the resulting suspension was stirred overnight at rt. In the morning the reaction mixture had become clear. The reaction mixture was concentrated. Since the crude product could not be easily purified it was used as is in the subsequent step. ESI-MS calc. for C8H12N2O2: 168; Found: 169 (M+).

EXAMPLE 1

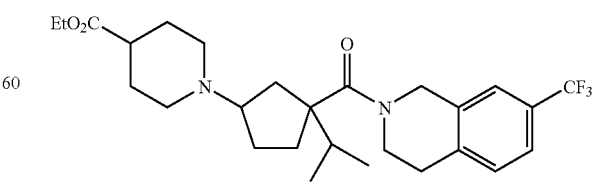

To a solution of Intermediate 3 (150 mg, 0.425 mmol), 4-carbethoxypiperidine (125 mg, 0.425 mmol), and DCM (25 mL) was added molecular sieves (4 Å) and NaBH(OAc)$_3$ (450 mg, 2.12 mmol). The reaction mixture was stirred at room temperature for 18 h before being filtered through celite, diluted with saturated NaHCO$_3$, and extracted with DCM (3×). The combined organic layers were dried over Na$_2$SO$_4$ and purified by preparative TLC (3/96.7/0.3, MeOH/DCM/ NH$_4$OH) to yield Example 1 (220 mg, 97.8%). LC-MS for C$_{27}$H$_{38}$F$_3$N$_2$O$_3$ [M$^+$H$^+$] calculated 495.28, found 495.25. A number of compounds were prepared as detailed in Example 1 using various amines. These compounds are summarized in the table below.

TABLE 1

(EXAMPLES 2 to 6)

| Example | R | Molecular Formula | Calculated [M$^+$H$^+$] | Found [M$^+$H$^+$] |
|---|---|---|---|---|
| 2 | MeO$_2$C-(4-piperidinylmethyl) | C$_{27}$H$_{38}$F$_3$N$_2$O$_3$ | 495.28 | 495.15 |
| 3 | EtO$_2$C-(3-piperidinyl) | C$_{27}$H$_{38}$F$_3$N$_2$O$_3$ | 485.28 | 495.15 |
| 4 | EtO$_2$C-(3-piperidinylmethyl) | C$_{28}$H$_{40}$F$_3$N$_2$O$_3$ | 509.29 | 509.35 |
| 5 | MeO$_2$C-(3-pyrrolidinyl) | C$_{25}$H$_{34}$F$_3$N$_2$O$_3$ | 467.24 | 467.1 |
| 6 | MeO$_2$C-(3-pyrrolidinylmethyl) | C$_{26}$H$_{36}$F$_3$N$_2$O$_3$ | 481.26 | 481.2 |

EXAMPLE 7

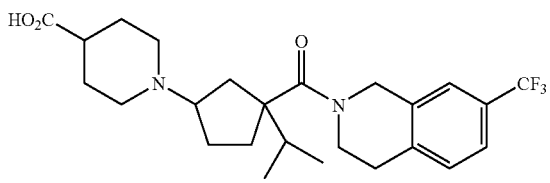

A mixture of the product from Example 1 (185 mg, 0.349 mmol), 5 N NaOH (200 μL, 1.04 mmol), and MeOH (5 mL) was heated at 60° C. for 3 hours before adding a solution of 4N HCl in dioxane to neutralize the base. The reaction solution was concentrated and purified by reverse phase HPLC to yield Example 7 (115 mg, 65.7%). LC-MS for C$_{25}$H$_{34}$F$_3$N$_2$O$_3$ [M$^+$H$^+$] calculated 467.24, found 467.35.

Examples 8-12 were prepared as detailed in Example 7 using Examples 2-6 as starting materials. These compounds are summarized in the table below.

TABLE 2

(EXAMPLES 8 to 12)

| Example | R | Molecular Formula | Calculated [M$^+$H$^+$] | Found [M$^+$H$^+$] |
|---|---|---|---|---|
| 8 | HO$_2$C-(4-piperidinylmethyl) | C$_{26}$H$_{36}$F$_3$N$_2$O$_3$ | 481.26 | 481.3 |
| 9 | HO$_2$C-(3-piperidinyl) | C$_{25}$H$_{34}$F$_3$N$_2$O$_3$ | 467.24 | 467.3 |
| 10 | HO$_2$C-(3-piperidinylmethyl) | C$_{26}$H$_{36}$F$_3$N$_2$O$_3$ | 481.26 | 481.3 |
| 11 | HO$_2$C-(3-pyrrolidinyl) | C$_{24}$H$_{32}$F$_3$N$_2$O$_3$ | 453.23 | 453.25 |
| 12 | HO$_2$C-(3-pyrrolidinylmethyl) | C$_{25}$H$_{33}$F$_3$N$_2$O$_3$ | 467.24 | 467.25 |

EXAMPLE 13

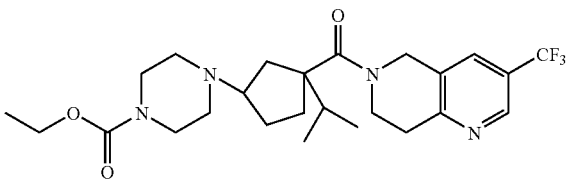

To a solution of Intermediate 4 (50 mg, 0.14 mmol) in methylene chloride (20 mL) was added 1-ethoxycarbonylpiperazine (23 mg, 0.14 mmol). After adding powdered 4 Å molecular sieves (25 mg), sodium triacetoxyborohydride (180 mg, 0.84 mmol) was added and the reaction mixture was stirred overnight. The mixture was diluted with methylene chloride, washed with aqueous saturated sodium bicarbonate, dried under sodium sulfate and concentrated in vacuo. The crude product was purified by preparative TLC (7/92.31.7, methanol/methylene chloride/ammonium hydroxide) to yield Example 13 as a mixture of 4 diastereomers (55 mg, 79%). LC-MS: MW calculated 496.27, found 497.3.

A number of compounds were prepared as detailed in Example 13 using various piperazines instead of 1-ethoxycarbonylpiperazine. These compounds, prepared as mixtures of 4 diastereomers each, are summarized in the table below.

TABLE 3

(EXAMPLES 14 to 16)

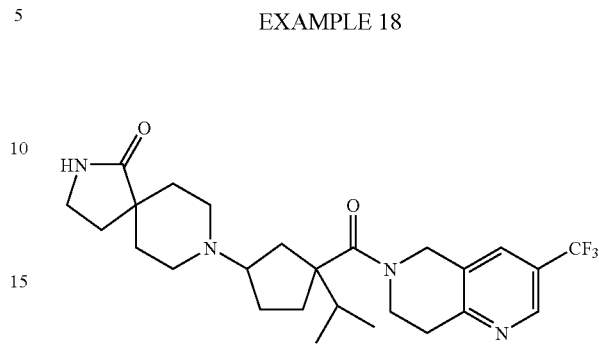

| Example | R | Molecular Formula | Calculated [M+H+] | Found [M+H+] |
|---|---|---|---|---|
| 14 | phenylpiperazinyl | C28H36F3N4O | 501.28 | 501.25 |
| 15 | o-tolylpiperazinyl | C29H37F3N4O | 515.29 | 515.3 |
| 16 | benzoylpiperazinyl | C29H35F3N4O | 528.27 | 529.25 |

EXAMPLE 17

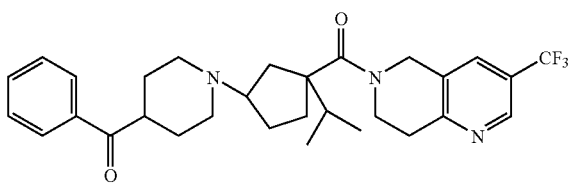

To a solution of Intermediate 4 (50 mg, 0.14 mmol) in methylene chloride (20 mL) was added 4-benzoylpiperidine hydrochloride (32 mg, 0.14 mmol) and N,N-diisopropylethylamine (73 μL, 0.42 mmol). After adding 4 Å powdered molecular sieves (25 mg), sodium triacetoxyborohydride (180 mg, 0.84 mmol) was added and the reaction mixture was stirred overnight. The mixture was extracted with methylene chloride, washed with sodium bicarbonate, dried under sodium sulfate and concentrated in vacuo. The crude product was purified by preparative TLC (7/92.3/0.7, methanol/methylene chloride/ammonium hydroxide) to yield Example 17 (30 mg, 43%) as a mixture of 4 diastereomers.

ESI-MS: calculated MW: 527.28, found 528.25.

EXAMPLE 18

A mixture of the Intermediate 4 (176 mg, 0.5 mmol), the spiropiperidine (as HCl salt, 115 mg, 0.6 mmol), DIEA (100 mg, 0.8 mmol), molecular sieves (4 Å, 200 mg) and sodium triacetoxyborohydride (212 mg, 1.0 mmol) in dichloromethane (10 mL) was stirred overnight. The reaction was quenched with sat. aq. sodium carbonate. The solid was removed by filtration through celite. The crude product was extracted into dichloromethane and purified on preparative TLC (1000 micron, 10%[aq. NH4OH/MeOH 1/9]/DCM). The title compound was obtained as a mixture of cis and trans racemic isomers (155 mg, 63%). LC-MS calc. for C26H35F3N4O2: 492; Found: 493 (M+H).

C. ZHOU

EXAMPLE 19

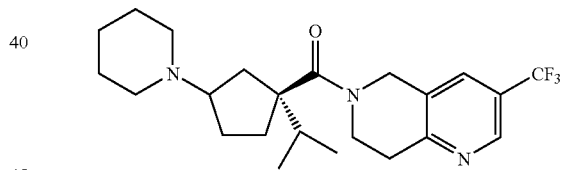

To a stirred solution of Intermediate 5 (50 mg, 0.14 mmol) and piperidine (28 μL, 0.28 mmol), in DCM (10 mL), was added 4 Å powdered molecular sieves (50 mg) and sodium triacetoxyborohydride (150 mg, 0.71 mmol). The resulting solution was allowed to stir at room temperature for 3 days before being filtered through celite and washed with saturated aqueous sodium bicarbonate and brine. The organic layer was dried over Na2SO4, filtered, and concentrated under reduced pressure to give a crude oil that was purified by preparative TLC (0.5% NH4OH/4.5% MeOH/95% DCM) to give 16 mg of a colorless solid as a mixture of 2 diastereomers. A small portion of this free base was converted to its hydrochloride salt by the addition of 2 N HCl in ethyl ether. ESI-MS calc. for C23H32F3N3O: 423.25; found 424 (M+H).

Several other examples were made according to the procedure described in Example 19 except that various substituted piperidines where used as the amine component in place of piperidine. The examples are compiled in Table 4.

TABLE 4
(EXAMPLES 20 to 28)
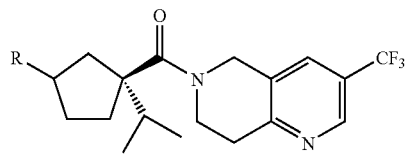
| Example | Structure | Molecular Formula | Calculated MW | Found MW [M + H] |
|---|---|---|---|---|
| 20 | HN-CH₃, C(=O), piperidine (4-position) | C25H35F3N4O2 | 480.27 | 481 |
| 21 | ethyl ester, piperidine (4-position) | C26H36F3N3O3 | 495.27 | 496 |
| 22 | ethyl ester, piperidine (3-position) | C26H36F3N3O3 | 495.27 | 496 |
| 23 | 4-methylpiperidine | C24H34F3N3O | 437.27 | 438 |
| 24 | 3-methylpiperidine | C24H34F3N3O | 437.27 | 438 |
| 25 | 3,5-dimethylpiperidine | C25H36F3N3O | 451.28 | 452 |
| 26 | 3-hydroxypiperidine | C23H32F3N3O2 | 439.24 | 440 |
| 27 | 4-hydroxypiperidine | C23H32F3N3O2 | 439.24 | 440 |
| 28 | azabicyclic | C24H32F3N3O | 435.25 | 436 |

EXAMPLE 29 AND EXAMPLE 30

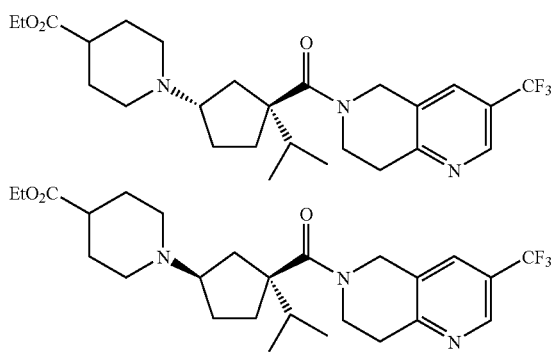

The free base of the product prepared in Example 22 (55 mg) was resolved into its individual diastereomers using an HPLC equipped with a ChiralCel OD column, eluting with 25% ethanol/hexanes. Each compound was converted to its hydrochloride salt by the addition of 2 N HCl in ethyl ether. 27 mg of the faster eluting diastereomer (Example 29) and 20 mg of the slower eluting diastereomer (Example 30) were recovered.

Example 29: ESI-MS calc. for $C_{26}H_{36}F_3N_3O_3$: 495.27; found 496 (M+H).

Example 30: ESI-MS calc. for $C_{26}H_{36}F_3N_3O_3$: 495.27; found 496 (M+H).

EXAMPLE 31

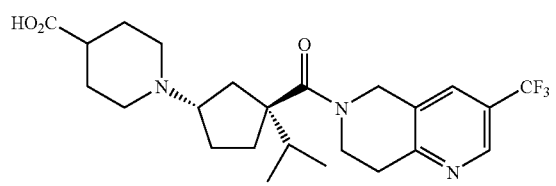

EXAMPLE 29 (10 mg, 0.018 mmol), was dissolved in a mixture of methanol (1 mL) and THF (1 mL), and treated with a solution of lithium hydroxide monohydrate (5 mg, 0.12 mmol) in water (1 mL). The resulting solution was stirred for 18 h at room temperature before being concentrated under reduced pressure. The product was purified by reverse phase HPLC (C18, 20-100% MeCN/H$_2$O) and converted to its hydrochloride salt by addition of 2 N HCl in ethyl ether to give 6.8 mg of product (70%).

ESI-MS calc. for $C_{24}H_{32}F_3N_3O_3$: 467.24; found 468 (M+H).

EXAMPLE 32

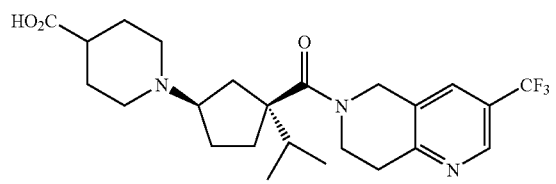

EXAMPLE 30 (10 mg, 0.018 mmol), was dissolved in a mixture of methanol (1 mL) and THF (1 mL), and treated with a solution of lithium hydroxide monohydrate (5 mg, 0.12 mmol) in water (1 mL). The resulting solution was stirred for 18 h at room temperature before being concentrated under reduced pressure. The product was purified by reverse phase HPLC (C18, 20-100% MeCN/H$_2$O) and converted to its hydrochloride salt by addition of 2 N HCl in ethyl ether to give 3.8 mg of product (39%).

ESI-MS calc. for $C_{24}H_{32}F_3N_3O_3$: 467.24; found 468 (M+H).

EXAMPLE 33

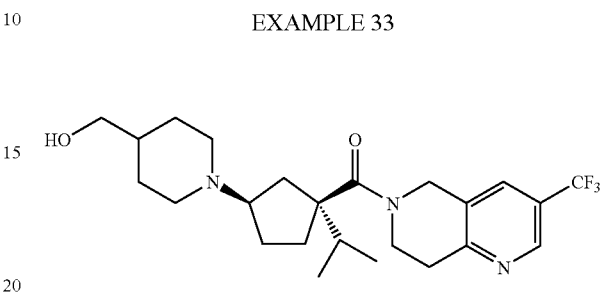

To a solution of Example 30 (15 mg, 0.026 mmol), in THF (2 mL) was added lithium triethylborohydride (1.0 M solution in THF, 150 µL, 0.15 mmol). After 18 h at room temperature an additional portion of lithium triethylborohydride (100 µL) was added and the resulting mixture was stirred for 24 h before being concentrated under reduced pressure. The resulting residue was dissolved in DCM and washed with aqueous saturated sodium bicarbonate, 1 N aqueous HCl, and then brine. The organic layer was dried over Na2SO4, filtered, treated with 2 N HCl in ether followed by hexanes and concentrated under reduced pressure to give 1.5 mg of the desired product as a hydrochloride salt (11%). ESI-MS calc. for $C_{24}H_{34}F_3N_3O_2$: 453.26; found 454 (M+H).

EXAMPLE 34 AND EXAMPLE 35

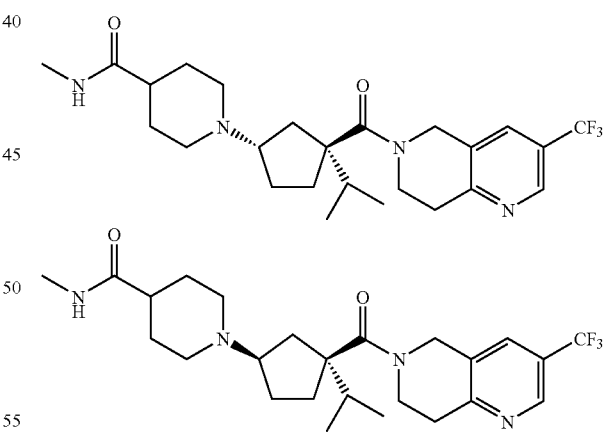

The free base of the product prepared in Example 20 (60 mg) was resolved into its individual diastereomers using an HPLC equipped with a ChiralCel OD column, eluting with 25% ethanol/hexanes. Each compound was converted to its hydrochloride salt by the addition of 2 N HCl in ethyl ether. 26 mg of the faster eluting diastereomer (Example 34) and 17 mg of the slower eluting diastereomer (Example 35) were recovered.

Example 34: ESI-MS calc. for $C_{25}H_{35}F_3N_4O_2$: 480.27; found 481 (M+H).

Example 35: ESI-MS calc. for C25H35F3N4O2: 480.27; found 481 (M+H).

EXAMPLE 36 AND EXAMPLE 37

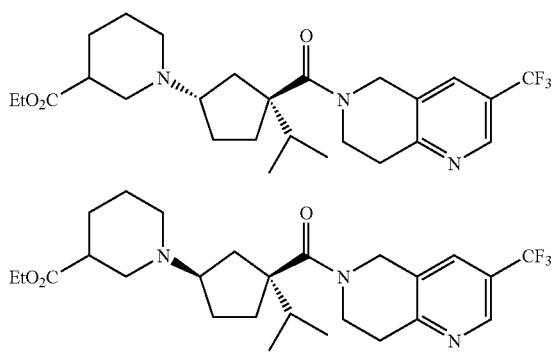

The free base of the product prepared in Example 22 (54 mg) was resolved into 2 mixtures of 2 diastereomers using an HPLC equipped with a ChiralCel OD column, eluting with 13% ethanol/hexanes. Each compound was converted to its hydrochloride salt by the addition of 2 N HCl in ethyl ether. 33 mg of the faster eluting diastereomers (Example 36) and 10 mg of the slower eluting diastereomers (Example 37) were recovered.

Example 36: ESI-MS calc. for C26H36F3N3O3: 495.27; found 496 (M+H).

Example 37: ESI-MS calc. for C26H36F3N3O3: 495.27; found 496 (M+H).

EXAMPLES 38-41

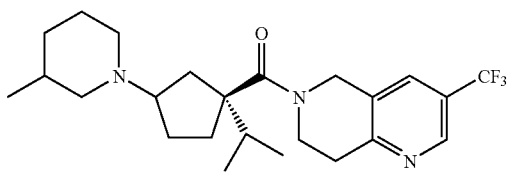

The free base of the product prepared in Example 24 (40 mg) was resolved into its individual diastereomers using an HPLC equipped with a ChiralCel OD column, eluting with 20% ethanol/hexanes. Each compound was converted to its hydrochloride salt by the addition of 2 N HCl in ethyl ether. 15 mg of the fastest eluting diastereomer (Example 38), 1.5 mg of diastereomer 2 (Example 39), 7 mg of diastereomer 3 (Example 40), and 6 mg of the slowest eluting diastereomer (Example 41) were recovered.

Example 38: ESI-MS calc. for C24H34F3N3O: 437.27; found 438 (M+H).

Example 39: ESI-MS calc. for C24H34F3N3O: 437.27; found 438 (M+H).

Example 40: ESI-MS calc. for C24H34F3N3O: 437.27; found 438 (M+H).

Example 41: ESI-MS calc. for C24H34F3N3O: 437.27; found 438 (M+H).

EXAMPLES 42-46

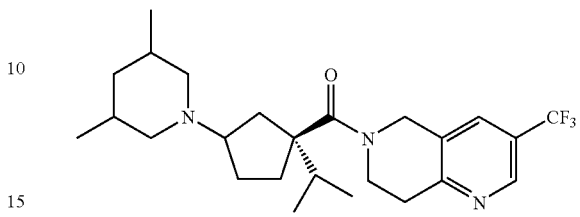

The free base of the product prepared in Example 25 (40 mg) was resolved into its individual diastereomers using an HPLC equipped with a ChiralCel OD column, eluting with 20% ethanol/hexanes. Each compound was converted to its hydrochloride salt by the addition of 2 N HCl in ethyl ether. All 6 diastereomers were resolved, but peaks 2 and 6 were combined in overlapping runs to give 4 pure diatereomers and one mixture of 2.

Example 42: Peak 1: ESI-MS calc. for C25H36F3N3O: 451.28; found 452 (M+H).

Example 43: Peak 2/6: ESI-MS calc. for C25H36F3N3O: 451.28; found 452 (M+H).

Example 44: Peak 3: ESI-MS calc. for C25H36F3N3O: 451.28; found 452 (M+H).

Example 45: Peak 4: ESI-MS calc. for C25H36F3N3O: 451.28; found 452 (M+H).

Example 46: Peak 5: ESI-MS calc. for C25H36F3N3O: 451.28; found 452 (M+H).

EXAMPLE 47 AND EXAMPLE 48

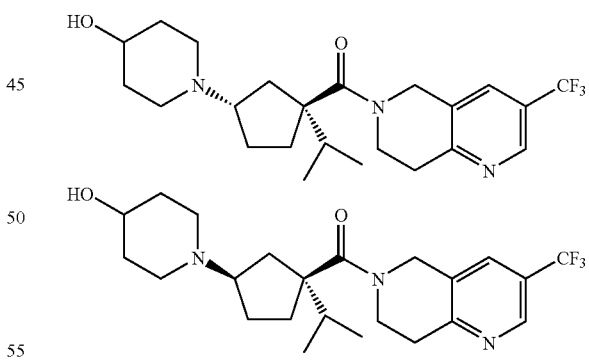

The free base of the product prepared in Example 27 (20 mg) was resolved into its individual diastereomers using an HPLC equipped with a ChiralCel OD column, eluting with 25% ethanol/hexanes. Each compound was converted to its hydrochloride salt by the addition of 2 N HCl in ethyl ether. 7 mg of the faster eluting diastereomer (Example 47) and 6 mg of the slower eluting diastereomer (Example 48) were recovered.

Example 47: ESI-MS calc. for C23H32F3N3O2: 439.24; found 440 (M+H).

Example 48: ESI-MS calc. for C23H32F3N3O2: 439.24; found 440 (M+H).

EXAMPLE 49

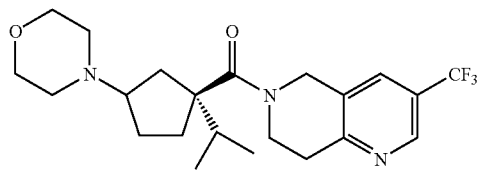

To a stirred solution of Intermediate 5 (50 mg, 0.14 mmol) and morpholine (25 µL, 0.28 mmol), in DCM (10 mL), was added 4 Å powdered molecular sieves (50 mg) and sodium triacetoxyborohydride (150 mg, 0.71 mmol). The resulting solution was stirred at room temperature for 3 days before being filtered through celite and washed with saturated aqueous sodium bicarbonate and brine. The organic layer was dried over Na$_2$SO$_4$, filtered, and concentrated under reduced pressure to give a crude oil that was purified by preparative TLC (0.5% NH$_4$OH/4.5% MeOH (95% DCM) to give 57 mg of a colorless solid as a mixture of 2 diastereomers. A small portion of this free base was converted to its hydrochloride salt by the addition of 2 N HCl in ethyl ether.

ESI-MS calc. for C22H30F3N3O0: 425.23; found 426 (M+H).

Several other examples were made according to the procedure described in Example 49 except that various substituted morpholines where used as the amine component in place of morpholine. The examples are compiled in Table 5.

TABLE 5
(EXAMPLES 50 to 53)

| Example | Structure | Molecular Formula | Calculated MW | Found MW [M + H] |
|---|---|---|---|---|
| 50 | 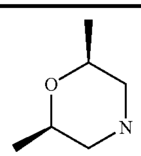 | C24H34F3N3O2 | 453.26 | 454 |
| 51 | 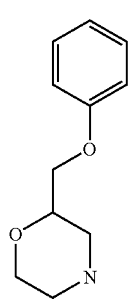 | C29H36F3N3O3 | 531.27 | 532 |
| 52 | | C23H30F3N3O2 | 437.23 | 438 |

EXAMPLE 53 AND EXAMPLE 54

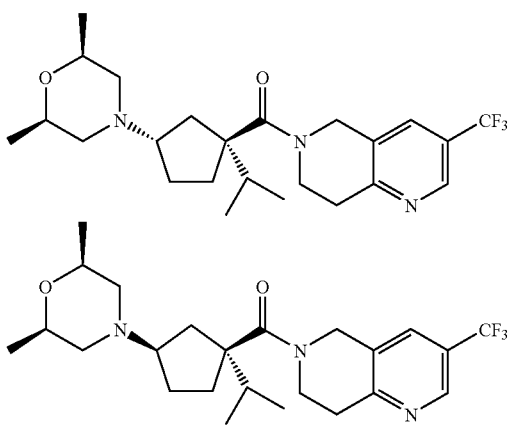

The free base of the product prepared in Example 50 (60 mg) was resolved into its individual diastereomers using an HPLC equipped with a ChiralCel OD column, eluting with 20% ethanol/hexanes. Each compound was converted to its hydrochloride salt by the addition of 2 N HCl in ethyl ether. 26 mg of the faster eluting diastereomer (Example 53) and 27 mg of the slower eluting diastereomer (Example 54) were recovered.

Example 53: ESI-MS calc. for C24H34F3N3O2: 453.26; found 454 (M+H).

Example 54: ESI-MS calc. for C24H34F3N3O2: 453.26; found 454 (M+H).

EXAMPLE 55 AND EXAMPLE 56

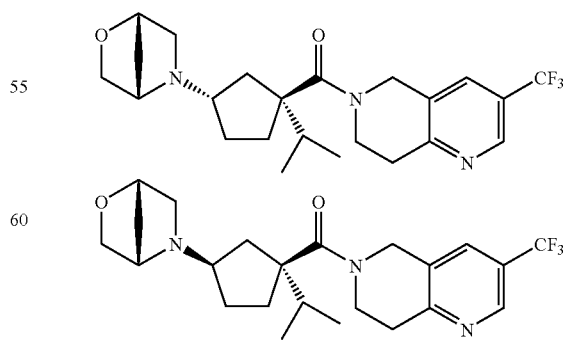

The free base of the product prepared in Example 52 (48 mg) was resolved into its individual diastereomers using an HPLC equipped with a ChiralCel OD column, eluting with 25% ethanol/hexanes. Each compound was converted to its hydrochloride salt by the addition of 2 N HCl in ethyl ether. 18 mg of the faster eluting diastereomer (Example 53) and 23 mg of the slower eluting diastereomer (Example 54) were recovered.

Example 55: ESI-MS calc. for C23H30F3N3O2: 437.23; found 438 (M+H).

Example 56: ESI-MS calc. for C23H30F3N3O2: 437.23; found 438 (M+H).

EXAMPLE 57

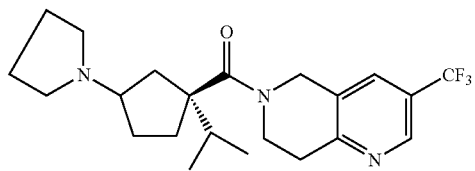

To a stirred solution of Intermediate 5 (50 mg, 0.14 mmol) and pyrrolidine (23 µL, 0.28 mmol), in DCM (10 mL), was added 4 Å powdered molecular sieves (50 mg) and sodium triacetoxyborohydride (150 mg, 0.71 mmol). The resulting solution was stirred at room temperature for 3 days before being filtered through celite and washed with saturated aqueous sodium bicarbonate and brine. The organic layer was dried over Na$_2$SO$_4$, filtered, and concentrated under reduced pressure to give a crude oil that was purified by preparative TLC (0.5% NH$_4$OH/4.5% MeOH/95% DCM) to give 15 mg of a higher running diastereomer and 35.5 mg of a lower running isomer both of which where recoved as colorless solid. A small portion of the free base was converted to its hydrochloride salt by the addition of 2 N HCl in ethyl ether.

Top: ESI-MS calc. for C22H30F3N3O: 409.23; found 410 (M+H).

Bottom: ESI-MS calc. for C22H30F3N3O: 409.23; found 410 (M+H).

Several other examples were made according to the procedure described in Example 57 except that various substituted pyrollidines where used as the amine component in place of pyrrolidine. The examples are compiled in Table 6.

TABLE 6

(EXAMPLES 58 to 62)

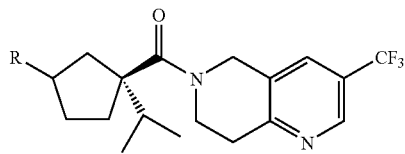

| Example | Structure | Molecular Formula | Calculated MW | Found MW [M + H] |
|---|---|---|---|---|
| 58 | 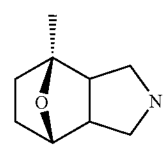 | C27H36F3N3O2 | 491.28 | 492 |
| 59 | 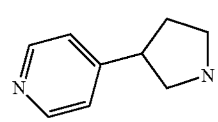 | C27H33F3N4O | 486.26 | 487 |
| 60 | 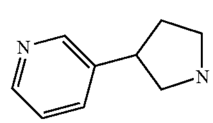 | C27H33F3N4O | 486.26 | 487 |
| 61 | 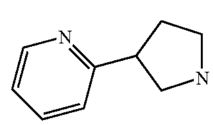 | C27H33F3N4O | 486.26 | 487 |
| 62 | 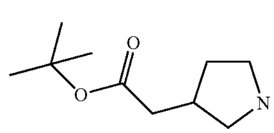 | C28H40F3N3O3 | 523.30 | 524 |

EXAMPLE 63

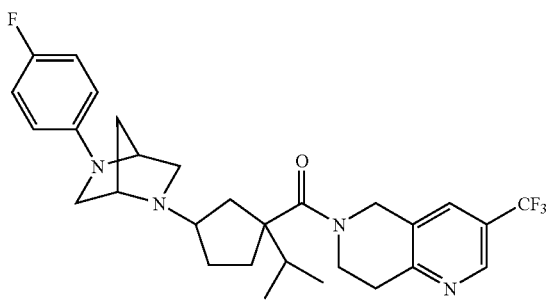

A mixture of the Intermediate 3 (55 mg, 0.15 mmol), (1S,4S)-(−)-2-(4-fluorophenyl)-2,5-diazabicyclo[2.2.1]heptane (as HBr salt, 85 mg, 0.3 mmol), DIEA (65 mg, 0.5 mmol), molecular sieves (4 Å, 250 mg) and sodium triacetoxyborohydride (212 mg, 1.0 mmol) in dichloromethane (5 mL) was stirred overnight. The reaction was quenched with sat. aq. sodium carbonate. The solid was removed by filtration through celite. The crude product was extracted into dichloromethane and purified on preparative TLC (1000 micron, 5%[aq. NH4OH/MeOH 1/9]/DCM). The title compound was obtained as a mixture of cis and trans racemic isomers (75 mg, 95%). LC-MS calc. for C30H35F4N3O: 529; Found: 530 (M+H).

EXAMPLE 64

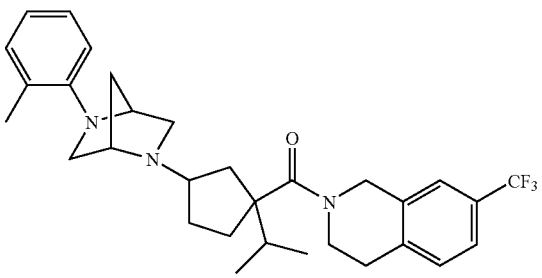

A mixture of the Intermediate 3 (55 mg, 0.15 mmol), (1S,4S)-(−)-2-(2-methyl)-2,5-diazabicyclo[2.2.1]heptane (as maleic acid salt, 100 mg, 0.3 mmol), DIEA (65 mg, 0.5 mmol), molecular sieves (4 Å, 250 mg) and sodium triacetoxyborohydride (212 mg, 1.0 mmol) in dichloromethane (5 mL) was stirred overnight. The reaction was quenched with sat. aq. sodium carbonate. The solid was removed by filtration through celite. The crude product was extracted into dichloromethane and purified on preparative TLC (1000 micron, 5%[aq. NH4OH/MeOH 1/9]/DCM). The title compound was obtained as a mixture of cis and trans racemic isomers (52 mg, 66%). LC-MS calc. for C31H38F3N3O: 525; Found: 526 (M+H).

EXAMPLE 65

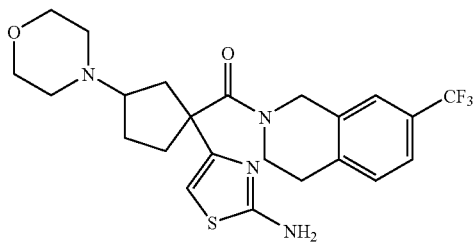

Step A:

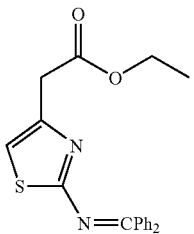

A neat mixture of 54 g (0.29 mole) ethyl (2-aminothiazol-4-yl)acetate and 50 g (0.276 mole) benzophenone imine was stirred at 190° C. for 5 h and then cooled at RT and diluted with 100 mL of CH2Cl2. The entire mixture was transferred onto a silica gel column and eluted with 20% EtOAc/Hexane. The title compound was obtained as light-yellow solid (70 g, 69% yield). $^1$H NMR (300 MHz, CDCl$_3$): δ1.26 (t, 3H), 3.74 (s, 2H), 4.15 (q, 2H), 6.87 (s, 1H), 77.25-7.86 (m, 10H); Mass Spectrum (NH$_3$—Cl): m/z 351 (M+1).

Step B:

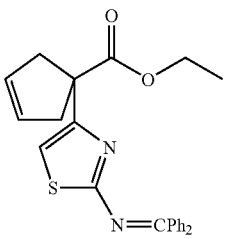

To a mixture of 35 g (0.10 Mole) of the Schiff base ester form Step A, cis-1,3-dichloro-2-butene (13 mL, 0.11 Mole) in 500 mL of DME at RT was added in multiple portions solid NaH (60% oil, 10.0 g, 0.25 Mole). The resulting mixture was stirred for 2 days, poured into 2000 mL of ice-water, extracted with 1500 mL of ether. The ether layer was washed with water (3×500 mL), dried over Na2SO4 and evaporated. FC (Silica Gel, 5% EtOAc/Hexane) afforded the title compound as an oil (24 g, 59%). $^1$H NMR (300 MHz, CDCl$_3$): δ 1.20 (t, 3H), 2.87 (d, 2H), 3.19 (d, 2H), 4.14 (q, 2H), 5.29 (s, 2H), 6.71 (s, 1H), 7.26-7.81 (m, 10H). Mass Spectrum (NH$_3$—Cl): m/z 403 (M+1).

Step C:

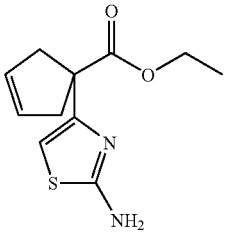

24.0 g (0.059 mol) of the cyclopentene Schiff base from Step B was dissolved in 100 mL of 4 N HCl/dioxane. After 1 h, 1.8 mL of water was added. The mixture was stirred for 3 h, evaporated to dryness. The residue was dissolved in 100 mL of CH₂Cl₂ and added 15 mL of DIEA. The entire mixture was dumped onto a silica gel column, eluted with 20% EtOAc/Hexane to remove benzophenone, then eluted with 40% EtOAc/Hexane to give the title compound as a light yellow solid (12.0 g, 85%). $^1$H NMR (300 MHz, CDCl₃): δ 1.19 (t, 3H), 2.79 (d, 2H), 3.15 (d, 2H), 4.13 (q, 2H), 5.66 (s, 2H), 5.82 (wide, 2H), 6.19 (s, 1H).

Step D:

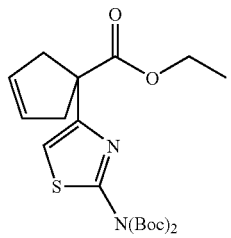

A mixture of 12 g (50 mmol) of the aminothiazole from Step C, 28 g (130 mmol) of di-tert-butyl dicarbonate and 0.6 g of DMAP in 250 mL of DCM was stirred overnight, and evaporated. The title compound (21.0 g, 96%) was obtained as a yellow oil after flash chromatography purification on silica gel (10% EtOAc/Hexane). $^1$H NMR (300 MHz, CDCl₃): δ1.18 (t, 3H), 1.49 (d, 18H), 2.88 (d, 2H), 3.18 (d, 2H), 4.13 (q, 2H), 5.65 (s, 2H), 6.83 (s, 1H). Mass Spectrum (NH₃—CI): mz 439 (M+1).

Step E:

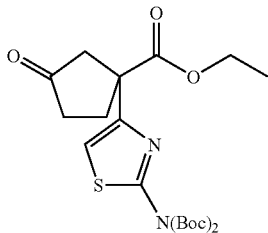

To a solution of 13.1 g (30.0 mmol) of the ester from Step D in 50 mL of anhydrous ether at −78° C. was added dropwise a solution of BH₃.DMS in THF (14 mL, 24 mmol). The cooling bath was removed and the mixture was stirred at room temperature for 3 h, diluted with 250 mL of DCM, added 25 g of sodium acetate and 55 g of PCC. The mixture was stirred overnight. The entire mixture was applied to a silica gel column and eluted with in 10% EtOAc/Hexane and then 30% EtOAc/Hexane. Two components were obtained. The fast-eluted isomer (yellow oil, 6.0 g) was identified as the title compound. $^1$H NMR (300 MHz, CDCl₃): δ1.21 (t, 3H), 1.50 (s, 18H), 2.33 (t, 2H), 2.42-2.70 (m, 2H), 2.78-3.10 (dd, 2H), 4.18 (q, 3H), 6.88 (s, 1H). Mass Spectrum (NH3-CI): m/z 455 (M+1).

Step F:

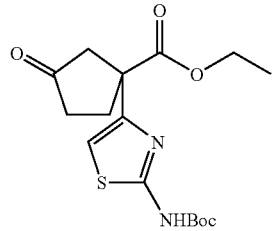

The slow-eluted component from above was proved to be the title compound (gummy material, 1.80 g).
$^1$H NMR (300 MHz, CDCl₃): δ(t, 3H), 1.46 (s, 9H), 2.27 (3, 2H), 2.38-2.62 (m, 2H), 2.64-3.00 (dd, 2H), 4.11 (q, 2H), 6.66 (s, 1H). Mass Spectrum (NH₃-CI): m/z 355 (M+1).

Step G:

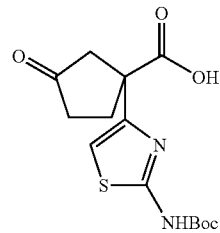

A mixture of 1.40 g (4.00 mmol) of the keto ester from Step F and 0.82 g (13 mmol) of lithium hydroxide monohydrate in a solution of 20 mL of MeOH and 2 mL of water was stirred at room temperature overnight. The entire mixture was applied to a silica gel column and eluted with 10% MeOH/CH₂Cl₂. Evaporation in vacuo afforded a light yellow solid. 1.30 g of the title product was obtained as a fluffy solid. $^1$H NMR (300 MHz, CDCl₃): δ(t, 9H), 2.10-3.20 (m, 8H), 6.60 (s, 1H).

Step H:

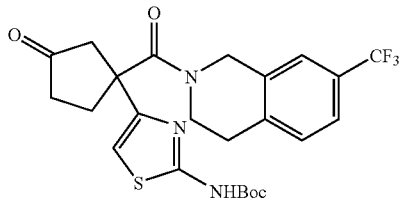

A mixture of the keto acid prepared in Step G (1.0 g, 3.0 mmol), Intermediate 1 (as HCl salt, 0.66 g, 3.0 mmol) and EDC (0.95 g, 5.0 mmol) in dichloromethane (10 mL) was stirred for 2 days. The mixture was diluted with dichloromethane and washed with 1 N aq. HCl, dried over sodium sulfate and evaporated. The residue was purified on preparative TLC (1500 micron, 10%[aq. NH₄OH/MeOH 1/9]/DCM) to yield the title product as a yellow solid (0.52 g, 34%). LC-MS calc. for C25H27F3N2O4S: 508; Found: 509 (M+H).

Step I:

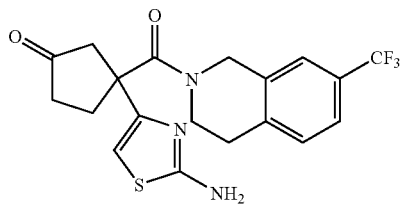

The product from step H (510 mg, 1.0 mmol) was mixed with TFA (10 mL) for 30 min. TFA was removed and the residue was purified on preparative TLC (10%[aq. NH4OH/MeOH 1/9]/DCM) to yield the desired product as a white solid (223 mg, 55%). LC-MS calc. for C20H19F3N2O2S: 408; Found: 409 (M+H).

Step J:

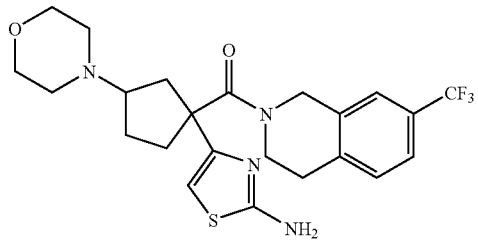

A mixture of the product from Step I (210 mg, 0.50 mmol), morpholine (440 mg, 5.0 mmol), molecular sieves (4 Å, 500 mg) and sodium triacetoxyborohydride (420 mg, 2.0 mmol) in dichloromethane (15 mL) was stirred overnight. The reaction was quenched with sat. aq. sodium carbonate. The solid was removed by filtration through celite. The crude product was extracted into dichloromethane and purified on preparative TLC (1000 micron, 10%[aq. NH4OH/MeOH 1/9]/DCM). The title compound was obtained as a mixture of cis and trans racemic isomers (200 mg, 84%). LC-MS calc. for C24H28F3N3O2S: 479; Found: 480 (M+H).

EXAMPLE 66

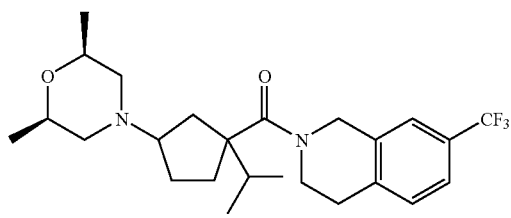

A mixture of the Intermediate 3 (70 mg, 0.20 mmol), cis-2,6-dimethylmorpholine (23 μL, 0.20 mmol), molecular sieve (4 μL, 200 mg), and sodium triacetoxyborohydride (210 mg, 0.99 mmol) in DCM was stirred for 5 days. The reaction mixture was diluted by DCM, filtered, and washed with sat. aq. NaHCO₃, water and brine. DCM layers were dried over Na₂SO₄, filtered and concentrated. The residue was purified on preparative TLC (1000 micron) (developed by 3% [aq. NH4OH/MeOH 1/9]/DCM) to yield the final title compound as a free base. Its HCl salt (62.2 mg) was formed by treatment with 4 N HCl/dioxane. ESI-MS calc. for C25H35F3N2O2: 452.27; Found: 453 (M+H). The diastereoisomers were separated into one mixture of 2 cis diastereoisomers and two single diastereomers using HPLC (AD column, 5% EtOH/hexane).

EXAMPLE 67

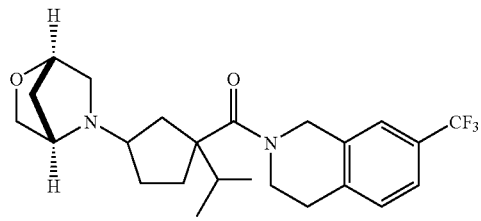

Example 68 was prepared starting from Intermediate 3 and (1S,4S)-(+)-2-aza-5-oxabiclclo[2.2.1]heptane hydrochloride as detailed in Example 66. The cis and trans isomers were resolved on preparative TLC (4/95.6/0.4, MeOH/DCM/NH₄OH). Top spot: ESI-MS calc. for C24H31F3N2O2: 436.23; Found: 437 (M+H). Bottom spot: ESI-MS calc. for C24H31F3N2O2: 436.23; Found: 437 (M+H).

EXAMPLE 68

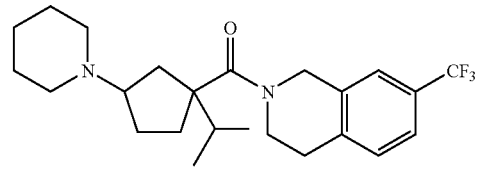

Example 68 was prepared starting from piperidine and Intermediate 3 as detailed in Example 49. ESI-MS calc. for C24H33F3N2O: 422.25; Found: 423 (M+H).

EXAMPLE 69

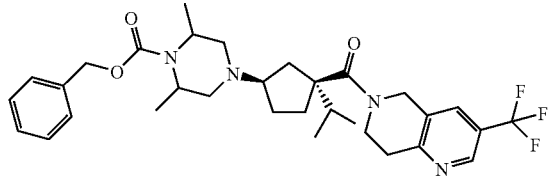

Intermediate 22 (563 mg, 2.43 mmol) was dissolved in dichloromethane and cooled to −78° C. Ozone was bubbled into the solution until a blue color persisted. Nitrogen gas was then bubbled through the solution until disappearance of the blue color. Na$_2$SO$_4$ was added into the stirring solution. The reaction mixture was filtered into a flask containing Intermediate 23. Dichloromethane (20 mL), triethylamine (136 µL, 0.974 mmol), and NaB(OAc)$_3$H (929 mg, 4.38 mmol) were added to the reaction flask. The reaction mixture was stirred at room temperature under N$_2$ gas for two hours and then diluted with dichloromethane and washed with saturated sodium bicarbonate solution (2×100 mL) and brine (1×100 mL). The organic layers were dried over MgSO$_4$, filtered, and concentrated. The crude products were divided into three batches and loaded onto three ion exchange column. Impurities were flushed away with using 40% MeOH/hexanes (100 mL). The desired product was then eluted from the columns with a 30% solution 2N NH$_3$ in MeOH further diluted in dichloromethane. Example 69 (131 mg, 0.223 mmol, 46% yield) was purified by preparatory TLC using 32% EtOAc/hex. The diastereomers were then isolated through preparatory TLC using 45% EtOAc/hex (top isomer: 20 mg, 0.034 mmol, 7% yield; middle isomer: 45 mg, 0.076 mmol, 16% yield; bottom isomer: 54 mg, 0.092 mmol, 19% yield). ESI-MS calculated for C$_{32}$H$_{41}$F$_3$N$_4$O$_3$: 586.69, found 587 (M+H).

Several other piperazines and homo-piperazines where made according to the same procedure described in Example 69. Table 7 summarizes these compounds.

EXAMPLE 73

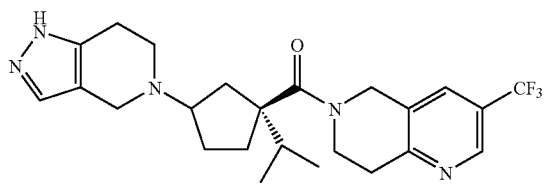

The above compound was prepared from Intermediate 5 and 4,5,6,7-tetrahydro-1H-pyrazolo[4,3-]pyridine according to the procedure described in Example 49. ESI-MS calc. for C24H30F3N5O: 461.24; found 462 (M+H).

EXAMPLE 74

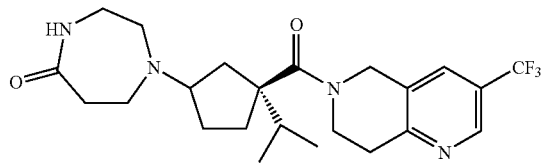

TABLE 7

(EXAMPLES 70 to 72)

| Example | Structure | Molecular Formula | Calculated MW | Found MW [M + H] |
|---|---|---|---|---|
| 70 | 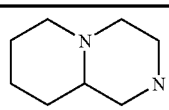 | C26H37F3N4O | 478.29 | 479 |
| 71 | 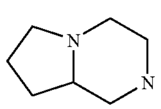 | C25H35F3N4O | 464.28 | 465 |
| 72 | 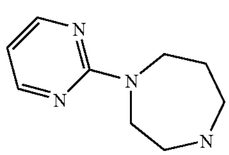 | C27H35F3N6O | 516.28 | 517 |

The above compound was prepared from Intermediate 5 and 1,4-diazepan-5-one according to procedure described in Example 49. ESI-MS calc. for C23H31F3N4O2: 452.24; found 453 (M+H).

EXAMPLE 75

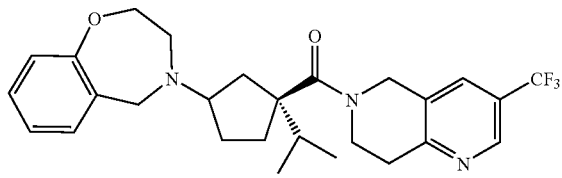

The above compound was prepared from Intermediate 5 and 2,3,4,5-tetrahydro-1,4-benzoxazepine according to the procedure described in Example 57. Top spot: ESI-MS calc. for C27H32F3N3O2: 487.24; found 488 (M+H). Bottom spot: ESI-MS calc. for C27H32F3N3O2: 487.24; found 488 (M+H).

EXAMPLE 76

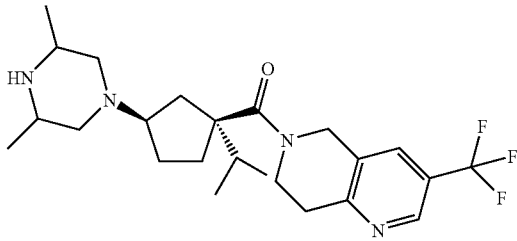

Palladium catalyst on carbon (top: 6 mg, middle: 18 mg, bottom: 20 mg) was added to three flasks each containing one of the three diastereomers of Example 70 (top: 29.6 mg, middle: 89.9 mg, bottom: 102.3 mg). The mixtures were dissolved in MeOH (3-6 mL), and the reaction vessels were flushed repeatedly with hydrogen gas. The reaction was stirred at room temperature under a hydrogen atmosphere for 4.5 hours and then passed through an Acrodisc® syringe filter with a 0.45 μm PTFE membrane. Compound 76 (top isomer: 16.0 mg, 0.0354 mmol, 71% yield; middle isomer: 42.7 mg, 0.0943 mmol, 62% yield; bottom isomer: 34.5 mg, 0.0762 mmol, 44% yield) was isolated through preparatory TLC using a 10% NH4OH/MeOH (1:9) in dichloromethane solvent system. ESI-MS calculated for C24H35F3N4O: 452.56, found 453 (M+H).

EXAMPLE 77

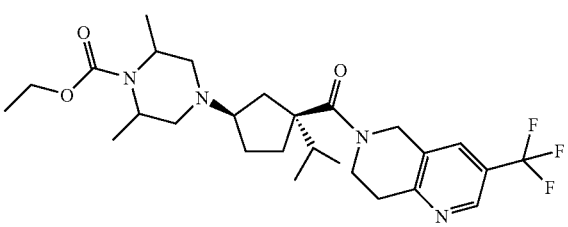

Example 76 (middle stereoisomer on TLC, 11 mg, 0.024 mmol) was dissolved in dichloromethane (3 mL) and cooled to 0° C. Ethylchloroformate (5 μL, 0.05 mmol), triethylamine (10 μL, 0.07 mmol), and a catalytic amount of DMAP (1-2 mg) was added to the reaction flask. The reaction was warmed to room temperature and stirred for two hours under a nitrogen atmosphere. Thereafter, the reaction was diluted with DCM and washed with saturated sodium bicarbonate solution (1×25 mL) and brine (1×25 mL). The organic layer was dried over MgSO4, filtered, and concentrated. Example 77 (4.2 mg, 0.0080 mmol, 33% yield) was purified through preparatory TLC using a 2% NH4OH/MeOH (1:9) in dichloromethane solvent system. ESI-MS calculated for C27H39F3N4O3: 524.62, found: 525 (M+H).

EXAMPLE 78

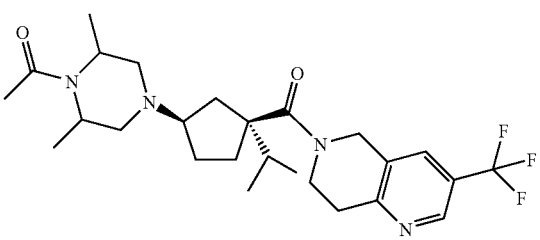

Example 76 (middle stereoisomer on TLC, 11 mg, 0.024 mmol) was dissolved in dichloromethane (3 mL) and cooled to 0° C. Acetic anhydride (11 μL, 0.12 mmol), triethylamine (23 μL, 0.17 mmol), and a catalytic amount of DMAP (1-2 mg) was added to the reaction flask. The reaction was warmed to room temperature and stirred for 2.5 hrs. under a nitrogen atmosphere. The reaction was then diluted with DCM and washed with saturated sodium bicarbonate solution (1×25 mL) and brine (1×25 mL). The organic layer was dried over MgSO4, filtered, and concentrated. Example 78 (5.3 mg, 0.011 mmol, 45% yield) was purified through preparatory TLC using a 2% NH4OH/MeOH (1:9) in dichloromethane solvent system. ESI-MS calculated for C26H37F3N4O2: 494.59, found: 495 (M+H).

EXAMPLE 79

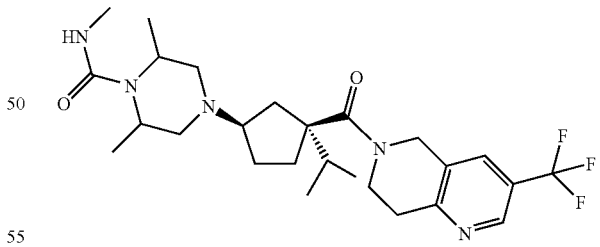

Dichloromethane (2-3 mL per flask) was added to three separate flasks containing the three diastereomers of Example 77 (top: 16 mg, 0.035 mmol, middle: 11 mg, 0.023 mmol, bottom: 14 mg, 0.031 mmol). Methylisocyanate (top: 21 μL, 0.35 mmol, middle: 14 μL, 0.23 mmol, bottom: 19 μL, 0.31 mmol) was added to each reaction vessel. The reactions were stirred for three hours and then concentrated before isolating Example 79 (top isomer: 12.8 mg, 0.0251 mmol, 72% yield; middle isomer: 10.4 mg, 0.0204 mmol, 89% yield; bottom isomer: 11.1 mg, 0.0218 mmol, 70% yield) by preparatory TLC using a 2% NH₄OH/MeOH (1:9) in dichloromethane solvent system. ESI-MS calculated for $C_{26}H_{38}F_3N_5O_2$: 509.61, found: 510 (M+H).

EXAMPLE 80

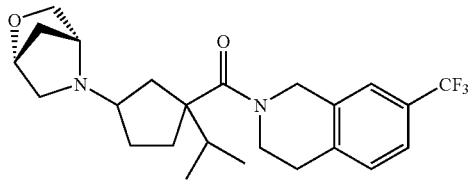

Step A

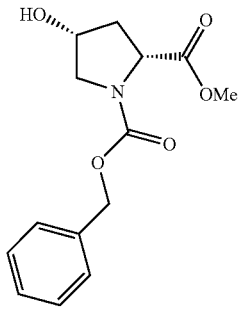

A solution of cis-hydroxy-D-proline (2.98 g, 22.7 mmol) in methanol (20 mL) was treated with thionyl chloride (1.78 mL, 24.4 mmol) and stirred at room temperature for 1 h. The reaction mixture was then heated to 65° C. overnight. Evaporation of the volatiles gave the crude methyl ester (4.0816 g), which was dissolved in dichloromethane (50 mL) and diisopropyl ethyl amine (9.59 mL, 55.1 mmol) was added. The reaction mixture was cooled to 0° C. and neat benzyl chloroformate (3.71 mL, 26.0 mmol) was added via syringe. After stirring at 0° C. for 30 minutes the cooling bath was removed. The reaction was quenched by pouring into an aqueous solution of citric acid (10%, 50 mL) and the product was extracted into dichloromethane. The combined organic phases were back-washed with brine, dried with anhydrous sodium sulfate, and the solvent was removed in vacuo. The crude product was purified by flash chromatography (silica gel, ethyl acetate:hexanes/4:6) to yield 4.0717 g (69%) of the pure product. ¹H NMR (500 MHz, CDCl₃): δ 7.35 m (5H), 5.21 (d, J=12.6 Hz, 2H), 5.10 (d, J=13 Hz, 1H), 5.06 (d, J=12.35 Hz, 1H), 4.45 (m, 2H), 3.80 (s, 3H), 2.35 (m, 1H), 2.15 (m, 1H).

Step B

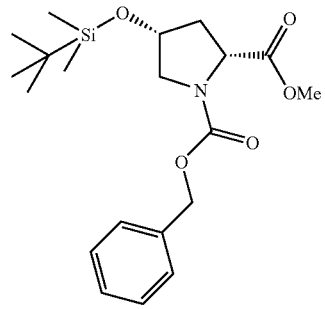

A solution of the alcohol from the previous step (2.63 g, 9.42 mmol) and diisopropylethylamine (3.28 mL, 18.8 mmol) in dichloromethane 40 mL was cooled to −78° C. and tert-butyldimethylsilyl trifluoromethane sulfonate (2.596 mL, 11.30 mmol) was added via syringe. The reaction mixture was stirred at −78° C. for 2 h, and quenched by pouring onto 50 mL of saturated solution of sodium bicarbonate. The organic phase was separated, dried with magnesium sulfate and the volatiles were removed in vacuo. The residue (6.0 g) was further purified by column chromatography (silica gel, ethyl acetate:hexanes/1:4) to afford 2.8355 g (76%) of the pure product. ¹H NMR (500 MHz, CDCl₃): 7.35 m (5H), 5.20 (m=2H), 4.45 (m, 2H), 3.70 (m, 4H), 3.45 (m, 1H), 2.23 (m, 2H) 0.87 (bs, 9H), 0.05 (m, 6H).

Step C

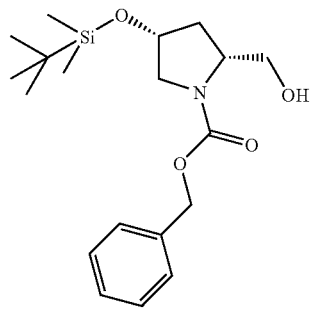

A solution of the ester from previous step (2.83 g, 7.19 mmol) in THF (10 mL) was treated with lithium borohydride (250 mg, 11.5 mmol) at 0° C. and the reaction mixture was stirred at room temperature for 72 h. It was then diluted with diethyl ether, washed with water and a 1 M solution of phosphoric acid. The combined organic extracts were dried (sodium sulfate) and the solvent was removed in vacuo. The crude product was further purified by column chromatography (silica gel, ethyl acetate:hexanes/3:7) to yield 1.5636 g (60%) of the pure product. LC MS: for $C_{19}H_{31}NO_4Si$ calculated 365.20, found 366.25 [M+H]⁺.

Step D

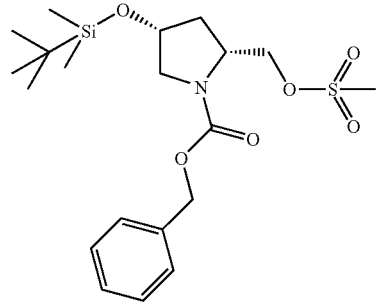

A solution of the alcohol from the previous step (1.56 g, 4.27 mmol) and diisopropylethylamine (1.49 mL, 8.53 mmol) in dichloromethane (20 mL) was treated with methanesulfonyl chloride (496 μL, 6.41 mmol) at 0° C. The reaction mixture was stirred at cold for 15 minutes, then at room temperature for another 30 minutes. It was diluted with dichloromethane, washed with water and dried with magnesium sulfate. The solvent was removed in vacuo and the crude product was used without any delay in the next step as obtained. LC MS: for $C_{20}H_{33}NSO_6Si$ calculated 443.18, found 444.25 $[M+H]^+$.

Step E

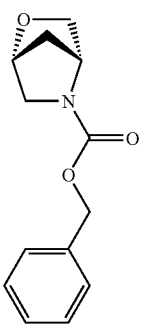

A solution of the TBS-ether from the previous step (1.82 g, 4.10 mmol) in THF (50 mL) was treated with tetrabutylammonium fluoride (4.51 mL, 1 M solution in THF). And the reaction mixture was stirred at room temperature until LC MS analysis indicated complete removal of the TBS group, about 15 minutes. The reaction mixture was then cooled to 0° C. and sodium hydride (180 mg, 60% suspension, 45.1 mmol) was added. Stirring at room temperature was continued for 24 h. The reaction was quenched by pouring onto water, and the crude product was extracted into ethyl acetate. The solvent was removed in vacuo, and the crude product was purified by flash chromatography (dichloromethane:ether/7:3) to afford 595 mg (59%) of the desired product. $^1$H NMR (500 MHz, $CDCl_3$): 7.38 (m, 5H), 5.30 (m, 2H), 4.52 (m, 2H), 3.80 (m, 2H), 3.40 (m, 2H), 1.70 (m, 2H).

Step F

A solution of the CBZ-amine from the previous step (590 mg, 2.53 mmol) in ethyl alcohol (30 mL) was hydrogenated in the presence of Pd/C (142 mg, 10%) under balloon pressure. The reaction was monitored by LC by the disappearance of the starting material and appearance of toluene. The catalyst was filtered off and the filtrate was evaporated to dryness to leave 321 mg (94%) of the desired product.

Step G

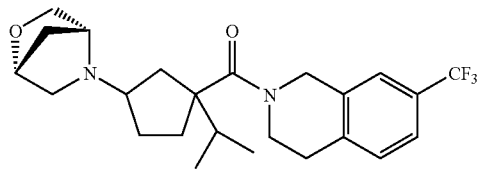

A solution of Intermediate 3 (120 mg, 0.340 mmol), amine hydrochloride from previous step (46 mg, 0.34 mmol), diisopropyl ethylamine (60 µL, 0.34 mmol) and 4 Å molecular sieves (crushed, 360 mg) in dichloroethane (10 mL) was treated with sodium triacetoxyborohydride, and stirred at room temperature for 24 h. The reaction was quenched by pouring onto saturated solution of sodium bicarbonate and the crude product was extracted with dichloromethane. The volatiles were removed in vacuo, and preparative TLC (ethyl acetate:ethyl alcohol:ammonium hydroxide/90:8:2 gave the pure product (118 mg, 80%). LC MS: for $C_{24}H_{31}N_2F_3O_2$ calculated 436.23, found 437.20 $[M+H]^+$.

EXAMPLE 81

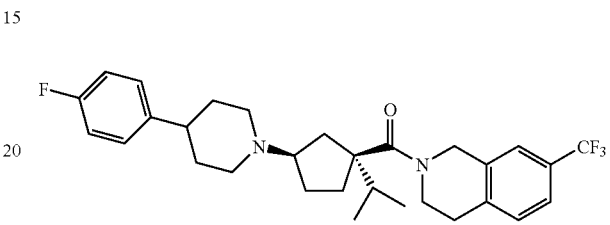

To a solution of Intermediate 21 (150 mg, 0.43 mmol) in dichloromethane (10 mL) was added EDC (414 mg, 2.16 mmol), HOAt (59 mg, 0.43 mmol) and Intermediate 1 (87 mg, 0.43 mmol) and the resulting mixture was stirred at room temperature for 4 days. The reaction was quenched with water and diluted with 20 mL of dichloromethane. The organic layer was separated and the aqueous layer was extracted with DCM (2×20 mL). The organics were combined, dried over sodium sulfate, filtered and evaporated under reduced pressure. The residue was purified by preparative TLC (eluant: 10% methanol: 89.5% dichloromethane: 0.5% $NH_4OH$) to yield 40 mg (17%) of the final pure desired product as a mixture of two cis isomers. LC-MS for $C_{30}H_{36}N_2OF_4$ calculated 516.28, found $[M+H]^+$ 517.

EXAMPLE 82

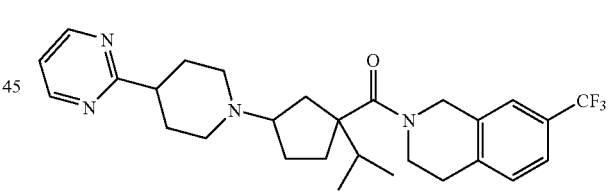

The hydrochloride salt of the pyrimidyl piperidine (Intermediate 8) (67 mg, 0.34 mmol) was combined with Intermediate 4 (100 mg, 0.28 mmol), triethylamine (46 µL, 0.35 mmol), and 4 Å powdered molecular sieves (100 mg) in DCM. After 15 minutes at room temperature, sodium triacetoxyborohydride (240 mg, 1.13 mmol) was added and the resulting mixture was stirred for 3 days before being filtered through celite, diluted with DCM and washed with saturated sodium bicarbonate and brine. The organic layer was dried over $MgSO_4$, filtered and concentrated under reduced pressure to give a crude oil that was purified by preparative TLC (silica gel, 0.3% $NH_4OH/2.7\%$ MeOH/97% DCM) to give 110 mg of a colorless oil. Resolution of the individual diastereomers was accomplished by HPLC using a ChiralPak AD column eluting with 30% isopropanol/hexanes to give 2 single diastereomers and a single mixture of the 2 other diastereomers.

First peak 10 mg: ESI-MS calc. for C28H35F3N4O: 500.28; found 504 (M+H).

Second peak 11 mg: ESI-MS calc. for C28H35F3N4O: 500.28; found 504 (M+H).

Third peak 7.0 mg ESI-MS calc. for C28H35F3N4O: 500.28; found 504 (M+H).

EXAMPLES 83-91

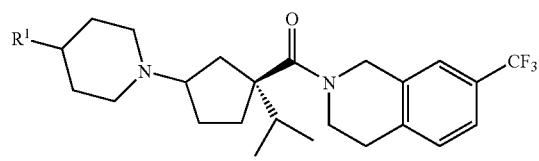

Several other examples where prepared in a similar fashion to Example 82, utilizing different piperidine intermediates. These Examples (83-91) are shown below.

| Example | R¹ | Molecular Formula | Calculated [M] | Found [M + H] |
|---------|----|-------------------|----------------|---------------|
| 83 | (pyrazol-1-yl) | C27H36F3N4O | 488.27 | 489 |
| 84 | (pyrazol-3-yl) | C27H36F3N4O | 488.27 | 489 |
| 85 | (imidazol-1-yl) | C27H36F3N4O | 488.27 | 489 |
| 86 | (1,2,3-triazol-1-yl) | C26H35F3N5O | 489.27 | 490 |
| 87 | (1,2,3-triazol-2-yl) | C26H35F3N5O | 489.27 | 490 |
| 88 | (1,2,4-triazol-1-yl) | C26H35F3N5O | 489.27 | 490 |
| 89 | (tetrazol-1-yl) | C25H34F3N6O | 490.26 | 491 |
| 90 | (tetrazol-2-yl) | C25H34F3N6O | 490.26 | 491 |
| 91 | (methyltetrazolyl) | C26H36F3N6O | 504.26 | 505 |

EXAMPLE 92

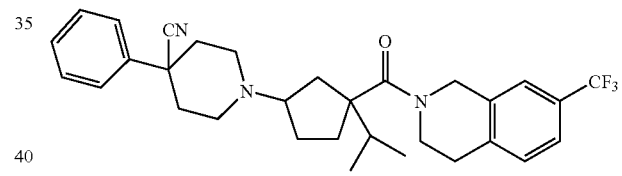

This product was prepared in an analogous fashion to that of Example 81, except Intermediate 21 was replaced with commercially available 4-cyano-4-phenylpiperidine. The crude product was purified by preparative TLC (eluant: 5% methanol: 94.5% DCM: 0.5% NH₄OH) to yield Example 92 as a mixture of four isomers. LC-MS for $C_{31}H_{36}F_3N_3O$ calculated 523.28, found [M+H]⁺524.

EXAMPLE 93

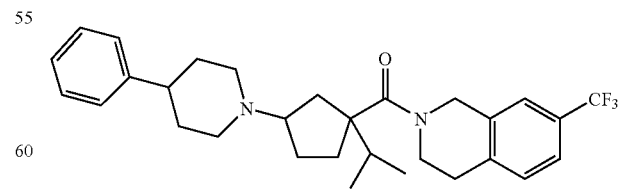

This product was prepared in an analogous fashion to that of Example 81, except Intermediate 21 was replaced with commercially available 4-phenylpiperidine. The crude product was purified by preparative TLC (eluant: 10% methanol:

89.5% DCM: 0.5% NH$_4$OH) to yield Example 93 as a mixture of four isomers. LC-MS for C$_{30}$H$_{37}$F$_3$N$_2$O calculated 498.29, found [M+H]$^+$ 499.

EXAMPLE 94

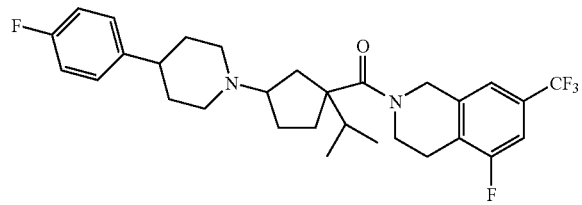

Step A

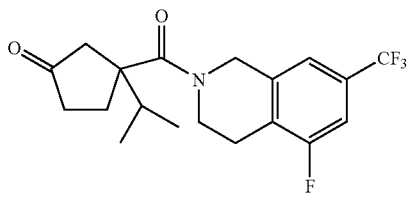

To a solution of the cyclopentanone carboxylic acid (from Step C, Intermediate 3) (2.3 g, 14 mmol) in dichloromethane (70 mL) was added oxalyl chloride (1.8 mL, 21 mmol) followed by 2 drops of DMF. The solution was stirred at room temperature for 80 minutes and then evaporated under reduced pressure. The residue was dissolved in DCM (20 mL) and added via syringe to a prepared solution of Intermediate 3 (3.0 g, 14 mmol) and triethylamine (2.1 mL, 15 mmol) in DCM (50 mL). The resulting mixture was stirred at room temperature for 18 h and then quenched with water (25 mL). The organics were separated, washed with 1 N HCl, saturated sodium bicarbonate solution, and brine, dried over anhydrous magnesium sulfate, filtered, and evaporated. The residue was purified on a Biotage Flash 40 (eluant: 40% ethyl acetate/60% hexane) to afford 2.2 g (43%) of the title compound.

Step B

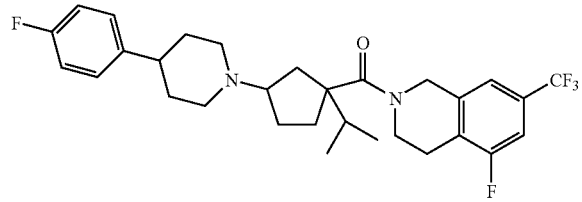

A solution of the product described in Step A (200 mg, 0.54 mmol) commercially available 4-fluorophenylpiperidine hydrochloride (120 mg, 0.54 mmol), diisopropylethylamine (94 μL, 0.54 mmol) and crushed molecular sieves (4 Å, 100 mg) in dichloromethane (10 mL) was treated with sodium triacetoxyborohydride (343 mg, 1.60 mmol) and stirred at room temperature overnight. The reaction was quenched with saturated sodium bicarbonate (10 mL) and diluted with an additional 10 mL of DCM. The organic layer was separated and the aqueous washed with dichloromethane (2×5 mL). The organics were combined, dried over anhydrous sodium sulfate, filtered and evaporated. The residue was purified by preparative TLC (eluent: 8% ethanol: 90% ethyl acetate: 2% NH$_4$OH) to yield two isomers, higher eluting (25 mg, 5%) and lower eluting (37.2 mg, 7.6%) of unknown absolute stereochemistry. LC-MS for C$_{30}$H$_{35}$N$_2$OF$_5$ calculated 534.28, found [M+H]$^+$ 535.

EXAMPLE 95

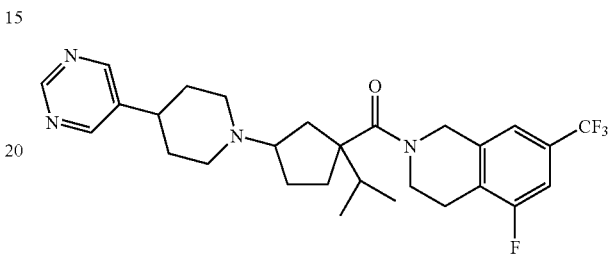

This product was prepared in an analogous fashion to that of Example 94, except 4-fluorophenylpiperidine hydrochloride was replaced with Intermediate 9. The crude product was purified by preparative TLC (eluent: 90% ethyl acetate: 8% ethanol: 2% NH$_4$OH) to yield 450 mg (66%) of the title product as a mixture of four isomers. LC-MS for C$_{28}$H$_{34}$N$_4$OF$_4$ calculated 518.27, found [M+H]$^+$ 519.

EXAMPLES 96-104

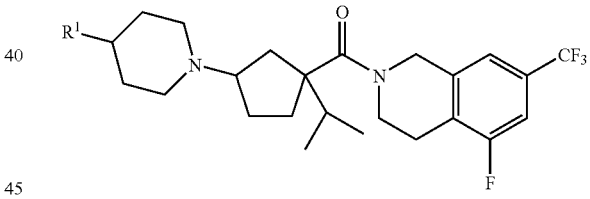

Several other examples where prepared in a similar fashion to Example 94, utilizing different piperidine intermediates. These Examples (96-104) are shown below.

| Example | R$^1$ | Molecular Formula | Calculated [M] | Found [M + H] |
|---|---|---|---|---|
| 96 | (tetrazole) | C25H33F4N6O | 508.26 | 509 |
| 97 | (tetrazole) | C25H33F4N6O | 508.26 | 509 |

-continued

| Example | R¹ | Molecular Formula | Calculated [M] | Found [M + H] |
|---|---|---|---|---|
| 98 | 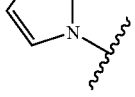 | C27H35F4N4O | 506.27 | 507 |
| 99 | 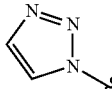 | C26H34F4N5O | 507.27 | 507 |
| 100 | 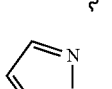 | C26H34F4N5O | 507.27 | 508 |
| 101 | 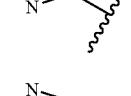 | C26H34F4N5O | 507.27 | 508 |
| 102 | 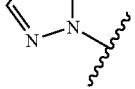 | C27H35F4N4O | 506.27 | 507 |
| 103 | 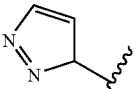 | C27H35F4N4O | 506.27 | 507 |
| 104 |  | C26H35F4N6O | 522.28 | 523 |

EXAMPLE 105

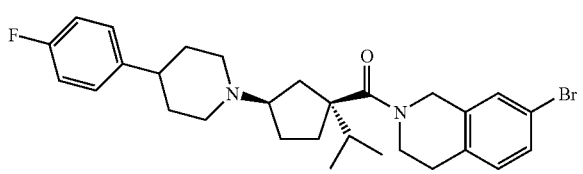

To a solution of Intermediate 21 (150 mg, 0.43 mmol) in dichloromethane (10 mL) was added EDC (170 mg, 0.86 mmol), HOAt (59 mg, 0.43 mmol) and Intermediate 21 (91 mg, 0.43 mmol) and the resulting mixture was stirred at room temperature for 3 days. The reaction was quenched with water and diluted with 20 mL of dichloromethane. The organic layer was separated and the aqueous layer was extracted with DCM (2×20 mL). The organics were combined, dried over sodium sulfate, filtered and evaporated under reduced pressure. The residue was purified by preparative TLC (eluant: 7% ethanol: 92% dichloromethane: 1.0% NH₄OH) to yield 121 mg (50%) of the final desired product as a mixture of two cis isomers. LC-MS for $C_{29}H_{36}BrFN_2O$ calculated 526.28, found [M+H]⁺ 527 and [(M+2)+H]⁺ 529.

EXAMPLE 106

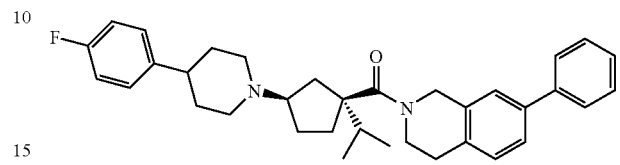

To a solution of Example 105 (100 mg, 0.210 mmol), phenylboronic acid (30 mg, 0.23 mmol), toluene (1.4 mL), and MeOH (0.6 mL) was added a solution of Na₂CO₃ (80 mg, 0.74 mmol) and Pd(PPh₃)₂Cl₂ (8 mg, 0.01 mmol) in H₂O (0.4 μL). The reaction mixture was heated at 80° C. in a high pressure tube for 12 h before filtered through celite and concentrated to dryness. The concentrate was diluted with DCM, washed with 1 N NaOH solution (3×), dried over Na₂SO₄, and concentrated in vacuo. The crude product was purified by preparative TLC (eluent: 5/94.5/0.5, MeOH/DCM/NH₄OH) to yield Example 106 (63.3 mg, 63.3%) a mixture of 2 cis isomers. LC-MS for $C_{35}H_{41}FN_2O$ calculated 524.29, found [M+H]⁺ 525.4.

EXAMPLE 107

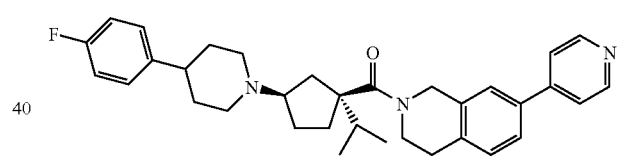

This product was prepared in an analogous fashion to that of Example 106, except phenylboronic acid was replaced with 4-pyridylboronic acid. The crude product was purified by preparative TLC (eluent: 10/89/1.0, MeOH/DCM/NH₄OH) to yield Example 107 as a mixture of two cis isomers. LC-MS for $C_{34}H_{40}F_3O$ calculated 525.26, found [M+H]⁺ 526.3.

EXAMPLE 108

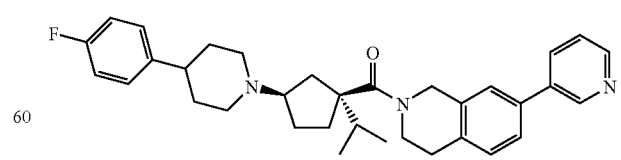

This product was prepared in an analogous fashion to that of Example 106, except phenylboronic acid was replaced with 3-pyridylboronic acid. The crude product was purified by preparative TLC (eluent: 10/89/1.0, MeOH/DCM/

NH$_4$OH) to yield Example 108 as a mixture of two cis isomers. LC-MS for C$_{34}$H$_{40}$FN$_3$O calculated 525.26, found [M+H]$^+$ 526.3.

EXAMPLE 109

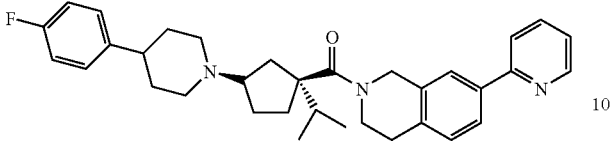

This product was prepared in an analogous fashion to that of Example 106, except phenylboronic acid was replaced with 2-pyridylboronic acid. The crude product was purified by preparative TLC (eluent: 10/89/1.0, MeOH/DCM/NH$_4$OH) to yield Example 109 as a mixture of two cis isomers. LC-MS for C$_{34}$H$_{40}$FN$_3$O calculated 525.26, found [M+H]$^+$ 526.3.

EXAMPLE 110

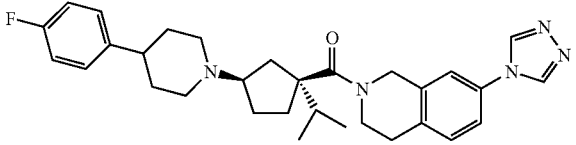

Step A

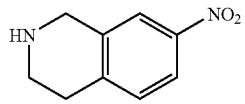

To ice cold concentrated sulfuric acid was added in a dropwise manner 1,2,3,4-tetrahydroisoquinoline (23 mL, 170 mmol), followed by potassium nitrate (18.8 g, 186 mmol) at such a rate that the temperature did not rise above 5° C. After complete addition the mixture was stirred at room temperature for 18 h then poured onto a stirred mixture of ice (700 g) and NH$_4$OH (150 mL). The mixture was extracted with CHCl$_3$ (3×300 mL). The combined CHCl$_3$ layers were washed with saturated NaCl (200 mL), dried over Na$_2$SO$_4$, filtered and concentrated in vacuo. The residue was dissolved in ethanol (130 mL) and cooled in an ice bath as concentrated hydrochloric acid (22 mL) was added. The formed precipitate was removed by filtration and recrystallized from methanol to give the product (12.45 g, 34%); $^1$H NMR 500 MHz (DMSO-d$_6$) δ=3.13 (2H, t, J=6.2 Hz), 3.35 (2H, t, J=6.2 Hz), 4.35 (2H, s), 7.50 (1H, d, J=8.5 Hz), 8.07 (1H, dd, J=2.3 and 8.5 Hz), 8.19 (1H, d, J=2.3 Hz) 10.02 (2H, br s).

Step B

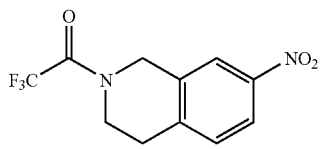

To a suspension of the product from Step A (12 g, 58 mmol), and pyridine (23.7 mL, 293 mmol) in anhydrous CH$_2$Cl$_2$ (50 ml) cooled at 0° C. was added in a dropwise manner trifluoroacetic anhydride (12 mL, 87 mmol), and the resulting mixture was stirred at room temperature for 18 h. The reaction mixture was poured onto ice (500 g) and extracted with CH$_2$Cl$_2$ (4×150 mL). The combined CH$_2$Cl$_2$ layers were washed with 1 N HCl (4×100 mL), saturated NaCl (100 mL), dried over Na$_2$SO$_4$, filtered and evaporated in vacuo to give the product (15.92 g, 89%); $^1$H NMR 500 MHz (CDCl$_3$) δ=3.07 (2H, m), 3.91 and 3.94 (2H, t, J=6.2 Hz), 4.85 and 4.88 (2H, s), 7.36 (1H, dd, J=8.7 and 11.9 Hz), 8.07 (1H, dd, J=2.3 and 8.5 Hz), 8.01-8.08 (2H m).

Step C

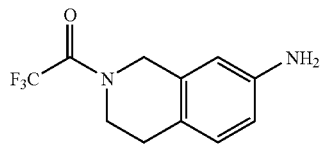

A solution of the product from Step B (16 g, 58 mmol) in ethanol (200 mL) was hydrogenated in a Parr Apparatus at 50 psi over PtO$_2$ until hydrogen uptake ceased. The catalyst was removed by filtration through celite and the filtrate was concentrated in vacuo to give to the product (14.2 g, 100%); $^1$H NMR 500 MHz (CDCl$_3$) δ=2.84 (2H, t, J=5.7 Hz), 3.35 (2H, br s), 3.80 and 3.84 (2H, t, J=6.0 Hz), 4.64 and 4.69 (2H, s), 6.45 (1H, d, J=10.0 Hz), 6.57 (1H, t d, J=2.4 and 8.5 Hz), 6.95 (1H, d, J=8.5 Hz).

Step D

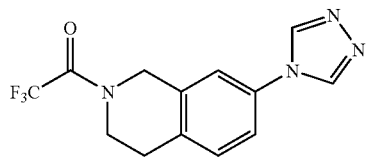

To a solution of the product from Step C (2.0 g, 8.7 mmol) in toluene (50 mL) was added N,N-dimethylformamide azine (2.3 g, 16 mmol) and a spatula end of toluene sulfonic acid, and the resulting mixture was heated at reflux for 24 h. The mixture was concentrated in vacuo and the residue was partitioned between CH$_2$Cl$_2$ (50 mL) and water (50 mL). The organic layer was separated and washed with saturated NaHCO$_3$ (25 mL) and saturated NaCl (25 mL), dried over MgSO$_4$, filtered and concentrated in vacuo. The residue was triturated with CH$_2$Cl$_2$ (4 mL), filtered and dried to give the product (1.0 g, 39%); $^1$H NMR 500 MHz (CDCl$_3$) δ=3.05 (2H, t, J=5.7 Hz), 3.90 and 3.95 (2H, t, J=6.0 Hz), 4.83 and 4.89 (2H, s), 7.20 (1H, d), 7.26 (1H, t), 7.38 (1H, t) 8.45 (2H, s).

Step E

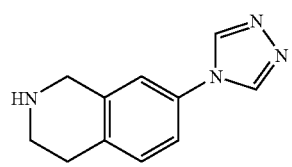

To a solution of the product from Step D (1.0 g, 3.4 mmol) in ethanol (50 mL) was added a solution of potassium carbonate (2.3 g, 17 mmol) in water (10 mL) and the resulting mixture was heated at reflux for 90 minutes. The cooled reaction mixture was concentrated in vacuo and the solid residue was extracted with $CH_2Cl_2$ (3×10 mL). The combined $CH_2Cl_2$ layers were evaporated in vacuo and the residue was purified by column chromatography on silica eluting with 10% $CH_3OH$ in $CH_2Cl_2$ containing 0.5% $NH_4OH$ to give the product (550 mg, 82%); $^1H$ NMR 500 MHz ($CDCl_3$) δ=2.69 (1H, br s), 2.85 (2H, t, J=5.9 Hz), 3.17 (2H, t, J=6.0 Hz), 4.07 (2H, s), 7.20 (1H, d, J=1.8 Hz), 7.14 (1H, dd, J=1.8 and 8.0 Hz), 7.23 (1H, d, J=8.0 Hz), 8.43 (2H, s).

Step F

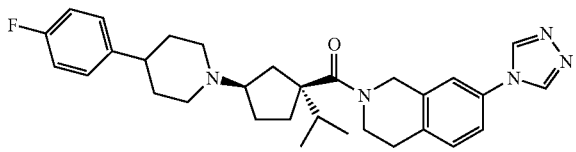

This product was prepared in an analogous fashion to that of Example 81, except Intermediate I was replaced with the product described in Step E. The crude product was purified by preparative TLC (eluant: 10% methanol: 89.5% DCM: 0.5% $NH_4OH$) to yield Example 30 as a mixture of two cis isomers. LC-MS for $C_{31}H_{39}FN_5O$ calculated 515.31, found $[M+H]^+$ 516.

EXAMPLE 111

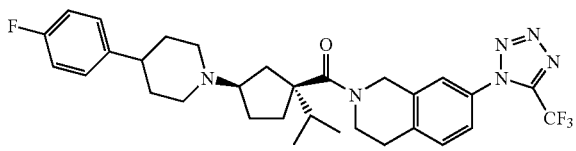

Step A

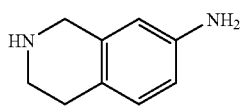

To a solution of the trifluoroacetamide produced in Step C of Example 110 (7.5 g, 31 mmol) in ethanol (200 mL) was added a solution of potassium carbonate (17 g, 120 mmol) in water (50 mL), and the resulting mixture was heated at reflux for 90 minutes. The cooled reaction mixture was concentrated in vacuo, and the residue was diluted with water (200 mL). The mixture was extracted with $CH_2Cl_2$ (3×100 mL). The combined $CH_2Cl_2$ layers were dried over $Na_2SO_4$, filtered and concentrated to give the product (3.76 g, 83%); $^1H$ NMR 500 MHz ($CDCl_3$) δ=2.69 (2H, t, J=6.0 Hz), 3.11 (2H, t, J=6.0 Hz), 3.45 (2H, br s), 3.92 (2H, s), 6.36 (1H, d, J=2.3 Hz), 6.52 (1H, dd, J=2.3 and 8.0 Hz), 6.89 (1H, d, J=8.0 Hz).

Step B

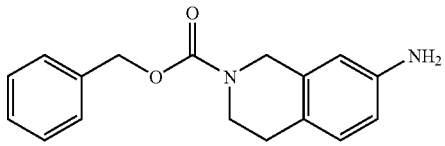

To a solution of the product from Step A (3.76 g, 25.4 mmol) in tetrahydrofuran (100 mL) was added triethylamine (4.24 mL, 30.5 mmol), and benzyl chloroformate (4.0 mL, 28 mmol), and the resulting mixture was stirred at room temperature for 4 h. Ethyl acetate (100 mL) was added to the reaction mixture and the whole was washed with water (250 mL), 5% citric acid solution (150 mL), saturated $NaHCO_3$ (150 mL), and saturated NaCl (100 mL), dried over $MgSO_4$, filtered and concentrated in vacuo to give the product (7.2 g, 100%).

Step C

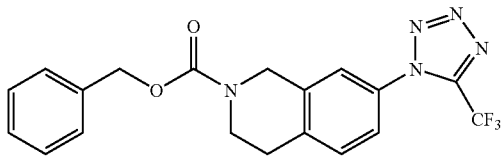

To a solution of the product from Step B (7.2 g, 25 mmol) and pyridine (5.1 mL, 64 mmol) in $CH_2Cl_2$ (150 mL) cooled in an ice bath was added trifluoroacetic anhydride (5.38 mL, 38.1 mmol), and the resulting mixture was stirred at room temperature for 5 h. The mixture was poured onto ice (150 g) and extracted with $CH_2Cl_2$ (4×100 mL). The combined $CH_2Cl_2$ layers were washed with 1 N HCl (4×75 mL), saturated NaCl (100 mL), dried over $MgSO_4$, filtered and evaporated. The residue was dissolved in $CCl_4$ (200 mL) and triphenylphosphine (10 g, 38 mmol) was added and the resulting mixture was heated at reflux for 15 h, cooled and concentrated in vacuo. The residue was dissolved in anhydrous N,N-dimethyl formamide (150 mL) and this solution was added to a solution of sodium azide (1.65 g, 25.4 mmol) in anhydrous N,N-dimethyl formamide (75 mL), and the resulting mixture was stirred at room temperature for 3 h. The reaction mixture was poured into water (500 mL) and extracted with $Et_2O$ (3×100 mL). The combined $Et_2O$ layers were washed with water (2×250 mL), saturated NaCl (100 mL), dried over $MgSO_4$, filtered and concentrated in vacuo. The residue was purified by column chromatography on silica eluting with a gradient ranging from 10% EtOAc in hexanes to 20% EtOAc in hexanes to give the product (3.4 g, 33%); $^1H$ NMR 500 MHz ($CDCl_3$) δ=2.99 (2H, br m), 3.80 (2H, t, J=6.0 Hz), 4.75 (2H, s), 5.21 (2H, s), 7.20-7.45 (8H, m).

Step D

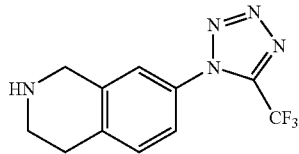

To a nitrogen flushed solution of the product from step C (3.4 g, 8.4 mmol) in methanol (100 mL) was added 10% palladium on carbon (500 mg) and the resulting mixture was stirred under a balloon of hydrogen for 5 h. The catalyst was removed by filtration through celite and the filtrate was evaporated in vacuo to give the product (2.2 g, 97%); $^1$H NMR 500 MHz (CDCl$_3$) δ=2.33 (1H, br s), 2.91 (2H, t, J=6.0 Hz), 3.19 (2H, t, J=6.0 Hz), 4.08 (2H, s), 7.14 (1H, d, 1.8 Hz), 7.22 (1H, dd, J=1.8 and 8.2 Hz), 7.31 (1H, d, J=8.2 Hz).

Step E

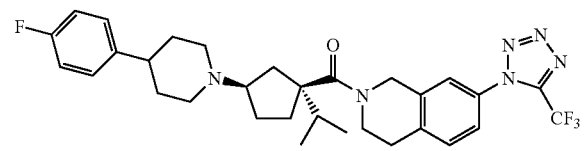

This product was prepared in an analogous fashion to that of Example 81, except Intermediate I was replaced with the product described in Step D. The crude product was purified by preparative TLC (eluant: 10% methanol: 89.5% DCM: 0.5% NH$_4$OH) to yield Example 31 as a mixture of two cis isomers. LC-MS for C$_{31}$H$_{36}$F$_3$N$_6$O calculated 584.29, found [M+H]$^+$ 585.

EXAMPLE 112

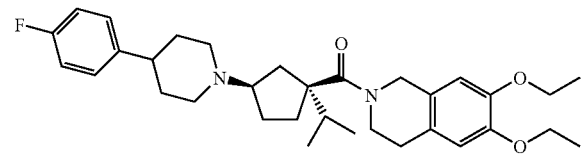

This product was prepared in an analogous fashion to that of Example 81, except Intermediate 1 was replaced with commercially available 6,7-diethoxy-tetrahydroisoquinoline. The crude product was purified by preparative TLC (eluant: 5% ethanol: 94% DCM: 1.0% NH$_4$OH) to yield Example 32 as a mixture of two cis isomer. LC-MS for C$_{33}$H$_{45}$FN$_2$O$_3$ calculated 536.34, found [M+H]$^+$ 537.

EXAMPLE 113

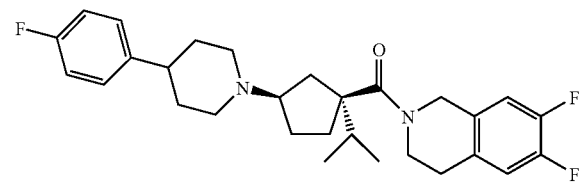

Step A

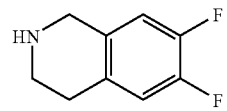

This product was prepared in a similar manner to Intermediate 1, except 2-Fluoro-4-trifluoromethyl phenylacetonitrile was replaced with 3,4-di-fluoromethyl phenylacetonitrile. LC-MS for C$_9$H$_9$F$_2$N calculated 169.07, found [M+H]$^+$ 170.1

Step B

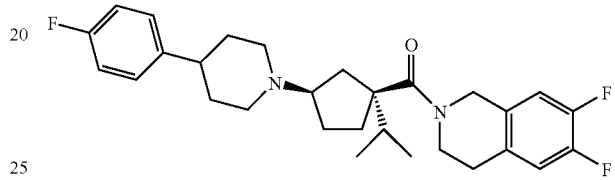

This product was prepared in an analogous fashion to that of Example 81, except Intermediate 1 was replaced with the product described in Step A. The crude product was purified by preparative TLC (eluant: 6% ethanol: 93% DCM: 1.0% NH$_4$OH) to yield Example 33 as a mixture of two cis isomers. LC-MS for C$_{29}$H$_{35}$F$_3$N$_2$O calculated 484.27, found [M+H]$^+$ 485.

EXAMPLE 114

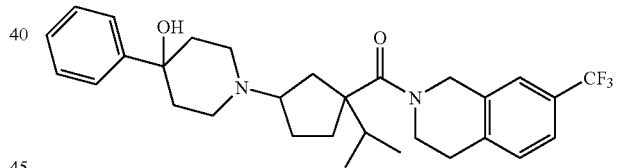

This product was prepared in an analogous fashion to that of Example 82, except Intermediate 8 was replaced with commercially available 4-hydroxy-4-phenylpiperidine. The crude product was purified by preparative TLC (eluant: 10% methanol: 89% DCM: 1.0% NH$_4$OH) to yield Example 114 as a mixture of four isomers. LC-MS for C$_{30}$H$_{37}$F$_3$N$_2$O$_2$ calculated 514.28, found [M+H]$^+$ 515.

EXAMPLE 115 AND 116

EXAMPLE 115

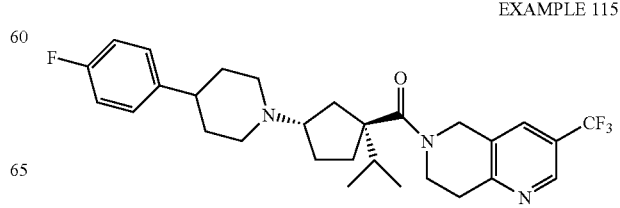

EXAMPLE 116

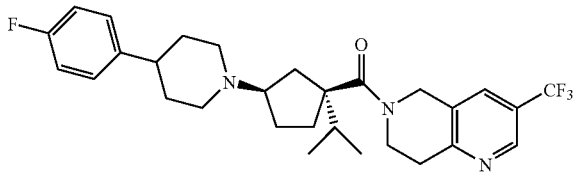

A solution of Intermediate 5 (100 mg, 0.22 mmol), 4-fluorophenylpiperidine hydrochloride (57 mg, 0.26 mmol), diisopropylethylamine (45 µL, 0.26 mmol) and crushed molecular sieves (4 Å, 50 mg) in dichloroethane (5 mL) was treated with sodium triacetoxyborohydride (233 mg, 1.10 mmol) and stirred at room temperature overnight. The reaction was quenched with saturated sodium bicarbonate (10 mL) and diluted with an additional 10 mL of DCE. The organic layer was separated and the aqueous layer was washed with dichloromethane (2×5 mL). The organics were combined, dried over anhydrous sodium sulfate, filtered and evaporated. The residue was purified by preparative TLC (eluent: 0.5% NOH: 5% MeOH: 94.5% $CH_2Cl_2$) to yield 72.3 mg (63%) of the final product as a mixture of two diastereomers. The separation was accomplished by using a HPLC equipped with a preparatory ChiralCel OD column eluting with an eluant of 15% ethanol and 85% hexane with a flow rate of 9 mL/min. This afforded the undesired trans isomer (35 mg, 50%) and the desired cis isomer (25 mg, 36%). Total recovery 86%. LC-MS for both: $C_{29}H_{35}N_3OF_4$ calculated 517.28, found $[M+H]^+$ 518.3.

Example 115: $^1$H NMR (1st isomer, undesired) (500 MHz, $CDCl_3$) δ 8.73 (s, 1H), 7.69 (s, 1H), 7.20 (app dd, J=5.5, 8.6 Hz, 2H) 6.98 (app t, J=8.6 Hz, 2H), [4.88 (d, J=17.5 Hz, 1H), 4.80 (d, J=17.5 Hz, 1H) (ABx q)]4.05-3.96 (m, 1H), 3.88 (app dt, J=5.9, 13.1 Hz, 1H), 3.27 (br d, J=11.4 Hz, 1H), 3.12 (br t, J=5.6 Hz, 3H), 2.83 (dd, J=5.7, 11.9 Hz, 1H), 2.52-2.44 (m, 1H), 2.43-2.34 (m, 1H), 2.16-1.95 (m, 6H), 1.86-1.74 (m, 4H), 1.45 (br t, J=10.0, 3H), 1.03 (d, J=6.6 Hz, 3H), 0.83 (d, J=6.6 Hz, 3H).

Example 116: $^1$H NMR (2$^{nd}$ isomer, desired) (500 MHz, $CDCl_3$) δ 8.72 (s, 1H), 7.69 (s, 1H), 7.19 (app dd, J=5.5, 8.6 Hz, 2H) 6.98 (app t, J=8.6 Hz, 2H), [4.94 (br s, 1H), 4.69 (br d, J=17.6 Hz, 1H) (ABx q)]4.05-3.80 (m, 1H), 3.20-3.08 (m, 4H), 2.68 (dd, J=6.6, 12.8 Hz, 1H), 2.52-2.43 (m, 2H), 2.28 (dd, J=7.3, 12.8 Hz, 1H), 2.14-2.00 (m, 3H), 1.97-1.87 (m, 2H), 1.83 (br d, J=12.8 Hz, 2H) 1.75 (br d, 12.4 Hz, 2H), 1.56-1.48 (m, 1H), 1.42-1.34 (m, 1H), 1.01 (d, J=6.5 Hz, 3H), 0.80 (d, J=6.6 Hz, 3H).

EXAMPLE 117

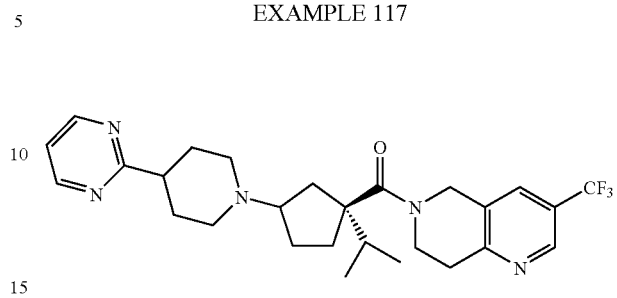

The hydrochloride salt of the pyrimidyl piperidine (Intermediate 8, 133 mg, 0.564 mmol) was combined with Intermediate 5 (100 mg, 0.282 mmol), DIEA (240 µL, 1.40 mmol), and 4 Å powdered molecular sieves (200 mg) in DCM. After 15 minutes at room temperature, sodium triacetoxyborohydride (300 mg, 1.41 mmol) was added and the resulting mixture was stirred for 3 days before being filtered through celite, diluted with DCM and washed with saturated sodium bicarbonate and brine. The organic layer was dried over $Na_2SO_4$, filtered and concentrated under reduced pressure to give a crude oil that was purified by preparative TLC (silica gel, 0.5% $NH_{40}OH$/4.5% MeOH/95% DCM) to give 126 mg of a colorless oil. Resolution of the cis/trans isomers was accomplished by HPLC using a ChiralPak OD column eluting with 20% ethyl alcohol/hexanes to give 57 mg of the trans isomer and 45 mg of the cis isomer.

First peak 57 mg: ESI-MS calc. for C27H34F3N5O: 501.27; found 502 (M+H).

Second peak 45 mg: ESI-MS calc. for C27H34F3N5O: 501.27; found 502 (M+H).

EXAMPLES 118-129

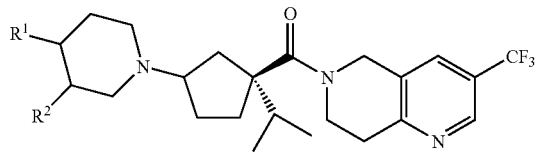

Several other examples were prepared in a similar fashion to Example 117, utilizing different piperidine intermediates. These Examples (118-129) are shown below.

| Example | R$^1$ | R$^2$ | Molecular Formula | Calculated [M] | Found [M + H] |
|---------|-------|-------|-------------------|----------------|---------------|
| 118 | ![pyrimidinyl] | H | C27H34F3N5O | 501.27 | 502 |

-continued
| Example | R¹ | R² | Molecular Formula | Calculated [M] | Found [M + H] |
|---|---|---|---|---|---|
| 119 | 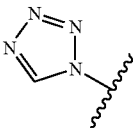 | H | C24H32F3N7O | 491.26 | 492 |
| 120 | 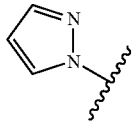 | H | C26H34F3N5O | 489.27 | 490 |
| 121 | 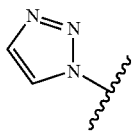 | H | C25H33F3N6O | 490.27 | 491 |
| 122 | 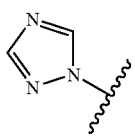 | H | C25H33F3N6O | 490.27 | 491 |
| 123 | 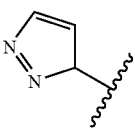 | H | C26H34F3N5O | 489.27 | 490 |
| 124 | 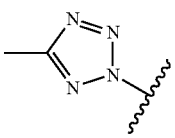 | H | C25H34F3N7O | 505.28 | 506 |
| 125 | 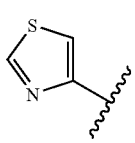 | H | C26H33F3N4OS | 506.23 | 507 |
| 126 | 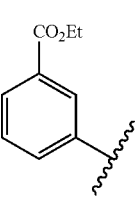 | H | C32H43F3N3O3 | 574.33 | 575 |
| 127 | 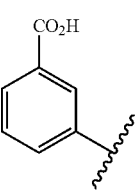 | H | C30H39F3N3O3 | 546.29 | 547 |
| 128 | 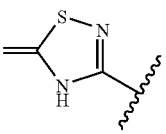 | H | C25H32F3N5O2S | 523.22 | 524 |

-continued

| Example | R¹ | R² | Molecular Formula | Calculated [M] | Found [M + H] |
|---|---|---|---|---|---|
| 129 | H | (4-methyl-1,2,4-triazol-3-yl) | C26H35F3N6O | 504.28 | 505 |

EXAMPLE 130

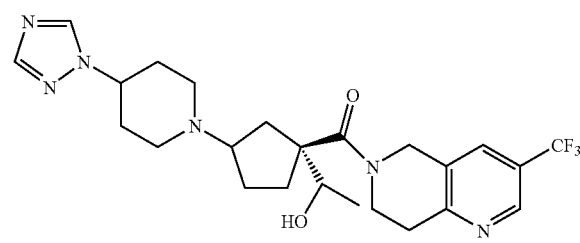

Step A

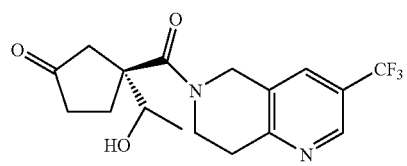

This ketone was obtained from the racemic Intermediate 6 by resolution on the ChiralCel OD preparative column, eluting with 15% ethyl alcohol in hexanes at 9.0 mL/min. The faster eluting enantiomers retention time under analogous analytical conditions (1.0 mL/min) was 11.25 minutes. LC MS for $C_{17}H_{19}F_3N_2O_3$ calculated 356.13, found 357.05 $[M+H]^+$.

Step B

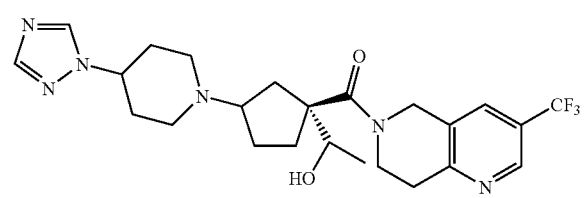

The final compound was synthesized starting from the faster eluting ketone described in Step A of this example and Intermediate 10 according to the procedure described in Example 19. The respective cis- and trans-diastereoisomeric mixtures were separated by preparative TLC. LC MS for $C_{24}H_{31}F_3N_6O_2$ calculated 492.25, found 493.30 $[M+H]^+$.

EXAMPLE 131

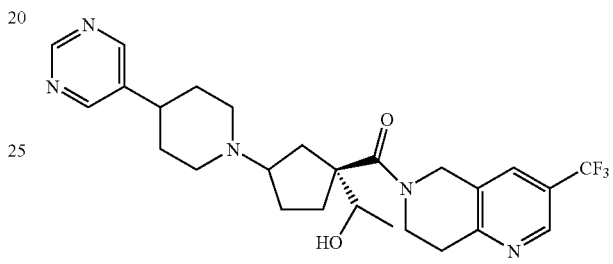

This compound was synthesized starting from the ketone preparation of which was described in Example 130, Step A and Intermediate 9 according to the procedure described in Example 19. LC MS for $C_{26}H_{32}F_3N_5O_2$ calculated 503.25, found 504.25 $[M+H]^{30}$.

EXAMPLE 132

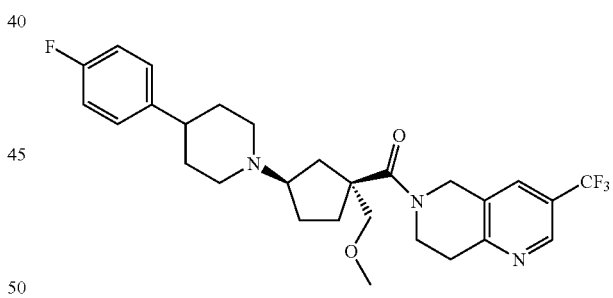

Step A

This ketone was synthesized following procedures described in Intermediates 6, except that methoxymethyl chloride was used instead of acetaldehyde in Step C, Intermediate 6. The respective enantiomers were obtained by HPLC separation using a ChiralCel OD preparative column (eluent hexane:ethyl alcohol/85:15, 9.0 mL/min). LC MS for $C_{26}H_{32}F_3N_5O_2$ calculated 503.25, found 504.25 [M+H]+.

Step B

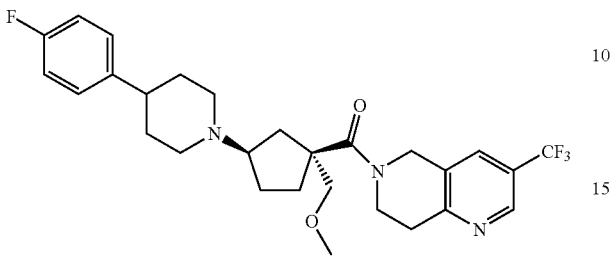

The final compound was prepared starting from the ketone from Step A and 4-(4-fluorophenyl)piperidine according to the procedure described in Example 19. The respective isomers were obtained by preparative TLC (eluent ethyl acetate: ethyl alcohol:ammonium hydroxide/90:9:1). LC MS for $C_{26}H_{32}F_3N_5O_2$ calculated 503.25, found 504.70 [M+H]+.

EXAMPLE 133

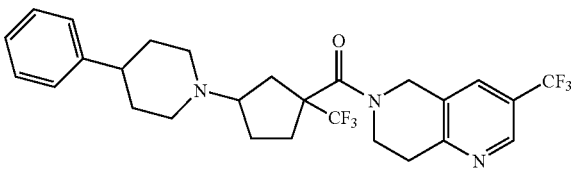

Step A

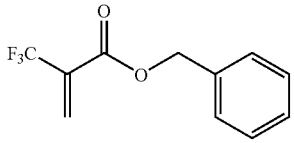

To a mixture of 2-(trifluorormethyl)acrylic acid (20.0 g, 143 mmol) and benzyl alcohol (14.8 mL, 142 mmol) in DCM (150 mL), was added EDC (40.93 g, 214.2 mmol) in portions. The reaction mixture was stirred for 2 h, diluted by DCM, washed with water and brine, dried over $Na_2SO_4$, filtered and concentrated. The residue was purified by flash column chromatography (silica gel, 5% EtOAc/hexane) to yield the product (13.7 g, 42%) as a viscous oil. $^1$H-NMR (400 MHz, CDCl$_3$) δ 7.36-7.43 (m, 5H), 6.78 (d, 1H), 6.48 (d, 1H), 5.32 (s, 2H).

Step B

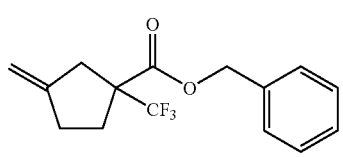

To a flamed dried flask was added 2-[(trimethylsilyl)methyl]-2-propen-1-yl acetate (12.18 mL, 57.35 mmol) and the intermediate described in Step A, Example 52 (13.2 g, 57.4 mmol), and tetrakis(triphenylphosphine)palladium(0) (13.3 g, 11.5 mmol) in THF (200 mL) under nitrogen. The reaction mixture was refluxed overnight, diluted by DCM (150 mL), filtered, and concentrated. The residue was purified by flash column chromatography (silica gel, 100% hexane to 2.5% EtOAc/hexane to 5% EtOAc/hexane) to afford the product (11.68 g, 71.7%). $^1$H-NMR (400 MHz, CDCl$_3$) δ 7.33-7.42 (m, 5H), 5.23 (s, 2H), 4.93 (m, 2H), 3.03 (m, 1H), 2.78 (m, 1H), 2.36-2.52 (m, 3H), 2.12-2.24 (m, 1H).

Step C

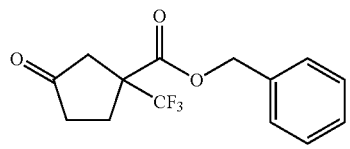

A solution of the product described in Step B (11.6 g, 40.8 mmol) in DCM (150 mL) was cooled to −78° C. and saturated with nitrogen. Ozone was bubbled into the reaction mixture until the solution became blue, then triphenylphosphine (12.8 g, 49.0 mmol) was added to the mixture. The reaction mixture was stirred overnight, and then evaporated under reduced pressure. The residue was purified by flash column chromatography (silica gel, 30% EtOAc/hexane) to yield the title compound (8.49 g, 72.7%). $^1$H-NMR (400 MHz, CDCl$_3$) δ 7.33-7.42 (m, 5H), 5.26 (s, 2H), 2.92 (m, 1H), 2.65 (m, 1H), 2.35-2.54 (m, 4H).

Step D

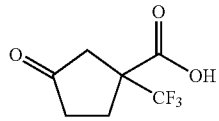

To a solution of the intermediate described in Step C (1.00 g, 3.49 mmol) in ethanol (60 mL), was added Pd—C (10%, 100 mg). The reaction mixture was placed in a Parr-shaker and shaken under 50lb pressure of $H_2$ for 1.5 h. The solution was diluted by methanol, filtered through celite and evaporated under vacuum to afford the acid (692 mg, 100%) as a yellow oil. LC-MS calc. for $C_7H_7F_3O3$: 196.03; Found: 197 (M+H).

Step E

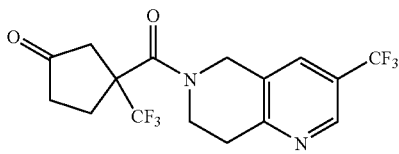

To a mixture of the product described in Step D (684 mg, 3.49 mmol), EDC (2.01 g, 10.5 mmol), and Intermediate 2

(916 mg, 3.84 mmol) in DCM (30 mL) was added DIEA (670 µL, 3.84 mmol) and the resulting solution was stirred overnight at room temperature. The reaction mixture was diluted with DCM, washed by water and brine, dried over Na₂SO₄, filtered and evaporated in vacuo. The residue was purified by column chromatography (silica gel, 50% EtOAc/hexane) to afford the title compound. ¹H-NMR (400 MHz, CDCl₃) δ 8.75 (s, 1H), 7.71 (s, 1H), 4.86 (d, J=5.5 Hz, 2H), 3.91-4.08 (m, 2H), 3.18 (t, J=5.0 Hz, 2H), 2.98 (s, 2H), 2.64-2.85 (m, 2H), 2.43-2.56 (m, 2H). LC-MS calc. for C16H14F6N2O2: 380.10; Found: 381 (M+H).

Step F

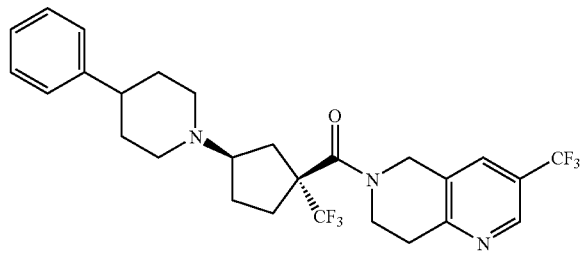

To a mixture of the compound described in Step E (100 mg, 0.263 mmol), 4-phenylpiperidine HCl salt (52 mg, 0.26 mmol), molecular sieve (4 Å, 180 mg), DIEA (46 µL, 0.26 mmol) in DCM (5 mL), was added sodium triacetoxyborohydride (167 mg, 0.789 mmol) and the resulting mixture was stirred overnight at room temperature. The reaction was diluted with DCM, filtered through celite, and evaporated under reduced pressure. The residue was purified by preparative TLC (1000 micron, eluant: 0.4% aqueous NH₄OH: 4% MeOH: 95.6% DCM) to yield a mixture of cis- and trans-isomers as a free base. The cis- and trans-isomers were separated by preparative chiral HPLC (chiral OD column, eluant: 5% EtOH/hexane) to yield the final product of the title compound as the desired cis isomers. Its HCl salt (20.4 mg) was formed by treatment with 4 N HCl/dioxane. ¹H-NMR (400 MHz, CDCl₃) δ 8.74 (s, 1H), 7.70 (s, 1H), 7.20-7.35 (m, 5H), 4.85 (m, 2H), 3.99 (m, 2H), 3.14-3.24 (m, 5H), 2.46-2.56 (m, 3H), 2.02-2.22 (m, 5H), 1.70-1.91 (m, 5H). LC-MS calc. for C27H29F6N3O: 525.22; Found: 526 (M+H).

EXAMPLE 134

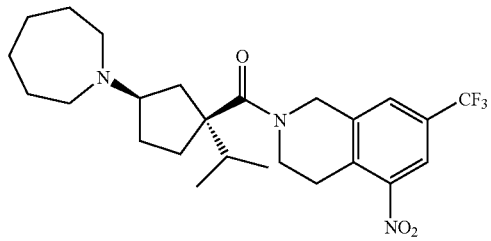

Step A

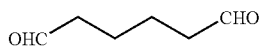

To a stirred, −78° C. solution of cyclohexene (15 mL) in 100 mL of dichloromethane was bubbled in ozone until light blue color appeared. Excessive ozone was removed by a nitrogen flow, then 60 mL of dimethyl sulfide was added. The mixture was left overnight, dried over sodium sulfate. The solvent and DMS were removed under low vacuum. The crude product was used in next step without further purification.

Step B

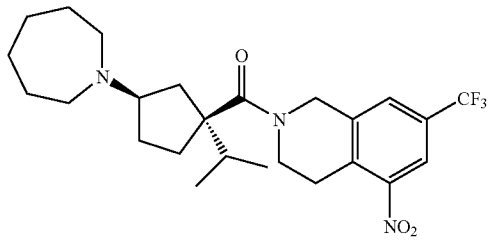

A mixture of Intermediate 27 (135 mg, 0.3 mmol), the 1,6-hexane-dialdehyde from Step A (~100 mg), molecular sieve (4 Å, 50 mg), DIEA (130 mg, 1.0 mmol) in DCM (10 mL crude material) was stirred for 5 min. Then sodium triacetoxyborihydride (424 mg, 2.0 mmol) was added. The resulting mixture was stirred for 2 h, quenched with sat. aq. Na₂CO₃, filtered, washed with DCM. The filtrates were separated, the aq. solution was extracted with DCM. The combined DCM layers were dried over Na₂SO₄, evaporated. The residue was purified on preparative TLC (1000 micron) (developed by 10% [aq. NH₄OH/MeOH 1/9]/DCM) to yield the final product of the title compound as a free base. Its HCl salt (42 mg) was formed by treatment with 4 M HCl/dioxane. ESI-MS calc. For C25H34F3N3O3: 481; Found: 482 (M+H).

EXAMPLE 135

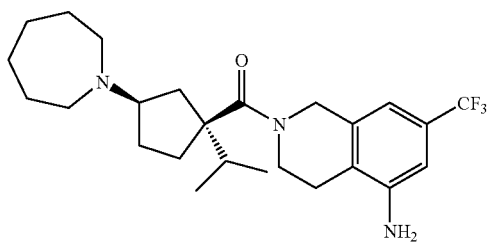

A mixture of the Example 134 (35 mg), Pd/C (5%, 5 mg) and methanol (20 mL) was hydrogenated on a Parr Apparatus for one hour. The catalyst was removed by filtration. The filtrate was evaporated to afford the title product as a white solid (32 mg). ESI-MS calc. For C25H36F3N3O: 451; Found: 452 (M+H).

EXAMPLE 136

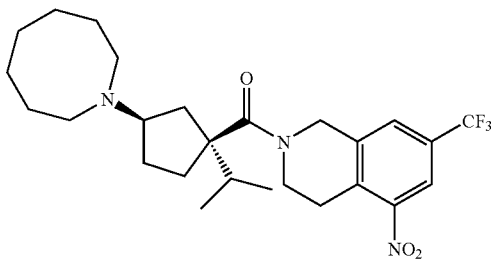

Step A

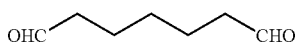

To a stirred, −78° C. solution of cycloheptene (5 mL) in 50 mL of dichloromethane was bubbled in ozone until light blue color appeared. Excessive ozone was removed by a nitrogen flow, then 20 mL of dimethyl sulfide was added. The mixture was left overnight, dried over sodium sulfate. The solvent and DMS were removed under low vacuum. The crude product was used in next step without further purification.

Step B

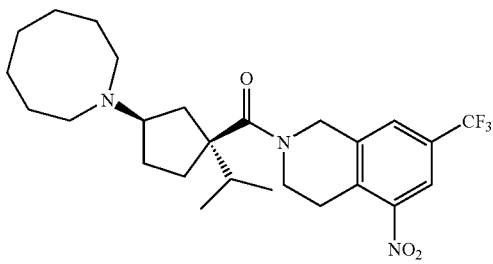

A mixture of the Intermediate 27 (135 mg, 0.3 mmol), 1,7-heptane-dialdehyde from Step A) (~100 mg), molecular sieve (4 Å, 50 mg), DIEA (130 mg, 1.0 mmol) in DCM (10 mL crude material) was stirred for 5 min. Then sodium triacetoxyborohydride (424 mg, 2.0 mmol) was added. The resulting mixture was stirred for 2 h, quenched with sat. aq. Na2CO3, filtered, washed with DCM. The filtrates were separated, the aq. solution was extracted with DCM. The combined DCM layers were dried over Na2SO4, evaporated. The residue was purified on preparative TLC (1000 micron) (developed by 10% [aq. NH4OH/MeOH 1/9]/DCM) to yield the final product of the title compound as a free base. Its HCl salt (50 mg) was formed by treatment with 4 M HCl/dioxane. ESI-MS calc. For C26H36F3N3O3: 485; Found: 486 (M+H).

EXAMPLE 137

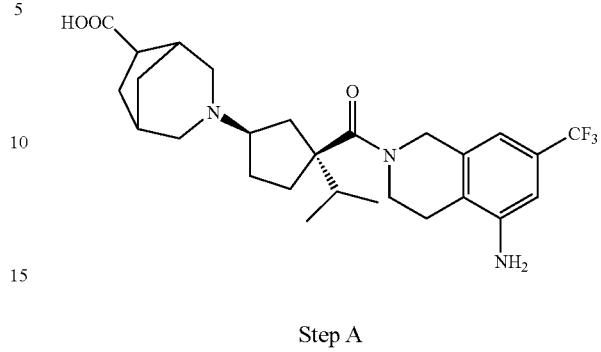

Step A

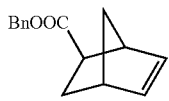

5-Norbornene-2-carboxylic acid (5.4 g, 40 mmol), benzyl alcohol (4.3 g, 40 mmol), EDAC.HCl (9.5 g, 50 mmol), DIEA (5.2 g, 40 mmol) were weighed into a flask. 50 mL of dichloromethane was added. The mixture was stirred overnight, washed with 2 M aq. HCl, water and sat. aq. sodium carbonate, dried over sodium sulfate, evaporated. The residue was purified on MPLC (10% EtOAc/Hexane). The title compound was obtained as a mixture of exo and endo isomers (5.2 g).

Step B

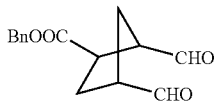

To a stirred, −78° C. solution of benzyl 5-norbornene-2-carboxylate (1.2 g, 5 mmol) in 50 mL of dichloromethane was bubbled in ozone until light blue color appeared. Excessive ozone was removed by a nitrogen flow, then 20 mL of dimethyl sulfide was added. The mixture was left overnight, dried over sodium sulfate. The solvent and DMS were removed under low vacuum. The crude product was used in next step without further purification.

Step C

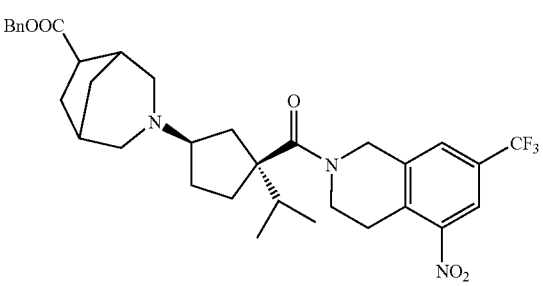

A mixture of the Intermediate 27 (86 mg, 0.2 mmol), the di-aldehyde ester from Step B (~200 mg), molecular sieve (4 Å, 500 mg), DIEA (130 mg, 1.0 mmol) in DCM (10 mL crude material) was stirred for 5 min. Then sodium triacetoxyborohydride (420 mg, 2.0 mmol) was added. The resulting mixture was stirred for 2 h, quenched with sat. aq. $Na_2CO_3$, filtered, washed with DCM. The filtrates were separated, the aq. solution was extracted with DCM. The combined DCM layers were dried over $Na_2SO_4$, evaporated. The residue was purified on preparative TLC (1000 micron) (developed by 10% [aq. NH4OH/MeOH 1/9]/DCM) to yield the final product of the title compound as a free base. Its HCl salt (62 mg) was formed by treatment with 4N HCl/dioxane. ESI-MS calc. For C34H40F3N3O5: 627; Found: 428 (M+H).

Step D

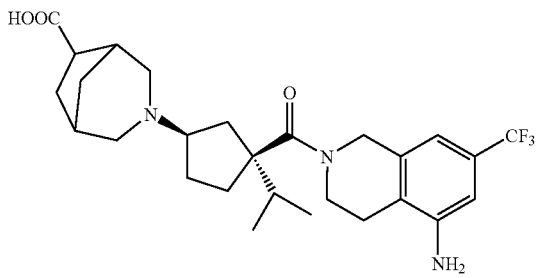

A mixture of the amino ester from Step C (60 mg), Pd/C (5%, 100 mg) and methanol (20 mL) was hydrogenated on a Parr Aparatus under 50 lbs of hydrogen for one hour. The catalyst was removed by filtration. The filtrate was evaporated, the residue was purified on preparative TLC (developed by methanol) to afford the title product as a white solid (18 mg). ESI-MS calc. For C27H36F3N3O: 507; Found: 508 (M+H).

EXAMPLE 138

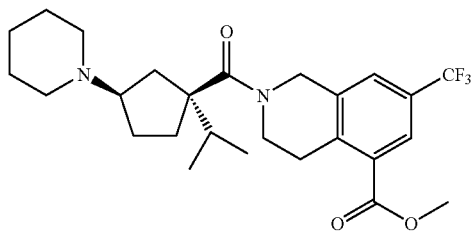

Step A

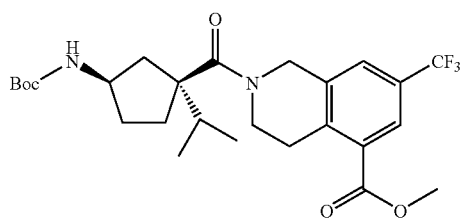

A mixture of Intermediate 26 (as HCl salt, 1.2 g, 4.0 mmol), Intermediate 23 (1.1 g, 4.0 mmol), PyBrOP (1.9 g, 4.0 mmol), DMAP (0.29 g, 2.4 mmol) and DIEA (2.8 mL, 16 mmol) in 10 mL of dichloromethane was stirred at room temperature overnight. The entire mixture was applied to a silica gel column and eluted with 20% ethyl acetate/hexane. The title compound was obtained as a white solid (1.7 g, 83%). LC-MS for C26H35F3N2O5 calculated 512, found [M+H−100][30] 413.

Step B

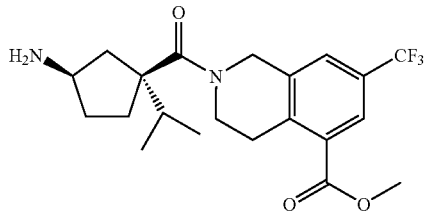

The above amide from Step A (1.7 g, 3.3 mmol) was mixed with 20 mL of 4 M HCl/dioxane. The resulting solution was stirred for one hour, evaporated and dried under high vacuum to yield the title product as a white solid (1.45 g, 100%). LC-MS for C21H27F3N2O3 calculated 412, found [M+H]$^+$ 413.

Step C

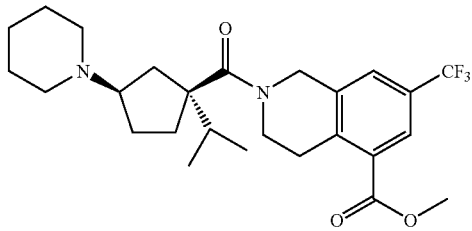

A mixture of the above intermediate from Step B (140 mg, 0.30 mmol), glutaric dialdehyde (50% $H_2O$, 120 mg, 0.60 mmol), molecular sieve (4 Å, 1500 mg), DIEA (52 mg, 0.40 mmol) in DCM (10 mL) was stirred for 5 min. Then sodium triacetoxyborohydride (212 mg, 1.00 mmol) was added. The resulting mixture was stirred for one hour, quenched with sat. aq. $Na_2CO_3$, filtered, washed with DCM. The filtrates were separated, the aq. solution was extracted with DCM. The combined DCM layers were dried over $Na_2SO_4$ and evaporated. The residue was purified on preparative TLC (1000 micron) (developed by 10% [aq. NH4OH/MeOH 1/9]/DCM) to yield the final product of the title compound as a free base. Its HCl salt (80 mg) was formed by treatment with 4N HCl/dioxane. ESI-MS calc. For C26H35F3N2O3: 480; Found: 481 (M+H).

EXAMPLE 139

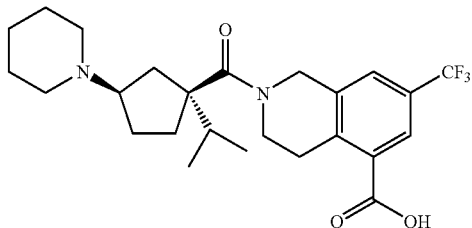

A mixture of Example 138 (45 mg, 0.090 mmol), lithium hydroxide monohydrate (50 mg), water (0.1 mL) and methanol (1.0 mL) was stirred at room temperature overnight, the entire mixture was loaded on preparative TLC and developed with methanol. The title compound as obtained as white solid (34 mg). LC-MS for C25H33F3N2O3 calculated 466, found [M+H]+ 467.

EXAMPLE 140

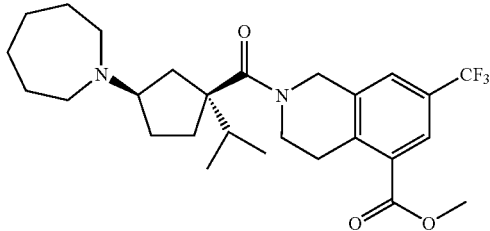

A mixture of the Intermediate from Example 138, Step B (140 mg, 0.30 mmol), 1,6-hexane dialdehyde from Example 136, Step A (~100 mg), molecular sieve (4 Å, 500 mg), DIEA (130 mg, 1.00 mmol) in DCM (20 mL) was stirred for 5 min. Then sodium triacetoxyborohydride (424 mg, 2.00 mmol) was added. The resulting mixture was stirred for one hour, quenched with sat. aq. Na2CO3, filtered, washed with DCM. The filtrates were separated, the aq. solution was extracted with DCM. The combined DCM layers were dried over Na2SO4, evaporated. The residue was purified on preparative TLC (1000 micron) (developed by 10% [aq. NH4OH/MeOH 1/9]/DCM) to yield the final product of the title compound as a free base. Its HCl salt (75 mg) was formed by treatment with 4 M HCl/dioxane. ESI-MS calc. For C27H37F3N2O3: 494; Found: 495 (M+H).

EXAMPLE 141

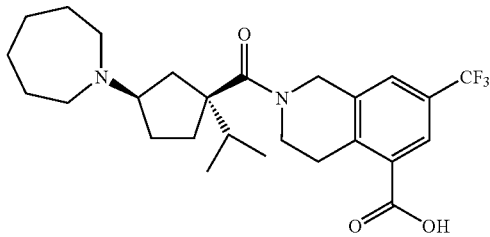

A mixture of the Example 140 (20 mg, 0.04 mmol), lithium hydroxide monohydrate (50 mg), water (0.1 mL) and methanol (1.0 mL) was stirred at room temperature overnight, the entire mixture was loaded on preparative TLC and developed with methanol. The title compound as obtained as white solid (15 mg). LC-MS for C26H35F3N2O3 calculated 480, found [M+H]+ 481.

EXAMPLE 142

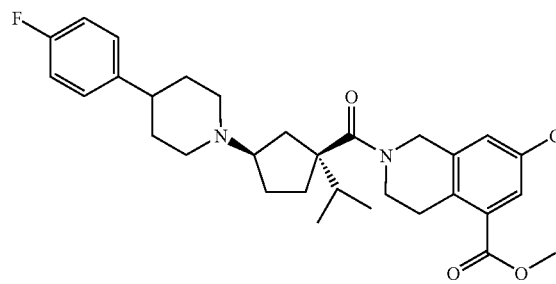

Step A

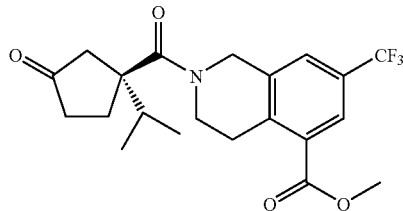

To a stirred solution of Intermediate 29 (190 mg, 1.1 mmol) in 1 mL of dichloromethane was added a solution of oxalyl chloride (2 M, 0.70 mL, 1.4 mmol) in dichloromethane, then a trace of DMF. The mixture was stirred at room temperature for 30 min. before being evaporated to remove the solvent and excessive reagent under vacuum. The residue was dissolved in 1 mL of dichloromethane and added into a solution of the Intermediate 2 (295 mg, 1.00 mmol) and DIEA (260 mg, 2.0 mmol) in dichloromethane (2 mL). The reaction was stirred for 2 h. The entire mixture was loaded onto preparative TLC plate (1000 micron) and developed with 10% MeOH/DCM. The title compound was obtained as yellow solid (300 mg). LC-MS for C21H24F3NO4 calculated 411, found [M+H]+ 412.

Step B

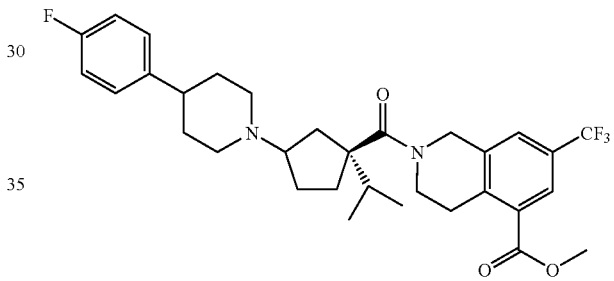

A mixture of the above ketone from Step A (300 mg, 0.73 mmol), 4-fluorophenylpiperidine hydrochloride (214 mg, 1.00 mmol), DIEA (129 mg, 1.00 mmol), molecular sieves (4 Å, 500 mg) and sodium triacetoxyborohydride (212 mg, 1.00 mmol) in 10 mL of dichloromethane was stirred at room temperature over the weekend, quenched with sat. aq. sodium carbonate, extracted with dichloromethane and purified on preparative TLC (1000 micron), eluting with 10% MeOH/ DCM. The title compound was obtained as a mixture of cis and trans isomers (270 mg). LC-MS for C32H38F4N2O3 calculated 574, found [M+H]+ 575.

EXAMPLE 143

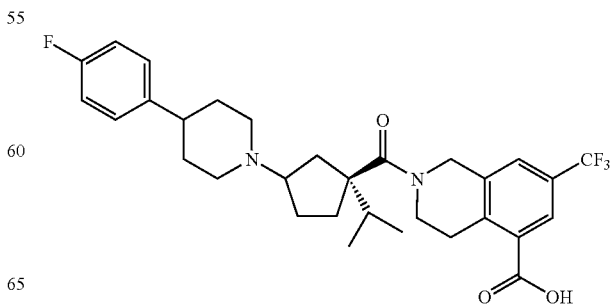

A mixture of the Example 142 (22 mg, 0.04 mmol), lithium hydroxide monohydrate (30 mg) in MeOH/H$_2$O (9/1, 0.5 mL) was stirred at 60° C. for 2 h., the entire mixture was loaded on a preparative TLC plate and developed with methanol. The title compound as obtained as white solid (12 mg). LC-MS for C31H34F4N2O3 calculated 560, found [M+H]$^+$ 561.

EXAMPLE 144

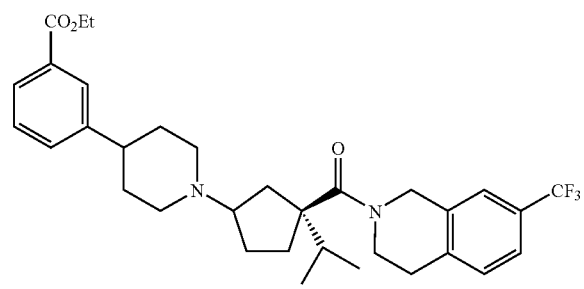

Step A:

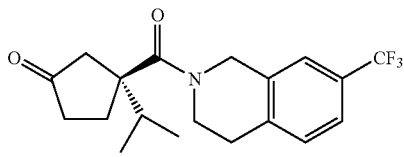

Intermediate 29 (100 mg, 0.588 mmol) was dissolved in DCM (20 mL) and treated sequentially with oxalyl chloride (153 μL, 1.76 mmol) and DMF (1 drop). The resulting solution was stirred at room temperature for 2 h, before being concentrated to dryness and dried under high vacuum for 30 min. The resulting residue was dissolved in DCM (5 mL) and added dropwise to a stirred solution of Intermediate 1 (177 mg, 0.882 mmol) in DCM (5 mL) and triethylamine (5 mL). The resulting reaction mixture was stirred at room temperature overnight, before being diluted with DCM and washed with bicarb, 1 N aqueous HCl, and brine. The organic layer was dried over MgSO$_4$, filtered, and concentrated under reduced pressure to give 230 mg of the desired crude product, which was used in the next step without further purification.

Step B:

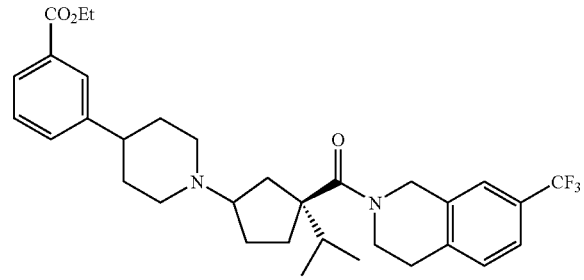

A mixture of the product from the previous step (115 mg, 0.326 mmol), ethyl 3-piperidin-4-ylbenzoate hydrochloride (131 mg, 0.489 mmol), DIEA (83 μL, 0.49 mmol), molecular sieves (4 Å, 100 mg) and sodium triacetoxyborohydride (346 mg, 1.63 mmol) in 10 mL of dichloromethane was stirred at RT over weekend, quenched with sat. aq. sodium bicarbonate, extracted with dichloromethane and purified on preparative TLC (silica gel, eluting with 40% THF/hexanes). The title compound was obtained as a mixture of cis and trans isomers (200 mg). LC-MS calc. for C33H41F3N2O3: 570.3; found [M+H]$^+$ 571.6. The individual stereosiomers were obtained by resolution on a ChiralCel OD column eluting with 10% ethanol/hexanes:

Peak 1: LC-MS calc. for C33H41F3N2O3: 570.3; found [M+H]$^+$ 571.6.

Peak 2: LC-MS calc. for C33H41F3N2O3: 570.3; found [M+H]$^+$ 571.6.

EXAMPLE 145

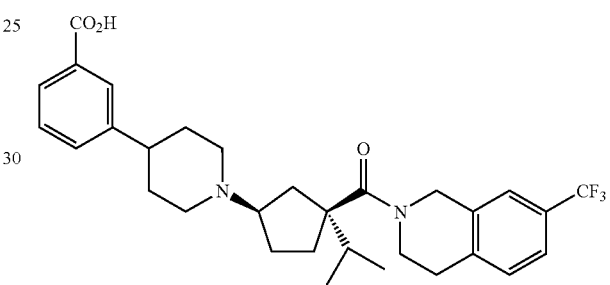

A mixture of the Example 144 Peak 2 (80 mg,), lithium hydroxide monohydrate (30 mg) in EtOH/H$_2$O (4/1, 4 mL) was stirred at room temperature overnight. The product was purified by reverse phase HPLC and converted to an HCl salt in the usual fashion. The title compound as obtained as white solid (45 mg). LC-MS calculated for C31H37F3N2O3: 542.28; found [M+H]$^+$ 543.

EXAMPLE 146

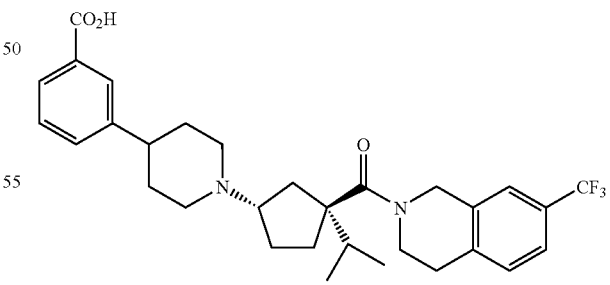

A mixture of the Example 144 Peak 1 (78 mg,), lithium hydroxide monohydrate (30 mg) in EtOH/H$_2$O (4/1, 4 mL) was stirred at room temperature overnight. The product was purified by reverse phase HPLC and converted to an HCl salt in the usual fashion. The title compound as obtained as white solid (49 mg). LC-MS calculated for C31H37F3N2O3: 542.28; found [M+H]$^+$ 543.

TABLE 8

Analogs Prepared in an Analogous Fashion to EXAMPLE 144

| EX. | Amine | X | Formula/calc. MW | ESI-MS observed M + H$^+$ (M + 1) |
|---|---|---|---|---|
| 147 | | C | C34H43F3N2O3 584 | 585 |
| 148 | | C | C34H43F3N2O3 584 | 585 |
| 149 | | C | C34H43F3N2O3 584 | 585 |
| 150 | | C | C34H43F3N2O3 584 | 585 |
| 151 | | N | C33H42F3N3O3 585 | 586 |
| 152 | | N | C33H42F3N3O3 585 | 586 |

TABLE 8-continued

Analogs Prepared in an Analogous Fashion to EXAMPLE 144

| EX. | Amine | X | Formula/calc. MW | ESI-MS observed M + H+ (M + 1) |
|---|---|---|---|---|
| 153 | (ethyl 3-(3-methylpiperidin-4-yl)benzoate) | N | C33H42F3N3O3 585 | 586 |
| 154 | (ethyl 3-(3-methylpiperidin-4-yl)benzoate, other stereoisomer) | N | C33H42F3N3O3 585 | 586 |
| 155 | (methyl 3-(piperidin-4-yl)benzoate) | N | C31H38F3N3O3 557 | 558 |
| 156 | (methyl 2-methyl-3-(piperidin-4-yl)benzoate) | N | C32H40F3N3O3 571 | 572 |
| 157 | (methyl 2-methoxy-5-(piperidin-4-yl)benzoate) | N | C32H38F3N3O4 585 | 586 |
| 158 | (methyl 2-methyl-3-(piperidin-4-yl)benzoate) | N | C32H38F3N3O3 569 | 570 |
| 159 | (2-(3-(piperidin-4-yl)phenyl)propan-2-ol) | N | C32H42F3N3O2 557 | 558 |

TABLE 8-continued

Analogs Prepared in an Analogous Fashion to EXAMPLE 144

| EX. | Amine | X | Formula/calc. MW | ESI-MS observed M + H+ (M + 1) |
|---|---|---|---|---|
| 160 | (3-isopropenylphenyl)piperidine | N | C32H40F3N3O 539 | 540 |
| 161 | methyl 4-fluoro-3-piperidinylbenzoate | N | C31H37F4N3O3 575 | 576 |
| 162 | methyl 3-fluoro-5-piperidinylbenzoate | N | C31H37F4N3O3 575 | 576 |
| 163 | 3-phenylpyrrolidine Mixture of 2 isomers | N | C28H34F3N3O 485 | 486 |
| 164 | methyl 2-fluoro-5-piperidinylbenzoate | N | C31H37F4N3O3 575 | 576 |
| 165 | 3-phenylpiperidine | N | C29H36F3N3O 499 | 500 |

TABLE 8-continued

Analogs Prepared in an Analogous Fashion to EXAMPLE 144

| EX. | Amine | X | Formula/calc. MW | ESI-MS observed M + H+ (M + 1) |
|---|---|---|---|---|
| 166 | (methyl 2-(3-(piperidin-4-yl)phenyl)acetate) | N | C32H40F3N3O3 571 | 572 |
| 167 | (methyl 2-fluoro-5-(piperidin-4-yl)benzoate) | C | C32H38F4N2O3 574 | 575 |
| 168 | (methyl 3-fluoro-5-(piperidin-4-yl)benzoate) | C | C32H38F4N2O3 574 | 575 |
| 169 | (3-hydroxy-5-(piperidin-4-yl)isoxazole) | N | C26H33F3N4O3 506 | 507 |
| 170 | (3-fluoropiperidine) mix. of 2 diastereomers | N | C23H31F4N3O 441 | 442 |
| 171 | (4-fluoropiperidine) | C | C24H32F4N2O 440 | 441 |
| 172 | ((S)-3-fluoropyrrolidine) | C | C23H30F4N2O 426 | 427 |
| 173 | ((R)-3-fluoropyrrolidine) | C | C23H30F4N2O 426 | 427 |

TABLE 8-continued

Analogs Prepared in an Analogous Fashion to EXAMPLE 144

[Structure: Amine—[cyclopentyl with isopropyl]—C(=O)—N(tetrahydropyridine fused to pyridine ring with CF3, with X in ring)]

| EX. | Amine | X | Formula/calc. MW | ESI-MS observed M + H+ (M + 1) |
|---|---|---|---|---|
| 174 | piperidine | C | C24H33F3N2O 422 | 423 |
| 175 | 4-(trifluoroacetamido)piperidine | C | C26H33F6N3O2 533 | 534 |
| 176 | 3,3-difluoropyrrolidine | C | C23H29F5N2O 444 | 445 |
| 177 | 3-(trifluoromethyl)pyrrolidine (Mix. of 2 diastereomers) | C | C24H30F6N2O 476 | 477 |
| 178 | pyrrolidine | C | C23H31F3N2O 408 | 409 |
| 179 | 3-(trifluoromethyl)piperidine (Mix. of 2 diastereomers) | C | C25H32F6N2O 490 | 491 |
| 180 | 3,3-difluoropiperidine | C | C24H31F5N2O 458 | 459 |
| 181 | 4,4-difluoropiperidine | C | C24H31F5N2O 458 | 459 |
| 182 | 4-(trifluoromethyl)piperidine | C | C25H32F6N2O 490 | 491 |

In many cases the analogs listed in TABLE 8 could be further modified to generate new target chemokine receptor modulators. For example, the ester groups of the analogs in this table were hydrolyzed to give the corresponding carboxylic acids which were themselves potent modulators. These hydrolyses were usually accomplished under the conditions shown in EXAMPLE 145 or with minor modifications to those conditions. A representative list of the resulting carboxylic acid containing chemokine receptor modulators is presented in TABLE 9.

TABLE 9

Carboxylic Acid Containing Analogs From Esters in Table 8

| EX. | Amine | X | Formula/calc. MW | ESI-MS observed M + H+ (M + 1) |
|---|---|---|---|---|
| 183 | 3-carboxyphenyl, 3-methylpiperidine | C | C32H39F3N2O3 556 | 557 |
| 184 | 3-carboxyphenyl, 3-methylpiperidine | C | C32H39F3N2O3 556 | 557 |
| 185 | 3-carboxyphenyl, 3-methylpiperidine | C | C32H39F3N2O3 556 | 557 |
| 186 | 3-carboxyphenyl, 3-methylpiperidine | C | C32H39F3N2O3 556 | 557 |
| 187 | 3-carboxyphenyl, 3-methylpiperidine | N | C31H38F3N3O3 556 | 558 |
| 188 | 3-carboxyphenyl, 3-methylpiperidine | N | C31H38F3N3O3 557 | 558 |
| 189 | 3-carboxyphenyl, 3-methylpiperidine | N | C31H38F3N3O3 557 | 558 |

TABLE 9-continued

Carboxylic Acid Containing Analogs From Esters in Table 8

| EX. | Amine | X | Formula/calc. MW | ESI-MS observed M + H+ (M + 1) |
|---|---|---|---|---|
| 190 | 3-carboxyphenyl-(3-methylpiperidin-4-yl) | N | C31H38F3N3O3 557 | 558 |
| 191 | 3-(piperidin-4-yl)benzoic acid | N | C30H36F3N3O3 543 | 544 |
| 192 | 2-methyl-3-(piperidin-4-yl)benzoic acid | N | C31H38F3N3O3 557 | 558 |
| 193 | 4-fluoro-3-(piperidin-4-yl)benzoic acid | N | C30H35F4N3O3 561 | 562 |
| 194 | 3-fluoro-5-(piperidin-4-yl)benzoic acid | N | C30H35F4N3O3 561 | 562 |
| 195 | 2-fluoro-5-(piperidin-4-yl)benzoic acid | N | C30H35F4N3O3 561 | 562 |

TABLE 9-continued

Carboxylic Acid Containing Analogs From Esters in Table 8

| EX. | Amine | X | Formula/calc. MW | ESI-MS observed M + H+ (M + 1) |
|---|---|---|---|---|
| 196 | (structure with -CH2-COOH on phenyl-piperidine) | N | C31H38F3N3O3<br>557 | 558 |
| 197 | (2-fluoro-benzoic acid phenyl-piperidine) | N | C31H36F4N2O3<br>560 | 561 |
| 198 | (3-fluoro-benzoic acid phenyl-piperidine) | N | C31H36F4N2O3<br>560 | 561 |

EXAMPLE 199

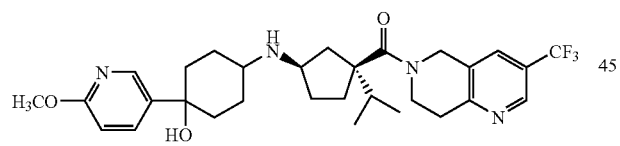

Example 199 was prepared using intermediate 24 and 4-hydroxy-4-(6-methoxypyridin-3-yl)cyclohexanone (Xue, C.; et. al. WO2004/050024) in an analogous fashion to example 82. LC-MS calculated for C30H39F3N4O3: 560.67; found [M+H]+ 562.

EXAMPLE 200

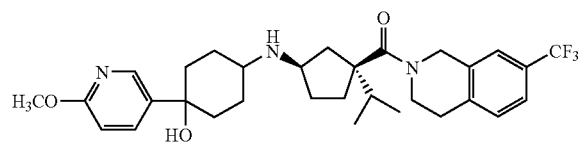

Example 200 was prepared using intermediate 25 and 4-hydroxy-4-(6-methoxypyridin-3-yl)cyclohexanone in an analogous fashion to example 82. LC-MS calculated for C31H40F3N3O3: 559.68; found [M+H]+ 561.

EXAMPLE 201

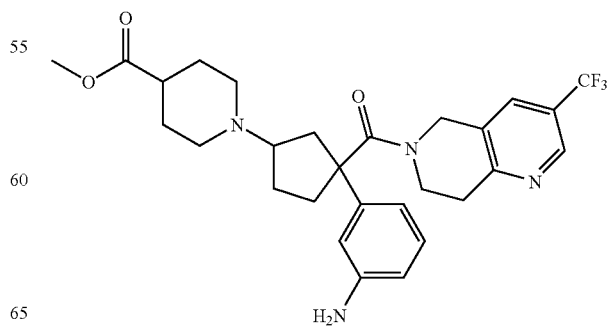

Step A

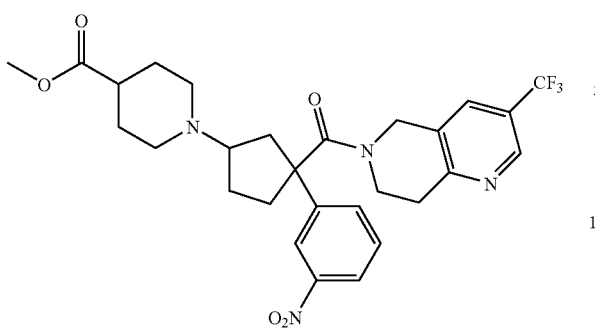

This product was prepared in an analogous fashion to that of Example 65, except the intermediate from Step A was replaced with commercially available 3-nitrophenyl acetic acid ethyl ester. The crude product was purified via silica gel chromatography, eluting with a 1% to 10% gradient of MeOH in DCM. LC/MS (ESI) 561.4 (M+H$^+$).

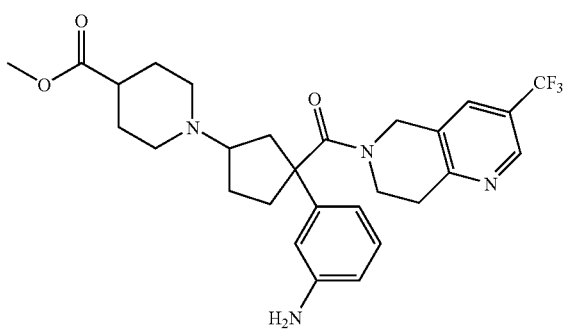

1.15 g (2.05 mmol) of the product from step A was stirred in MeOH at room temperature with N,N-dimethyl hydrazine (20.5 mmol, 1.23 g) and 60 mg activated charcoal. To this was added ~5-10% FeCl$_3$ (~20-50 mg, spatula tip addition), and reaction was warmed to reflux. After 2 hrs, additional portions of N,N-dimethyl hydrazine (20.5 mmol, 1.23 g) and FeCl$_3$ (~20-50 mg, spatula tip addition) were added. TLC analysis 2 hrs later showed complete reaction. Crude mixture was filtered through celite and concentrated in vacuo with no further purification necessary. LC/MS (ESI) 531.5 (M+H$^+$).

EXAMPLE 202

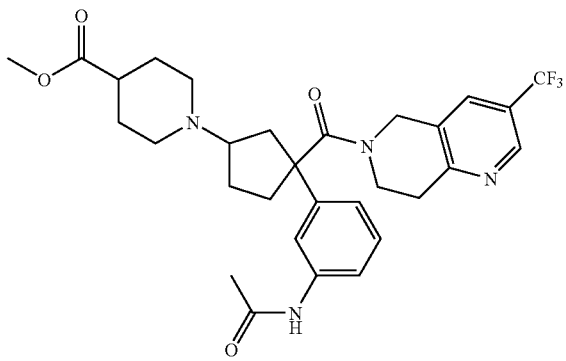

The aniline product from example 201 (265 mg, 0.5 mmol) was stirred with DIEA (260 µL, 1.5 mmol) in DCM (5 mL). To this was added acetic anhydride (72 µL, 0.75 mmol) neat, via syringe. TLC analysis after 20 min showed complete conversion to product. The crude reaction is diluted with 50 mL DCM and washed 2× with H$_2$O (25 mL each). The DCM layer was dried over MgSO$_4$, filtered, and concentrated in vacuo. The residue was purified by reverse phase preparative HPLC, to afford the product as a colorless solid. LC/MS (ESI) 573.5 (M+H$^+$).

EXAMPLE 203

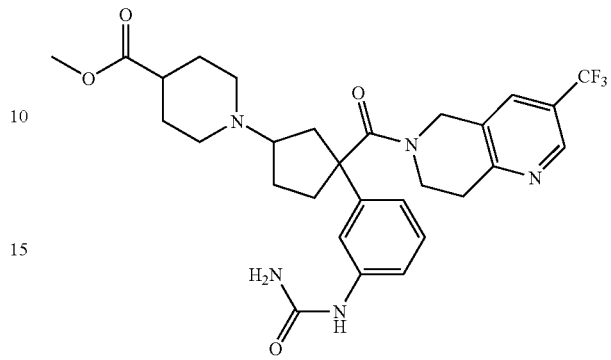

The aniline product from example 201 (265 mg, 0.5 mmol) was stirred at room temperature in 8 mL of 1:1 AcOH:H$_2$O. To this was added 81 mg (1.0 mmol) of potassium cyanate. After 30 minutes, TLC showed complete reaction. The resulting mixture was concentrated to dryness in vacuo, and the crude residue was purified by reverse phase preparative HPLC, to afford the product as a colorless solid. LC/MS (ESI) 574.4 (M+H$^+$).

EXAMPLE 204

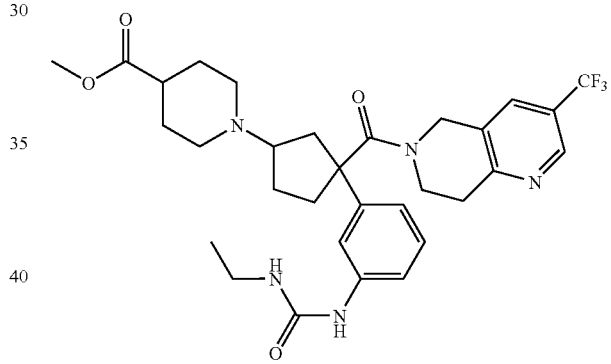

The aniline product from example 201 (265 mg, 0.5 mmol) was stirred at room temperature in dioxane. To this was added 120 µL (1.5 mmol) of ethyl isocyanate. After 18 hrs, TLC analysis showed complete reaction. The resulting mixture was concentrated to dryness in vacuo, and the crude residue was purified by reverse phase preparative HPLC, to afford the product as a colorless solid. LC/MS (ESI) 602.7 (M+H$^+$).

EXAMPLE 205

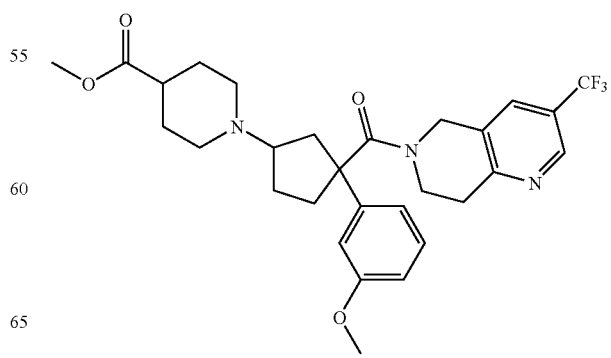

This product was prepared in an analogous fashion to that of example 65, except the intermediate from Step A was replaced with commercially available 3-methoxyphenyl acetic acid ethyl ester. The crude product was purified by reverse phase preparative HPLC, to afford the product as a colorless solid. LC/MS (ESI) 546.3 (M+H+).

EXAMPLE 206

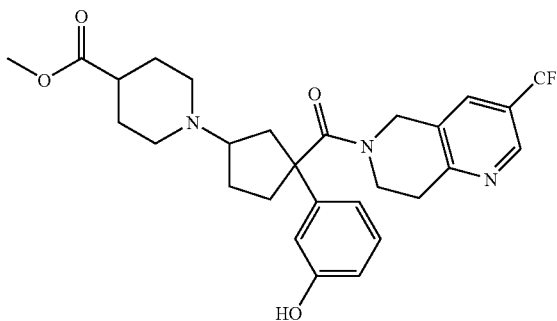

The TFA salt (583 mg, 0.88 mmol) of the methoxyphenyl product from example 205 was stirred in dry DCM (20 mL) at room temperature. To this was added boron tribromide (360 µL, 3.5 mmol) neat, via syringe. After 20 min, analysis of the reaction via LC/MS showed complete conversion to product. The reaction was quenched with MeOH (5 mL), then diluted with 100 mL DCM. The crude mixture was washed 2× with H$_2$O (50 mL each), then dried over MgSO$_4$, filtered, and concentrated in vacuo. The residue was purified by reverse phase preparative HPLC, to afford the product as a colorless solid. LC/MS (ESI) 532.6 (M+H+).

EXAMPLE 207

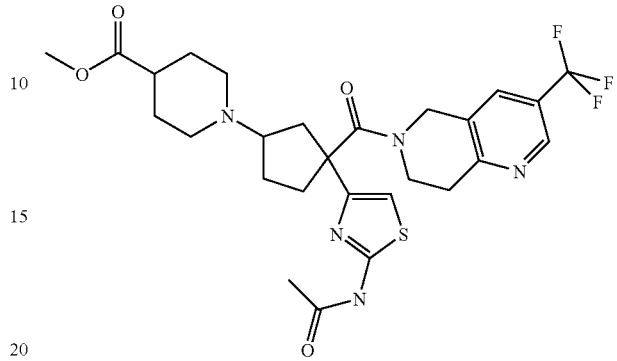

This product was prepared in an analogous fashion to that of example 65 using methyl piperidine-4-carboxylate. The crude product was purified by reverse phase preparative HPLC, to afford the product as a colorless solid. LC/MS (ESI) 580.5 (M+H+).

Selected analogs above (Examples 201, 205, 206, 207) could be further modified to generate new target chemokine receptor modulators. For example, the ester groups of these analogs were hydrolyzed to give the corresponding carboxylic acids which were themselves potent modulators. These hydrolyses were usually accomplished under the conditions shown in example 145. A representative list of the resulting carboxylic acid containing chemokine receptor modulators is presented in Table 10.

TABLE 10

Analogs Prepared in an Analogous Fashion to EXAMPLE 145

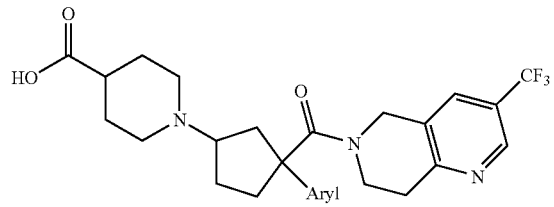

| EX. | Aryl | Formula/Calc. MW | ESI-MS observed M + H+ (M + 1) |
|---|---|---|---|
| 208 | 3-aminophenyl (NH$_2$) | C27H31F3N4O3 516.6 | 517.5 |
| 209 | 3-methoxyphenyl (OMe) | C28H32F3N3O4 531.6 | 532.4 |

TABLE 10-continued

Analogs Prepared in an Analogous Fashion to EXAMPLE 145

| EX. | Aryl | Formula/Calc. MW | ESI-MS observed M + H⁺ (M + 1) |
|---|---|---|---|
| 210 | 3-hydroxy-5-methylphenyl | C27H30F3N3O4 517.6 | 518.5 |
| 211 | 2-acetamidothiazol-4-yl | C26H30F3N5O4S 565.6 | 566.6 |

EXAMPLE 212

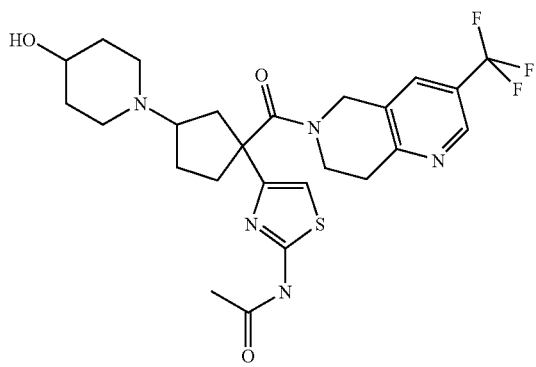

This product was prepared in an analogous fashion to that of example 65 using 4-hydroxypiperidine. The crude product was purified by reverse phase preparative HPLC, to afford the product as a colorless solid. LC/MS (ESI) 538.4 (M+H⁺).

EXAMPLE 213

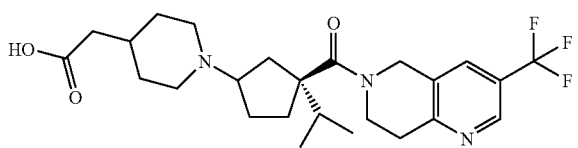

Step A

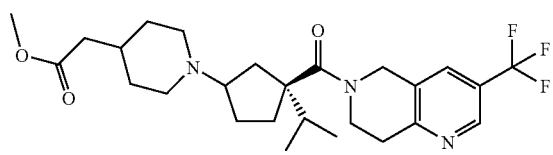

Compound was synthesized using commercially available piperidin-4-yl-acetic acid methyl ester in an analogous fashion to example 19.

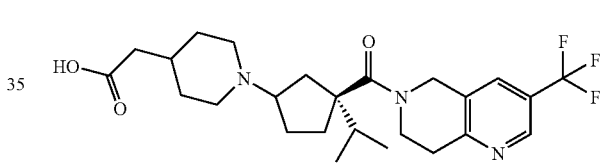

To a solution of methyl [1-((3S)-3-isopropyl-3-{[3-(trifluoromethyl)-7,8-dihydro-1,6-naphthyridin-6(5H)-yl]carbonyl}cyclopentyl)piperidin-4-yl]acetate (470 mgs, 0.92 mmol) in methanol (5 ml) was added 2N Lithium Hydroxide solution (1.8 ml, 3.7 mmol), the reaction was then stirred overnight at room temperature. The reaction was neutralized to pH=5 using 3N HCl. The crude was purified on reverse phase HPLC using 5%-100% ACN/H₂O to yield [1-((3S)-3-{[3-(1,1-difluoroethyl)-7,8-dihydro-1,6-naphthyridin-6(5H)-yl]carbonyl}-3-isopropylcyclopentyl)piperidin-4-yl]acetic acid (320 mgs, 91%), LC-MS 482 (M⁺+1).

EXAMPLE 214

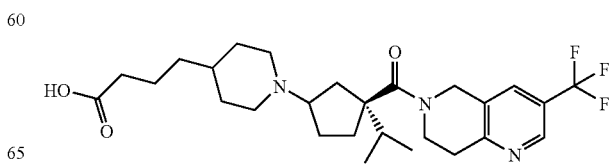

Compound was synthesized using commercially available 4-piperidine butyric acid hydrochloride in an analogous fashion to example 19. LCMS 511 (M⁺+1).

EXAMPLE 215

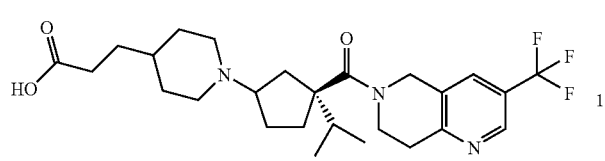

Step A

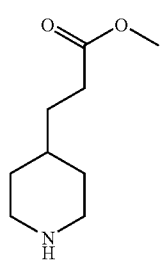

To a solution of N-Boc-4-piperidinylpropionic acid methyl ester (300 mg, 1.1 mmol) in dichloromethane (2 ml) was added a solution of 1N HCl in ethyl ether (5 ml, 5 mmol), and the resulting mixture was stirred for 2 hours. Solvent was removed under reduced pressure to afford crude desired methyl 3-piperidin-4-ylpropanoate (242 mg, 100%)

Step B

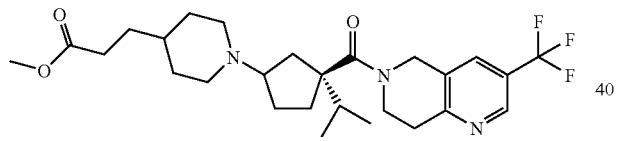

This compound was synthesized using the reductive amination procedure already described in previous examples by reacting the product from step A with (3S)-3-isopropyl-3-{[3-(trifluoromethyl)-7,8-dihydro-1,6-naphthyridin-6(5H)-yl]carbonyl}cyclopentanone to yield desired compound.

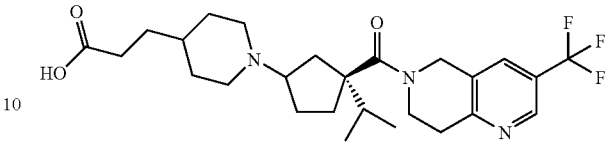

Step C

The desired compound was prepared in the same procedure from the product in step B as in example 204. (310 mgs, 60% overall). LC-MS 497 (M⁺+1).

EXAMPLE 216

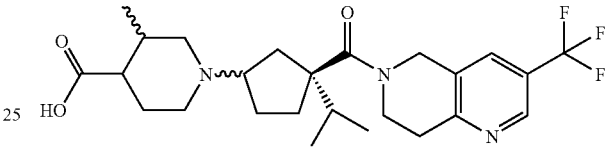

Compound was synthesized using the in an analogous fashion to example 215 using methyl 3-methylpiperidine-4-carboxylate LC-MS 482 (M⁺+1).

EXAMPLES 217-219

Examples 217-219 were prepared using the recemic form of example 32 and commercially available amino ester intermediates by the following procedure: To a solution of example 32 (250 mgs, 0.54 mmol) in dichloromethane (2 ml), was added corresponding amino ester (1.2 mmol), BOP (240 mgs, 1.0 mmol), triethyl amine (90 mgs, 0.89 mmol), the reaction was stirred overnight. The reaction was added sat. NaHCO₃ as well as ethyl acetate (50 ml). The organic layer was washed with brine (10 ml), dried, concentrated, the residue was purified on HPLC to afford the desired compound. (Table 11)

TABLE 11

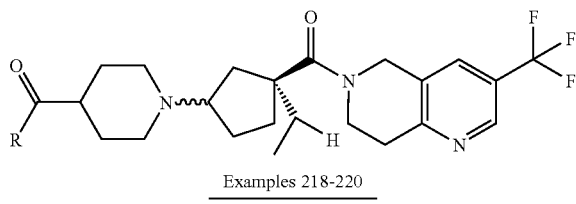

Examples 218-220

| EXAMPLE | R | M.F. | M.W. | Found (M + H) |
|---------|---|------|------|---------------|
| 217 | 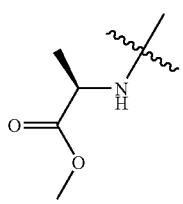 | C₂₇H₃₇F₃N₄O₄ | 538.62 | 539 |

TABLE 11-continued

Examples 218-220

| EXAMPLE | R | M.F. | M.W. | Found (M + H) |
|---|---|---|---|---|
| 218 | (3-methoxycarbonyl-phenyl-NH-) | $C_{31}H_{37}F_3N_4O_4$ | 586.66 | 587 |
| 219 | (4-methoxycarbonyl-phenyl-NH-) | $C_{31}H_{37}F_3N_4O_4$ | 586.66 | 587 |

EXAMPLE 220

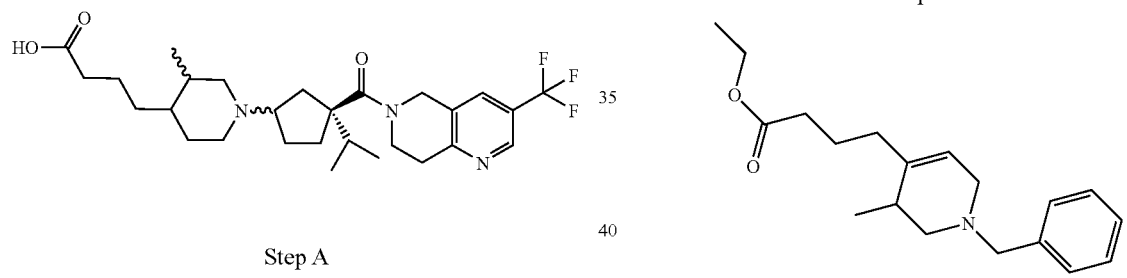

Step A

At −78° C., the solution of 1-Benzyl-3-methyl-4-piperidone (4.5 g, 22.6 mmol), was added dropwise to LDA (2N solution in THF/n-Heptane, 12.5 ml, 24.8 mmol)), the reaction was stirred for a half hour, then a solution of N-phenylbis (trifluoromethanesulfonimide) (8.9 g, 24.8 mmol) in THF(50 ml) added to it. The reaction was then warmed to room temperature for two hours. THF was removed under reduced pressure. The residue was purified on silica gel using 5% ethyl acetate/hexane as eluant to afford the desired compound as yellow oil (6.5 g, 87%), LC-MS 336 ($M^+$+1).

Step B

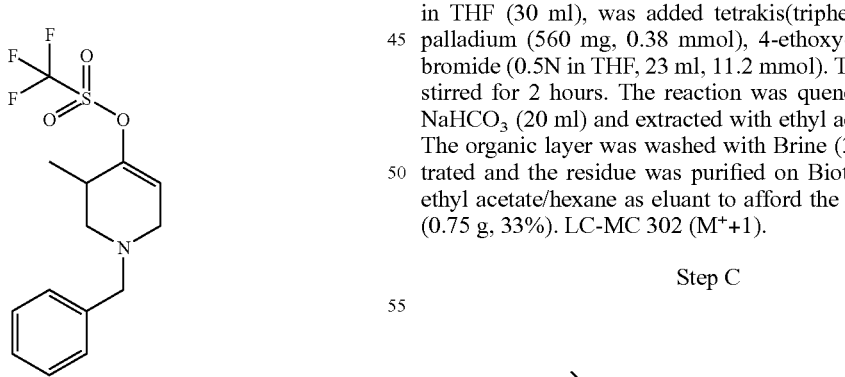

At 0° C., to a solution of above compound (2.5 g, 7.5 mmol) in THF (30 ml), was added tetrakis(triphenyl phosphine) palladium (560 mg, 0.38 mmol), 4-ethoxy-4-oxobutylzinc bromide (0.5N in THF, 23 ml, 11.2 mmol). The reaction was stirred for 2 hours. The reaction was quenched using Sat. $NaHCO_3$ (20 ml) and extracted with ethyl acetate (100 ml). The organic layer was washed with Brine (30 ml), concentrated and the residue was purified on Biotage using 10% ethyl acetate/hexane as eluant to afford the desired product (0.75 g, 33%). LC-MC 302 ($M^+$+1).

Step C

To the solution of above product (0.75 mg, 2.5 mmol) in methanol (10 ml) was added palladium hydroxide (300 mg, 1.9 mmol). The reaction was stirred in $H_2$ 1 atm overnight. The catalyst was filtered and the filtrate was concentrated to afford the desired product as yellow oil (490 mg, 100%).

Step D

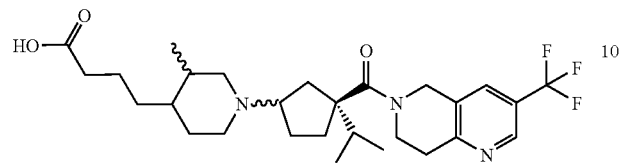

The final product was obtained by reacting the product from step C in an analogous fashion as in example 82 then hydrolyzing using 2N lithium hydroxide as in example 145 to afford the final product as off-white solid (0.75 g, 52%). LC-MS 552($M^+$+1).

EXAMPLE 221

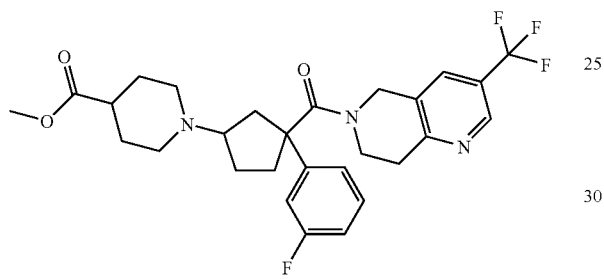

Compound was synthesized in an analogous manner to example 201 using 3-fluorophenyl acetic acid ethyl ester. ESI MS ($M+H^+$) calc 534.6 found 534.3.

EXAMPLE 222

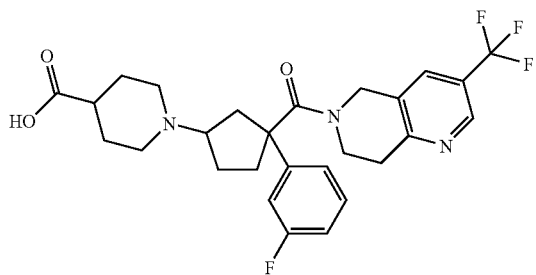

Compound was synthesized in an analogous manner to example 208 using example 221. ESI MS ($M+H^+$) calc 520.5 found 520.4.

EXAMPLE 223

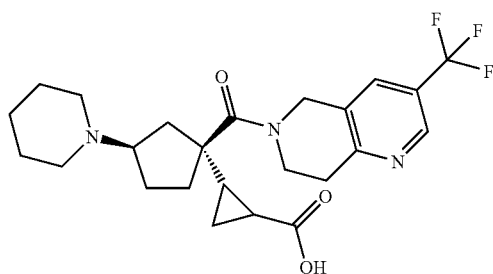

Step A

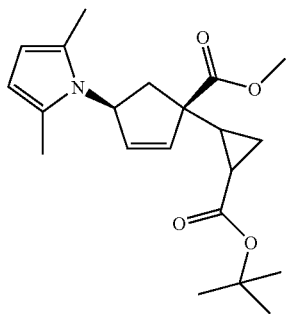

Methyl (1R,4S)-4-(2,5-dimethyl-1H-pyrrol-1-yl)cyclopent-2-ene-1-carboxylate (0.44 g, 2 mmol) and LHMDS (1.8 mL of 20% solution in THF, 2.2 mmol) were stirred at −78° C. for 30 minutes. To this solution was added 4 bromo-t-butyl crotonate (0.48 g, 2.2 mmol). The solution was allowed to warm to room temperature over 1 hour, quenched with water and extracted with ethyl acetate. The solvent was dried, filtered and evaporated to yield a brown oil. ESI MS ($M+H^+$) calc 360.5 found 360.2.

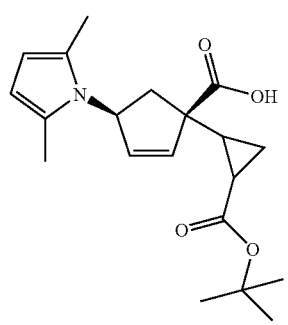

Step B

Methyl (1R,4S)-1-[2-(tert-butoxycarbonyl)cyclopropyl]-4-(2,5-dimethyl-1H-pyrrol-1-yl)cyclopent-2-ene-1-carboxylate (0.63 g, 1.8 mmol) and LiOH (0.09 g, 3.9 mmol) were stirred in methanol/water at 60° C. for 30 minutes. The solution was neutralized and extracted with ethyl acetate and water. The organic layer was dried, filtered, and evaporated to yield a brown solid.

Step C

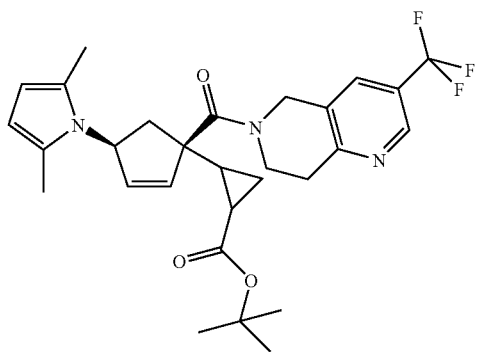

To (1R,4S)-1-[2-(tert-butoxycarbonyl)cyclopropyl]-4-(2, 5-dimethyl-1H-pyrrol-1-yl)cyclopent-2-ene-1-carboxylic acid (0.46 g, 1.8 mmol) in DMF, was added HATU (0.73 g, 1.9 mmol), and N-methyl morpholine (0.55 g. 5.4 mmol) and was allowed to stir for 30 minutes. 3-(trifluoromethyl)-7,8-dihydro-1,6-naphthyridine (0.46 g, 1.93 mmol) was added and stirred at room temperature for 12 hours. The solution was extracted with ethyl acetate and water, dried, filtered and evaporated. The crude material was chromatographed on silica with ethyl acetate/hexanes (10-50%) to yield and off white solid. ESI MS (M+H$^+$) calc 530.6 found 530.4.

Step D

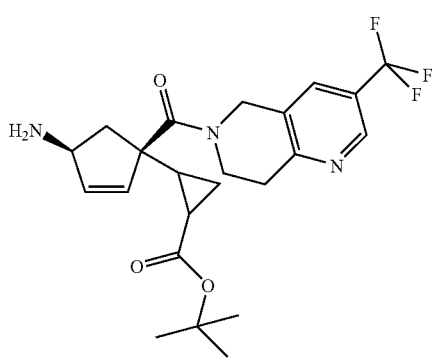

tert-Butyl 2-((1R,4S)-4-(2,5-dimethyl-1H-pyrrol-1-yl)-1-{[3-(trifluoromethyl)-7,8-dihydro-1,6-naphthyridin-6(5H)-yl]carbonyl}cyclopent-2-en-1-yl)cyclopropanecarboxylate (0.9 g, 1.7 mmol), hydroxylamine (50% in water, 0.7 g, 10.5 mmol), hydroxylamine hydrochloride (0.7 g, 10.5 mmol) and methanol (10 mL) were stirred at 70° C. for 6 hours. The solution was cooled to ambient temperature, extracted with ethyl acetate and water. The organic layer was dried, filtered and evaporated to yield an off white solid. ESI MS (M+H$^+$) calc 452.5 found 452.3.

Step E

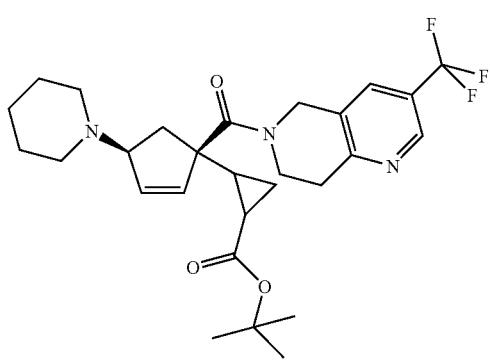

tert-Butyl 2-((1R,4S)-4-amino-1-{[3-(trifluoromethyl)-7,8-dihydro-1,6-naphthyridin-6(5H)-yl]carbonyl}cyclopent-2-en-1-yl)cyclopropanecarboxylate (0.15 g, 0.33 mmol), THF (2 mL), H$_2$SO$_4$ (0.3 mL), glutardialdehyde (50% in water, 0.64 g, 3.2 mmol), and sodium triacetoxy borohydride (0.7 g, 3.3 mmol) were stirred at room temperature for 1 hour. The solution was basified with sodium hydroxide, extracted with ethyl acetate, the organic layer dried, and evaporated. The crude material was purified on RPHPLC to yield a white solid. ESI MS (M+H$^+$) calc 520.6 found 520.7.

Step F

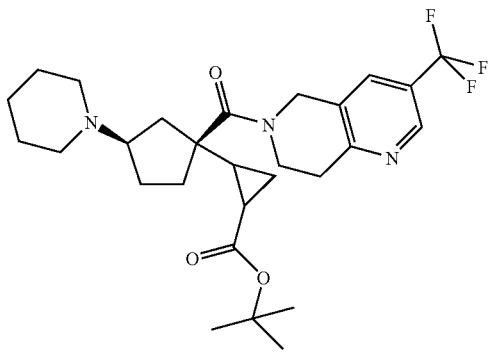

6-({(1R,4S)-1-[2-(tert-butoxycarbonyl)cyclopropyl]-4-piperidinium-1-ylcyclopent-2-en-1-yl}carbonyl)-3-(trifluoromethyl)-5,6,7,8-tetrahydro-1,6-naphthyridin-1-ium bis(trifluoroacetate) (0.1 g), Pd/C (0.05 g) in methanol (10 mL) was added hydrogen. The solution was stirred at room temperature for 5 hours. The solution was filtered and evaporated to yield and off white solid. ESI MS (M+H$^+$) calc 522.6 found 522.5.

Step G

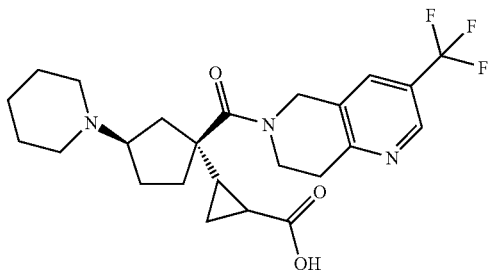

6-({(1S,3R)-1-[2-(tert-butoxycarbonyl)cyclopropyl]-3-piperidinium-1-ylcyclopentyl}carbonyl)-3-(trifluoromethyl)-5,6,7,8-tetrahydro-1,6-naphthyridin-1-ium bis(trifluoroacetate) (0.1 g) in methylene chloride (5 mL) was added TFA (2 mL). The solution was stirred at room temperature for 2 hours, then the solvent was evaporated to yield an off white solid. ESI MS (M+H$^+$) calc 466.5 found 466.4.

EXAMPLE 224

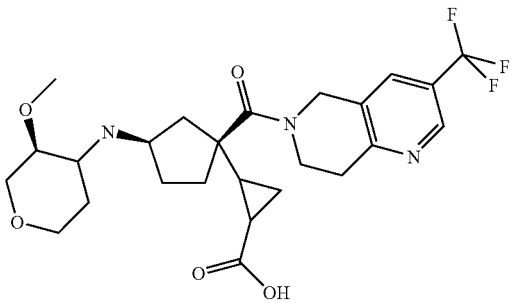

Step A

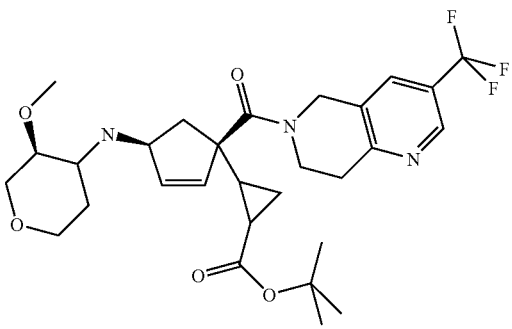

Intermediate tert-Butyl 2-((1R,4S)-4-amino-1-{[3-(trifluoromethyl)-7,8-dihydro-1,6-naphthyridin-6(5H)-yl]carbonyl}cyclopent-2-en-1-yl)cyclopropanecarboxylate (0.37 mmol), triacetoxy borohydride (0.087 g, 0.41 mmol), and triethylamine (0.05 mL) in DCE (5 mL) were stirred at room temperature for 18 hours, filtered, evaporated and purified by RPHPLC to yield a white solid. ESI MS (M+H$^+$) calc 566.7 found 566.5.

Step B

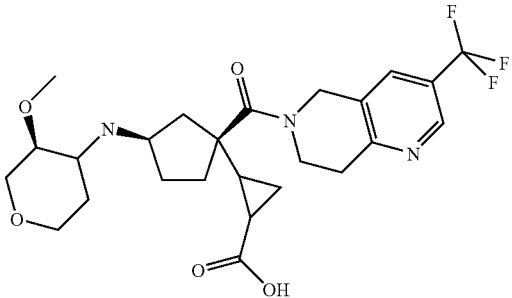

1,5-anhydro-3-[((1S,4R)-4-[2-(tert-butoxycarbonyl)cyclopropyl]-4-{[3-(trifluoromethyl)-7,8-dihydro-1,6-naphthyridin-1-ium-6(5H)-yl]carbonyl}cyclopent-2-en-1-yl)ammonio]-2,3-dideoxy-4-O-methyl-D-glycero-pentitol bis (trifluoroacetate) (0.15 g), Pd/C (0.05 g) were stirred under hydrogen for 2 hours, filtered and evaporated. The residue was dissolved in methylene chloride (4 mL) and TFA (2 mL) was added and the solution stirred for 2 hours. The solvent was evaporated and the product purified by RPHPLC to yield an off white solid. ESI MS (M+H$^+$) calc 512.6 found 512.4.

EXAMPLE 225

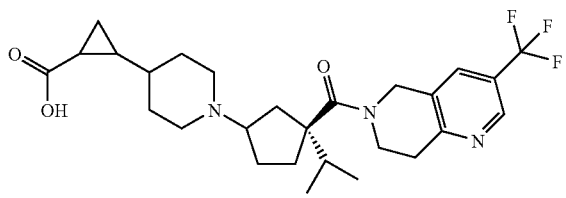

Step A

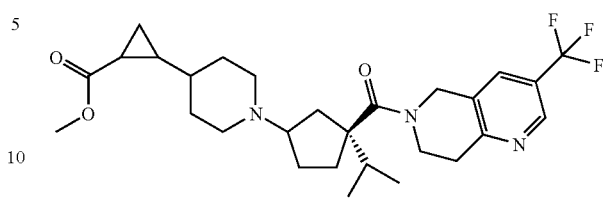

(3S)-3-isopropyl-3-{[3-(trifluoromethyl)-7,8-dihydro-1,6-naphthyridin-6(5H)-yl]carbonyl}cyclopentanone (0.12 g, 0.34 mmol), methyl 2-piperidin-4-ylcyclopropanecarboxylate (0.1 g, 0.34 mmol), sodium triacetoxy borohidride (0.14 g, 0.67 mmol), triethylamine (0.05 mL), in DCE were stirred at room temperature for 18 hours. The solution was filtered, evaporated and purified on RPHPLC to an off white solid. ESI MS (M+H$^+$) calc 522.6 found 522.5.

Step B

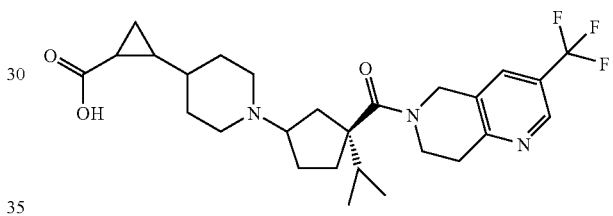

methyl 2-[1-((3S)-3-isopropyl-3-{[3-(trifluoromethyl)-7,8-dihydro-1,6-naphthyridin-6(5H)-yl]carbonyl}cyclopentyl)piperidin-4-yl]cyclopropanecarboxylate (0.08 g), LiOH (0.025 g) were stirred in water/methanol for 3 hours. The solution was neutralized, extracted with ethyl acetate, dried, filtered and evaporated to yield an off white solid. ESI MS (M+H$^+$) calc 508.6 found 508.5.

EXAMPLE 226

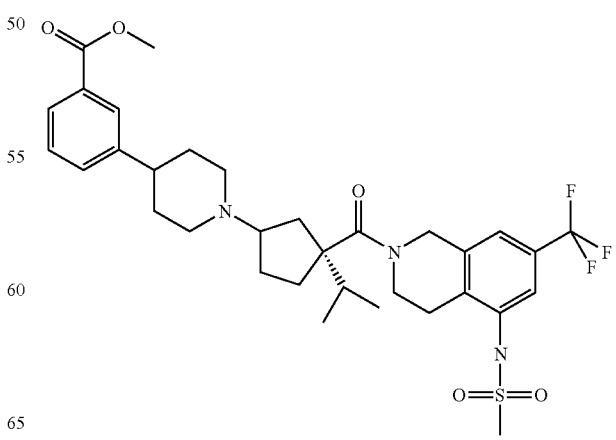

Step A

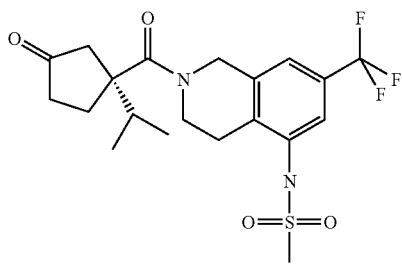

To a solution of 3-{[5-amino-7-(trifluoromethyl)-3,4-dihydroisoquinolin-2(1H)-yl]carbonyl}-3-isopropylcyclopentanone (500 mg, 1.35 mmol) in dry methylene chloride (10 mL) was added diisopropylethylamine (0.8 mL, 4.0 mmol). The reaction was stirred at room temperature for 5 minutes and then methane sulfonyl chloride was added via syringe (219 mg, 1.9 mmol). After 2 hrs the reaction was diluted with ethyl acetate. The solution was washed with aqueous NaHCO3 and the organic layer was dried (anhydrous Na2SO4), filtered and the solvent evaporated. The residue was chromatographed on silica gel eluting with a 30-70% ethyl acetate/hexane gradient to give the title compound as a pale yellow oil (420 mg) 69% yield. $^1$H-NMR (500 MHz, MeOD): 8.17 (1H, s), 7.95 (1H, s), 4.93 (2H, s), 3.93-3.80 (3H, m3), 3.49 (3H, s), 3.36-3.21 (3H, m), 3.28-3.31 (3H, m), 2.73-2.68 (1H, m), 2.22-2.19 (1H, d, m), 1.50 (1H, s), 0.85-0.82 (6H, d, J=10 Hz).

Step B

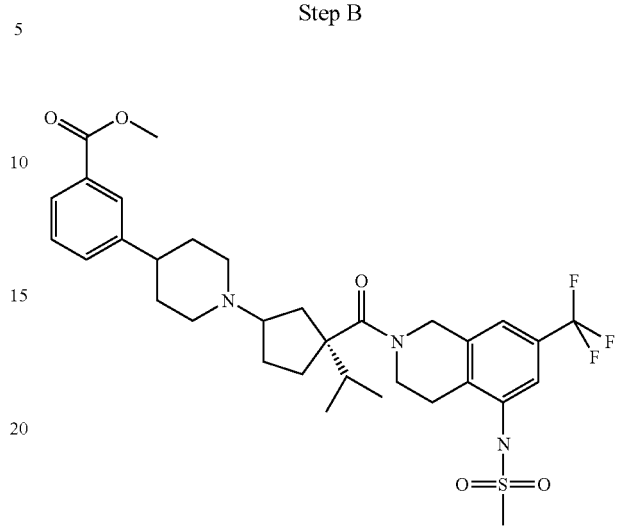

A similar procedure as in example 82 was followed with the product obtained from step A to give the desired compound. 1H-NMR (500 MHz, MeOD): 7.90-7.86 (2H, m), 7.50 (1H, s), 7.49 (1H, m), 7.49-7.43 (2H, m), 3.87-3.85 (6H, m), 3.68 (1H, s), 3.49-3.48 (6H, m), 3.27-2.94 (5H, m) 2.6 (2H, m), 2.23-1.50 (10H, m), 1.05-0.70 (6H, m).

TABLE 12

Analogs are Prepared in an Analogous Fashion to EXAMPLE 145 (followed by ester hydrolysis as described in EXAMPLE 145)

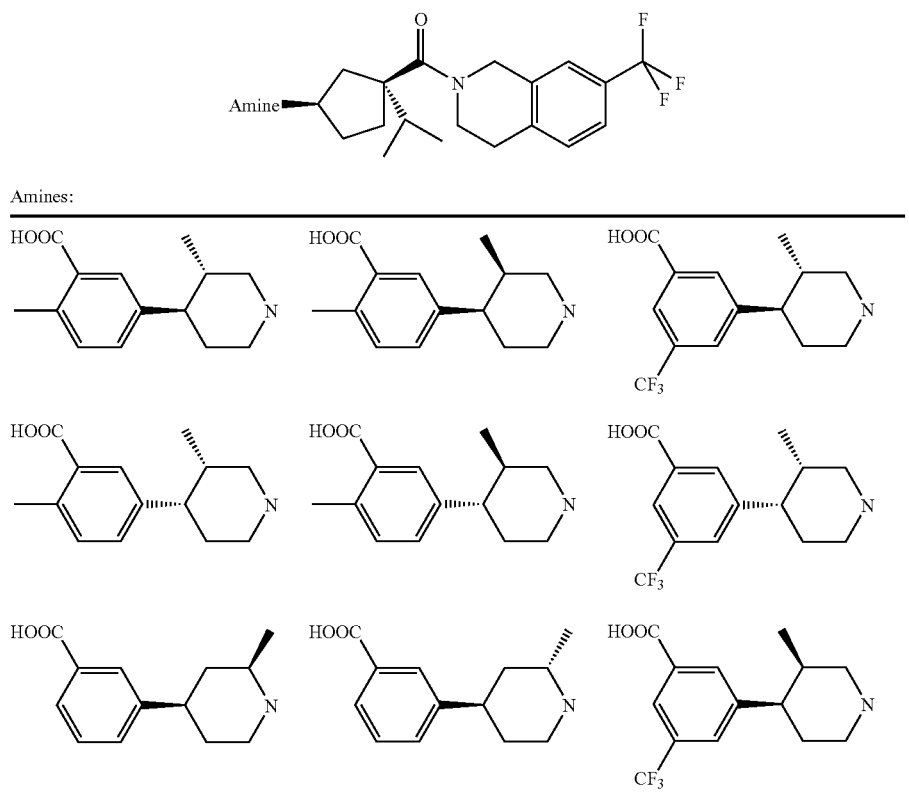

TABLE 12-continued
Analogs are Prepared in an Analogous Fashion to EXAMPLE 145 (followed by ester hydrolysis as described in EXAMPLE 145)
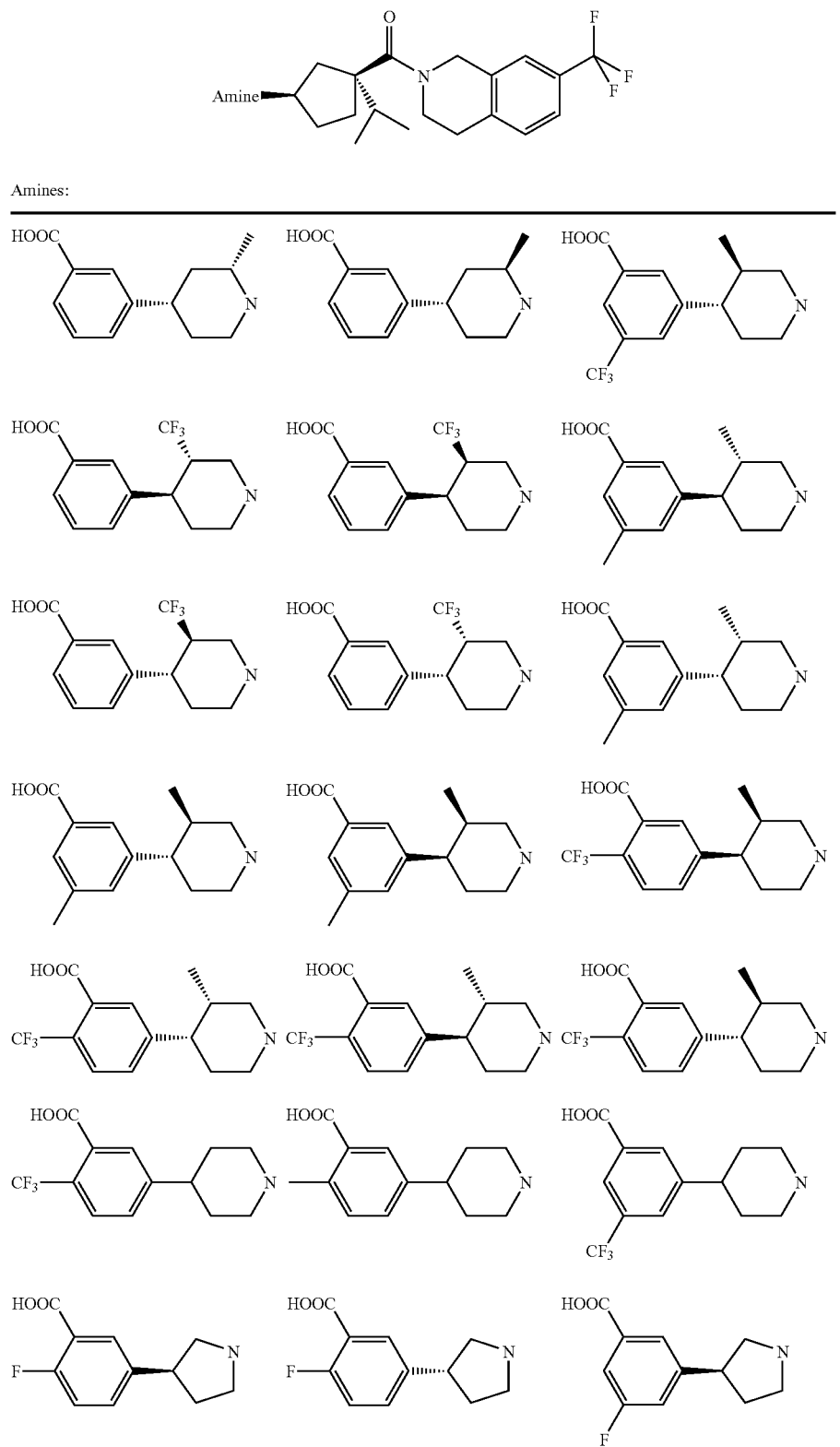
Amines:

TABLE 12-continued
Analogs are Prepared in an Analogous Fashion to EXAMPLE 145 (followed by ester hydrolysis as described in EXAMPLE 145)
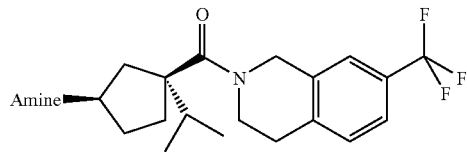
Amines:
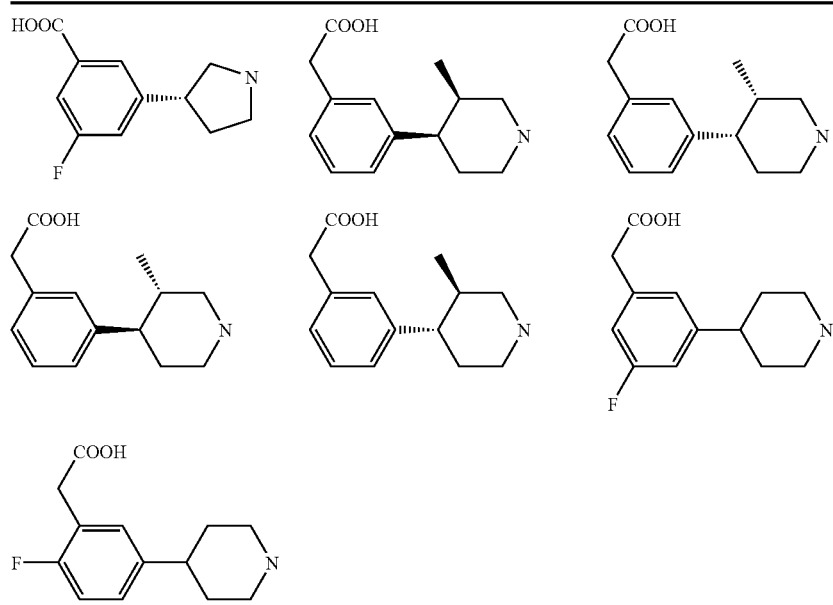
TABLE 13
Analogs are Prepared in an Analogous Fashion to EXAMPLE 145 (followed by ester hydrolysis as described in EXAMPLE 145)
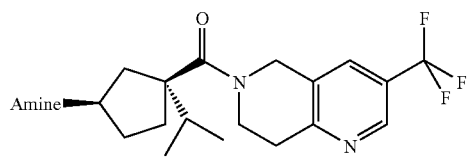
Amines:
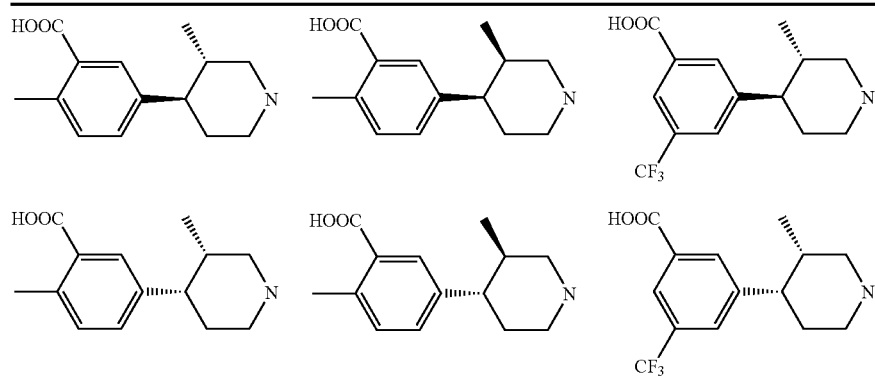

TABLE 13-continued
Analogs are Prepared in an Analogous Fashion to EXAMPLE 145 (followed by ester hydrolysis as described in EXAMPLE 145)
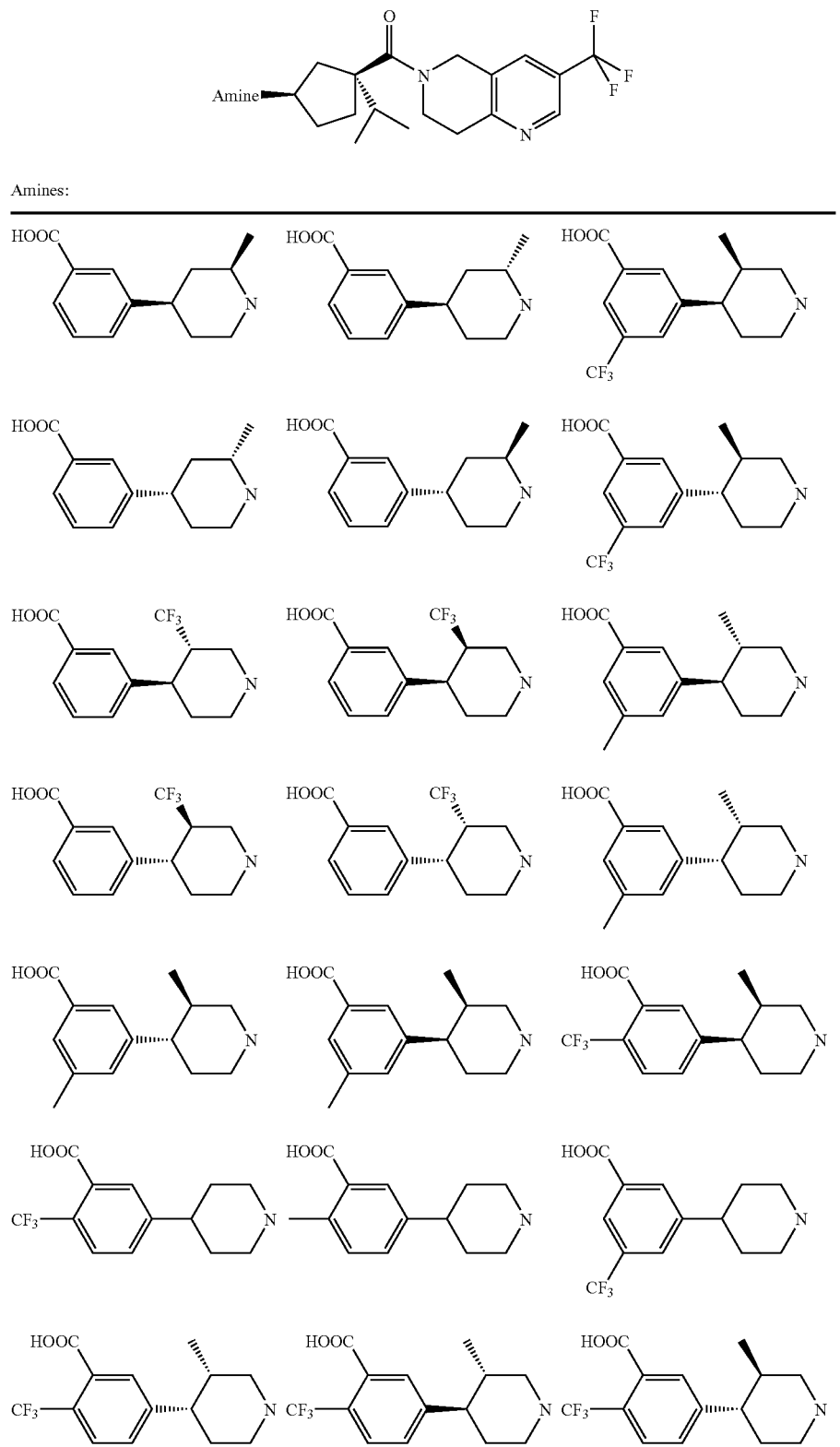
Amines:

TABLE 13-continued
Analogs are Prepared in an Analogous Fashion to EXAMPLE 145 (followed by ester hydrolysis as described in EXAMPLE 145)
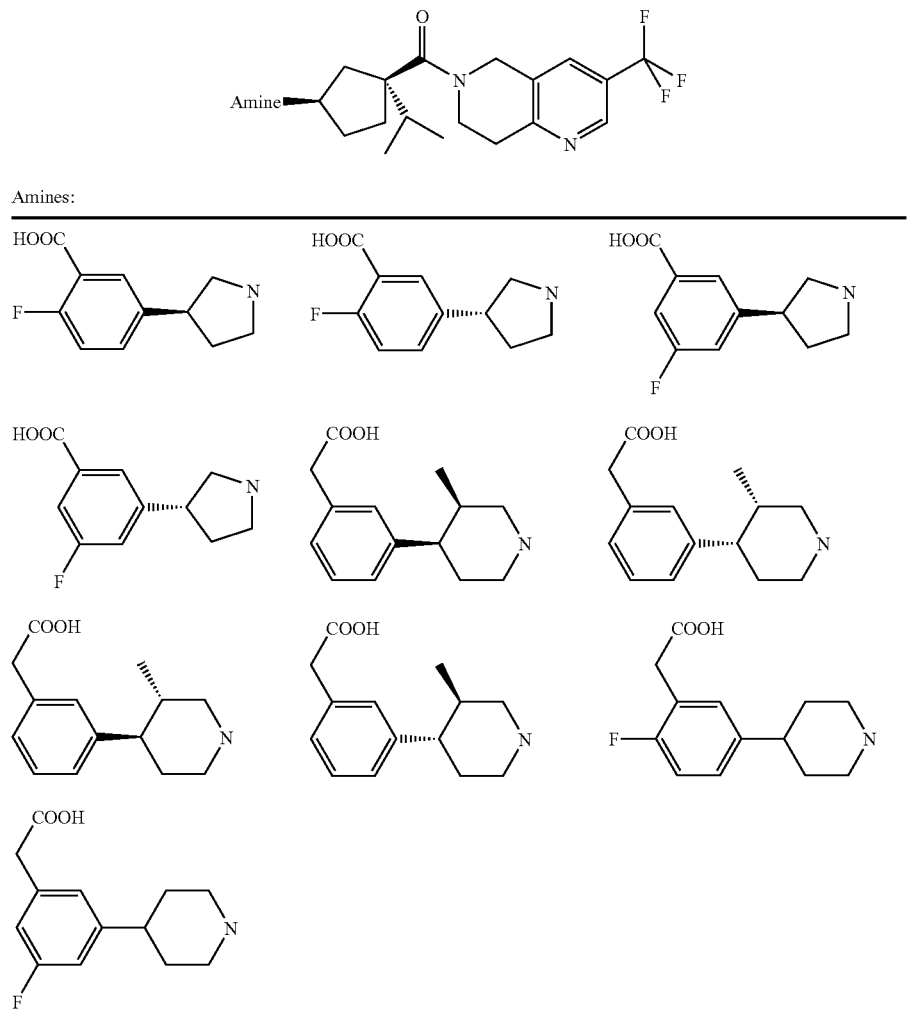
Amines:
TABLE 15
Analogs are Prepared in an Analogous Fashion to EXAMPLE 199
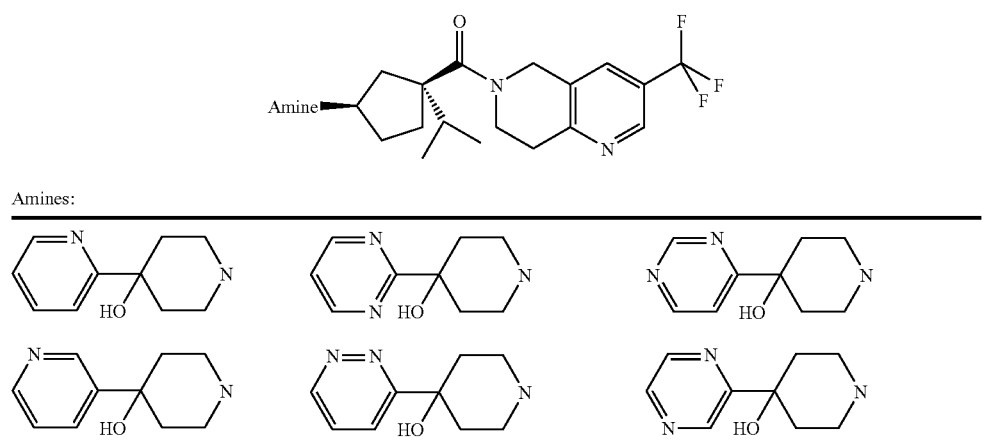
Amines:

TABLE 15-continued
Analogs are Prepared in an Analogous Fashion to EXAMPLE 199
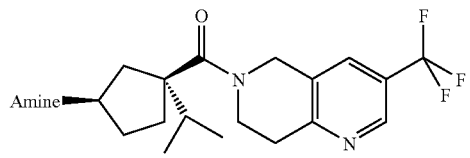
Amines:
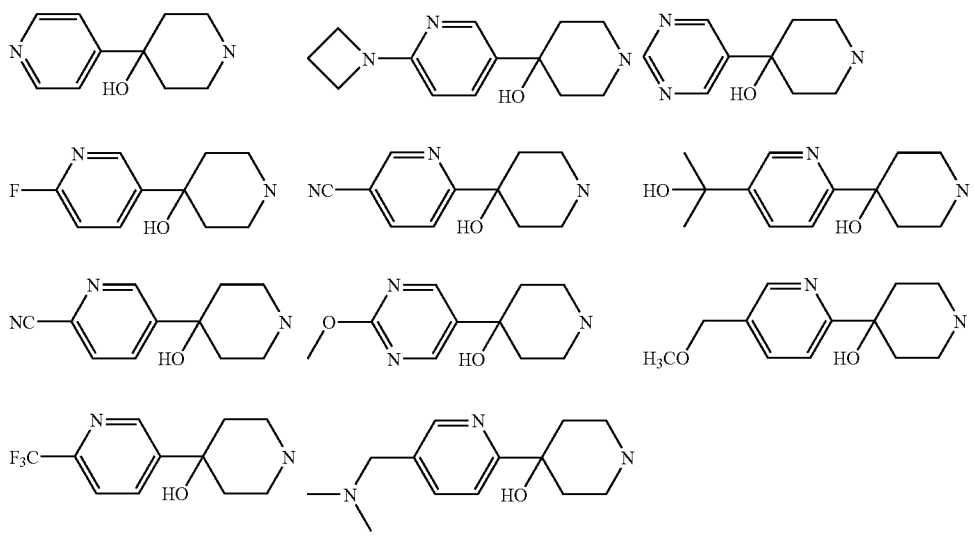
TABLE 16
Analogs are Prepared in an Analogous Fashion to EXAMPLE 200
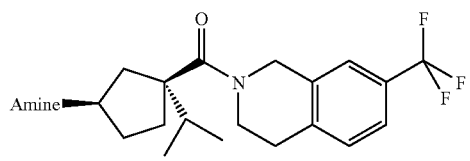
Amines:
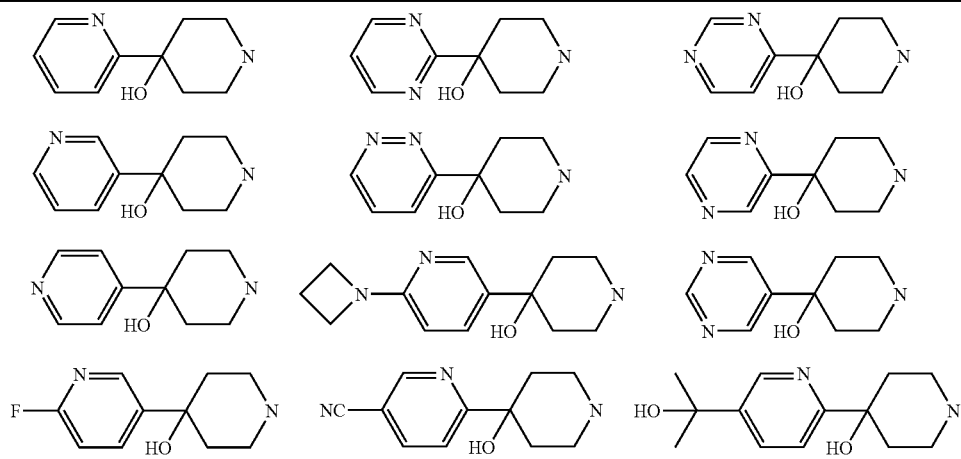

TABLE 16-continued

Analogs are Prepared in an Analogous Fashion to EXAMPLE 200

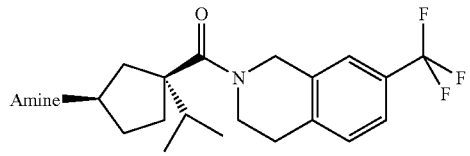

Amines:

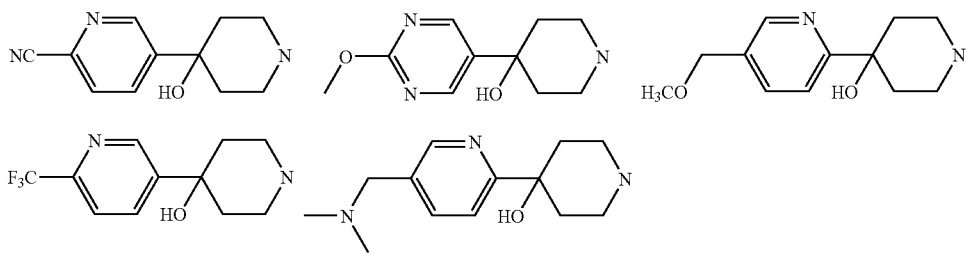

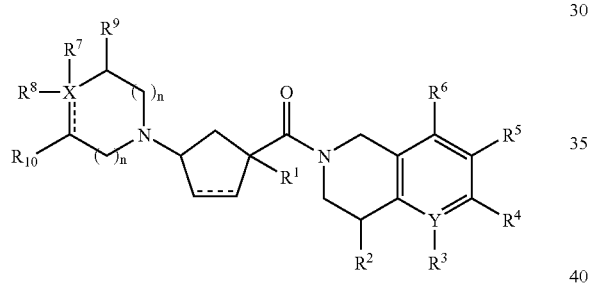

What is claimed is:

1. A compound of formula I:

Formula I wherein:

X is selected from the group consisting of:
  N, O, S and $SO_2$;

Y is N or C;

$R^1$ is selected from the group consisting of:
  hydrogen, $-C_{1-6}$alkyl, $-C_{0-6}$alkyl-O-$C_{1-6}$alkyl, $-C_{0-6}$alkyl-S-$C_{1-6}$alkyl, $-(C_{0-6}$alkyl)-$(C_{3-7}$cycloalkyl)-$(C_{0-6}$alkyl), hydroxy, heterocycle, $-CN$, $-NR^{12}R^{12}$, $-NR^{12}COR^{13}$, $-NR^{12}SO_2R^{14}$, $-COR^{11}$, $-CONR^{12}R^{12}$, and phenyl, where $R^{11}$ is independently selected from the group consisting of: hydroxy, hydrogen, $C_{1-6}$alkyl, $-O-C_{1-6}$alkyl, benzyl, phenyl and $C_{3-6}$ cycloalkyl where the alkyl, phenyl, benzyl, and cycloalkyl groups can be unsubstituted or substituted with 1-3 substituents where the substituents are independently selected from the group consisting of: halo, hydroxy, $C_{1-3}$alkyl, $C_{1-3}$alkoxy, $-CO_2H$, $-CO_2-C_{1-6}$ alkyl, and trifluoromethyl, and where $R^{12}$ is selected from the group consisting of: hydrogen, $C_{1-6}$ alkyl, benzyl, phenyl and $C_{3-6}$ cycloalkyl where the alkyl, phenyl, benzyl and cycloalkyl groups can be unsubstituted or substituted with 1-3 substituents where the substituents are independently selected from the group consisting of: halo, hydroxy, $C_{1-3}$alkyl, $C_{1-3}$alkoxy, $-CO_2H$, $-CO_2-C_{1-6}$ alkyl, and trifluoromethyl, and where $R^{13}$ is selected from the group consisting of: hydrogen, $C_{1-6}$ alkyl, $-O-C_{1-6}$alkyl, benzyl, phenyl and $C_{3-6}$ cycloalkyl where the alkyl, phenyl, benzyl, and cycloalkyl groups can be unsubstituted or substituted with 1-3 substituents where the substituents are independently selected from the group consisting of: halo, hydroxy, $C_{1-3}$alkyl, $C_{1-3}$alkoxy, $-CO_2H$, $-CO_2-C_{1-6}$ alkyl, and trifluoromethyl, and where $R^{14}$ is selected from the group consisting of: hydroxy, $C_{1-6}$ alkyl, $-O-C_{1-6}$alkyl, benzyl, phenyl and $C_{3-6}$ cycloalkyl where the alkyl, phenyl, benzyl, and cycloalkyl groups can be unsubstituted or substituted with 1-3 substituents where said substituents are independently selected from the group consisting of: halo, hydroxy, $C_{1-3}$alkyl, $C_{1-3}$alkoxy, $-CO_2H$, $-CO_2-C_{1-6}$ alkyl, and trifluoromethyl, and where said alkyl and said cycloalkyl are unsubstituted or substituted with 1-7 substituents where said substituents are independently selected from the group consisting of:

(a) halo,
(b) hydroxy,
(c) $-O-C_{1-3}$alkyl,
(d) trifluoromethyl,
(f) $C_{1-3}$alkyl,
(g) $-O-C_{1-3}$alkyl,
(h) $-COR^{11}$,
(i) $-SO_2R^{14}$,
(j) $-NHCOCH_3$,
(k) $-NHSO_2CH_3$,
(l) -heterocycle,
(m) $=O$ and
(n) $-CN$, and where said phenyl and heterocycle are unsubstituted or substituted with 1-3 substituents where said substituents are independently selected from the group consisting of: halo, $C_{1-3}$alkyl, $C_{1-3}$alkoxy and trifluoromethyl;

$R^2$ is selected from the group consisting of:
 (a) hydrogen,
 (b) hydroxy,
 (c) halo,
 (d) $C_{1-3}$alkyl, where the alkyl is unsubstituted or substituted with 1-6 substituents independently selected from fluoro and hydroxy,
 (e) —$NR^{12}R^{12}$,
 (f) —$COR^{11}$,
 (g) —$CONR^{12}R^{12}$,
 (h) —$NR^{12}COR^{13}$,
 (i) —$OCONR^{12}R^{12}$,
 (j) —$NR^{12}CONR^{12}R^{12}$,
 (k) -heterocycle,
 (l) —CN,
 (m) —$NR^{12}$—$SO_2$—$NR^{12}R^{12}$,
 (n) —$NR^{12}$—$SO_2$—$R^{14}$,
 (o) —$SO_2$—$NR^{12}R^{12}$, and
 (p) =O, where $R^2$ is connected to the ring via a double bond;
$R^3$ is oxygen or is absent when Y is N;
$R^3$ is selected from the following groups when Y is C:
 (a) hydrogen,
 (b) hydroxy,
 (c) halo,
 (d) $C_{1-3}$alkyl, where said alkyl is unsubstituted or substituted with 1-6 substituents independently selected from: fluoro, hydroxy, and —$COR^{11}$,
 (e) —$NR^{12}R^{12}$,
 (f) —$COR^{11}$,
 (g) —$CONR^{12}R^{12}$,
 (h) —$NR^{12}COR^{13}$,
 (i) —$OCONR^{12}R^{12}$,
 (j) —$NR^{12}CONR^{12}R^{12}$,
 (k) -heterocycle,
 (l) —CN,
 (m) —$NR^{12}$—$SO_2$—$NR^{12}R^{12}$,
 (n) —$NR^{12}$—$SO_2$—$R^{14}$,
 (o) —$SO_2$—$NR^{12}R^{12}$ and
 (p) nitro;
$R^4$ is selected from the group consisting of:
 (a) hydrogen,
 (b) $C_{1-6}$alkyl,
 (c) trifluoromethyl,
 (d) trifluoromethoxy,
 (e) chloro,
 (f) fluoro,
 (g) bromo, and
 (h) phenyl;
$R^5$ is selected from the group consisting of:
 (a) $C_{1-6}$alkyl, where alkyl may be unsubstituted or substituted with 1-6 fluoro and optionally substituted with hydroxyl,
 (b) —O—$C_{1-6}$alkyl, where alkyl may be unsubstituted or substituted with 1-6 fluoro,
 (c) —CO—$C_{1-6}$alkyl, where alkyl may be unsubstituted or substituted with 1-6 fluoro,
 (d) —S—$C_{1-6}$alkyl, where alkyl may be unsubstituted or substituted with 1-6 fluoro,
 (e) -pyridyl, which may be unsubstituted or substituted with one or more substituents selected from the group consisting of: halo, trifluoromethyl, $C_{1-4}$alkyl, and $COR^{11}$,
 (f) fluoro,
 (g) chloro,
 (h) bromo,
 (i) —$C_{4-6}$cycloalkyl,
 (j) —O—$C_{4-6}$cycloalkyl,
 (k) phenyl, which may be unsubstituted or substituted with one or more substituents selected from the group consisting of: halo, trifluoromethyl, $C_{1-4}$alkyl, and $COR^{11}$,
 (l) —O-phenyl, which may be unsubstituted or substituted with one or more substituents selected from the group consisting of: halo, trifluoromethyl, $C_{1-4}$alkyl, and $COR^{11}$,
 (m) —$C_{3-6}$cycloalkyl, where alkyl may be unsubstituted or substituted with 1-6 fluoro,
 (n) —O—$C_{3-6}$cycloalkyl, where alkyl may be unsubstituted or substituted with 1-6 fluoro,
 (o) -heterocycle,
 (p) —CN, and
 (q) —$COR^{11}$;
$R^6$ is selected from:
 (a) hydrogen,
 (b) $C_{1-6}$alkyl,
 (c) trifluoromethyl,
 (d) fluoro,
 (e) chloro, and
 (f) bromo;
$R^7$ is selected from:
hydrogen, ($C_{0-6}$alkyl)-phenyl, ($C_{0-6}$alkyl)-heterocycle, ($C_{0-6}$alkyl)-$C_{3-7}$cycloalkyl, ($C_{0-6}$alkyl)-$COR^{11}$, ($C_{0-6}$alkyl)-(alkene)-$COR^{11}$, ($C_{0-6}$alkyl)-$SO_3H$, ($C_{0-6}$alkyl)-W—$C_{0-4}$alkyl, ($C_{0-6}$alkyl)-$CONR^{12}$-phenyl, ($C_{0-6}$alkyl)-$CONR^{15}$—V—$COR^{11}$, and nothing (when X is O, S, or $SO_2$), where V is $C_{1-6}$alkyl or phenyl,
 where W is selected from the group consisting of: a single bond, —O—, —S—, —SO—, —$SO_2$—, —CO—, —$CO_2$—, —$CONR^{12}$— and —$NR^{12}$—,
 where the $R^{15}$ can be hydrogen, $C_{1-4}$alkyl, or where $R^{15}$ is joined via a 1-5 carbon tether to one of the carbons of V to form a ring,
 where the $C_{0-6}$alkyl is unsubstituted or substituted with 1-5 substituents, where said substituents are independently selected from:
 (a) halo,
 (b) hydroxy,
 (c) —$C_{0-6}$alkyl
 (d) —O—$C_{1-3}$alkyl,
 (e) trifluoromethyl, and
 (f) —$C_{0-2}$alkyl-phenyl,
 where said phenyl, heterocycle, cycloalkyl, and $C_{0-4}$alkyl is unsubstituted or substituted with 1-5 substituents where said substituents are independently selected from the group consisting of:
 (a) halo,
 (b) trifluoromethyl,
 (c) hydroxy,
 (d) $C_{1-3}$alkyl,
 (e) —O—$C_{1-3}$alkyl,
 (f) —$C_{0-3}$—$COR^{11}$,
 (g) —CN,
 (h) —$NR^{12}R^{12}$,
 (i) —$CONR^{12}R^{12}$, and
 (j) —$C_{0-3}$-heterocycle,
 or where the phenyl and heterocycle may be fused to another heterocycle, which itself may be unsubstituted or substituted with 1-2 substituents independently selected from hydroxy, halo, —$COR^{11}$, and —$C_{1-3}$alkyl, and where alkene is unsubstituted or substituted with 1-3 substituents which are independently selected from the group consisting of:
(a) halo,
(b) trifluoromethyl,
(c) $C_{1-3}$alkyl,
(d) phenyl, and
(e) heterocycle;

$R^8$ is nothing;
or $R^7$ and $R^9$ may be joined together to form a ring which is heterocycle,
wherein said ring is unsubstituted or substituted with 1-7 substituents where said substituents are independently selected from the group consisting of:
(a) halo,
(b) trifluoromethyl,
(c) hydroxy,
(d) $C_{1-3}$alkyl,
(e) —O—$C_{1-3}$alkyl,
(f) —$COR^{11}$,
(g) —CN,
(h) —$NR^{12}R^{12}$, and
(i) —$CONR^{12}R^{12}$;

$R^9$ and $R^{10}$ are independently selected from the group consisting of:
(a) hydrogen,
(b) hydroxy,
(c) $C_{1-6}$alkyl
(d) $C_{1-6}$alkyl-$COR^{11}$,
(e) $C_{1-6}$alkyl-hydroxy,
(f) —O—$C_{1-3}$alkyl,
(g) =O, when $R^9$ or $R^{10}$ is connected to the ring via a double bond, and
(h) halo;

n is 1;
the dashed line represents a single or a double bond;
or a pharmaceutically acceptable salt thereof.

2. The compound of claim 1 having formula If:

If wherein X is N or O,
or a pharmaceutically acceptable salt thereof.

3. The compound of claim 2, wherein
X is O;
$R^3$ is absent when Y is N and hydrogen when Y is C;
$R^7$ is nothing; and
$R^2$ is hydrogen;
or a pharmaceutically acceptable salt thereof.

4. The compound of claim 1 wherein $R^1$ is selected from the group consisting of:
—$C_{1-6}$alkyl, —$C_{0-6}$alkyl-O—$C_{1-6}$alkyl, and —($C_{0-6}$alkyl)-($C_{3-7}$cycloalkyl)-($C_{0-6}$alkyl),
where the alkyl and the cycloalkyl are unsubstituted or substituted with 1-7 substituents where the substituents are independently selected from:
(a) halo,
(b) hydroxy,
(c) —O—$C_{1-3}$alkyl,
(d) trifluoromethyl,
(f) $C_{1-3}$alkyl,
(g) —O—$C_{1-3}$alkyl,
(h) —$COR^{11}$,
(i) —CN,
(j) —$NR^{12}R^{12}$, and
(k) —$CONR^{12}R^{12}$,
or a pharmaceutically acceptable salt thereof.

5. The compound of claim 1 wherein $R^1$ is selected from the group consisting of:
(1) —$C_{1-6}$alkyl, which is unsubstituted or substituted with 1-6 substituents where the substituents are independently selected from the group consisting of:
(a) halo,
(b) hydroxy,
(c) —O—$C_{1-3}$alkyl,
(d) trifluoromethyl, and
(e) —$COR^{11}$,
(2) —$C_{0-6}$alkyl-O—$C_{1-6}$alkyl-, which is unsubstituted or substituted with 1-6 substituents where the substituents are independently selected from the group consisting of:
(a) halo,
(b) trifluoromethyl, and
(c) —$COR^{11}$,
(3) and —($C_{3-5}$cycloalkyl)-($C_{0-6}$alkyl), which is unsubstituted or substituted with 1-7 substituents where the substituents are independently selected from the group consisting of:
(a) halo,
(b) hydroxy,
(c) —O—$C_{1-3}$alkyl,
(d) trifluoromethyl, and
(e) —$COR^{11}$,
or a pharmaceutically acceptable salt thereof.

6. The compound of claim 5 wherein $R^1$ is selected from the group consisting of:
(a) $C_{1-6}$alkyl,
(b) $C_{1-6}$alkyl substituted with hydroxy and
(c) $C_{1-6}$alkyl substituted with 1-6 fluoro,
or a pharmaceutically acceptable salt thereof.

7. The compound of claim 6 wherein $R^1$ is selected from the group consisting of:
(a) —$CH(CH_3)_2$,
(b) —$CH(OH)CH_3$, and
(c) —$CH_2CF_3$,
or a pharmaceutically acceptable salt thereof.

8. A pharmaceutical composition which comprises an inert carrier and a compound of claim 1.

9. A method for treating rheumatoid arthritis which comprises the administration to a patient of an effective amount of the compound of claim 1, wherein treating does not include preventing or prophylactic therapy.

10. The compound of claim 1 selected from the following compounds, or a pharmaceutically acceptable salt or individual diastereomer thereof:

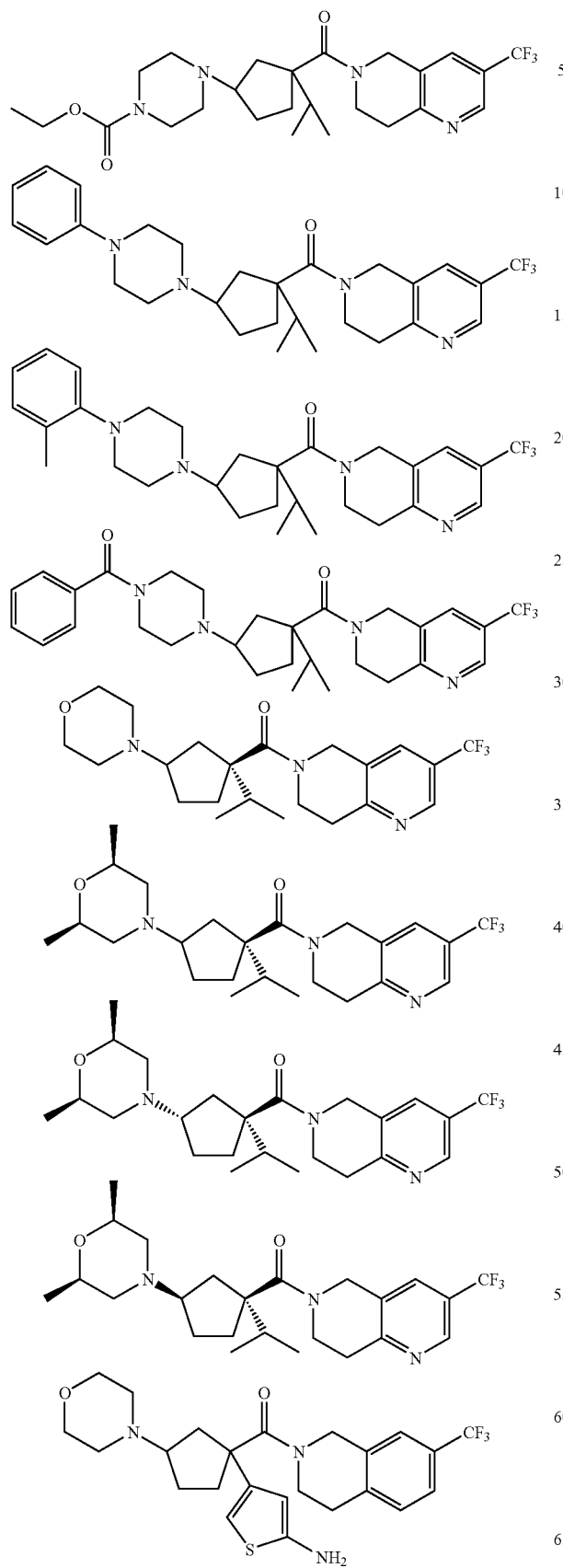
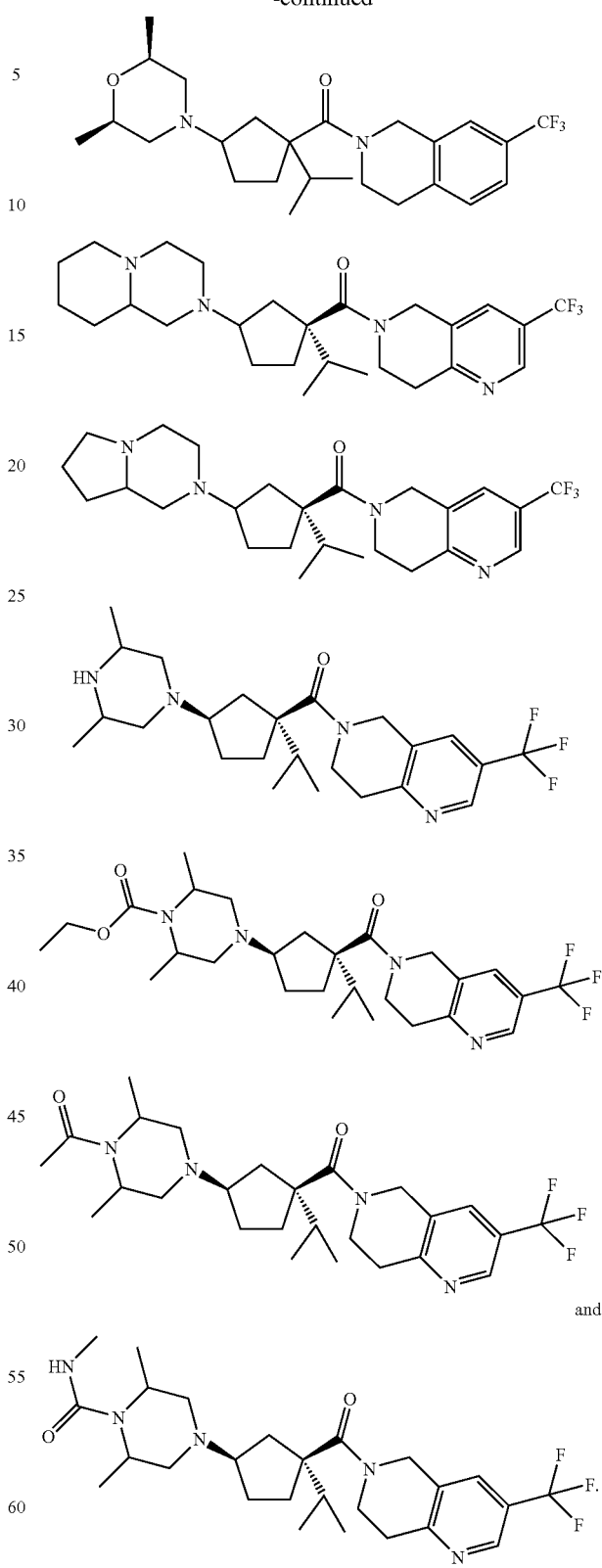
11. The compound of claim 1 wherein $R^5$ is —$CF_3$.
* * * * *

UNITED STATES PATENT AND TRADEMARK OFFICE
CERTIFICATE OF CORRECTION

| | |
|---|---|
| PATENT NO. | : 7,598,243 B2 |
| APPLICATION NO. | : 10/260008 |
| DATED | : October 6, 2009 |
| INVENTOR(S) | : Butora et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1389 days.

Signed and Sealed this

Twenty-eighth Day of September, 2010

David J. Kappos
*Director of the United States Patent and Trademark Office*